US008580781B2

(12) United States Patent
Dorsch et al.

(10) Patent No.: US 8,580,781 B2
(45) Date of Patent: Nov. 12, 2013

(54) PYRIDAZINONE DERIVATIVES

(75) Inventors: Dieter Dorsch, Ober-Ramstadt (DE);
Frank Stieber, Heidelberg (DE); Oliver Schadt, Rodenbach (DE); Andree Blaukat, Muehltal (DE)

(73) Assignee: Merck Patent GmbH, Darmstadt (DE)

( * ) Notice: Subject to any disclaimer, the term of this patent is extended or adjusted under 35 U.S.C. 154(b) by 683 days.

(21) Appl. No.: 12/668,535

(22) PCT Filed: Apr. 29, 2008

(86) PCT No.: PCT/EP2008/003473
§ 371 (c)(1),
(2), (4) Date: Jan. 11, 2010

(87) PCT Pub. No.: WO2009/006959
PCT Pub. Date: Jan. 15, 2009

(65) Prior Publication Data
US 2010/0234354 A1 Sep. 16, 2010

(30) Foreign Application Priority Data
Jul. 12, 2007 (DE) .................. 10 2007 032 507

(51) Int. Cl.
*C07D 403/10* (2006.01)
*C07D 403/14* (2006.01)
*C07D 401/14* (2006.01)
*C07D 413/14* (2006.01)
*A61K 31/501* (2006.01)
*A61K 31/5355* (2006.01)
*A61K 31/551* (2006.01)
*A61P 35/00* (2006.01)

(52) U.S. Cl.
USPC .............. 514/217.06; 514/252.02; 514/236.5; 540/601; 544/238; 544/122

(58) Field of Classification Search
USPC .................. 544/238, 122; 514/252.02, 236.5, 514/217.06; 540/601
See application file for complete search history.

(56) References Cited

U.S. PATENT DOCUMENTS

| 6,242,461 | B1 | 6/2001 | Goldstein |
| 6,403,586 | B1 | 6/2002 | Ohkuchi et al. |
| 8,071,593 | B2 | 12/2011 | Schadt et al. |
| 8,173,653 | B2 | 5/2012 | Dorsch et al. |
| 2004/0152739 | A1 | 8/2004 | Hanau |
| 2004/0259863 | A1 | 12/2004 | Eggenweiler et al. |
| 2005/0107391 | A1 | 5/2005 | Cui et al. |
| 2007/0015771 | A1 | 1/2007 | Matteucci et al. |
| 2007/0043057 | A1 | 2/2007 | Matteucci et al. |
| 2007/0203136 | A1 | 8/2007 | Lu et al. |
| 2007/0265272 | A1 | 11/2007 | Cheng et al. |
| 2008/0293719 | A1 | 11/2008 | Dorsch et al. |
| 2009/0098181 | A1 | 4/2009 | Lu et al. |
| 2009/0124612 | A1 | 5/2009 | Albrecht et al. |
| 2010/0197690 | A1 | 8/2010 | Schadt et al. |
| 2010/0234354 | A1 | 9/2010 | Dorsch et al. |
| 2010/0273796 | A1 | 10/2010 | Dorsch et al. |
| 2010/0280030 | A1 | 11/2010 | Schadt et al. |
| 2010/0286390 | A1 | 11/2010 | Shigeta et al. |
| 2011/0034474 | A1 | 2/2011 | Dorsch et al. |
| 2011/0092498 | A1 | 4/2011 | Dorsch et al. |
| 2011/0098269 | A1* | 4/2011 | Becknell et al. ............ 514/210.2 |
| 2011/0112061 | A1* | 5/2011 | Hu et al. .................... 514/210.2 |
| 2011/0263596 | A1 | 10/2011 | Schadt et al. |
| 2011/0269957 | A1* | 11/2011 | Fandrick et al. ................ 544/96 |
| 2012/0028988 | A1* | 2/2012 | Sakamoto et al. ....... 514/252.03 |
| 2012/0040949 | A1* | 2/2012 | Berthel et al. ........... 514/210.16 |

FOREIGN PATENT DOCUMENTS

| DE | 196 04 388 | 8/1997 |
| DE | 10 2005 057 924 | 6/2007 |
| EP | 1 061 077 | 12/2000 |
| JP | 10 259176 | 9/1998 |
| JP | 2001 192384 | 7/2001 |
| WO | WO-2003 037349 | 5/2003 |
| WO | WO-2004 058762 | 7/2004 |
| WO | WO-2005 004607 | 1/2005 |
| WO | WO-2006 015263 | 2/2006 |
| WO | WO-2007 044796 | 4/2007 |
| WO | WO-2007 0570932 | 5/2007 |
| WO | WO-2007 064797 | 6/2007 |
| WO | WO-2007 065518 | 6/2007 |
| WO | WO 2007/065518 A | 6/2007 |
| WO | WO-2007 075567 | 7/2007 |
| WO | WO-2007 130383 | 11/2007 |
| WO | WO-2007 132308 | 11/2007 |
| WO | WO-2008 008539 | 1/2008 |
| WO | WO-2008 075068 | 6/2008 |
| WO | WO-2009 006959 | 1/2009 |
| WO | WO-2009 007074 | 1/2009 |
| WO | WO-2009 050197 | 4/2009 |
| WO | WO-2009 053737 | 4/2009 |

(Continued)

OTHER PUBLICATIONS

Glen, et al., BMC Cancer 2011, 11:309.*
Smolen, et al., Proc Natl Acad Sci U S A. Feb. 14, 2006; 103(7): 2316-2321.*
Wang, et al., Clin Cancer Res. Mar. 15, 2012;18(6)1663-71.*
Chen, et al., Circulation, 2008; 118: 84-95.*
"International Search Report," International Application PCT/EP2008/003473, Date of completion Jul. 28, 2008, Date of Mailing Aug. 6, 2008, 2pages.
"Cancer" MedLine Plus (2009). Accessed Mar. 17, 2009. http://www.nlm.nih.gov/medlineplus/cancer.html.
Buchanan, Sean G. "SGX523 is an exquisitely selectively, ATP-competitive inhibitor of the MET receptor tyrosine kinase with anti-tumor activity in vivo" Molecular Cancer Therapeutics, Dec. 2009;8(12): 3181-3190.

(Continued)

*Primary Examiner* — James O Wilson
*Assistant Examiner* — Cecilia M Jaisle
(74) *Attorney, Agent, or Firm* — Millen, White, Zelano & Branigan, P.C.

(57) ABSTRACT

Compounds of the formula (I), in which $R^1$, $R^2$, $R^3$, $R^4$, $R^{4'}$ have the meanings indicated in claim 1, are inhibitors of tyrosine kinases, in particular Met kinase, and can be employed, inter alia, for the treatment of tumors.

29 Claims, No Drawings

(56) References Cited

FOREIGN PATENT DOCUMENTS

| | | |
|---|---|---|
| WO | WO-2009 063061 | 5/2009 |
| WO | WO-2009 080314 | 7/2009 |
| WO | WO-2009 080364 | 7/2009 |
| WO | WO-2009 080533 | 7/2009 |
| WO | WO-2009 080534 | 7/2009 |
| WO | WO-2009 080555 | 7/2009 |
| WO | WO-2009 080721 | 7/2009 |
| WO | WO-2009 080725 | 7/2009 |
| WO | WO-2009 081197 | 7/2009 |
| WO | WO-2009 083076 | 7/2009 |
| WO | WO-2009 083105 | 7/2009 |
| WO | WO-2009 085659 | 7/2009 |
| WO | WO-2009 086041 | 7/2009 |
| WO | WO-2009 086264 | 7/2009 |

OTHER PUBLICATIONS

Cancer Drug Design and Discovery, Neidle, Stephen, ed. (Elsevier/Academic Press), pp. 427-431, 2008.
Database CA (Online) Chemical Abstracts Service, Columbus, Ohio US:2002, Dushamov, D.A.et al., Acylation of 6-halobenzoxazolin-2-ones by acid chlorides in the presence of a small quantity of iron(III) chloride hexahydrate, XP002496356.
Database CA (Online) Chemical Abstracts Service, Columbus, Ohio US:1979, Domagalina, Eugenia et al, "Acylation of benzoxazolin—2-ones and 3-hydroxyl-1, 2 benzisoxazoles," XP002496357 Polish Journal of Pharmacology and Pharmacy.
Database CA (Online) Chemical Abstracts Service, Columbus, Ohio US; 1967, Nitta, yoshihiro et al: "Benzoxazolone derivatives," XP002496358.
Ettmayer et al. "Lessons Learned from Marketed and Investigational Prodrugs" J. Med. Chem., (2004), 47(10):2393-2404.
Flouzat, Christine et al. "Synthesis and N-substitution of an uncommon heterocyclic system: oxazolo[5,4-b]pyridin-2(1H)-one," Tetrahedron Letters, Bd. 33, Nr. 32, 1992 Seiten 4571-4574, XP00249354.
Golub et al. "Molecular Classification of Cancer: Class Discovery and Class Prediction by Gene Expression Monitoring" Science (1999), 286:521-537.
Guessous, Fadila et al. "An orally Bioavailable c-Met Kinase Inhibitor Potently Inhibits Brain Tumor Malignancy and Growth", Anti-Cancer in Medicinal Chemistry, 2010, 10(1):28-35.
H. Refaat et al., "Synthesis and Anti-Inflammatory Activity of Certain Piperazinylthienylpyridazine Derivatives," Arch Pharm Res., vol. 30, No. 7 (2007) pp. 803-811.
http://www.uspto.gov/wb/offices/pac/dapp/1pecba.htm#7 last accessed on Nov. 22, 2011.
International Search Report "International Application No. PCT/EP2008/003696," Date of Completion Sep. 18, 2008, Date of Mailing Oct. 1, 2008, 4 pages.
International Search Report of PCT/EP2008/009970 dated Jan. 28, 2009.
International Search Report of PCT/EP2009/002137 (Jun. 4, 2009).
International Search Report of PCT/EP2009/003675 (Aug. 26, 2009).
Jin et al., Mol. Cancer Ther., Jul. 2006, vol. 5, pp. 1754-1763.
Jin, Hongkui et al. "MetMAb, the One-Armed 5D5 Anti-c-Met Antibody, Inhibits Orthotopic Pancreatic Tumor Growth and Improves Survival", Cancer Res 2008;68(11):4360-4368; Jun. 1, 2008. www.aacrjournals.org.
Johnson et al. "Relationships between drug activity in NCI preclinical in vitro and in vivo models and early clinical trials." British Journal of Cancer (2001) 84(10):1424-1431.
Knowles, Lynn M. et al. "HGF and c-Met Participate in Paracrine Tumorigenic Pathways in Head and Neck Squamous Cell Cancer", Clin Cancer Res, Jun. 1, 2009; 15(11):3740-3750. www.aacrjournals.org.
Lala et al. "Role of nitric oxide in tumor progression: Lessons from experimental tumors." Cancer and Metastasis Review (1998), 17(1), 91-106.
Lima, L. M. et al., "Bioisosterism: a useful strategy for molecular modification and drug design," Current Medicinal Chemistry, 2005, vol. 12, No. 1, pp. 23-49.
Liu, Xiangdong et al. "A novel kinase inhibitor INCB28060 blocks c-MET-dependent signaling, neoplastic activities, and crosstalk with EGFR and HER-3", Clin Cancer Res (45 pages); Published: Sep. 14, 2011.
Locatelli et al., J. Biol. Chem., Jun. 17, 2011, vol. 286, No. 24, pp. 21062-21072.
M. Goekce et al., "Synthesis of New Mannich Bases of Arylpyridazinones as Analgesic and Anti-Inflammatory Agents," Drug Research, vol. 55, No. 6 (2005) pp. 318-325.
Morissette et al. "High-throughput crystallization: polymorphs, salts, co-crystals and solvates of pharmaceutical solids." Advanced Drug Deliver Reviews 2004, 56 275-300.
Qian, Fawn et al. "Inhibition of Tumor Cell Growth, Invasion, and Metastasis by EXEL-2880 (XL880, GSK1363089), a Novel Inhibitor of HGF and VEGF Receptor Tyrosine Kinases", Cancer Res 2009;69(20):8009-8016. Dated: Oct. 15, 2009. www.aacrjournals.org.
Samlowski et al., BJU Int., 2008, vol. 102, No. 2, pp. 162-165, Abstract.
Sampson, Erik R. et al. "The Orally Bioavailable Met Inhibitor PF-2341066 Inhibits Osteosarcoma Growth and Osteolysis/Matrix Production in a Xenograft Model", Journal of Bone and Mineral Research, 26(6):1283-1294; Dated: Jun. 2011.
Sausville et al. "Contributions of Human Tumor Xenografts to Anticancer Drug Development" Cancer Res. 2006, 66(7), Apr. 1, 2006.
Search Report for Chilean Patent Application No. 3854-08 filed Dec. 19, 2008.
Singapore Written Opinion for Application No. 201007486-2 (Sep. 26, 2011).
Souillac et al. Characterization of Delivery Systems, Differential Scanning Calorimetry, pp. 217-218 (in Encyclopedia of Controlled Drug Delivery, 1999, John Wiley & Sons, pp. 212-227).
Stella, V. "Prodrugs as therapeutics" Expert Opin. Ther. Patents (2004), 14(3):277-280.
Testa, B. "Prodrug research: futile or fertile?" Biochemical Pharmacology, 68 (2004): 2097-2106.
Tuynman et al., Br. J. Cancer, 2008, vol. 98, No. 6, pp. 1102-1108, Abstract.
Ucar, Huseyin et al., "Fries Like Rearragement: a novel and efficient metod for the sythesis of 6-acyl-2(3H)-benzoxazolones and 6-acyl-2(3H)-benzothiazolones" Tetrahedron, Bd. 54, Nr. 9, 1998, Seiten 1763-1772 XP002496355.
Underiner et al., Anti-Cancer Agents in Medicinal Chemistry, 2010, vol. 10, pp. 7-27.
Vippagunta, S.R. "Crystalline Solids" Advanced Drug Delivery Reviews 48(2001):3-26.
Zillhardt, Marion et al. "Foretinib (GSK1363089), an Orally Available Multikinase Inhibitor of c-Met and VEGFR-2, Blocks Proliferation, Induces Anoikis, and Impairs Ovarian Cancer Metastasis", Clin Cancer Res 2011;17:4042-4051. Published: May 6, 2011. www.aacrjournals.org.
Zou, Helen Y. et al. "An Orally Available Small-Molecule Inhibitor of c-Met, PF-2341066, Exhibits Cytoreductive Antitumor Efficacy through Antiproliferative and Antiangiogenic Mechanisms", Cancer Res 2007; 67:(9)4408-4417. Dated: May 1, 2007. www.aacrjournals.org.
Zou, Helen Y. et al. "Sensitivity of Selected Human tumor Models to PF-04217903, a Novel Selective c-Met Kinase Inhibitor", Molecular Cancer Therapeutics, American Association for Cancer Research. 32 pages. Published: Mar. 2, 2012.
Merck Patent GMBH, "New Aryl-alkyl diazinone derivatives," Espacenet, Publication Date: Aug. 14, 1997; English Abstract of DE-196 04 388.
Japan Tobacco Inc., "New Amide derivative having vascularization inhibiting action and its use," Patent Abstracts of Japan, Publication Date: Sep. 29, 1998; English Abstracts of JP-10 259176.

(56) References Cited

OTHER PUBLICATIONS

Fujisawa Pharmaceut Co Ltd., "Pyrazolopyridine compound and pharmaceutical use thereof," Patent Abstracts of Japan, Publication Date: Jul. 17, 2001.
Office Action for Related Columbian Patent Application No. 09-138245 dated Sep. 21, 2012.
Berthou, S. et al., "The Met kinase inhibitor SU11274 exhibits a selective inhibition pattern toward different receptor mutated variants," Oncogene, 2004, vol. 23, pp. 5387-5393.
Database Beilstein, Beilstein Institute for Organic Chemistry, Frankfurt, DE, XP002506064M 1991.
Databse Beilstein, Beilstein Institute for Organic Chemistry, Frankfurt, DE, XP002506065, 2008.
Hackh's Chem Dict., $3^{rd}$. Ed., 1944, p. 18.
Hawley's Condensed Chem Dict., $14^{th}$ Ed., 2002.
Hill, K. S. et al., "Met Receptor Tyrosine Kinase Signaling Induces Secretion of the Angiogenic Chemokine Interleukin-8/CXCL8 in Pancreatic Cancer," PLoS ONE, Jul. 1, 2012, vol. 7, No. 7, e40420.
http://www.iupac.org/goldbook/A00123.pdf, downloaded Oct. 29, 2010.
International Search Report for PCT/EP2008/005928 dated Dec. 11, 2008.
International Search Report of PCT/EP2009/005172 dated Jan. 26, 2010.
Wolff et al. Burger's Medicinal Chemistry and Drug Discovery. $5^{th}$ Ed. vol. 1 Principles and Practice, 1995, pp. 975-977.
Ziegler, D. S. et al., "Resistance of human glioblastoma multiforme cells to growth factor inhibitors is overcome by blockade of inhibitors of apoptosis proteins," Journal of Clinical Investigation, Sep. 9, 2008, vol. 118, pp. 3109-3122.

* cited by examiner

PYRIDAZINONE DERIVATIVES

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of signal transduction by kinases, in particular tyrosine kinases and/or serine/threonine kinases, plays a role, furthermore to pharmaceutical compositions which comprise these compounds, and to the use of the compounds for the treatment of kinase-induced diseases.

In particular, the present invention relates to compounds and to the use of compounds in which the inhibition, regulation and/or modulation of signal transduction by Met kinase plays a role.

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of disease states and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88, 229-279).

The role of the receptor tyrosine kinase Met in human oncogenesis and the possibility of inhibition of HGF (hepatocyte growth factor)dependent Met activation are described by S. Berthou et al. in Oncogene, Vol. 23, No. 31, pages 5387-5393 (2004). The inhibitor SU11274 described therein, a pyrrole-indoline compound, is potentially suitable for combating cancer. Another Met kinase inhibitor for cancer therapy is described by J. G. Christensen et al. in Cancer Res. 2003, 63(21), 7345-55.

A further tyrosine kinase inhibitor for combating cancer is reported by H. Hov et al. in Clinical Cancer Research Vol. 10, 6686-6694 (2004). The compound PHA-665752, an indole derivative, is directed against the HGF receptor c-Met. It is furthermore reported therein that HGF and Met make a considerable contribution to the malignant process of various forms of cancer, such as, for example, multiple myeloma.

The synthesis of small compounds which specifically inhibit, regulate and/or modulate signal transduction by tyrosine kinases and/or serine/|threonine kinases, in particular Met kinase, is therefore desirable and an aim of the present invention.

It has been found that the compounds according to the invention and salts thereof have very valuable pharmacological properties while being well tolerated.

The present invention specifically relates to compounds of the formula I which inhibit, regulate and/or modulate signal transduction by Met kinase, to compositions which comprise these compounds, and to processes for the use thereof for the treatment of Met kinase-induced diseases and complaints, such as angiogenesis, cancer, tumour formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic diseases and diseases of the immune system, also autoimmune diseases, cirrhosis, diabetes and diseases of the blood vessels, also instability and permeability and the like in mammals.

Solid tumours, in particular fast-growing tumours, can be treated with Met kinase inhibitors. These solid tumours include monocytic leukaemia, brain, urogenital, lymphatic system, stomach, laryngeal and lung carcinoma, including lung adenocarcinoma and small-cell lung carcinoma.

The present invention is directed to processes for the regulation, modulation or inhibition of Met kinase for the prevention and/or treatment of diseases in connection with unregulated or disturbed Met kinase activity. In particular, the compounds of the formula I can also be employed in the treatment of certain forms of cancer. The compounds of the formula I can furthermore be used to provide additive or synergistic effects in certain existing cancer chemotherapies, and/or can be used to restore the efficacy of certain existing cancer chemotherapies and radiotherapies.

The compounds of the formula I can furthermore be used for the isolation and investigation of the activity or expression of Met kinase. In addition, they are particularly suitable for use in diagnostic methods for diseases in connection with unregulated or disturbed Met kinase activity.

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In scintillation proximity assay (Sorg et al., J. of. Biomolecular Screening, 2002, 7, 11-19) and flash-plate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

There are many diseases associated with deregulation of cellular proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, peri-anastomatic prosthetic restenosis, restenosis after angioplasty or stent placement, and the like.

PRIOR ART

Other pyridazine derivatives are described as MET kinase inhibitors in WO 2007/065518.

Thiadiazinones are described in DE19604388, WO2003/037349 WO2007/057093 or WO2007/057092.

Dihydropyridazinones for combating cancer are described in WO 03/037349 A1.

Other pyridazines for the treatment of diseases of the immune system, ischaemic and inflammatory diseases are known from EP 1 043 317 A1 and EP 1 061 077 A1.

EP 0 738 716 A2 and EP 0 711 759 B1 describe other dihydropyridazinones and pyridazinones as fungicides and insecticides.

Other pyridazinones are described as cardiotonic agents in U.S. Pat. No. 4,397,854. JP 57-95964 discloses other pyridazinones.

The use of other MET kinase inhibitors for combating cancer is described in WO 2007/075567.

SUMMARY OF THE INVENTION

The invention relates to compounds of the formula I

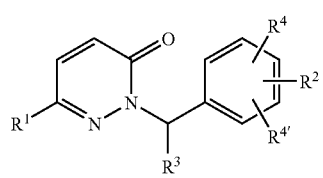

in which
$R^1$ denotes Ar or Het,
$R^2$ denotes an unsaturated, saturated or aromatic 6-membered heterocycle having 1 to 4 N, O and/or S atoms, which may be unsubstituted or mono-, di- or trisubstituted by Hal, A, $[C(R^3)_2]_nOR^3$, $N=CR^3N(R^3)_2$, $SR^3$, $NO_2$, $CN$, $COOR^3$, $CON(R^3)_2$, $NR^3COA$, $NR^3SO_2A$, $SO_2N(R^3)_2$, $S(O)_mA$, $[C(R^3)_2]_nN(R^3)_2$, $[C(R^3)_2]_n$Het, $O[C(R^3)_2]_pOR^3$, $O[C(R^3)_2]_nN(R^3)_2$, $O[C(R^3)_2]_nC\equiv C[C(R^3)_2]_nN(R^3)_2$, $O[C(R^3)_2]_nN^{+O-}(R^3)_2$, $O[C(R^3)_2]_n$Het, $S[C(R^3)_2]_nN(R^3)_2$, $S[C(R^3)_2]_n$Het, $NR^3[C(R^3)_2]_nN(R^3)_2$, $NR^3[C(R^3)_2]_n$Het, $NHCON(R^3)_2$, $NHCONH[C(R^3)_2]_nN(R^3)_2$, $NHCONH[C(R^3)_2]_n$Het, $NHCO[C(R^3)_2]_nN(R^3)_2$, $NHCO[C(R^3)_2]_n$Het, $CONR^3)_2$, $CONR^3[C(R^3)_2]_nN(R^3)_2$, $CONR^3[C(R^3)_2]_n NR^3COOA$, $CONR^3[C(R^3)_2]_nOR^3$, $CONR^3[C(R^3)_2]_n$Het, $COHet$, $COA$, $CH=CH-COOR^3$, $CH=CH-N(R^3)_2$ and/or $=O$ (carbonyl oxygen),
$R^3$ denotes H or A,
$R^4$, $R^{4'}$ each, independently of one another, denote H, Hal, A, $OR^3$, $CN$, $COOR^3$, $CON(R^3)_2$, $NR^3COA$, $NR^3SO_2A$, $SO_2N(R^3)_2$ or $S(O)_mA$,
Ar denotes phenyl, naphthyl or biphenyl, each of which is unsubstituted or mono-, di- or trisubstituted by Hal, A, $[C(R^3)_2]_nOR^3$, $[C(R^3)_2]_nN(R^3)_2$, $SR^3$, $NO_2$, $CN$, $COOR^3$, $CON(R^3)_2$, $NR^3COA$, $NR^3SO_2A$, $SO_2N(R^3)_2$, $S(O)_mA$, $CO$-Het, Het, $O[C(R^3)_2]_nN(R^3)_2$, $O[C(R^3)_2]_n$Het, $NHCOOA$, $NHCON(R^3)_2$, $NHCOO[C(R^3)_2]_nN(R^3)_2$, $NHCOO[C(R^3)_2]_n$-Het, $NHCONH[C(R^3)_2]_nN(R^3)_2$, $NHCONH[C(R^3)_2]_n$Het, $OCONH[C(R^3)_2]_nN(R^3)_2$, $OCONH[C(R^3)_2]_n$Het, $CONR^3[C(R^3)_2]_nN(R^3)_2$, $CONR^3[C(R^3)_2]_n$Het and/or $COA$,
Het denotes a mono-, bi- or tricyclic saturated, unsaturated or aromatic heterocycle having 1 to 4 N, O and/or S atoms, which may be unsubstituted or mono-, di-, tri-, tetra- or pentasubstituted by Hal, A, $[C(R^3)_2]_nOR^3$, $[C(R^3)_2]_nN(R^3)_2$, $SR^3$, $NO_2$, $CN$, $COOR^3$, $CON(R^3)_2$, $NR^3COA$, $NR^3SO_2A$, $SO_2N(R^3)_2$, $S(O)_mA$, $CO$-Het$^1$, $[C(R^3)_2]_n$Het$^1$, O[C(R³)₂]ₙN(R³)₂, O[C(R³)₂]ₙHet¹, NHCOOA, NHCON(R³)₂, NHCOO[C(R³)₂]ₙN(R³)₂, NHCOO[C(R³)₂]ₙHet¹, NHCONH[C(R³)₂]ₙN(R³)₂, NHCONH[C(R³)₂]ₙHet¹, OCONH[C(R³)₂]ₙN(R³)₂, OCONH[C(R³)₂]ₙHet¹, CO-Het¹, CHO, COA, =S, =NH, =NA and/or =O (carbonyl oxygen), and where a ring nitrogen may be oxidised, Het¹ denotes a monocyclic saturated heterocycle having 1 to 2 N and/or O atoms, which may be mono- or disubstituted by A, OA, OH, Hal and/or =O (carbonyl oxygen), A denotes unbranched or branched alkyl having 1-10 C atoms, in which 1-7 H atoms may be replaced by F and/or in which one or two non-adjacent CH₂ groups may be replaced by O, NH, S, SO, SO₂ and/or by CH=CH groups, or cyclic alkyl having 3-7 C atoms, Hal denotes F, Cl, Br or I, m denotes 0, 1 or 2, n denotes 0, 1, 2, 3 or 4, p denotes 1, 2, 3 or 4, and pharmaceutically usable derivatives, solvates, salts, tautomers and stereoisomers thereof, including mixtures thereof in all ratios.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force solvates are, for example, mono- or dihydrates or alkoxides.

The term pharmaceutically usable derivatives is taken to mean, for example, the salts of the compounds according to the invention and also so-called prodrug compounds.

The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to Claims 1-10 and pharmaceutically usable derivatives, salts, solvates, tautomers and stereoisomers thereof, characterised in that a) a compound of the formula II

II in which R¹ has the meaning indicated in Claim 1, is reacted with a compound of the formula III

III in which R², R³, R⁴ and R⁴' have the meanings indicated in Claim 1 and L denotes Cl, Br, I or a free or reactively functionally modified OH group, or b) a radical R² is converted into another radical R² by
i) converting an oxadiazole radical into a pyrimidinyl radical,
ii) acylating or alkylating an amino group,
iii) etherifying a hydroxyl group, or c) that it is liberated from one of its functional derivatives by treatment with a solvolysing or hydrogenolysing agent, and/or a base or acid of the formula I is converted into one of its salts.

Above and below, the radicals R¹, R², R³, R⁴, R⁴' have the meanings indicated for the formula I, unless expressly stated otherwise.

A denotes alkyl, this is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cyclic alkyl(cycloalkyl) preferably denotes cyclopropyl, cyclobutyl, cyclopentyl, cyclohexyl or cycloheptyl.

Ar denotes, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-di-methylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-methylsulfanylphenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-(morpholin-4-ylcarbonyl)phenyl, o-, m- or p-(morpholin-4-ylcarbonyl)phenyl, o-, m- or p-(3-oxomorpholin-4-yl)phenyl, o-, m- or p-(piperidinylcarbonyl)phenyl, o-, m- or p-[2-(morpholin-4-yl)ethoxy]phenyl, o-, m- or p-[3-(N,N-diethylamino)propoxy]phenyl, o-, m- or p-[3-(3-diethylaminopropyl)ureido]phenyl, o-, m- or p-(3-diethylaminopropoxycarbonylamino)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar furthermore preferably denotes phenyl, naphthyl or biphenyl, each of which is unsubstituted or mono-, di- or trisubstituted by A, Hal, CN, S(O)$_m$A, NR$^3$COA, CON(R$^3$)$_2$, O[C(R$^3$)$_2$]$_n$N(R$^3$)$_2$, [C(R$^3$)$_2$]$_n$OR$^3$, CONR$^3$[C(R$^3$)$_2$]$_n$N(R$^3$)$_2$ and/or CONR$^3$[C(R$^3$)$_2$]$_n$Het.

Irrespective of further substitutions, Het denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, azabicyclo-[3.2.1]octyl or dibenzofuranyl.

The heterocyclic radicals may also be partially or fully hydrogenated.

Irrespective of further substitutions, Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-,-2-,-3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Het preferably denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, azabicyclo[3.2.1]octyl, azabicyclo[2.2.2]octyl, imidazolidinyl, azepanyl or benzo-2,1,3-thiadiazolyl, each of which is unsubstituted or mono-, di-, tri-, tetra- or pentasubstituted by A, CHO, COOR$^3$, CON(R$^3$)$_2$, [C(R$^3$)$_2$]$_n$Het$^1$, [C(R$^3$)$_2$]$_n$OR$^3$, [C(R$^3$)$_2$]$_n$N(R$^3$)$_2$, O[C(R$^3$)$_2$]$_n$Het$^1$ and/or =O (carbonyl oxygen), and where a ring nitrogen may be oxidised.

Het$^1$ preferably denotes pyrrolidine, piperidine, piperazine or morpholine, each of which is unsubstituted or mono- or disubstituted by A and/or =O (carbonyl oxygen).

R$^1$ preferably denotes Ar or benzo-2,1,3-thiadiazolyl.

The unsaturated, saturated or aromatic 6-membered heterocycle having 1 to 4 N and/or O atoms in the meaning for R$^2$ has, for example, the following meanings: pyrimidine, pyridazine, pyridine, 1,3-oxazinane, morpholine, piperidine, piperazine, 1,4-dihydropyridine, 1,2,3,4-tetrahydro-6-pyridine, tetrahydropyran, 1,4-dioxane, 1,3-dioxane, hexahydropyridazine or hexahydropyrimidine.

R$^2$ preferably denotes pyrimidinyl, pyridazinyl, pyridinyl, 1,3-oxazinanyl, morpholinyl, piperidinyl or piperazinyl, each of which is unsubstituted or mono-, di- or trisubstituted by Hal, A, [C(R$^3$)$_2$]$_n$OR$^3$, N=CR$^3$N(R$^3$)$_2$, CN, COOR$^3$, [C(R$^3$)$_2$]$_n$N(R$^3$)$_2$, [C(R$^3$)$_2$]$_n$Het, O[C(R$^3$)$_2$]$_p$OR$^3$, O[C(R$^3$)$_2$]$_n$N(R$^3$)$_2$, O[C(R$^3$)$_2$]$_n$C=C[C(R$^3$)$_2$]$_n$N(R$^3$)$_2$, O[C(R$^3$)$_2$]$_n$N$^+$O$^-$(R$^3$)$_2$, O[C(R$^3$)$_2$]$_n$Het, NR$^3$[C(R$^3$)$_2$]$_n$N(R$^3$)$_2$, NR$^3$[C(R$^3$)$_2$]$_n$Het, [C(R$^3$)$_2$]$_n$NHCO[C(R$^3$)$_2$]$_n$N(R$^3$)$_2$, [C(R$^3$)$_2$]$_n$NHCO[C(R$^3$)$_2$]$_n$Het, CONR$^3$[C(R$^3$)$_2$]$_n$N(R$^3$)$_2$, CONR$^3$[C(R$^3$)$_2$]$_n$NR$^3$COOA, CONR$^3$[C(R$^3$)$_2$]$_n$OR$^3$, CONR$^3$[C(R$^3$)$_2$]$_n$Het, COHet, CH=CH—COOR$^3$, CH=CH—N(R$^3$)$_2$ and/or =O (carbonyl oxygen).

R$^3$ preferably denotes H, methyl, ethyl or propyl.

R$^4$, R$^{4'}$ preferably denote H.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to II, which conform to the formula I and in which the radicals not designated in greater detail have the meaning indicated for the formula I, but in which in Ia $R^2$ denotes an unsaturated, saturated or aromatic 6-membered heterocycle having 1 to 4 N and/or O atoms, which may be unsubstituted or mono-, di- or trisubstituted by Hal, A, $[C(R^3)_2]_nOR^3$, $N=CR^3N(R^3)_2$, CN, $COOR^3$, $[C(R^3)_2]_nN(R^3)_2$, $[C(R^3)_2]_n$Het, $O[C(R^3)_2]_pOR^3$, $O[C(R^3)_2]_nN(R^3)_2$, $O[C(R^3)_2]_nC\equiv C[C(R^3)_2]_nN(R^3)_2$, $O[C(R^3)_2]_nN^+O^-(R^3)_2$, $O[C(R^3)_2]_n$Het, $NR^3[C(R^3)_2]_nN(R^3)_2$, $NR^3[C(R^3)_2]_n$Het, $[C(R^3)_2]_nNHCO[C(R^3)_2]_nN(R^3)_2$, $[C(R^3)_2]_nNHCO[C(R^3)_2]_n$Het, $CONR^3[C(R^3)_2]_nN(R^3)_2$, $CONR^3[C(R^3)_2]_nNR^3COOA$, $CONR^3[C(R^3)_2]_nOR^3$, $CONR^3[C(R^3)_2]_n$Het, COHet, $CH=CH-COOR^3$, $CH=CH-N(R^3)_2$ and/or =O (carbonyl oxygen);

in Ib Ar denotes phenyl, naphthyl or biphenyl, each of which is unsubstituted or mono-, di- or trisubstituted by A, Hal, CN, $S(O)_mA$, $NR^3COA$, $CON(R^3)_2$, $O[C(R^3)_2]_nN(R^3)_2$, $[C(R^3)_2]_nOR^3$, $CONR^3[C(R^3)_2]_nN(R^3)_2$ and/or $CONR^3[C(R3)_2]_n$Het;

in Ic $R^4$, $R^{4'}$ denote H;

in Id Het denotes a mono-, bi- or tricyclic saturated, unsaturated or aromatic heterocycle having 1 to 4 N, O and/or S atoms, which may be unsubstituted or mono-, di-, tri-, tetra- or pentasubstituted by A, CHO, $COOR^3$, $CON(R^3)_2$, $[C(R^3)_2]_n$Het$^1$, $[C(R^3)_2]_nOR^3$, $[C(R^3)_2]_nN(R^3)_2$, $O[C(R^3)_2]_n$Het$^1$ and/or =O (carbonyl oxygen), and where a ring nitrogen may be oxidised;

in Ie Het$^1$ denotes a monocyclic saturated heterocycle having 1 to 2 N and/or O atoms, which may be mono- or disubstituted by A and/or =O (carbonyl oxygen);

in If A denotes unbranched or branched alkyl having 1-8 C atoms, in which 1-7 H atoms may be replaced by F and/or Cl;

in Ig $R^1$ denotes Ar or benzo-2,1,3-thiadiazolyl;

in Ih $R^3$ denotes H, methyl, ethyl or propyl;

in Ii $R^2$ denotes pyrimidinyl, pyridazinyl, pyridinyl, 1,3-oxazinanyl, morpholinyl, piperidinyl or piperazinyl, each of which is unsubstituted or mono-, di- or trisubstituted by Hal, A, $[C(R^3)_2]_nOR^3$, $N=CR^3N(R^3)_2$, CN, $COOR^3$, $[C(R^3)_2]_nN(R^3)_2$, $[C(R^3)_2]_n$Het, $O[C(R^3)_2]_pOR^3$, $O[C(R^3)_2]_nN(R^3)_2$, $O[C(R^3)_2]_nC\equiv C[C(R^3)_2]_nN(R^3)_2$, $O[C(R^3)_2]_nN^{+-}(R^3)_2$, $O[C(R^3)_2]_n$Het, $NR^3[C(R^3)_2]_nN(R^3)_2$, $NR^3[C(R^3)_{2]n}$Het, $[C(R^3)_2]_nNHCO[C(R^3)_2]_nN(R^3)_2$, $[C(R^3)_2]_nNHCO[C(R^3)_2]_n$Het, $CONR^3[C(R^3)_2]_nN(R^3)_2$, $CONR^3[C(R^3)_2]_nNR^3COOA$, $CONR^3[C(R^3)_2]_nOR^3$, $CONR^3[C(R^3)_2]_n$Het, COHet, $CH=CH-COOR^3$, $CH=CH-N(R^3)_2$ and/or =O (carbonyl oxygen);

in Ij Het denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, azabicyclo[3.2.1]octyl, azabicyclo[2.2.2]octyl, imidazolidinyl, azepanyl or benzo-2,1,3-thiadiazolyl, each of which is unsubstituted or mono-, di-, tri-, tetra- or pentasubstituted by A, CHO, $COOR^3$, $CON(R^3)_2$, $[C(R^3)_2]_n$Het$^1$, $[C(R^3)_2]_nOR^3$, $[C(R^3)_2]_nN(R^3)_2$, $O[C(R^3)_2]_n$Het$^1$ and/or =O (carbonyl oxygen), and where a ring nitrogen may be oxidised;

in Ik Het$^1$ denotes pyrrolidine, piperidine, piperazine or morpholine, each of which is unsubstituted or mono- or disubstituted by A and/or =O (carbonyl oxygen);

in Il $R^1$ denotes Ar or Het,
$R^2$ denotes pyrimidinyl, pyridazinyl, pyridinyl, 1,3-oxazinanyl, morpholinyl, piperidinyl or piperazinyl, each of which is unsubstituted or mono-, di- or trisubstituted by Hal, A, $[C(R^3)_2]_nOR^3$, $N=CR^3N(R^3)_2$, CN, $COOR^3$, $[C(R^3)_2]_nN(R^3)_2$, $[C(R^3)_2]_n$Het, $O[C(R^3)_2]_pOR^3$, $O[C(R^3)_2]_nN(R^3)_2$, $O[C(R^3)_2]_nC\equiv C[C(R^3)_2]_nN(R^3)_2$, $O[C(R^3)_2]_nN^+O^-(R^3)_2$, $O[C(R^3)_2]_n$Het, $NR^3[C(R^3)_2]_nN(R^3)_2$, $NR^3[C(R^3)_2]_n$Het, $[C(R^3)_2]_nNHCO[C(R^3)_2]_nN(R^3)_2$, $[C(R^3)_2]_nNHCO[C(R^3)_2]_n$Het, $CONR^3[C(R^3)_2]_nN(R^3)_2$, $CONR^3[C(R^3)_2]_nNR^3COOA$, $CONR^3[C(R^3)_2]_nOR^3$, $CONR^3[C(R^3)_2]_n$Het, COHet, $CH=CH-COOR^3$, $CH=CH-N(R^3)_2$ and/or =O (carbonyl oxygen), $R^3$ denotes H, methyl, ethyl or propyl, $R^4$, $R^{4'}$ denote H, Ar denotes phenyl, naphthyl or biphenyl, each of which is unsubstituted or mono-, di- or trisubstituted by A, Hal, CN, $S(O)_mA$, $NR^3COA$, $CON(R^3)_2$, $O[C(R^3)_2]_nN(R^3)_2$, $[C(R^3)_2]_nOR^3$, $CONR^3[C(R^3)_2]_nN(R^3)_2$ and/or $CONR^3[C(R^3)_2]_n$Het, Het denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, azabicyclo[3.2.1]octyl, azabicyclo[2.2.2]octyl, imidazolidinyl, azepanyl or benzo-2,1,3-thiadiazolyl, each of which is unsubstituted or mono-, di-, tri-, tetra- or pentasubstituted by A, CHO, $COOR^3$, $CON(R^3)_2$, $[C(R^3)_2]_n$Het$^1$, $[C(R^3)_2]_nOR^3$, $[C(R^3)_2]_nN(R^3)_2$, $O[C(R^3)_2]_n$Het$^1$ and/or =O (carbonyl oxygen), and where a ring nitrogen may be oxidised, Het$^1$ denotes pyrrolidine, piperidine, piperazine or morpholine, each of which is unsubstituted or mono- or disubstituted by A and/or =O (carbonyl oxygen), A denotes unbranched or branched alkyl having 1-8 C atoms, in which 1-7 H atoms may be replaced by F and/or Cl, Hal denotes F, Cl, Br or I, m denotes 0, 1 or 2, n denotes 0, 1, 2, 3 or 4, p denotes 1, 2, 3 or 4;

and pharmaceutically usable derivatives, salts, solvates, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds of the formulae II and III are generally known. If they are novel, however, they can be prepared by methods known per se. The pyridazinones of the formula II used are, if not commercially available, generally prepared by the method of W. J. Coates, A. McKillop, Synthesis, 1993, 334-342.

Compounds of the formula I can preferably be obtained by reacting a compound of the formula II with a compound of the formula III. In the compounds of the formula III, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

The reaction is generally carried out in the presence of an acid-binding agent, preferably an organic base, such as DIPEA, triethylamine, dimethylaniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF.

The reaction of a compound of the formula II with a compound of the formula III in which L denotes OH, is preferably carried out in a Mitsunobu reaction by addition of, for example, triphenylphosphine and a dialkyl azodicarboxylate. THF is preferred as solvent.

It is furthermore possible to convert a compound of the formula I into another compound of the formula I, for example by reducing nitro groups to amino groups (for example by hydrogenation on Raney nickel or Pd/carbon in an inert solvent, such as methanol or ethanol).

Free amino groups can furthermore be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

The compounds of the formula I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an aminoprotecting group instead of an H atom bonded to an N atom, for example those which conform to the formula I, but contain an NHR' group (in which R' is an aminoprotecting group, for example BOC or CBZ) instead of an $NH_2$ group.

Preference is furthermore given to starting materials which carry a hydroxyl-protecting group instead of the H atom of a hydroxyl group, for example those which conform to the formula I, but contain an R"O-phenyl group (in which R" is a hydroxylprotecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "aminoprotecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the aminoprotecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred amino-protecting groups are BOC and Mtr, furthermore CBZ, Fmoc, benzyl and acetyl.

The term "hydroxylprotecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxylprotecting groups are not crucial since they are removed again after the desired chemical reaction or reaction sequence; preference is given to groups having 1-20, in particular 1-10, carbon atoms. Examples of hydroxylprotecting groups are, inter alia, tert-butoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

The trityl group is employed to protect the amino acids histidine, asparagine, glutamine and cysteine. They are cleaved off, depending on the desired end product, using TFA/10% thiophenol, with the trityl group being cleaved off from all the said amino acids; on use of TFA/anisole or TFA/thioanisole, only the trityl group of His, Asn and Gln is cleaved off, whereas it remains on the Cys side chain.

The Pbf (pentamethylbenzofuranyl) group is employed to protect Arg. It is cleaved off using, for example, TFA in dichloromethane.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate(besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine(benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine(tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds.

The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment of tyrosine kinase-induced diseases. These diseases include the proliferation of tumour cells, pathological neovascularisation (or angiogenesis) which promotes the growth of solid tumours, ocular neovascularisation (diabetic retinopathy, age-induced macular degeneration and the like) and inflammation (psoriasis, rheumatoid arthritis and the like).

The present invention encompasses the use of the compounds of the formula I and/or physiologically acceptable salts and solvates thereof for the preparation of a medicament for the treatment or prevention of cancer.

Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, pancreatic cancer, glioblastomas and breast carcinoma.

Also encompassed is the use of the compounds according to Claim 1 according to the invention and/or physiologically acceptable salts and solvates thereof for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The use of compounds of the formula I and/or physiologically acceptable salts and solvates thereof for the preparation of a medicament for the treatment or prevention of inflammatory diseases also falls within the scope of the present invention. Examples of such inflammatory diseases include rheumatoid arthritis, psoriasis, contact dermatitis, delayed hyper-sensitivity reaction and the like.

Also encompassed is the use of the compounds of the formula I and/or physiologically acceptable salts and solvates thereof for the preparation of a medicament for the treatment or prevention of a tyrosine kinase-induced disease or a tyrosine kinase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The compounds of the formula I can be administered to patients for the treatment of cancer, in particular fast-growing tumours.

The invention thus relates to the use of compounds of the formula I, and pharmaceutically usable derivatives, solvates and stereoisomers thereof, including mixtures thereof in all ratios, for the preparation of a medicament for the treatment of diseases in which the inhibition, regulation and/or modulation of kinase signal transduction plays a role.

Preference is given here to Met kinase.

Preference is given to the use of compounds of the formula I, and pharmaceutically usable derivatives, solvates and stereoisomers thereof, including mixtures thereof in all ratios, for the preparation of a medicament for the treatment of diseases which are influenced by inhibition of tyrosine kinases by the compounds according to Claim 1.

Particular preference is given to the use for the preparation of a medicament for the treatment of diseases which are influenced by inhibition of Met kinase by the compounds according to Claim 1.

Especial preference is given to the use for the treatment of a disease where the disease is a solid tumour.

The solid tumour is preferably selected from the group of tumours of the lung, squamous epithelium, the bladder, the stomach, the kidneys, of head and neck, the oesophagus, the cervix, the thyroid, the intestine, the liver, the brain, the prostate, the urogenital tract, the lymphatic system, the stomach and/or the larynx.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti- tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); anti-metabolites (for example antifolates such as fluoropyrimidines like 5-fluorouracil and tegafur, raltitrexed, methotrexate, cytosine arabinoside, hydroxyurea and gemcitabine); anti-tumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metalloproteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbbl antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy)quinazolin-4-amine (gefitinib, AZD1839), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds of the formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson |
| | Tetraplatin | Matthey) |
| | Ormiplatin | BBR-3464 |
| | Iproplatin | (Hoffmann-La Roche) |
| | | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |

TABLE 1-continued

| | | |
|---|---|---|
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharma) | BNP-1350 (BioNumerik) |
| | Rebeccamycin analogue (Exelixis) | CKD-602 (Chong Kun Dang) |
| | BBR-3576 (Novuspharma) | KW-2170 (Kyowa Hakko) |
| Antitumour antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanomorpholinodoxorubicin | |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku Hormone) | Azaepothilon B (BMS) |
| | BMS 247550 (BMS) | BNP-7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |

TABLE 1-continued

| | | |
|---|---|---|
| Pump inhibitors | CBT-1 (CBA Pharma)<br>Tariquidar (Xenova)<br>MS-209 (Schering AG) | Zosuquidar<br>trihydrochloride (Eli Lilly)<br>Biricodar dicitrate (Vertex) |
| Histone acetyl<br>transferase inhibitors | Tacedinaline (Pfizer)<br>SAHA (Aton Pharma)<br>MS-275 (Schering AG) | Pivaloyloxymethyl butyrate<br>(Titan)<br>Depsipeptide (Fujisawa) |
| Metalloproteinase<br>inhibitors | Neovastat (Aeterna Laboratories)<br>Marimastat (British Biotech) | CMT-3 (CollaGenex)<br>BMS-275291 (Celltech) |
| Ribonucleoside<br>reductase inhibitors | Gallium maltolate (Titan)<br>Triapin (Vion) | Tezacitabine (Aventis)<br>Didox (Molecules for<br>Health) |
| TNF-alpha<br>agonists/<br>antagonists | Virulizin (Lorus Therapeutics)<br>CDC-394 (Celgene) | Revimid (Celgene) |
| Endothelin-A receptor<br>antagonists | Atrasentan (Abbot)<br>ZD-4054 (AstraZeneca) | YM-598 (Yamanouchi) |
| Retinoic acid receptor<br>agonists | Fenretinide (Johnson &<br>Johnson)<br>LGD-1550 (Ligand) | Alitretinoin (Ligand) |
| Immunomodulators | Interferon<br>Oncophage (Antigenics)<br>GMK (Progenics)<br>Adenocarcinoma vaccine<br>(Biomira)<br>CTP-37 (AVI BioPharma)<br>JRX-2 (Immuno-Rx)<br>PEP-005 (Peplin Biotech)<br>Synchrovax vaccines (CTL<br>Immuno)<br>Melanoma vaccine (CTL<br>Immuno)<br>p21-RAS vaccine (Gem-<br>Vax) | Dexosome therapy (Anosys)<br>Pentrix (Australian Cancer<br>Technology)<br>JSF-154 (Tragen)<br>Cancer vaccine (Intercell)<br>Norelin (Biostar)<br>BLP-25 (Biomira)<br>MGV (Progenics)<br>!3-Alethin (Dovetail)<br>CLL-Thera (Vasogen) |
| Hormonal and<br>antihormonal<br>agents | Oestrogens<br>Conjugated oestrogens<br>Ethynyloestradiol<br>chlorotrianisene<br>Idenestrol<br>Hydroxyprogesterone<br>caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol (EntreMed)<br>Arzoxifen (Eli Lilly) |
| Photodynamic<br>agents | Talaporfin (Light Sciences)<br>Theralux (Theratechnologies)<br>Motexafin-Gadolinium<br>(Pharmacyclics) | Pd-Bacteriopheophorbid<br>(Yeda)<br>Lutetium-Texaphyrin<br>(Pharmacyclics)<br>Hypericin |
| Tyrosine kinase<br>inhibitors | Imatinib (Novartis)<br>Leflunomide(Sugen/Pharmacia)<br>ZDI839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmith-<br>Kline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |
| Various agents | SR-27897 (CCK-A inhibitor,<br>Sanofi-Synthelabo)<br>Tocladesine (cyclic AMP<br>agonist, Ribapharm)<br>Alvocidib (CDK inhibitor,<br>Aventis)<br>CV-247 (COX-2 inhibitor,<br>Ivy Medical)<br>P54 (COX-2 inhibitor, | BCX-1777 (PNP inhibitor,<br>BioCryst)<br>Ranpirnase (ribonuclease<br>stimulant, Alfacell)<br>Galarubicin (RNA synthesis<br>inhibitor, Dong-A)<br>Tirapazamine (reducing<br>agent, SRI International)<br>N-Acetylcysteine (reducing |

TABLE 1-continued

| | | |
|---|---|---|
| | Phytopharm)<br>CapCell ™ (CYP450 stimulant, Bavarian Nordic)<br>GCS-IOO (gal3 antagonist, GlycoGenesys)<br>G17DT immunogen (gastrin inhibitor, Aphton)<br>Efaproxiral (oxygenator, Allos Therapeutics)<br>PI-88 (heparanase inhibitor, Progen)<br>Tesmilifen (histamine antagonist, YM BioSciences)<br>Histamine (histamine H2 receptor agonist, Maxim)<br>Tiazofurin (IMPDH inhibitor, Ribapharm)<br>Cilengitide (integrin antagonist, Merck KGaA)<br>SR-31747 (IL-1 antagonist, Sanofi-Synthelabo)<br>CCI-779 (mTOR kinase inhibitor, Wyeth)<br>Exisulind (PDE-V inhibitor, Cell Pathways)<br>CP-461 (PDE-V inhibitor, Cell Pathways)<br>AG-2037 (GART inhibitor, Pfizer)<br>WX-UK1 (plasminogen activator inhibitor, Wilex)<br>PBI-1402 (PMN stimulant, ProMetic LifeSciences)<br>Bortezomib (proteasome inhibitor, Millennium)<br>SRL-172 (T-cell stimulant, SR Pharma)<br>TLK-286 (glutathione-S transferase inhibitor, Telik)<br>PT-100 (growth factor agonist, Point Therapeutics)<br>Midostaurin (PKC inhibitor, Novartis)<br>Bryostatin-1 (PKC stimulant, GPC Biotech)<br>CDA-II (apoptosis promoter, Everlife)<br>SDX-101 (apoptosis promoter, Salmedix)<br>Ceflatonin (apoptosis promoter, ChemGenex) | agent, Zambon)<br>R-Flurbiprofen (NF-kappaB inhibitor, Encore)<br>3CPA (NF-kappaB inhibitor, Active Biotech)<br>Seocalcitol (vitamin D receptor agonist, Leo)<br>131-I-TM-601 (DNA antagonist, TransMolecular)<br>Eflornithin (ODC inhibitor, ILEX Oncology)<br>Minodronic acid (osteoclast inhibitor, Yamanouchi)<br>Indisulam (p53 stimulant, Eisai)<br>Aplidin (PPT inhibitor, PharmaMar)<br>Rituximab (CD20 antibody, Genentech)<br>Gemtuzumab (CD33 antibody, Wyeth Ayerst)<br>PG2 (haematopoiesis promoter, Pharmagenesis)<br>Immunol ™ (triclosan mouthwash, Endo)<br>Triacetyluridine (uridine prodrug, Wellstat)<br>SN-4071 (sarcoma agent, Signature BioScience)<br>TransMID-107 ™ (immunotoxin, KS Biomedix)<br>PCK-3145 (apoptosis promoter, Procyon)<br>Doranidazole (apoptosis promoter, Pola)<br>CHS-828 (cytotoxic agent, Leo)<br>Trans-retinic acid (differentiator, NIH)<br>MX6 (apoptosis promoter, MAXIA)<br>Apomine (apoptosis promoter, ILEX Oncology)<br>Urocidin (apoptosis promoter, Bioniche)<br>Ro-31-7453 (apoptosis promoter, La Roche)<br>Brostallicin (apoptosis promoter, Pharmacia) |
| Alkylating agents | Cyclophosphamide<br>Busulfan<br>Ifosfamide<br>Melphalan<br>Hexamethylmelamine<br>Thiotepa<br>chloroambucil<br>Dacarbazine<br>Carmustine | Lomustine<br>Procarbazine<br>Altretamine<br>Estramustine phosphate<br>Mechloroethamine<br>Streptozocin<br>Temozolomide<br>Semustine |
| Platinum agents | Cisplatin<br>Oxaliplatin<br>Spiroplatin<br>Carboxyphthalatoplatinum<br>Tetraplatin<br>Ormiplatin<br>Iproplatin | Carboplatin<br>ZD-0473 (AnorMED)<br>Lobaplatin (Aeterna)<br>Satraplatin (Johnson Matthey)<br>BBR-3464 (Hoffmann-La Roche)<br>SM-11355 (Sumitomo)<br>AP-5280 (Access) |
| Antimetabolites | Azacytidine<br>Gemcitabine<br>Capecitabine<br>5-fluorouracil<br>Floxuridine<br>2-chlorodesoxyadenosine<br>6-Mercaptopurine<br>6-Thioguanine<br>Cytarabine<br>2-fluorodesoxycytidine | Tomudex<br>Trimetrexate<br>Deoxycoformycin<br>Fludarabine<br>Pentostatin<br>Raltitrexed<br>Hydroxyurea<br>Decitabine (SuperGen)<br>Clofarabine (Bioenvision)<br>Irofulven (MGI Pharma) |

TABLE 1-continued

| | | |
|---|---|---|
| | Methotrexate | DMDC (Hoffmann-La |
| | Idatrexate | Roche) |
| | | Ethynylcytidine (Taiho) |
| Topoisomerase inhibitors | Amsacrine | Rubitecan (SuperGen) |
| | Epirubicin | Exatecan mesylate |
| | Etoposide | (Daiichi) |
| | Teniposide or | Quinamed (ChemGenex) |
| | mitoxantrone | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharrna) | BNP-1350 (BioNumerik) |
| | Rebeccamycin analogue (Exelixis) | CKD-602 (Chong Kun Dang) |
| | BBR-3576 (Novuspharrna) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanomorpholinodoxorubicin | |
| | Mitoxantron (Novantron) | |
| Antimitotic agents | Paclitaxel | SB 408075 |
| | Docetaxel | (GlaxoSmithKline) |
| | Colchicine | E7010 (Abbott) |
| | Vinblastine | PG-TXL (Cell |
| | Vincristine | Therapeutics) |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | | ER-86526 (Eisai) |
| | Cemadotin (BASF) | Combretastatin A4 (BMS) |
| | RPR 109881A (Aventis) | Isohomohalichondrin-B |
| | TXD 258 (Aventis) | (PharmaMar) |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient |
| | Auristatin PE (Teikoku Hormone) | NeuroPharma) |
| | | Azaepothilon B (BMS) |
| | BMS 247550 (BMS) | BNP-7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar |
| | Tariquidar (Xenova) | trihydrochloride (Eli Lilly) |
| | MS-209 (Schering AG) | Biricodar dicitrate (Vertex) |

TABLE 1-continued

| | | |
|---|---|---|
| Histone acetyl transferase inhibitors | Tacedinaline (Pfizer) SAHA (Aton Pharma) MS-275 (Schering AG) | Pivaloyloxymethyl butyrate (Titan) Depsipeptide (Fujisawa) |
| Metalloproteinase inhibitors | Neovastat (Aeterna Laboratories) Marimastat (British Biotech) | CMT-3 (CollaGenex) BMS-275291 (Celltech) |
| Ribonucleoside reductase inhibitors | Gallium maltolate (Titan) Triapin (Vion) | Tezacitabine (Aventis) Didox (Molecules for Health) |
| TNF-alpha agonists/ antagonists | Virulizin (Lorus Therapeutics) CDC-394 (Celgene) | Revimid (Celgene) |
| Endothelin-A receptor antagonists | Atrasentan (Abbot) ZD-4054 (AstraZeneca) | YM-598 (Yamanouchi) |
| Retinoic acid receptor agonists | Fenretinide (Johnson & Johnson) LGD-1550 (Ligand) | Alitretinoin (Ligand) |
| Immuno- modulators | Interferon Oncophage (Antigenics) GMK (Progenics) Adenocarcinoma vaccine (Biomira) CTP-37 (AVI BioPharma) JRX-2 (Immuno-Rx) PEP-005 (Peplin Biotech) Synchrovax vaccines (CTL Immuno) Melanoma vaccine (CTL Immuno) p21-RAS vaccine (GemVax) | Dexosome therapy (Anosys) Pentrix (Australian Cancer Technology) JSF-154 (Tragen) Cancer vaccine (Intercell) Norelin (Biostar) BLP-25 (Biomira) MGV (Progenics) !3-Alethin (Dovetail) CLL-Thera (Vasogen) |
| Hormonal and antihormonal agents | Oestrogens Conjugated oestrogens Ethynyloestradiol chlorotrianisene Idenestrol Hydroxyprogesterone caproate Medroxyprogesterone Testosterone Testosterone propionate Fluoxymesterone Methyltestosterone Diethylstilbestrol Megestrol Tamoxifen Toremofin Dexamethasone | Prednisone Methylprednisolone Prednisolone Aminoglutethimide Leuprolide Goserelin Leuporelin Bicalutamide Flutamide Octreotide Nilutamide Mitotan P-04 (Novogen) 2-Methoxyoestradiol (EntreMed) Arzoxifen (Eli Lilly) |
| Photodynamic agents | Talaporfin (Light Sciences) Theralux (Theratechnologies) Motexafin-Gadolinium (Pharmacyclics) | Pd-Bacteriopheophorbid (Yeda) Lutetium-Texaphyrin (Pharmacyclics) Hypericin |
| Tyrosine kinase inhibitors | Imatinib (Novartis) Leflunomide(Sugen/Pharmacia) ZDI839 (AstraZeneca) Erlotinib (Oncogene Science) Canertjnib (Pfizer) Squalamine (Genaera) SU5416 (Pharmacia) SU6668 (Pharmacia) ZD4190 (AstraZeneca) ZD6474 (AstraZeneca) Vatalanib (Novartis) PKI166 (Novartis) GW2016 (GlaxoSmithKline) EKB-509 (Wyeth) EKB-569 (Wyeth) | Kahalide F (PharmaMar) CEP-701 (Cephalon) CEP-751 (Cephalon) MLN518 (Millenium) PKC412 (Novartis) Phenoxodiol O Trastuzumab (Genentech) C225 (ImClone) rhu-Mab (Genentech) MDX-H210 (Medarex) 2C4 (Genentech) MDX-447 (Medarex) ABX-EGF (Abgenix) IMC-1C11 (ImClone) |
| Various agents | SR-27897 (CCK-A inhibitor, Sanofi- Synthelabo) Tocladesine (cyclic AMP agonist, Ribapharm) Alvocidib (CDK inhibitor, Aventis) CV-247 (COX-2 inhibitor, Ivy Medical) | BCX-1777 (PNP inhibitor, BioCryst) Ranpirnase (ribonuclease stimulant, Alfacell) Galarubicin (RNA synthesis inhibitor, Dong- A) Tirapazamine (reducing agent, SRI International) |

TABLE 1-continued

| | |
|---|---|
| P54 (COX-2 inhibitor, Phytopharm) | N-Acetylcysteine (reducing agent, Zambon) |
| CapCell ™ (CYP450 stimulant, Bavarian Nordic) | R-Flurbiprofen (NF-kappaB inhibitor, Encore) |
| GCS-IOO (gal3 antagonist, GlycoGenesys) | 3CPA (NF-kappaB inhibitor, Active Biotech) |
| G17DT immunogen (gastrin inhibitor, Aphton) | Seocalcitol (vitamin D receptor agonist, Leo) |
| Efaproxiral (oxygenator, Allos Therapeutics) | 131-I-TM-601 (DNA antagonist, TransMolecular) |
| PI-88 (heparanase inhibitor, Progen) | Eflornithin (ODC inhibitor, ILEX Oncology) |
| Tesmilifen (histamine antagonist, YM BioSciences) | Minodronic acid (osteoclast inhibitor, Yamanouchi) |
| Histamine (histamine H2 receptor agonist, Maxim) | Indisulam (p53 stimulant, Eisai) |
| Tiazofurin (IMPDH inhibitor, Ribapharm) | Aplidin (PPT inhibitor, PharmaMar) |
| Cilengitide (integrin antagonist, Merck KGaA) | Rituximab (CD20 antibody, Genentech) |
| SR-31747 (IL-1 antagonist, Sanofi-Synthelabo) | Gemtuzumab (CD33 antibody, Wyeth Ayerst) |
| CCI-779 (mTOR kinase inhibitor, Wyeth) | PG2 (haematopoiesis promoter, Pharmagenesis) |
| Exisulind (PDE-V inhibitor, Cell Pathways) | Immunol ™ (triclosan mouthwash, Endo) |
| CP-461 (PDE-V inhibitor, Cell Pathways) | Triacetyluridine (uridine prodrug, Wellstat) |
| AG-2037 (GART inhibitor, Pfizer) | SN-4071 (sarcoma agent, Signature BioScience) |
| WX-UK1 (plasminogen activator inhibitor, Wilex) | TransMID-107 ™ (immunotoxin, KS Biomedix) |
| PBI-1402 (PMN stimulant, ProMetic LifeSciences) | PCK-3145 (apoptosis promoter, Procyon) |
| Bortezomib (proteasome inhibitor, Millennium) | Doranidazole (apoptosis promoter, Pola) |
| SRL-172 (T-cell stimulant, SR Pharma) | CHS-828 (cytotoxic agent, Leo) |
| TLK-286 (glutathione-S transferase inhibitor, Telik) | Trans-retinic acid (differentiator, NIH) |
| PT-100 (growth factor agonist, Point Therapeutics) | MX6 (apoptosis promoter, MAXIA) |
| Midostaurin (PKC inhibitor, Novartis) | Apomine (apoptosis promoter, ILEX Oncology) |
| Bryostatin-1 (PKC stimulant, GPC Biotech) | Urocidin (apoptosis promoter, Bioniche) |
| CDA-II (apoptosis promoter, Everlife) | Ro-31-7453 (apoptosis promoter, La Roche) |
| SDX-101 (apoptosis promoter, Salmedix) | Brostallicin (apoptosis promoter, Pharmacia) |
| Ceflatonin (apoptosis promoter, ChemGenex) | |

A combined treatment of this type can be achieved with the aid of simultaneous, consecutive or separate dispensing of the individual components of the treatment. Combination products of this type employ the compounds according to the invention.

Assays

The compounds of the formula I described in the examples were tested by the assays described below and were found to have kinase inhibitory activity. Other assays are known from the literature and could readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

Measurement of Met Kinase Activity

According to the manufacturer's data (Met, active, upstate, catalogue No. 14-526), Met kinase is expressed for the purposes of protein production in insect cells (Sf21; *S. frugiperda*) and subsequent affinity-chromatographic purification as "N-terminal 6His-tagged" recombinant human protein in a baculovirus expression vector.

The kinase activity can be measured using various available measurement systems. In the scintillation proximity method (Sorg et al., J. of Biomolecular Screening, 2002, 7, 11-19), the flashplate method or the filter binding test, the radioactive phosphorylation of a protein or peptide as substrate is measured using radioactively labelled ATP ($^{32}$P-ATP, $^{33}$P-ATP). In the case of the presence of an inhibitory compound, a reduced radioactive signal, or none at all, can be detected. Furthermore, homogeneous time-resolved fluorescence resonance energy transfer (HTR-FRET) and fluorescence polarisation (FP) technologies can be used as assay methods (Sills et al., J. of Biomolecular Screening, 2002, 191-214).

Other non-radioactive ELISA assay methods use specific phospho-antibodies (phospho-ABs). The phospho-antibody only binds the phosphorylated substrate. This binding can be detected by chemiluminescence using a second peroxidase-conjugated antibody (Ross et al., 2002, Biochem. J.).

Flashplate Method (Met Kinase)

The test plates used are 96-well Flashplate® microtitre plates from Perkin Elmer (Cat. No. SMP200). The components of the kinase reaction described below are pipetted into the assay plate. The Met kinase and the substrate poly Ala-Glu-Lys-Tyr, (pAGLT, 6:2:5:1), are incubated for 3 hrs at room temperature with radioactively labelled $^{33}$P-ATP in the presence and absence of test substances in a total volume of 100 µl. The reaction is terminated using 150 µl of a 60 mM EDTA solution. After incubation for a further 30 min at room temperature, the supernatants are filtered off with suction, and the wells are washed three times with 200 µl of 0.9% NaCl solution each time. The measurement of the bound radioactivity is carried out by means of a scintillation measuring instrument (Topcount NXT, Perkin-Elmer).

The full value used is the inhibitor-free kinase reaction. This should be approximately in the range 6000-9000 cpm. The pharmacological zero value used is staurosporin in a final concentration of 0.1 mM. The inhibitory values (IC50) are determined using the RS1_MTS program.

Kinase reaction conditions per well:
30 µl of assay buffer
10 µl of substance to be tested in assay buffer with 10% of DMSO
10 µl of ATP (final concentration 1 µM cold, 0.35 µCi of $^{33}$P-ATP)
50 µl of Met kinase/substrate mixture in assay buffer;
  (10 ng of enzyme/well, 50 ng of pAGLT/well)
  Solutions used:
  Assay buffer:
  50 mM HEPES
    3 mM magnesium chloride
    3 µM sodium orthovanadate
    3 mM manganese(II) chloride
    1 mM dithiothreitol (DTT)
  pH=7.5 (to be set using sodium hydroxide)
  Stop solution:
  60 mM Titriplex III (EDTA)
  $^{33}$P-ATP: Perkin-Elmer;
  Met kinase: Upstate, Cat. No. 14-526, Stock 1 µg/10 µl; spec. activity 954 U/mg;
  Poly-Ala-Glu-Lys-Tyr, 6:2:5:1:Sigma Cat. No. P1152

In-Vivo Tests

Experimental procedure: Female Balb/C mice (breeder: Charles River Wiga) were 5 weeks old on arrival. They were acclimatised to our keeping conditions for 7 days. Each mouse was subsequently injected subcutaneously in the pelvic area with 4 million TPR-Met/NIH3T3 cells in 100 µl of PBS (without Ca++ and Mg++). After 5 days, the animals were randomised into 3 groups, so that each group of 9 mice had an average tumour volume of 110 µl (range: 55-165). 100 µl of vehicle (0.25% methylcellulose/100 mM acetate buffer, pH 5.5) were administered daily to the control group, and 200 mg/kg of "A56" or "A91" dissolved in the vehicle (volume likewise 100 µl/animal) were administered daily to the treatment groups, in each case by gastric tube. After 9 days, the controls had an average volume of 1530 µl and the experiment was terminated.

Measurement of the tumour volume: The length (L) and breadth (B) were measured using a Vernier calliper, and the tumour volume was calculated from the formula L×B×B/2.

Keeping conditions: 4 or 5 animals per cage, feeding with commercial mouse food (Sniff).

The compounds "A18" and "A22" have a significant anti-tumoural action.

Above and below, all temperatures are indicated in° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

Mass spectrometry (MS): EI (electron impact ionisation) M$^+$
  FAB (fast atom bombardment) (M+H)$^+$
  ESI (electrospray ionisation) (M+H)$^+$
APCl-MS (atmospheric pressure chemical ionisation—mass spectrometry) (M+H)$^+$.

Mass spectrometry (MS): EI (electron impact ionisation) M$^+$
  FAB (fast atom bombardment) (M+H)$^+$
  ESI (electrospray ionisation) (M+H)$^+$
APCl-MS (atmospheric pressure chemical ionisation—mass spectrometry) (M+H)$^+$.

HPLC/MS Analyses
  are carried out in a 3µ Silica-Rod column with a 210 second gradient from 20 to 100% water/acetonitrile/0.01% of trifluoroacetic acid, at a flow rate of 2.2 ml/min, and detection at 220 nm.

HPLC Analyses (Method A)
Column: Chromolith RP18e 100*3 mm
Flow rate: 2 ml/min
Solvent A: H$_2$O+0.1% of trifluoroacetic acid
Solvent B: acetonitrile+0.1% of trifluoroacetic acid
Gradient 5 min
0-4 min: 99:1→1:99
4-5 min: 1:99-1:99

HPLC Analyses (Method B)
Column: Chromolith RP18e 100*3 mm
Flow rate: 4 ml/min
Solvent A: H$_2$O+0.05% of HCOOH
Solvent B: acetonitrile+10% of solvent A
Gradient 8 min
0-1 min: 99:1→99:1
1-7 min: 99:1→1:99
7-8 min: 1:99→1:99

HPLC Analysis (Method C)
Flow rate: 2 ml/min
99:01-0:100 water+0.1% (vol.) of TFA:acetonitrile+0.1% (vol.) of TFA
0.0 to 0.2 min: 99:01
0.2 to 3.8 min: 99:01→0:100
3.8 to 4.2 min: 0:100
Column: Chromolith Performance RP18e; 100 mm long, internal diameter 3 mm, wavelength: 220 nm
Retention time Rt in minutes [min].

Examples of the Preparation of the Pyradizinone Starting Compounds

The pyridazinones are generally prepared by processes from W. H. Coates, A. McKillop, Synthesis 1993, p. 334.

An example thereof is the synthesis of 3-(6-oxo-1,6-dihydropyridazin-3-yl)benzonitrile:

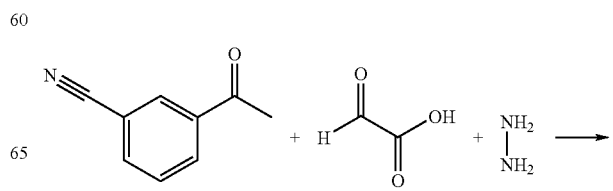

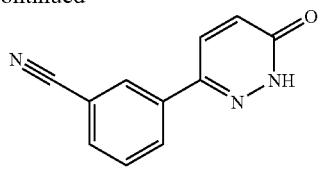

927 g (10.6 mol) of glyoxylic acid monohydrate are introduced in portions into a solution of 1278 g (8.80 mol) of 3-acetylbenzonitrile in 1.5 l of acetic acid. The resultant solution is heated at 95° C. for 18 hours. The mixture is allowed to cool to 30° C., and 7 l of water and 899 ml (18.5 mol) of hydrazinium hydroxide are added successively. The reaction mixture is stirred at 95° C. for 4 hours. The mixture is allowed to cool to 60° C., and the resultant precipitate is filtered off with suction and washed with 5 l of water and 2 l of acetone. The residue is heated to the boil in 5 l of acetone and filtered off with suction while hot. 5 l of acetic acid are added to the residue, and the mixture is heated at 90° C. for 2 hours with stirring. The mixture is allowed to cool to room temperature, and the residue is filtered off with suction and washed with acetone. The residue is again heated to 90° C. with 5 l of acetic acid, cooled to room temperature, filtered off with suction and washed with acetone. The residue is dried in vacuo: 3-(6-oxo-1,6-dihydropyridazin-3-yl)benzonitrile as beige crystals; ESI 198.

Some pyridazinones can be prepared in accordance with A. J. Goodman et al., Tetrahedron 55 (1999), 15067-15070. An example thereof is the alternative synthesis of 3-(6-oxo-1,6-dihydropyridazin-3-yl)benzonitrile:

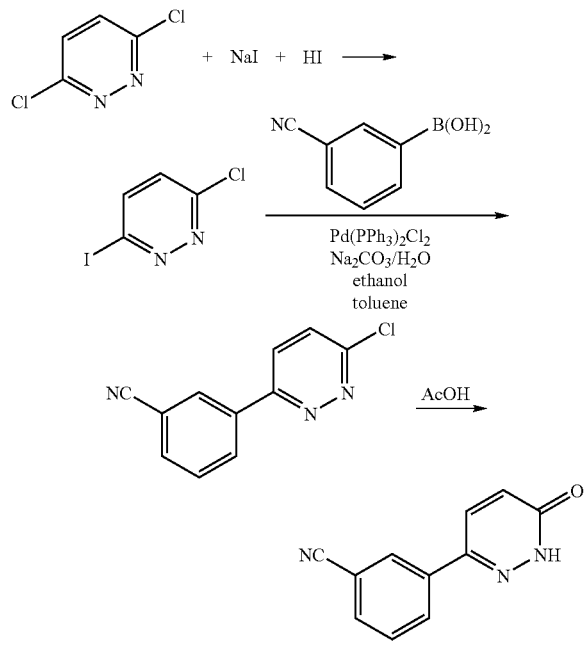

2.70 kg (18.0 mol) of sodium iodide are added in portions at room temperature to a mixture of 5.0 l of water and 11.3 l of 57% aqueous hydroiodic acid (75.2 mol). 2.00 kg (13.4 mol) of 3,6-dichloropyridazine are subsequently added in portions to the solution held at 20° C. The reaction mixture is stirred at 20° C. for 18 hours. 10 l of tert-butyl methyl ether and 4 l of water are added to the reaction mixture. The organic phase is separated off and washed with water and aqueous sodium sulfite solution. The organic phase is concentrated, heptane is added, and the resultant solid is filtered off with suction and washed with heptane. The residue is dried in vacuo: 3-chloro-6-iodopyridazine as colourless leaf-shaped crystals; ESI 241.

A solution of 212 mg (2.0 mmol) of sodium carbonate in 1 ml of water is added to a solution, kept under nitrogen, of 240 mg (1.00 mmol) of 3-chloro-6-iodopyridazine in 1 ml of toluene, and the mixture is heated to 80° C. 7.0 mg (0.010 mmol) of bis(triphenylphosphine)palladium(II) chloride are added, and a solution of 147 mg (1.00 mmol) of 3-cyanobenzeneboronic acid is subsequently added dropwise. The reaction mixture is stirred at 80° C. for 18 hours. The reaction mixture is cooled to room temperature, water is added, and the solid is filtered off with suction and washed with water. The residue is dried in vacuo: 3-(6-chloropyridazin-3-yl)benzonitrile as colourless crystals; ESI 216.

A suspension of 85 mg (0.396 mol) of 3-(6-chloropyridazin-3-yl)benzonitrile in 0.5 ml of acetic acid is heated to 80° C. and stirred at this temperature for 24 hours. The reaction mixture is cooled to room temperature, water is added, and the solid is filtered off with suction. The residue is washed with water and dried in vacuo: 3-(6-oxo-1,6-dihydropyridazin-3-yl)benzonitrile as colourless crystals.

The following pyridazinones are preferably prepared by this process:

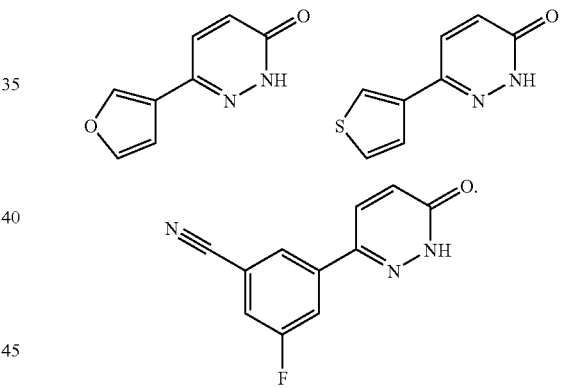

Some pyridazinones are prepared by the following process. An example thereof is the synthesis of 6-(1-methyl-1H-pyrazol-4-yl)-2H-pyridazin-3-one:

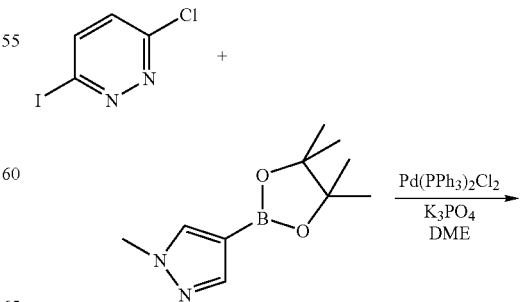

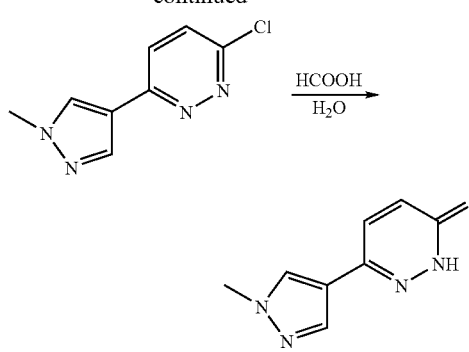

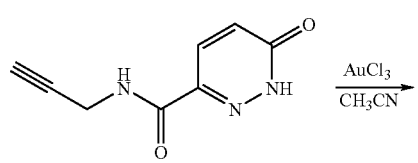

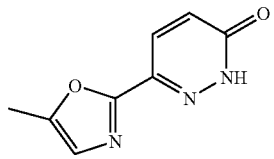

705 g (3.39 mol) of 1-methyl-1H-pyrazole-4-boronic acid pinacol ester and 1.44 kg of tripotassium phosphate trihydrate are added to a solution of 815 g (3.39 mol) of 3-chloro-6-iodopyridazine in 3.8 l of 1,2-dimethoxyethane. The resultant suspension is heated to 80° C. under nitrogen and with stirring, and 59.5 g (85 mmol) of bis(triphenylphosphine)palladium(II) chloride are added. The reaction mixture is stirred at 80° C. for 3 hours. The mixture is allowed to cool to room temperature, and 9 l of water are added. The resultant precipitate is filtered off with suction, washed with water and dried in vacuo: 3-chloro-6-(1-methyl-1H-pyrazol-4-yl)pyridazine as brown crystals; ESI 195.

A suspension of 615 g (2.90 mol) of 3-chloro-6-(1-methyl-1H-pyrazol-4-yl)pyridazine in a mixture of 1.86 l of formic acid and 2.61 l of water is heated to 80° C. with stirring and stirred at this temperature for 28 hours. The reaction mixture is cooled to room temperature, a little activated carbon is added, and the solid is filtered off with suction. The filtrate is adjusted to a pH of 7 using 40% aqueous sodium hydroxide solution with ice cooling and left at 6° C. for 16 h. The resultant precipitate is filtered off with suction, washed with water and dried in vacuo: 6-(1-methyl-1H-pyrazol-4-yl)-2H-pyridazin-3-one as colourless crystals; ESI 177.

The following pyridazinones are preferably prepared by this process:

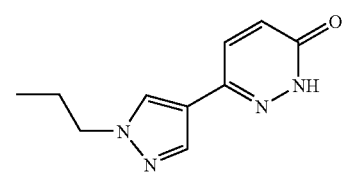

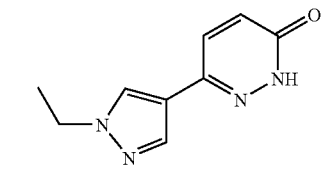

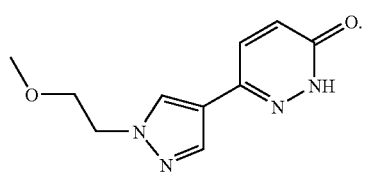

Preparation of 6-(5-methyloxazol-2-yl)-2H-pyridazin-3-one 10.6 g (69.2 mmol) of 1-hydroxybenzotriazole hydrate and 17.3 g of N-(3-dimethylaminopropyl)-N'-ethylcarbodiimide hydrochloride are added to a solution of 10.0 g (69.2 mmol) of 6-oxo-1,6-dihydropyridazine-3-carboxylic acid monohydrate and 3.85 g (69.2 mmol) of propargylamine in 200 ml of DMF, and the resultant solution is stirred at room temperature for 18 hours. The reaction mixture is partitioned between water and dichloromethane. The organic phase is washed with saturated sodium hydrogencarbonate solution, dried over sodium sulfate and evaporated: N-prop-2-ynyl-6-oxo-1,6-dihydropyridazine-3-carboxamide as colourless crystals; ESI 178.

622 mg (2.05 mmol) of gold(III) chloride are added to a solution of 3.69 g (20.5 mmol) of N-prop-2-ynyl-6-oxo-1,6-dihydropyridazine-3-carboxamide in 41 ml of acetonitrile, and the mixture is stirred at room temperature for 3 days. A further 622 mg (2.05 mmol) of gold(III) chloride are added, and the mixture is stirred at room temperature for 7 days. The reaction mixture is evaporated and chromatographed on a silica gel column with dichloromethane/methanol as eluent: 6-(5-methyloxazol-2-yl)-2H-pyridazin-3-one as yellowish crystals; ESI 178.

Preparation of 6-[4-(5-methyl-1,2,4-oxadiazol-3-yl)phenyl]-2H-pyridazin-3-one

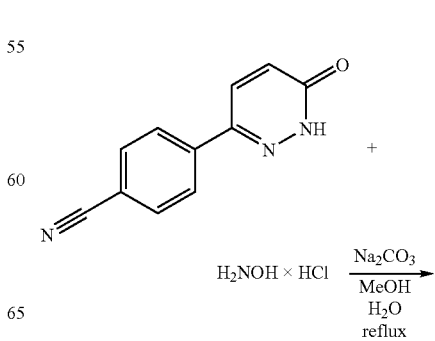

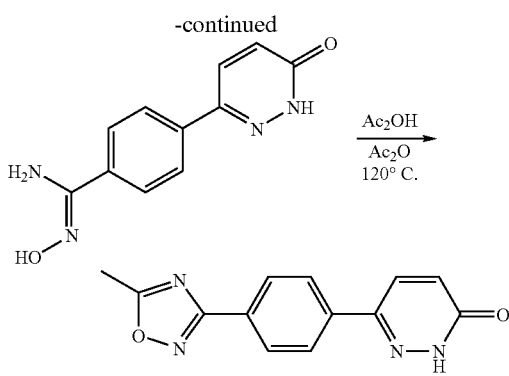

Preparation of tert-butyl 4-(6-oxo-1,6-dihydropy-ridazin-3-yl)piperazine-1-carboxylate

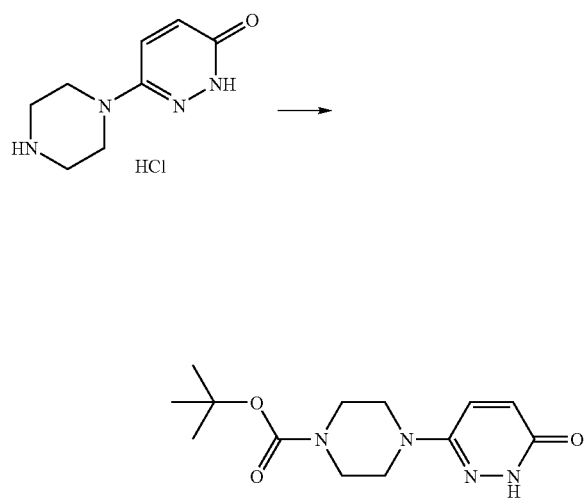

1 g (4.62 mmol) of 6-piperazin-1-yl-2H-pyridazin-3-one hydrochloride (*Eur. J. Med. Chem.* 1992, 27, 545-549) is suspended in 10 ml of THF, and 1.34 ml (9.69 mmol) of triethylamine and 1.09 ml (5.08 mmol) of di-tert-butyl dicarbonate are added. The mixture is stirred at RT for 15 h, and the solvent is removed. Ethyl acetate and water are added to the residue. A white solid remains undissolved. The residue is filtered off with suction and washed with water and ethyl acetate and dried in vacuo; yield 0.9 g; HPLC: Rt=2.27 min (method B); HPLC-MS: 281 (M+H).

Preparation of 6-(5-methyl-1,2,4-oxadiazol-3-yl)-2H-pyridazin-3-one

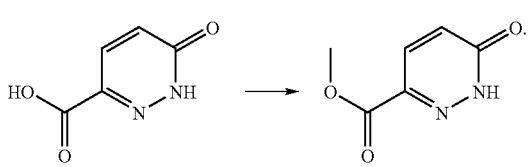

20 g (125 mmol) of 6-oxo-1,6-dihydropyridazine-3-carboxylic acid hydrate are suspended in 400 ml of methanol, and 10.7 ml (147 mmol) of thionyl chloride are slowly added with ice cooling. The suspension is stirred at 70° C. for 15 h, during which everything dissolves. The reaction mixture is concentrated to about 100 ml, during which a white precipitate forms. This precipitate is filtered off with suction and washed with methanol and dried in vacuo. Yield 19.2 g; HPLC: Rt=1.27 min (method B); HPLC-MS: 155 (M+H).

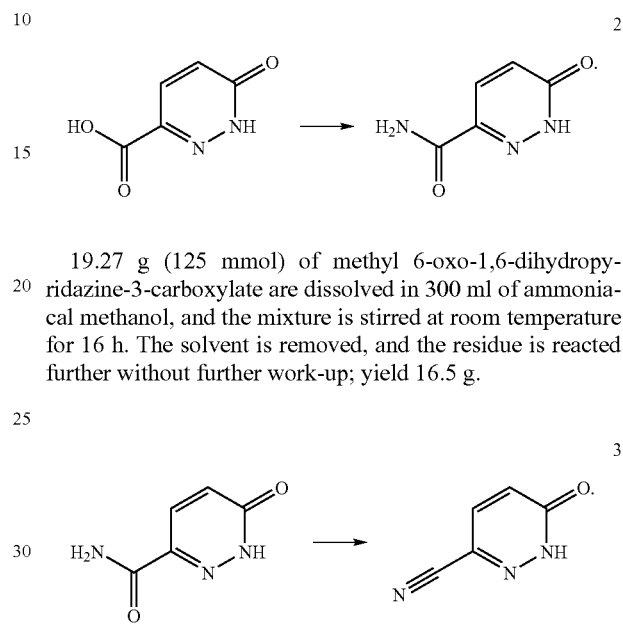

19.27 g (125 mmol) of methyl 6-oxo-1,6-dihydropyridazine-3-carboxylate are dissolved in 300 ml of ammoniacal methanol, and the mixture is stirred at room temperature for 16 h. The solvent is removed, and the residue is reacted further without further work-up; yield 16.5 g.

15 g (108 mmol) of 6-oxo-1,6-dihydropyridazine-3-carboxamide are suspended in 200 ml of dichloromethane. The suspension is cooled to 0° C., and 45 ml of pyridine and 18 ml (129 mmol) of trifluoroacetic anhydride are subsequently added dropwise. The mixture is stirred at RT for 5 days. 400 ml of water are added to the suspension, which is then extracted with 3×300 ml of DCM. The combined organic phases are dried using sodium sulfate and evaporated to dryness. A precipitate forms in the filtrate. This precipitate is filtered off with suction, washed with water and dried in vacuo. The aqueous phase is saturated with sodium chloride and extracted with 3×300 ml of ethyl acetate. The organic phase is dried and evaporated. All 3 fractions are combined and reacted further without further purification; yield: 14.3 g; GC-MS: 121 (M+).

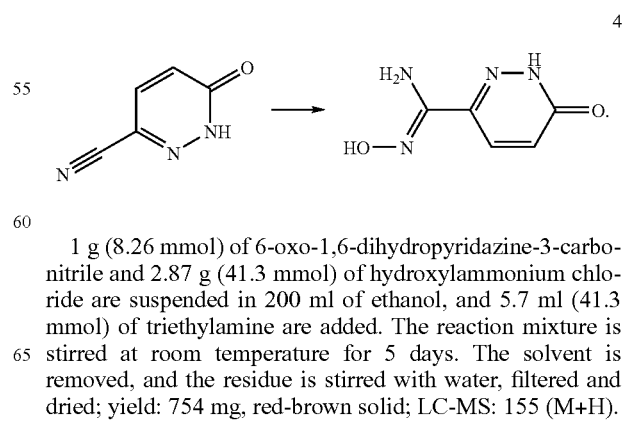

1 g (8.26 mmol) of 6-oxo-1,6-dihydropyridazine-3-carbonitrile and 2.87 g (41.3 mmol) of hydroxylammonium chloride are suspended in 200 ml of ethanol, and 5.7 ml (41.3 mmol) of triethylamine are added. The reaction mixture is stirred at room temperature for 5 days. The solvent is removed, and the residue is stirred with water, filtered and dried; yield: 754 mg, red-brown solid; LC-MS: 155 (M+H).

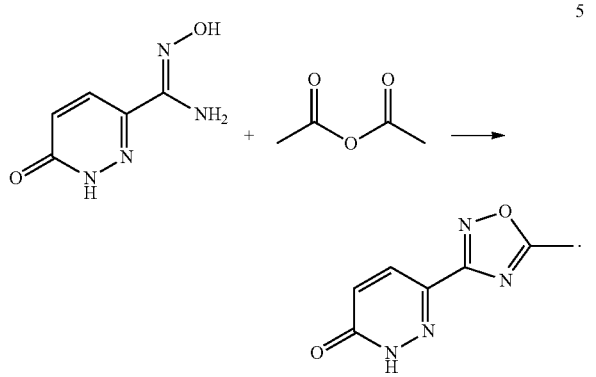

2.8 ml of glacial acetic acid, 2.3 ml of acetic anhydride and 200 μl of pyridine are added to 375 mg (2.43 mmol) of N-hydroxy-6-oxo-1,6-dihydropyridazine-3-carboxamidine, and the mixture is stirred at 90° C. for 15 h. During cooling of the reaction mixture, a precipitate forms, which is filtered off with suction, washed with water and dried in vacuo; yield: 253 mg, yellow solid; HPLC: Rt=1.51 min; LC-MS: 179 (M+H).

EXAMPLE 1

The preparation of 2-[3-(5-methylpyrimidin-2-yl)benzyl]-6-(3,4,5-trifluorophenyl)-2H-pyridazin-3-one ("A1") is carried out analogously to the following scheme

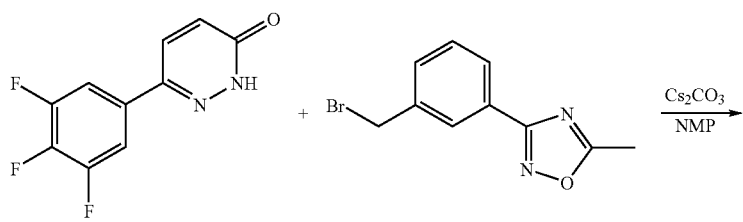

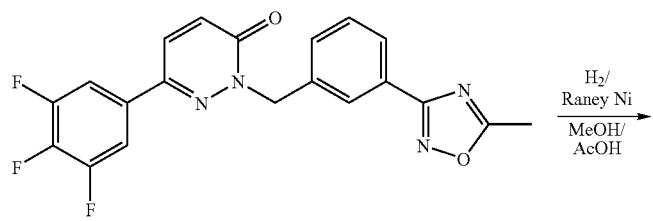

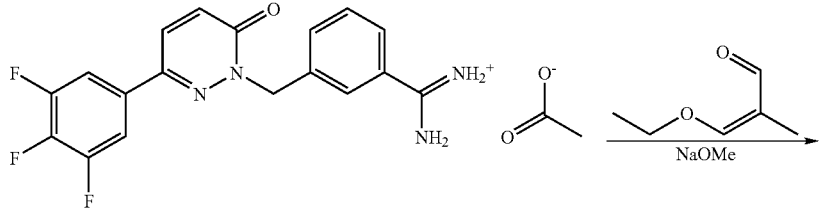

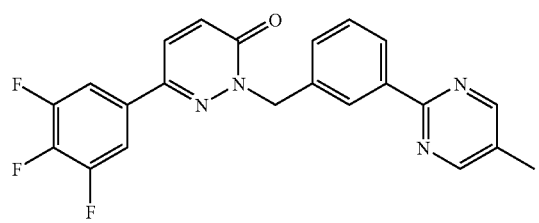

"A1"

1.1 6.52 g (20 mmol) of caesium carbonate are added to a solution of 4.52 g (20 mmol) of 6-(3,4,5-trifluorophenyl)-2H-pyridazin-3-one and 5.06 g (20 mmol) of 3-(3-bromomethylphenyl)-5-methyl-1,2,4-oxadiazole (prepared by the method of W. W. K. R. Mederski et al, Tetrahedron 55, 1999, 12757-12770) in 40 ml of 1-methylpyrrolidinone (NMP), and the resultant suspension is stirred at room temperature for 18 hours. Water is added to the reaction mixture, and the resultant precipitate is filtered off, washed with water and dried. The crude product is recrystallised from 2-propanol: 6-(3,4,5-trifluorophenyl)-2-[3-(5-methyl-1,2,4-oxadiazol-3-yl)benzyl]-2H-pyridazin-3-one as pale-yellowish crystals; ESI 399.

1.2 2 ml of acetic acid, 2 ml of water and 6 g of Raney nickel are added to a solution of 6.00 g (14.9 mmol) of 6-(3,4,5-trifluorophenyl)-2-[3-(5-methyl-1,2,4-oxadiazol-3-yl)benzyl]-2H-pyridazin-3-one in 60 ml of methanol, and the mixture is hydrogenated at room temperature and atmospheric pressure for 44 hours. The reaction mixture is filtered, and the filtrate is evaporated. The crystalline residue is boiled in tert-butyl methyl ether. The mixture is allowed to cool, and the solid is filtered off with suction and washed with tert-butyl methyl ether. The residue is dried in vacuo: and allowed to cool. 3-[6-oxo-3-(3,4,5-trifluorophenyl)-6H-pyridazin-1-ylmethyl]benzamidinium acetate as colourless crystals; ESI 359.

3-[6-Oxo-3-(3,5-difluorophenyl)-6H-pyridazin-1-ylmethyl]benzamidinium acetate, colourless crystals, is prepared analogously; ESI 341.

1.3 1.31 ml (11.0 mmol) of 3-ethoxymethacrolein and 2.04 ml (11.0 mmol) of a 30% sodium methoxide solution in methanol are added to a suspension of 4.18 g (10.0 mmol) of 3-[6-oxo-3-(3,4,5-trifluorophenyl)-6H-pyridazin-1-ylmethyl]benzamidinium acetate in 40 ml of methanol, and the mixture is heated at 50° C. for 18 hours. The mixture is allowed to cool, and the resultant precipitate is filtered off with suction, washed with methanol and dried in vacuo: 2-[3-(5-methylpyrimidin-2-yl)benzyl]-6-(3,4,5-trifluorophenyl)-2H-pyridazin-3-one ("A1") as colourless crystals; ESI 409; $^1$H-NMR (DMSO-$d_6$): δ [ppm]=2.32 (s, 3H), 5.45 (s, 2H), 7.16 (d, J=9.5 Hz, 1H), 7.52 (m, 2H), 7.90 (m, 2H), 8.13 (d, J=9.5 Hz, 1H), 8.30 (dt, $J_1$=7.5 Hz, $J_2$=1.5 Hz, 1H), 8.46 (t, J=1.5 Hz, 1H), 8.75 (s, 2H).

Analogous reaction of the benzamidinium acetate with 4-trimethylsilyl-3-butyn-1-one with potassium carbonate/acetonitrile at 120° C. in the microwave gives the following compounds 6-(3,5-difluorophenyl)-2-[3-(5-methylpyrimidin-2-yl)benzyl]-2H-pyridazin-3-one ("A2"), ESI 391;
2-[3-(4-methylpyrimidin-2-yl)benzyl]-6-(3,4,5-trifluorophenyl)-2H-pyridazin-3-one ("A3"), ESI 409.

Heating of the benzamidinium acetate at 175° C. with malondialdehyde bis-dimethyl acetal in an analogous manner gives the compound 2-(3-pyrimidin-2-ylbenzyl)-6-(3,4,5-trifluorophenyl)-2H-pyridazin-3-one ("A4"), ESI 395.

EXAMPLE 2

The preparation of 4-{3-[3-(3,5-difluorophenyl)-6-oxo-6H-pyridazin-1-yl-methyl]phenyl}morpholin-3-one ("A5") is carried out analogously to the following scheme

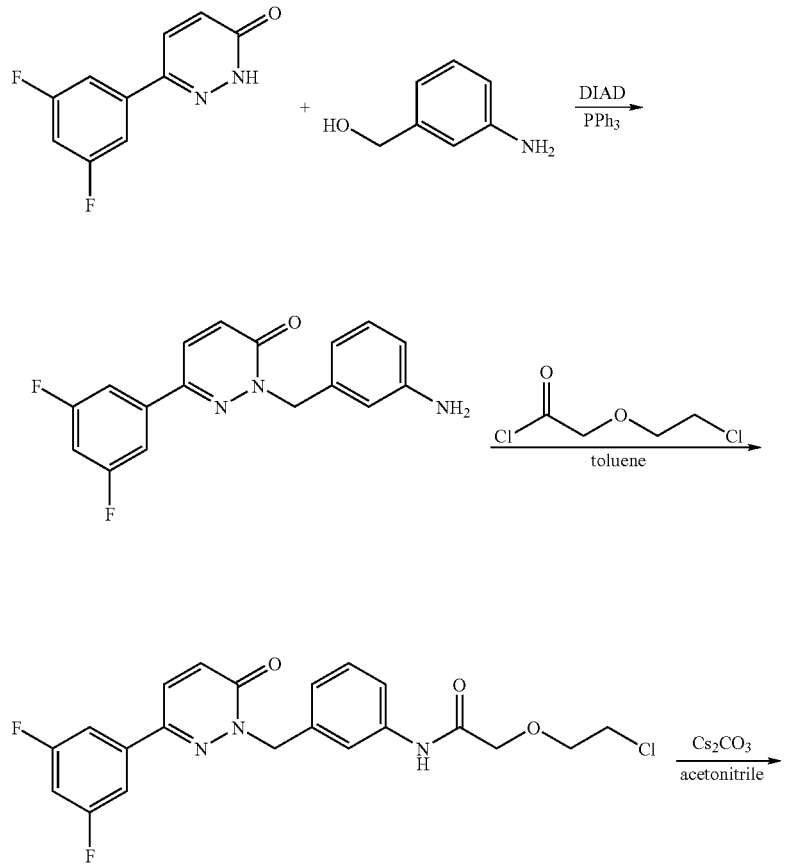

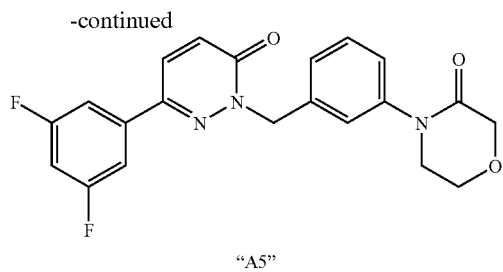

"A5"

2.1 2.83 g (22.5 mmol) of 3-aminobenzyl alcohol and 5.96 g (22.5 mmol) of triphenylphosphine are added to a suspension, kept under nitrogen, of 3.12 g (15.0 mmol) of 6-(3,5-difluorophenyl)-2H-pyridazin-3-one in 80 ml of THF, and the mixture is stirred at room temperature for 30 minutes. The suspension is cooled to 0° C., and 4.65 ml (22.5 mmol) of diisopropyl azodicarboxylate (DIAD) are added dropwise. The reaction mixture is stirred at room temperature for 18 hours. The reaction mixture is evaporated, and the residue is heated in 50 ml of isopropanol and allowed to cool. The resultant precipitate is filtered off with suction, washed with isopropanol and tert-butyl methyl ether and dried in vacuo: 2-(3-aminobenzyl)-6-(3,5-difluorophenyl)-2H-pyridazin-3-one as colourless crystals; ESI 314.

2.2 235 mg (1.5 mmol) of (2-chloroethoxy)acetyl chloride are added to a suspension 313 mg (1.00 mmol) of 2-(3-aminobenzyl)-6-(3,5-difluorophenyl)-2H-pyridazin-3-one in 2 ml of toluene, and the mixture is heated at the boil for 18 hours. The mixture is allowed to cool, and the resultant precipitate is filtered off with suction, washed with tert-butyl methyl ether and dried in vacuo: 2-(2-chloroethoxy)-N-{3-[3-(3,5-difluorophenyl)-6-oxo-6H-pyridazin-1-ylmethyl]phenyl}acetamide as colourless crystals; ESI 434.

2.3 509 mg (1.56 mmol) of caesium carbonate are added to a solution of 339 mg (0.78 mmol) of 2-(2-chloroethoxy)-N-{3-[3-(3,5-difluorophenyl)-6-oxo-6H-pyridazin-1-ylmethyl]phenyl}acetamide in 2 ml of acetonitrile, and the mixture is stirred at room temperature for 18 hours. The reaction mixture is filtered, and the filtrate is evaporated. The residue is taken up in tert-butyl methyl ether, filtered off with suction and washed with tert-butyl methyl ether: 4-{3-[3-(3,5-difluorophenyl)-6-oxo-6H-pyridazin-1-ylmethyl]phenyl}morpholin-3-one ("A5") as colourless crystals; ESI 398.

Analogous reaction of the aniline derivatives with 3-chloropropyl chloroformate gives the following compounds:

3-{3-[3-(3,5-difluorophenyl)-6-oxo-6H-pyridazin-1-ylmethyl]phenyl}-1,3-oxazinan-2-one ("A6"), ESI 398

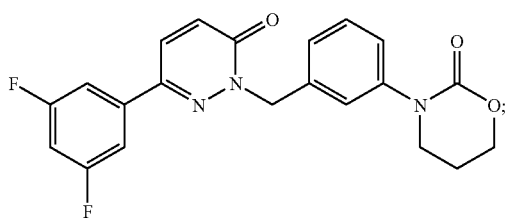

3-{3-[6-oxo-3-(3,4,5-trifluorophenyl)-6H-pyridazin-1-ylmethyl]phenyl}-1,3-oxazinan-2-one ("A7"), ESI 416.

EXAMPLE 3

The preparation of 1-{3-[3-(3,5-difluorophenyl)-6-oxo-6H-pyridazin-1-yl-methyl]phenyl}-3-methyl-6H-pyridazin-6-one ("A8") is carried out analogously to the following scheme

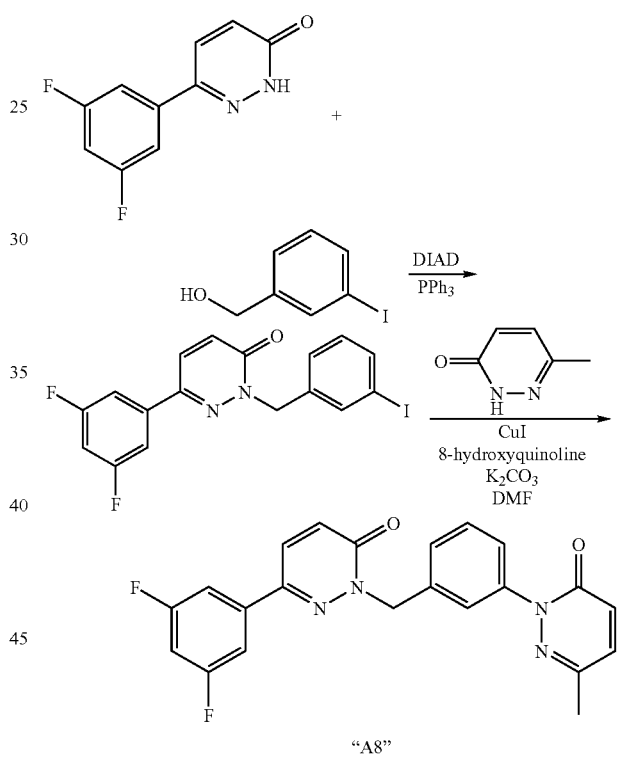

"A8"

3.1 5.03 g (21.1 mmol) of 3-iodobenzyl alcohol and 5.55 g (20.9 mmol) of triphenylphosphine are added to a suspension, kept under nitrogen, of 2.92 g (14.0 mmol) of 6-(3,5-difluorophenyl)-2H-pyridazin-3-one in 100 ml of THF, and the mixture is stirred at room temperature for 30 minutes. The suspension is cooled to 0° C., and 4.33 ml (20.9 mmol) of diisopropyl azodicarboxylate are added dropwise. The reaction mixture is stirred at room temperature for 1.5 hours. The reaction mixture is evaporated, and the residue is heated in 50 ml of isopropanol and allowed to cool. The resultant precipitate is filtered off with suction, washed with isopropanol and petroleum ether and dried in vacuo: 6-(3,5-difluorophenyl)-2-(3-iodobenzyl)-2H-pyridazin-3-one as colourless crystals; ESI 425.

3.2 14.3 mg (0.08 mmol) of copper(I) iodide, 76 mg (0.55 mmol) of potassium carbonate and 11 mg (0.08 mmol) of 8-hydroxyquinoline are added to a solution of 212 mg (0.50 mmol) of 6-(3,5-difluorophenyl)-2-(3-iodobenzyl)-2H-pyridazin-3-one and 55.1 mg (0.5 mmol) of 6-methylpyridazin-3(2H)-one in 2 ml of DMF, and the mixture is heated at 120° C. for 24 hours. The reaction mixture is allowed to cool, and 10% aqueous ammonia solution and ethyl acetate are added. The resultant precipitate is filtered off with suction, washed with water and dried. The residue is boiled in ethyl acetate, filtered off with suction and washed with ethyl acetate. The residue is dried in vacuo: 1-{3-[3-(3,5-difluorophenyl)-6-oxo-6H-pyridazin-1-yl-methyl]phenyl}-3-methyl-6H-pyridazin-6-one ("A8") as brownish crystals; ESI 407.

EXAMPLE 4

The preparation of 6-(3,5-difluorophenyl)-2-[3-(5-methylpyridin-2-yl)benzyl]-2H-pyridazin-3-one ("A9") is carried out analogously to the following scheme

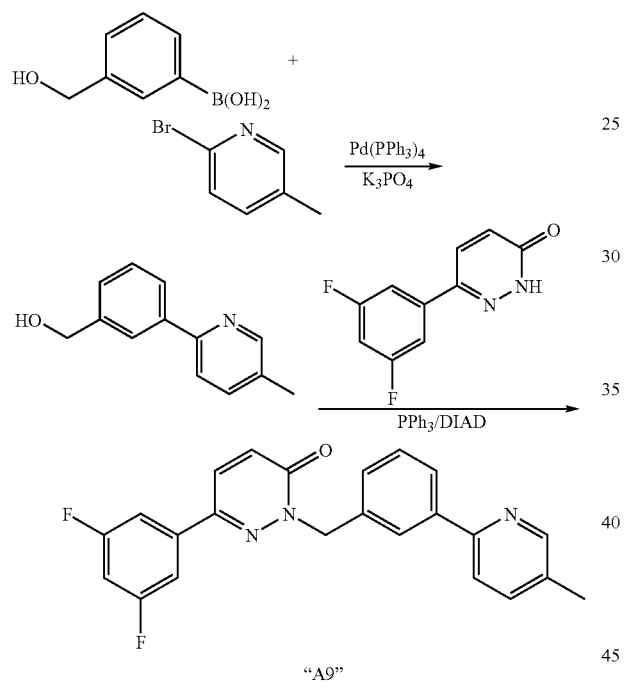

"A9"

4.1 92 mg (0.08 mmol) of tetrakis(triphenylphosphine) palladium are added to a suspension, kept under nitrogen, of 849 mg (4.0 mmol) of tripotassium phosphate, 344 mg (2.0 mmol) of 2-bromo-5-methylpyridine and 304 mg (2.0 mmol) of 3-hydroxymethylbenzeneboronic acid in 12 ml of dioxane and 1 ml of water, and the mixture is heated at the boil with stirring for 18 hours. The reaction mixture is cooled to room temperature and partitioned between water and ethyl acetate. The organic phase is dried over sodium sulfate and evaporated, and the residue is chromatographed on a silica gel column with dichloromethane/methanol as eluent: [3-(5-methylpyridin-2-yl)phenyl]methanol as yellowish oil; ESI 200.

4.2 134 mg (0.66 mmol) of diisopropyl azodicarboxylate are added to a solution of 88 mg (0.44 mmol) of [3-(5-methylpyridin-2-yl)phenyl]methanol, 138 mg (0.66 mmol) of 6-(3,5-difluorophenyl)-2H-pyridazin-3-one and 174 mg (0.66 mmol) of triphenylphosphine in 3.5 ml of THF. The reaction mixture is stirred at room temperature for 18 hours. The mixture is evaporated, and the residue is chromatographed on a silica gel column with dichloromethane/methanol as eluent: 6-(3,5-difluorophenyl)-2-[3-(5-methylpyridin-2-yl)benzyl]-2H-pyridazin-3-one ("A9") as colourless crystals; ESI 390.

The following compounds are obtained analogously 6-(3,5-difluorophenyl)-2-[3-(5-methoxypyridin-2-yl)benzyl]-2H-pyridazin-3-one

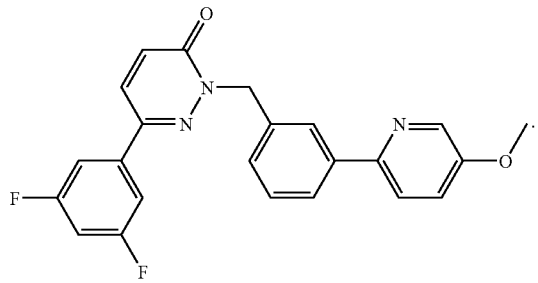

("A10"), ESI 406

EXAMPLE 5

The preparation of 2-[3-(5-aminopyridin-2-yl)benzyl]-6-(3,5-difluorophenyl)-2H-pyridazin-3-one ("A11") and of 6-(3,5-difluorophenyl)-2-{3-[5-(4-methylpiperazin-1-yl)pyridin-2-yl]benzyl}-2H-pyridazin-3-one ("A12") is carried out analogously to the following scheme

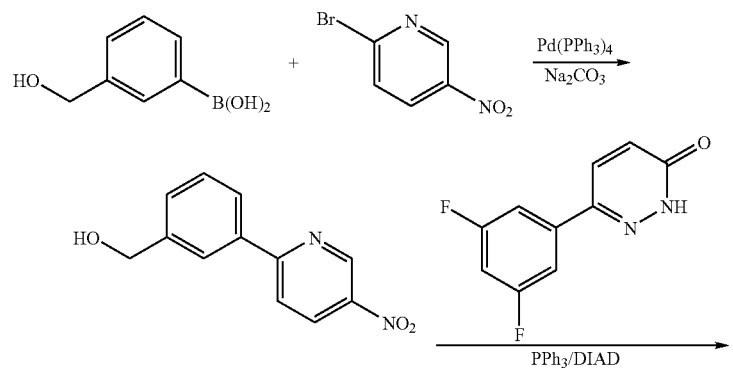

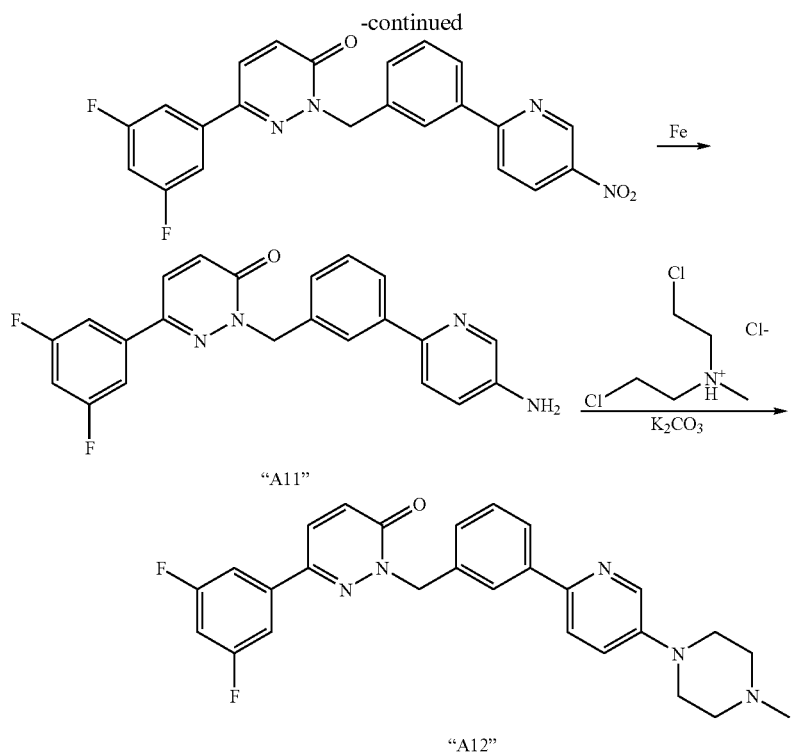

"A11"

"A12"

5.1 A suspension, kept under nitrogen, of 3.69 g (18.2 mmol) of 2-bromo-5-nitropyridine, 840 mg (0.73 mmol) of tetrakis(triphenylphosphine)palladium and 3.55 g (33.4 mmol) of sodium carbonate in 133 ml of toluene is heated to the boil. A solution of 5.07 g (32.7 mmol) of 3-(hydroxymethyl)benzeneboronic acid in 133 ml of toluene is then added dropwise, and the reaction mixture is heated at the boil for 18 hours. Water is added to the reaction mixture. The organic phase is separated off, and the aqueous is extracted a number of times with toluene. The combined organic phases are dried over sodium sulfate and evaporated. The residue is chromatographed on a silica gel column with dichloromethane/methanol: [3-(5-nitropyridin-2-yl)phenyl]methanol as yellow crystals; ESI 231.

5.2 4.46 g (22.0 mmol) of diisopropyl azodicarboxylate are added dropwise to a solution of 3.37 g (14.7 mmol) of [3-(5-nitropyridin-2-yl)phenyl]-methanol, 4.58 g (22.0 mmol) of 6-(3,5-difluorophenyl)-2H-pyridazin-3-one and 5.77 g (22.0 mmol) of triphenylphosphine in 120 ml of THF, and the reaction mixture is stirred at room temperature for 18 hours. The resultant precipitate is filtered off with suction, washed with THF and dried in vacuo: 6-(3,5-difluorophenyl)-2-[3-(5-nitropyridin-2-yl)benzyl]-2H-pyridazin-3-one as yellowish crystals; ESI 421.

5.3 220 µl of 2 N hydrochloric acid are added to a suspension of 420 mg (1.00 mmol) of 6-(3,5-difluorophenyl)-2-[3-(5-nitropyridin-2-yl)benzyl]-2H-pyridazin-3-one in 4 ml of ethanol, and the mixture is heated to 95° C. and cooled to room temperature. 402 mg (7.2 mmol) of iron powder is added, and the reaction mixture is stirred at 85° C. for 1 hour and at 60° C. for 17 hours. The reaction mixture is filtered, and the filtrate is partitioned between water and ethyl acetate. The organic phase is washed successively with sodium hydrogencarbonate solution, sodium carbonate solution and sodium chloride solution, dried over sodium sulfate and evaporated: 2-[3-(5-aminopyridin-2-yl)benzyl]-6-(3,5-difluorophenyl)-2H-pyridazin-3-one ("A11") as brownish foam; ESI 391.

5.4 The final step is carried out analogously to Example 9.3, giving 6-(3,5-difluorophenyl)-2-{3-[5-(4-methylpiperazin-1-yl)pyridin-2-yl]benzyl}-2H-pyridazin-3-one ("A12").

EXAMPLE 6

The preparation of 6-(3,5-difluorophenyl)-2-[3-(4-piperazin-1-ylpyrimidin-2-yl)benzyl]-2H-pyridazin-3-one ("A13") is carried out analogously to the following scheme

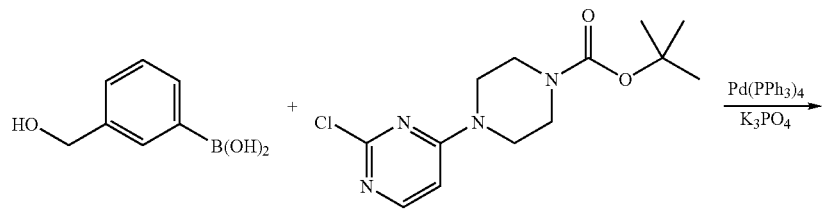

-continued

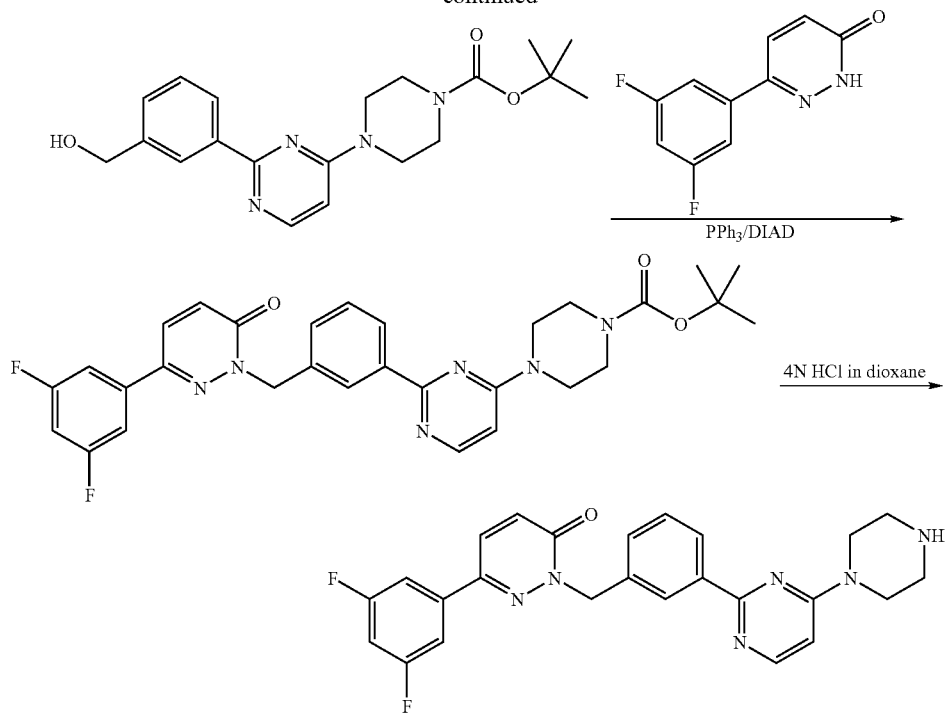

"A13"

6.1 A catalyst solution prepared by reaction of of 56 mg (0.08 mmol) of bis(triphenylphosphine)palladium(II) chloride and 3.0 mg (0.08 mmol) of sodium borohydride in 0.4 ml of THF at 55° C. is added to a suspension, kept under nitrogen, of 849 mg (4.0 mmol) of tripotassium phosphate, 598 mg (2.0 mmol) of tert-butyl 4-(2-chloropyrimidin-4-yl)piperazine-1-carboxylate (prepared in accordance with WO 03104225) and 304 mg (2.0 mmol) of 3-hydroxymethylbenzeneboronic acid in 12 ml of dioxane and 1 ml of water. The reaction mixture is stirred at 97° C. for 18 hours. The reaction mixture is cooled and partitioned between water and ethyl acetate. The organic phase is dried over sodium sulfate and evaporated, and the residue is chromatographed on a silica gel column with dichloromethane/methanol as eluent: tert-butyl 4-[2-(3-hydroxymethylphenyl)pyrimidin-4-yl]-piperazine-1-carboxylate as yellowish solid; ESI 371.

6.2 118 mg (0.582 mmol) of diisopropyl azodicarboxylate are added to a solution of 144 mg (0.388 mmol) of tert-butyl 4-[2-(3-hydroxymethylphenyl)pyrimidin-4-yl]piperazine-1-carboxylate, 122 mg (0.582 mmol) of 6-(3,5-difluorophenyl)-2H-pyridazin-3-one and 153 mg (0.582 mmol) of triphenylphosphine in 3 ml of THF. The reaction mixture is stirred at room temperature for 18 hours. The mixture is evaporated, and the residue is chromatographed on a silica gel column with dichloromethane/methanol as eluent: tert-butyl 4-(2-{3-[3-(3,5-difluorophenyl)-6-oxo-6H-pyridazin-1-yl-methyl]phenyl}pyrimidin-4-yl)piperazine-1-carboxylate as yellowish oil; ESI 561.

6.3 1.3 ml of 4 N HCl in dioxane are added to a solution of 81 mg (0.14 mmol) of tert-butyl 4-(2-{3-[3-(3,5-difluorophenyl)-6-oxo-6H-pyridazin-1-ylmethyl]phenyl}pyrimidin-4-yl)piperazine-1-carboxylate in 1 ml of dioxane, and the mixture is left at room temperature for 18 hours. The reaction mixture is partitioned between water and ethyl acetate. The aqueous phase is adjusted to a pH of 14 using 1 N NaOH and extracted with ethyl acetate. The organic phase is dried over sodium sulfate and evaporated: 6-(3,5-difluorophenyl)-2-[3-(4-piperazin-1-ylpyrimidin-2-yl)benzyl]-2H-pyridazin-3-one ("A13") hydrochloride as colourless amorphous solid; ESI 461.

The following compound is obtained analogously
6-(3,5-difluorophenyl)-2-{3-[4-(methylpiperidin-4-ylamino)pyrimidin-2-yl]benzyl}-2H-pyridazin-3-one

"A59"

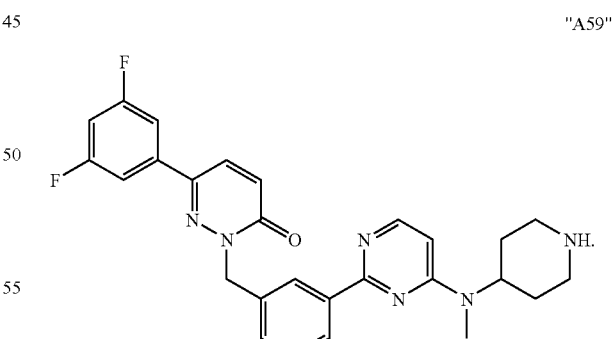

EXAMPLE 7

The preparation of 6-(3,5-difluorophenyl)-2-{3-[5-(4-methylpiperazin-1-yl-methyl)pyrimidin-2-yl]benzyl}-2H-pyridazin-3-one ("A14") is carried out analogously to the following scheme

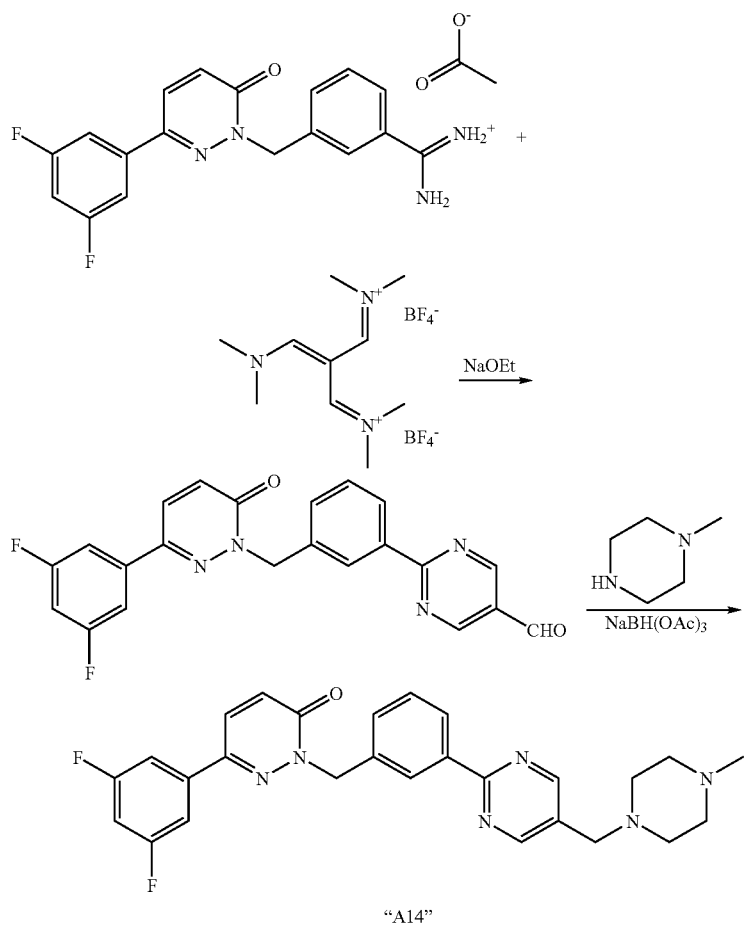

"A14"

7.1 12.0 ml (31.5 mmol) of a 20% solution of sodium ethoxide in ethanol are added to a suspension, kept under nitrogen, of 4.00 g (10.0 mmol) of 3-[6-oxo-3-(3,5-difluorophenyl)-6H-pyridazin-1-ylmethyl]benzamidinium acetate and 4.64 g (13.0 mmol) of 2-dimethylaminomethylene-1,3-bis-(dimethylimmonio)propane bistetrafluoroborate (prepared by the method of P. J. Coleman et al., J. Med. Chem. 2004, 47, 4829-4837) in 280 ml of ethanol, and the mixture is heated at the boil for 2 hours. The reaction mixture is cooled, evaporated in vacuo and digested with water. The resultant precipitate is filtered off with suction and washed with water. The residue is chromatographed on a silica gel column with dichloromethane/methanol: 2-{3-[3-(3,5-difluorophenyl)-6-oxo-6H-pyridazin-1-ylmethyl]-phenyl}pyrimidine-5-carbaldehyde as colourless crystals; ESI 405.

7.2 A suspension of 472 mg (1.17 mmol) of 2-{3-[3-(3,5-difluorophenyl)-6-oxo-6H-pyridazin-1-ylmethyl]phenyl}pyrimidine-5-carbaldehyde in 5 ml of dichloromethane is given succesively with 166 µl of 1-methylpiperazine, 495 mg (2.34 mmol) of sodium triacetoxyborohydride and 67 µl of acetic acid, and the reaction mixture is stirred at room temperature for 42 hours. The reaction mixture is partitioned between dichloromethane and 1 N NaOH. The organic phase is separated off, dried over sodium sulfate and evaporated. The residue is chromatographed on a silica gel column with dichloromethane/methanol as eluent: 6-(3,5-difluorophenyl)-2-{3-[5-(4-methylpiperazin-1-ylmethyl)pyrimidin-2-yl]benzyl}-2H-pyridazin-3-one ("A14") as colourless crystals; ESI 489;

$^1$H-NMR (CDCl$_3$): δ [ppm]=2.29 (s, 3H), 2.48 (m, 8H), 3.54 (s, 2H), 5.50 (s, 2H), 6.86 (tt, J$_1$=8.8 Hz, J$_2$=2.3 Hz, 1H), 7.04 (d, J =9.5 Hz, 1H), 7.34 (m, 2H), 7.47 (t, J=7.8 Hz, 1H), 7.58 (d, J=9.5 Hz, 1H), 7.58 (m, 1H), 8.38 (dt, J$_1$=7.8 Hz, J$_2$=1 Hz, 1H), 8.64 (t, J=1 Hz, 1H), 8.74 (s, 2H).

The following compound is obtained analogously
6-(3,5-difluorophenyl)-2-[3-(5-dimethylaminomethylpyrimidin-2-yl)-benzyl]-2H-pyridazin-3-one

"A58"

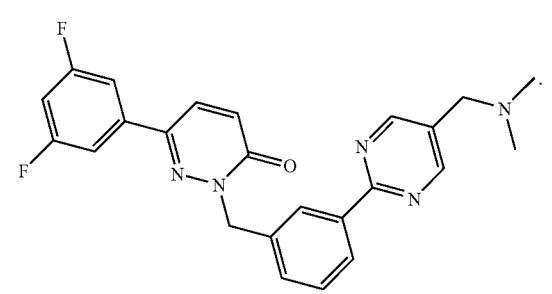

EXAMPLE 8

The preparation of 3-{1-[3-(5-methylpyrimidin-2-yl)benzyl]-6-oxo-1,6-dihydropyridazin-3-yl}benzonitrile ("A15") is carried out analogously to the following scheme

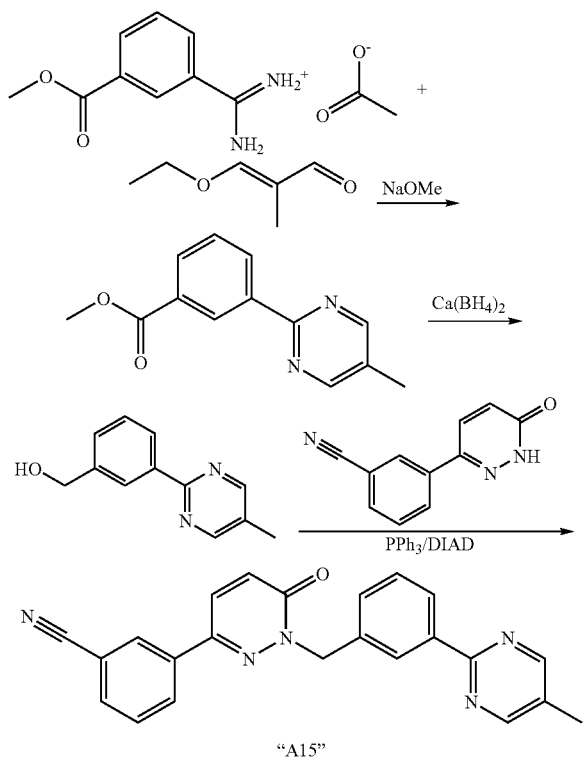

"A15"

8.1 1.31 ml (11.0 mmol) of 3-ethoxymethacrolein and 2.04 ml (11.0 mmol) of a 30% solution of sodium ethoxide in methanol are added to a suspension of 2.41 g (10.0 mmol) of methyl 3-carbamimidoylbenzoate acetate (preparation see Example 37) in 40 ml of methanol, and the resultant solution is stirred at 50° C. for 18 hours. The reaction mixture is evaporated in vacuo, and water is added. The resultant precipitate is filtered off with suction, washed with water and dried in vacuo: methyl 3-(5-methylpyrimidin-2-yl)benzoate as colourless crystals; ESI 229.

8.2 600 mg (5.41 mmol) of powdered calcium chloride are added to a suspension of 400 mg (10.6 mmol) of sodium borohydride in 20 ml of THF, and the mixture is stirred at room temperature for 1.5 hours. A solution of 751 mg (3.29 mmol) of methyl 3-(5-methylpyrimidin-2-yl)benzoate in 10 ml of THF is added dropwise to this suspension with stirring, and the mixture is stirred at room temperature for 18 hours. 10 ml of 1 N NaOH, water and dichloromethane are added to the reaction mixture, which is then filtered. The organic phase of the filtrate is separated off, dried over sodium sulfate and evaporated. The residue is chromatographed on a silica gel column with dichloromethane/methanol as eluent: [3-(5-methylpyrimidin-2-yl)-phenyl]methanol as colourless solid; ESI 201.

8.3 147 µl (0.75 mmol) of diisopropyl diazodicarboxylate are added dropwise to a suspension of 98.6 mg (0.50 mmol) of 3-(6-oxo-1,6-dihydropyridazin-3-yl)benzonitrile, 100 mg (0.50 mmol) of [3-(5-methylpyrimidin-2-yl)phenyl]methanol and 197 mg (0.75 mmol) of triphenylphosphine in 3 ml of THF, and the resultant solution is stirred at room temperature for 18 hours. The reaction mixture is evaporated in vacuo, and 2-propanol is added to the residue. The resultant precipitate is filtered off with suction and chromatographed on a silica gel column with dichloromethane/methanol as eluent: 3-{1-[3-(5-methylpyrimidin-2-yl)benzyl]-6-oxo-1,6-dihydropyridazin-3-yl}benzonitrile ("A15") as yellowish solid; ESI 380; $^1$H NMR (DMSO-d$_6$): δ [ppm]=2.31 (s, 3H), 5.46 (s, 2H), 7.16 (d, J=9.7 Hz, 1H), 7.51 (m, 2H), 7.72 (t, J=8.0 Hz, 1H), 7.93 (dt, J$_1$=7.5 Hz, J$_2$=1 Hz, 1H), 8.17 (d, J=9.7 Hz, 1H), 8.25 (dt, J$_1$=7.8 Hz, J$_2$=1 Hz, 1H), 8.30 (dt, J$_1$=6.8 Hz, J$_2$=1.6 Hz, 1H), 8.37 (t, J=1.6 Hz, 1H), 8.46 (bs, 1H), 8.75 (s, 2H).

The following compounds are obtained analogously
6-benzo-1,2,5-thiadiazol-5-yl-2-[3-(5-methylpyrimidin-2-yl)benzyl]-2H-pyridazin-3-one, ESI 413,

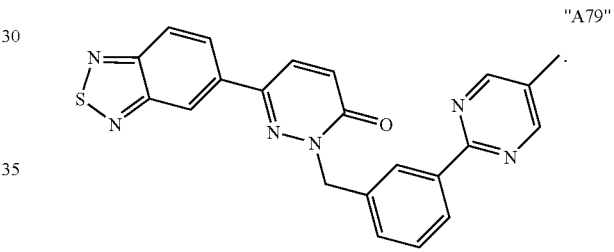

"A79"

EXAMPLE 9

The preparation of N'-(2-{3-[3-(3,5-difluorophenyl)-6-oxo-6H-pyridazin-1-ylmethyl]phenyl}-pyrimidin-5-yl)-N,N-dimethylformamidine ("A16"), 2-[3-(5-aminopyrimidin-2-yl)benzyl]-6-(3,5-difluorophenyl)-2H-pyridazin-3-one ("A17") and
6-(3,5-difluorophenyl)-2-{3-[5-(4-methylpiperazin-1-yl)pyrimidin-2-yl]-benzyl}-2H-pyridazin-3-one ("A18") is carried out analogously to the following scheme

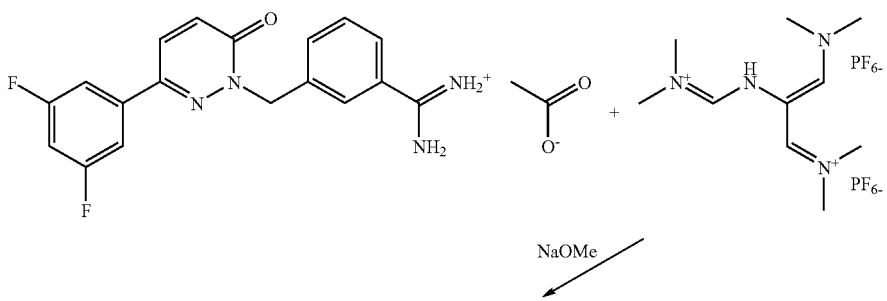

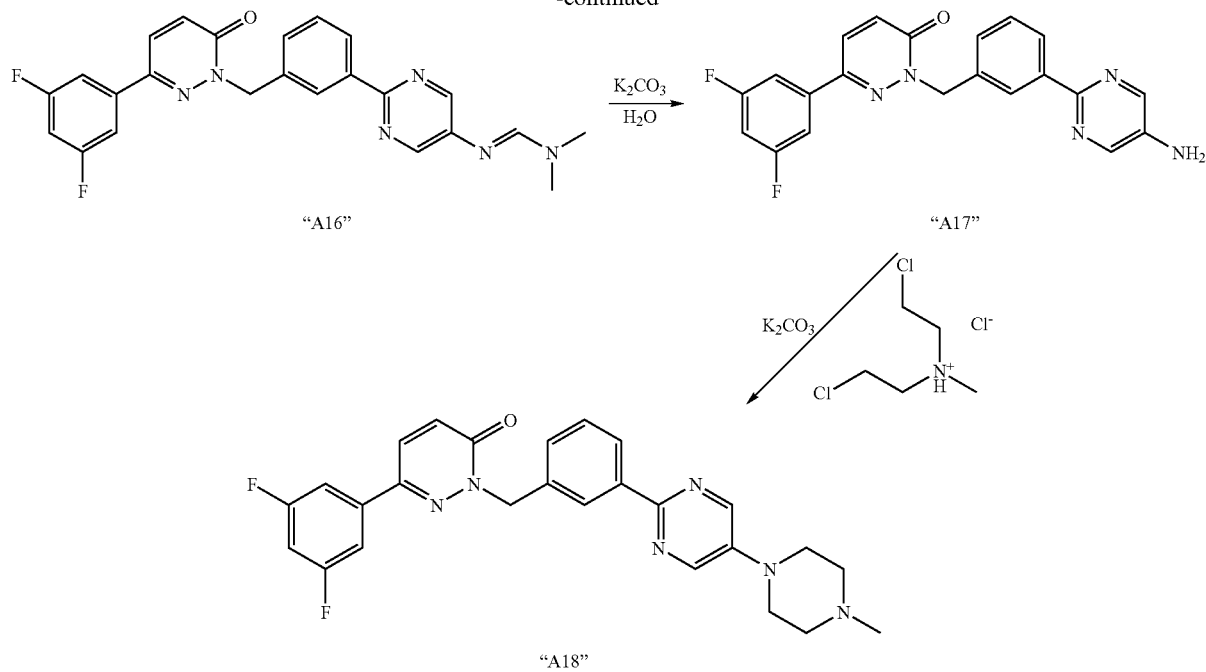

9.1 A sodium methoxide solution prepared by dissolution of 3.45 g (150 mmol) of sodium in 35 ml of methanol is added dropwise to a suspension, kept under nitrogen, of 20.0 g (50.0 mmol) of 3-[6-oxo-3-(3,5-difluorophenyl)-6H-pyridazin-1-ylmethyl]benzamidinium acetate and 24.4 g (50.0 mmol) of ({2-dimethylamino-1-[dimethylimmoniomethyl]vinyl-amino}-methylene)dimethylammonium dihexafluorophosphate in 20 ml of methanol. The reaction mixture is slowly warmed to 60° C. and stirred at this temperature for 20 minutes. The reaction mixture is cooled to room temperature and partitioned between water and dichloromethane. The organic phase is dried over sodium sulfate and evaporated. The residue is taken up in methanol, filtered off with suction, the residue is washed with ether and dried in vacuo: N'-(2-{3-[3-(3,5-difluorophenyl)-6-oxo-6H-pyridazin-1-yl-methyl]phenyl}pyrimidin-5-yl)-N,N-dimethylformamidine ("A16") as colourless crystals; ESI 447.

9.2 190 ml of dioxane and 17.4 g (39.0 mmol) of N'-(2-{3-[3-(3,5-difluorophenyl)-6-oxo-6H-pyridazin-1-ylmethyl]phenyl}pyrimidin-5-yl)-N,N-dimethylformamidine are added to a solution of 19.1 g (137 mmol) of potassium carbonate in 380 ml of water. The reaction mixture is heated at the boil for 3 days and subsequently cooled to room temperature. The resultant precipitate is filtered off with suction, washed with water and dried in vacuo: 2-[3-(5-aminopyrimidin-2-yl)benzyl]-6-(3,5-difluorophenyl)-2H-pyridazin-3-one ("A17") as colourless crystals; ESI 392.

9.3 501 mg (2.55 mmol) of bis(2-chloroethyl)methylammonium chloride are added to a solution, kept under nitrogen, of 587 mg (1.5 mmol) of 2-[3-(5-aminopyrimidin-2-yl)benzyl]-6-(3,5-difluorophenyl)-2H-pyridazin-3-one in 2 ml of 1-methylpyrrolidone, and the reaction mixture is heated at 130° C. for 32 hours. The reaction mixture is cooled, dichloromethane is added, and the mixture is filtered. The filtrate is evaporated in vacuo, and the residue is chromatographed on a silica gel column with dichloromethane/methanol. The product-containing fractions are combined and evaporated, and the residue is recrystallised from methanol. This material is suspended in methanol and converted into the hydrochloride using hydrogen chloride in diethyl ether, and the hydrochloride is precipitated using diethyl ether: 6-(3,5-difluorophenyl)-2-{3-[5-(4-methylpiperazin-1-yl)pyrimidin-2-yl]benzyl}-2H-pyridazin-3-one ("A18") hydrochloride as colourless crystals; ESI 475;

$^1$H-NMR (DMSO-$d_6$): δ [ppm]=2.81 (d, J=3.3 Hz, 3H), 3.19 (m 2H), 3.30 (m, 2H), 3.50 (m, 2H), 4.05 (m, 2H), 5.43 (s, 2H), 7.14 (d, J=9.5 Hz, 1H), 7.35 (tt, $J_1$=8.8 Hz, $J_2$=2.3 Hz, 1H), 7.47 (m, 2H), 7.66 (m, 2H), 8.15 (d, J=9.5 Hz, 1H), 8.22 (m, 1H) 8.34 (bs,1H), 8.65 (s, 2H), 11.0 (bs, 1H).

The following compounds are obtained analogously 6-(3,5-difluorophenyl)-2-[3-(5-piperazin-1-ylpyrimidin-2-yl)benzyl]-2H-pyridazin-3-one ("A19") hydrochloride, ESI 461, $^1$H-NMR ($d_6$-DMSO): δ [ppm]=3.25 (m, 4H), 3.59 (m, 4H), 5.44 (s, 2H), 7.16 (d, J=10 Hz, 1H), 7.37 (tt, $J_1$=9.2 Hz, $J_2$=2 Hz, 1H), 7.47 (m, 2H), 7.67 (m, 2H), 8.16 (d, J=10 Hz, 1H), 8.22 (m, 1H), 8.35 (bs, 1H), 8.65 (s, 2H), 9.38 (bs, 2H);

2-{3-[5-(4-methylpiperazin-1-yl)pyrimidin-2-yl]benzyl}-6-(3,4,5-trifluorophenyl)-2H-pyridazin-3-one ("A20"), hydrochloride, ESI 493;

2-{3-[5-(piperazin-1-yl)pyrimidin-2-yl]benzyl}-6-(3,4,5-trifluorophenyl)-2H-pyridazin-3-one ("A65");

N'-(2-{3-[3-(3,4,5-trifluorophenyl)-6-oxo-6H-pyridazin-1-ylmethyl]-phenyl}pyrimidin-5-yl)-N,N-dimethylformamidine ("A76"), ESI 465;

2-[3-(5-aminopyrimidin-2-yl)benzyl]-6-(3,4,5-trifluorophenyl)-2H-pyridazin-3-one ("A82"), ESI 410.

EXAMPLE 10

The preparation of 6-(3,5-difluorophenyl)-2-[3-(5-hydroxypyrimidin-2-yl)benzyl]-2H-pyridazin-3-one ("A21") and 6-(3,5-difluorophenyl)-2-{3-[5-(3-dimethylaminopropoxy)pyrimidin-2-yl]benzyl}-2H-pyridazin-3-one ("A22") is carried out analogously to the following scheme

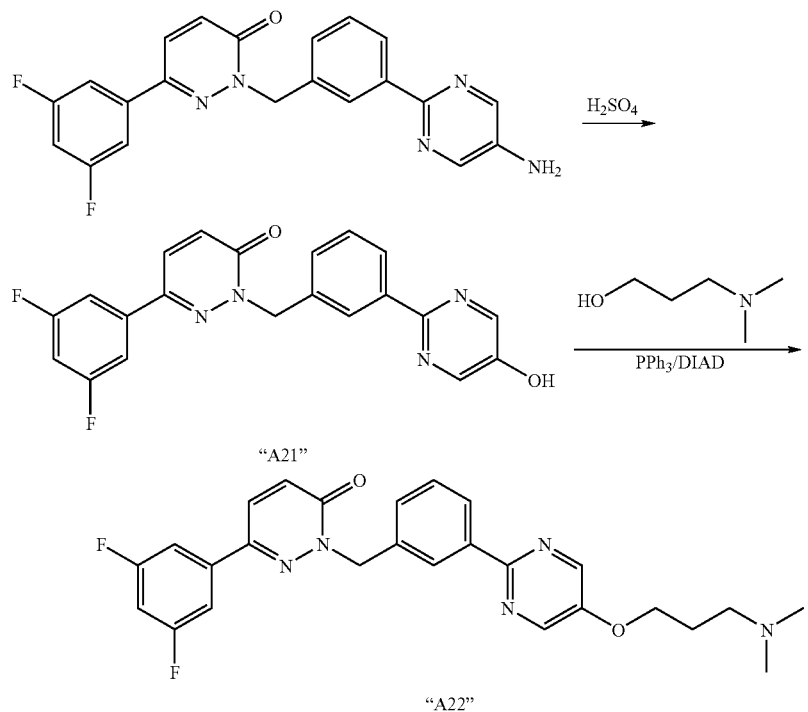

"A21"

"A22"

10.1 A suspension of 4.76 g (12.2 mmol) of 2-[3-(5-aminopyrimidin-2-yl)benzyl]-6-(3,5-difluorophenyl)-2H-pyridazin-3-one in a mixture of 5.40 ml of concentrated sulfuric acid and 44 ml of water is heated at the boil for 4 hours. The reaction mixture is cooled to room temperature, diluted with ice-cold water and rendered alkaline using conc. aqueous ammonia. The precipitate is filtered off with suction, washed with water and dried. The crude product is recrystallised from methanol: 6-(3,5-difluorophenyl)-2-[3-(5-hydroxypyrimidin-2-yl)benzyl]-2H-pyridazin-3-one ("A21") as colourless crystals; ESI 393.

10.2 98.3 μl (0.82 mmol) of 3-(dimethylamino)-1-propanol, 218 mg (0.82 mmol) of triphenylphosphine are added to a suspension, kept under nitrogen, of 215 mg (0.55 mmol) of 6-(3,5-difluorophenyl)-2-[3-(5-hydroxypyrimidin-2-yl)benzyl]-2H-pyridazin-3-one in 5 ml of THF, and the mixture is cooled in an ice bath. 170 μl (0.82 mmol) of diisopropyl azodicarboxylate are added dropwise, and the reaction mixture is stirred at room temperature for 2 hours. The reaction mixture is evaporated in vacuo, and the residue is chromatographed on a silica gel column with dichloromethane/methanol as eluent. The product-containing fractions are combined and evaporated. This material is dissolved in acetone and converted into the hydrochloride using hydrogen chloride in diethyl ether, and the hydrochloride is precipitated using diethyl ether: 6-(3,5-difluorophenyl)-2-{3-[5-(3-dimethylaminopropoxy)pyrimidin-2-yl]benzyl}-2H-pyridazin-3-one ("A22") hydrochloride as colourless crystals; ESI 478;

$^1$H-NMR (DMSO-$d_6$): δ [ppm]=2.21 (m, 2H), 2.78 (d, J=5 Hz, 6H), 3.22 (m 2H), 4.31 (t, J=6 Hz, 2H), 5.44 (s, 2H), 7.14 (d, J=9.5 Hz, 1H), 7.35 (tt, $J_1$=8.8 Hz, $J_2$=2.3 Hz, 1H), 7.49 (m, 2H), 7.66 (m, 2H), 8.15 (d, J=9.5 Hz, 1H), 8.24 (m, 1H) 8.38 (bs, 1H), 8.65 (s, 2H), 10.7 (bs, 1H).

The following compound are obtained analogously
6-(3,5-difluorophenyl)-2-{3-[5-(1-methylpiperidin-4-yloxy)pyrimidin-2-yl]benzyl}-2H-pyridazin-3-one ("A23")

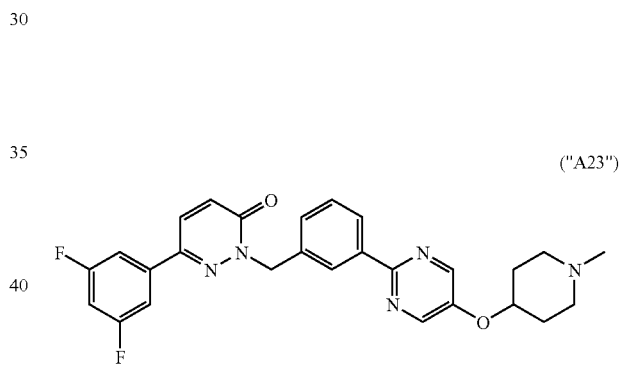

hydrochloride, ESI 490;

6-(3,5-difluorophenyl)-2-{3-[5-(3-pyrrolidin-1-ylpropoxy)pyrimidin-2-yl]-benzyl}-2H-pyridazin-3-one

"A56"

6-(3,5-difluorophenyl)-2-(3-{5-[2-(4-methylpiperazin-1-yl)ethoxy]-pyrimidin-2-yl}benzyl)-2H-pyridazin-3-one, hydrochloride,

"A57", ESI 519

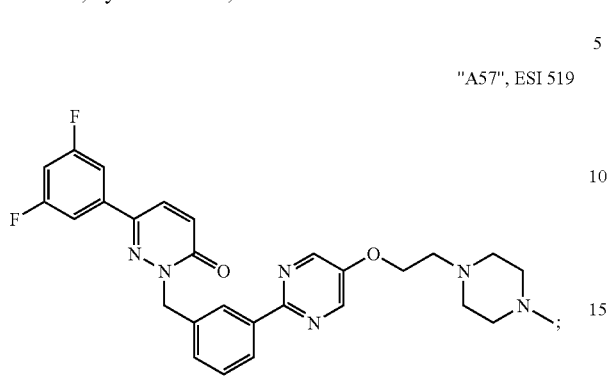

2-{3-[5-(3-dimethylaminopropoxy)pyrimidin-2-yl]benzyl}-6-(3,4,5-trifluorophenyl)-2H-pyridazin-3-one

"A60"

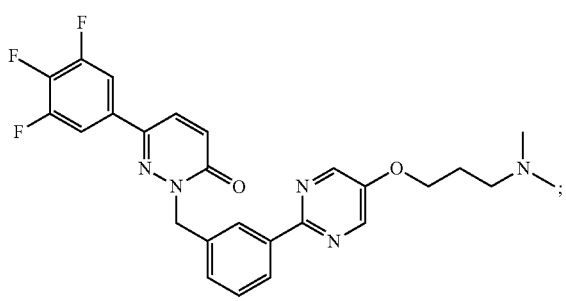

2-{3-[5-(2-dimethylaminoethoxy)pyrimidin-2-yl]benzyl}-6-(3,5-difluorophenyl)-2H-pyridazin-3-one ("A64") hydrochloride, ESI 464;

6-(3,5-difluorophenyl)-2-{3-[5-(1-methylpiperidin-4-ylmethoxy)pyrimidin-2-yl]benzyl}-2H-pyridazin-3-one, ESI 504,

"A66"

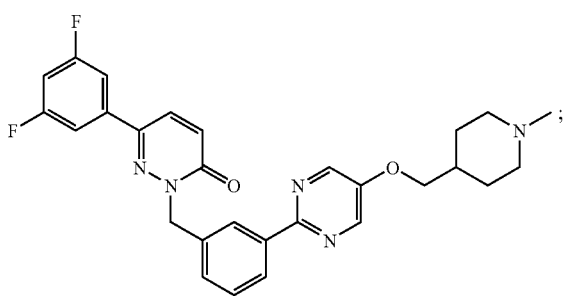

"A110"

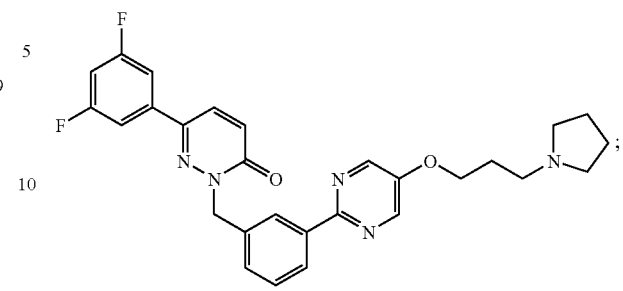

"A111"

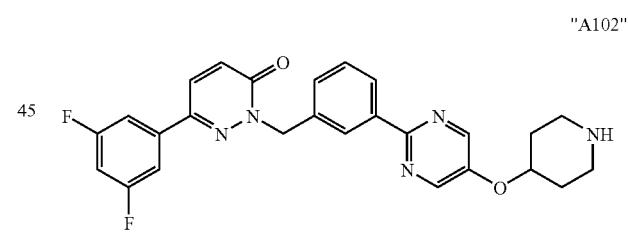

hydrochloride, ESI 450 (precursor BOC-protected compound);

6-(3,5-difluorophenyl)-2-{3-[5-(piperidin-4-yloxy)pyrimidin-2-yl]benzyl}-2H-pyridazin-3-one hydrochloride, ESI 476

"A102"

(precursor BOC-protected compound), $^1$H-NMR spectrum of "A102" hydrochloride:

$^1$H-NMR (d$_6$-DMSO): δ [ppm]=1.94 (m, 2H), 2.19 (m, 2H), 3.08 (m, 2H), 3.26 (m, 2H), 4.89 (m, 1H), 5.44 (s, 2H), 7.15 (d, J=10 Hz, 1H), 7.36 (tt, J$_1$=9.2 Hz, J$_2$=2 Hz, 1H), 7.50 (m, 2H), 7.66 (m, 2H), 8.16 (d, J=10 Hz, 1H), 8.24 (m, 1H), 8.37 (bs, 1H), 8.71 (s, 2H), 9.11 (bs, 1H), 9.19 (bs, 1H).

EXAMPLE 11

The preparation of 6-(3,5-difluorophenyl)-2-{3-[5-(3-dimethylaminopropoxy)pyridin-2-yl]benzyl}-2H-pyridazin-3-one ("A24"), ESI 477, is carried out analogously to the following scheme

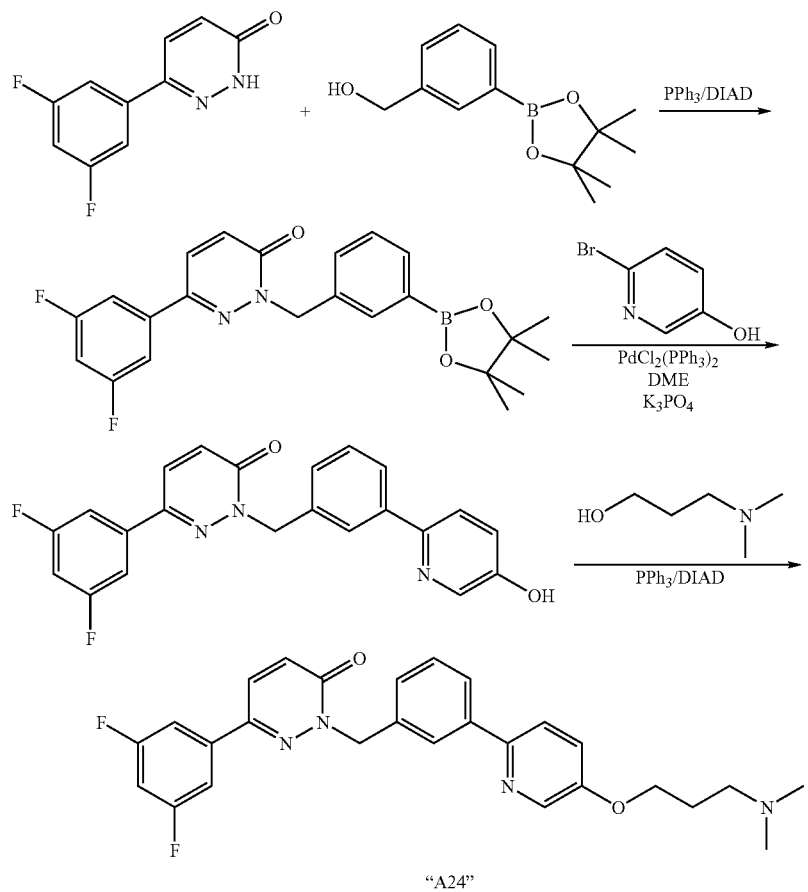
"A24"
EXAMPLE 12
The preparation of 2-[3-(5-bromopyrimidin-2-yl)benzyl]-6-(3,5-difluorophenyl)-2H-pyridazin-3-one ("A25") and 6-(3,5-difluorophenyl)-2-{3-[5-(1-methyl-1H-pyrazol-4-yl)pyrimidin-2-yl]benzyl}-2H-pyridazin-3-one ("A26") is carried out analogously to the following scheme
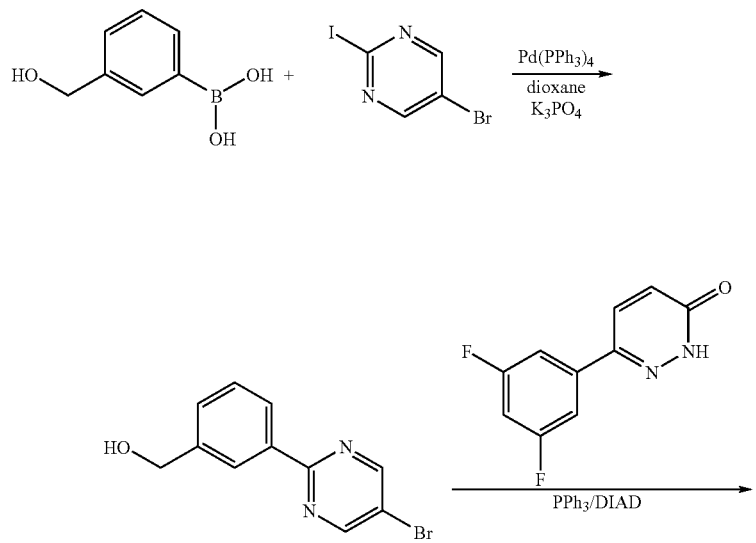

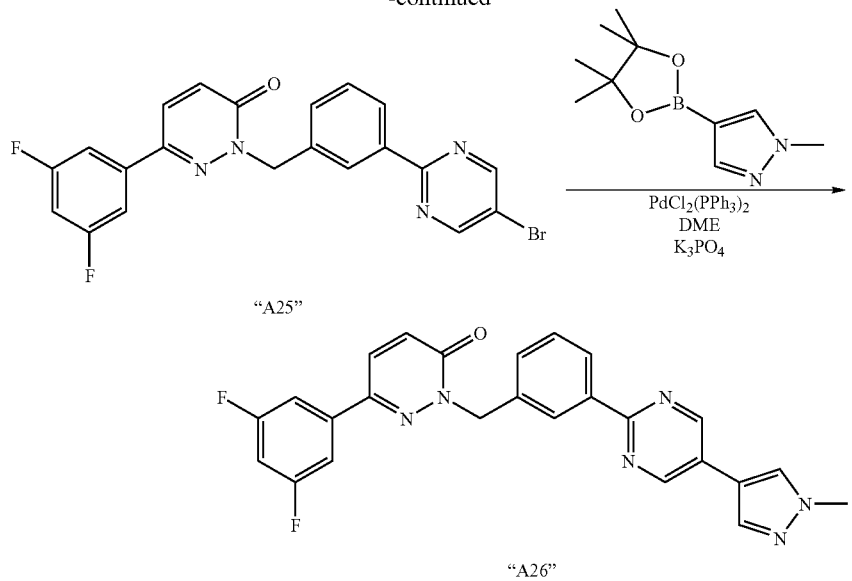

"A25"

"A26"

12.1 750 mg (0.65 mmol) of tetrakis(triphenylphosphine) palladium are added to a solution, kept under nitrogen, of 6.11 g (21.5 mmol) of 5-bromo-2-iodopyrimidine, 3.91 g (25.7 mmol) of 3-(hydroxymethyl)benzeneboronic acid and 9.11 g (42.9 mmol) of tripotassium phosphate trihydrate in 120 ml of dioxane and 14 ml of water, and the mixture is stirred at 90° C. for 18 hours. The reaction mixture is cooled to room temperature, tert-butyl methyl ether and water are added, and the mixture is filtered through kieselguhr. The organic phase of the filtrate is separated off, dried over sodium sulfate and evaporated. The residue is chromatographed on a silica gel column with dichloromethane/methanol as eluent: [3-(5-bromopyrimidin-2-yl)phenyl]methanol as pale-yellow crystals; ESI 265,267.

12.2 2.60 ml (13.2 mmol) of diisopropyl azodicarboxylate are added dropwise to a suspension of 2.76 g (13.2 mmol) of 6-(3,5-difluorophenyl)-2H-pyridazin-3-one, 2.49 g (8.83 mmol) of [3-(5-bromopyrimidin-2-yl)-phenyl]methanol, and 3.47 g (13.2 mmol) of triphenylphosphine in 30 ml of THF, and the reaction mixture is stirred at room temperature for 18 hours. The reaction mixture is evaporated in vacuo, taken up in 2-propanol, heated to the boil and allowed to cool. The resultant precipitate is filtered off with suction, washed with 2-propanol and re-recrystallised from 2-propanol: 2-[3-(5-bromopyrimidin-2-yl)benzyl]-6-(3,5-difluorophenyl)-2H-pyridazin-3-one ("A25") as colourless crystals; ESI 455,457;

$^1$H-NMR (DMSO-$d_6$): δ [ppm]=5.45 (s, 2H), 7.14 (d, J=9.5 Hz, 1H), 7.35 (tt, $J_1$=8.8 Hz, $J_2$=2.3 Hz, 1H), 7.53 (t, J=7.5 Hz, 1H), 7.59 (m, 1H), 7.66 (m, 2H), 8.14 (d, J=9.5 Hz, 1H), 8.29 (m, 1H), 8.38 (bs, 1H), 9.06 (s, 2H).

12.3 425 mg (2.0 mmol) of tripotassium phosphate trihydrate and 56.2 mg (0.08 mmol) of bis(triphenylphosphine) palladium chloride are added to a solution, kept under nitrogen, of 455 mg (1.00 mmol) of 2-[3-(5-bromopyrimidin-2-yl)benzyl]-6-(3,5-difluorophenyl)-2H-pyridazin-3-one and 229 mg (1.10 mmol) of 1-methyl-4-(4,4,5,5-tetramethyl-1,3,2-dioxaborolan-2-yl)-1H-pyrazole in 10 ml of 1,2-dimethoxyethane, and the mixture is stirred at 80° C. for 18 hours, during which a grey precipitate forms. The reaction mixture is diluted with water and filtered. The residue is chromatographed on a silica gel column with dichloromethane/methanol as eluent: 6-(3,5-difluorophenyl)-2-{3-[5-(1-methyl-1H-pyrazol-4-yl)pyrimidin-2-yl]-benzyl}-2H-pyridazin-3-one ("A26") as colourless crystals; ESI 457;

$^1$H-NMR (DMSO-$d_6$): δ [ppm]=3.80 (s, 3H), 5.44 (s, 2H), 7.13 (d, J=9.5 Hz, 1H), 7.29 (tt, $J_1$=8.8 Hz, $J_2$=2.3 Hz, 1H), 7.50 (m, 2H), 7.64 (m, 2H), 8.05 (s, 1H), 8.14 (d, J=9.5 Hz, 1H), 8.32 (m, 1H), 8.35 (s, 1H), 8.45 (bs,1H), 9.11 (s, 2H).

The following compounds are obtained analogously:

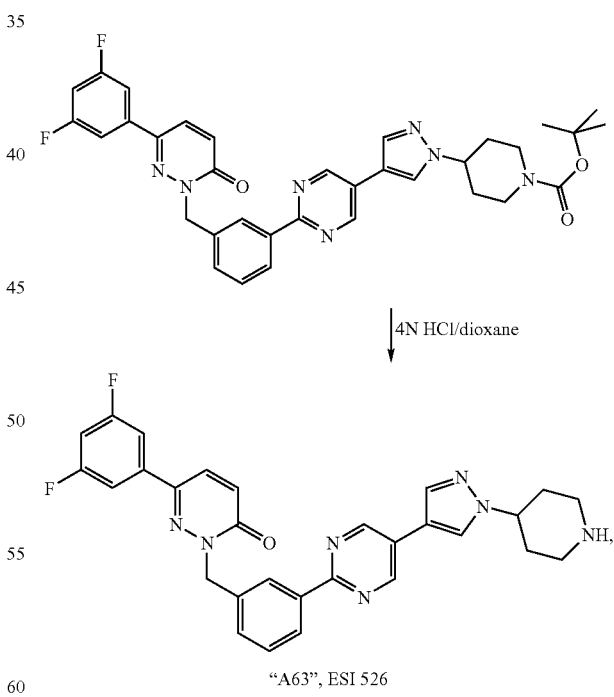

"A63", ESI 526

"A63": $^1$H-NMR (DMSO-$d_6$): δ [ppm]=1.81 (m, 2H), 2.01 (m, 2H), 2.15 (bs, 1H), 2.61 (m, 2H), 3.06 (m, 2H), 4.24 (m, 1H), 5.47 (s, 2H), 7.16 (d, J=9.5 Hz, 1H), 7.36 (tt, $J_1$=8.8 Hz, $J_2$=2.3 Hz, 1H), 7.53 (m, 2H), 7.68 (m, 2H), 8.10 (s, 1H), 8.16 (d, J=9.5 Hz, 1H), 8.33 (m, 1H), 8.46 (bs,1H), 8.48 (s, 1H), 9.14 (s, 2H);

| Compound No. | Name and/or structure | ESI [M + H]⁺ | HPLC (Rt in min) method |
|---|---|---|---|
| "A103" | 3-(3,4,5-trifluorophenyl)-pyridazinone with pyrimidine-pyrazole-piperidine | | |
| "A104" | 3-cyanophenyl-pyridazinone with pyrimidine-pyrazole-piperidine | | |
| "A105" | 3-fluorophenyl-pyridazinone with pyrimidine-pyrazole-piperidine | | |
| "A106" | 3,5-difluorophenyl-pyridazinone with pyrimidine-pyrazole-propyl-N,N-dimethylamine | | |
| "A107" | 3,5-difluorophenyl-pyridazinone with pyrimidine-pyrazole-ethanol | | |

-continued
| Compound No. | Name and/or structure | ESI [M + H]⁺ | HPLC (Rt in min) method |
|---|---|---|---|
| "A108" | 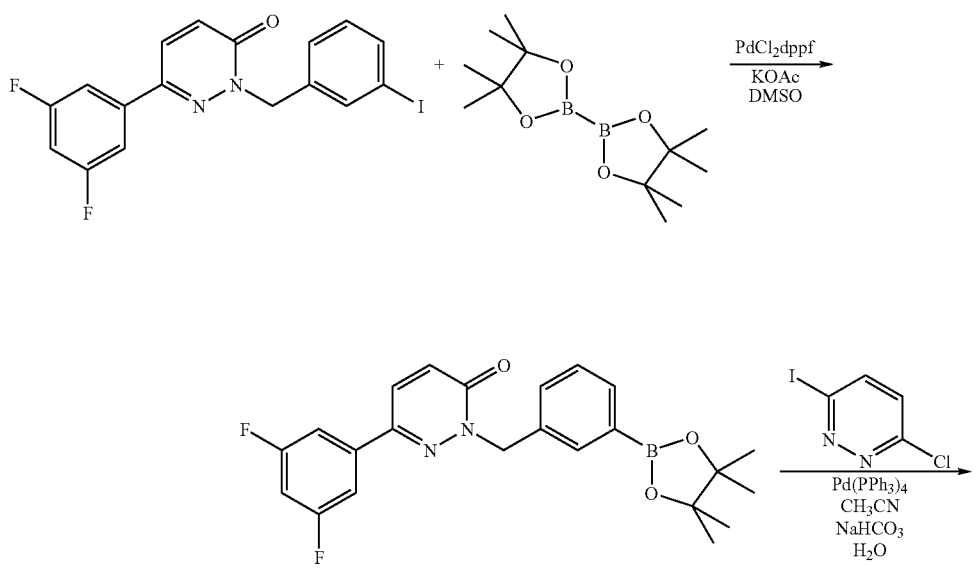 | | |
| "A109" | | | |
EXAMPLE 13
The preparation of 6-(3,5-difluorophenyl)-2-{3-[6-(4-methylpiperazin-1-yl)-pyridazin-3-yl]benzyl}-2H-pyridazin-3-one ("A27") and 6-(3,5-difluorophenyl)-2-{3-[6-(3-dimethylaminopropoxy)pyridazin-3-yl]benzyl}-2H-pyridazin-3-one ("A28") is carried out analogously to the following scheme

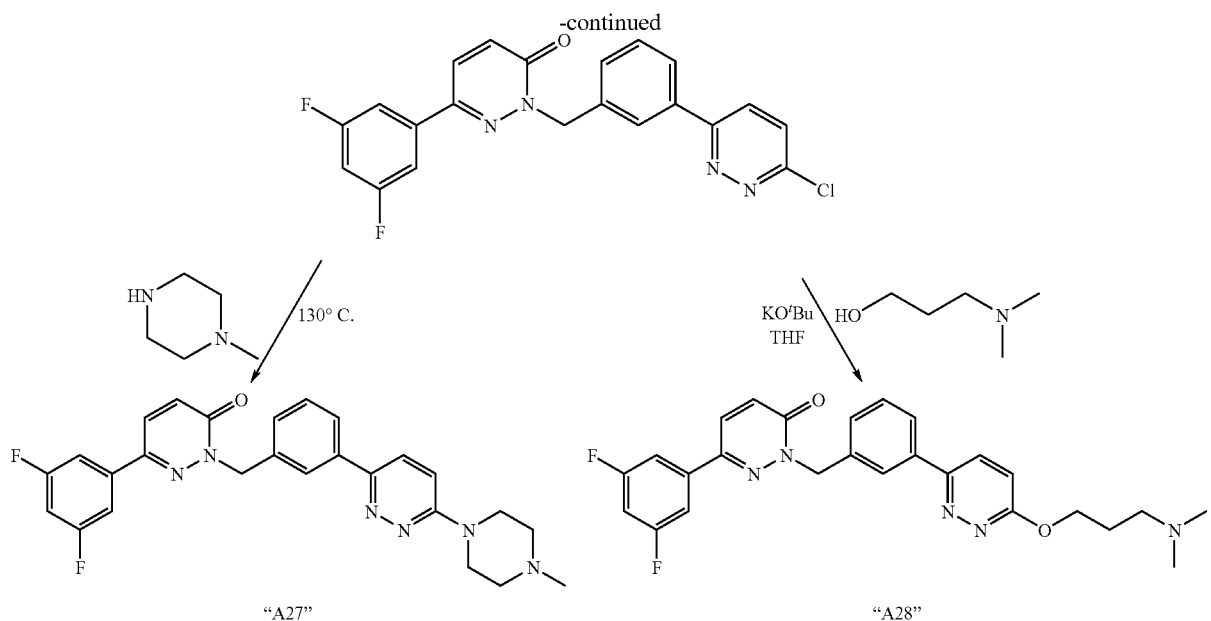

"A27"    "A28"

The following compounds are obtained analogously 6-(3,5-difluorophenyl)-2-{3-[6-(3-dimethylaminopropy-lamino)pyridazin-3-yl]benzyl}pyridazin-3-one ("A67") hydrochloride, ESI 477,

"A67"

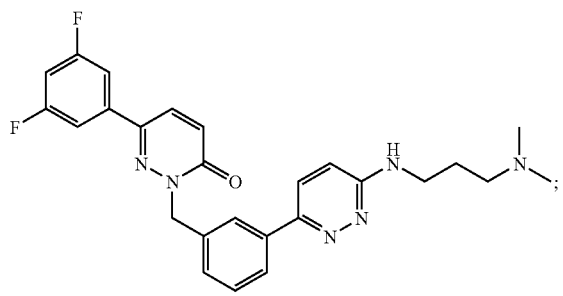

6-(3,5-difluorophenyl)-2-{3-[6-(2-dimethylaminoethy-lamino)pyridazin-3-yl]benzyl}pyridazin-3-one ("A68") hydrochloride, ESI 463;

6-(3,5-difluorophenyl)-2-{3-[6-(4-dimethylaminobuty-lamino)pyridazin-3-yl]benzyl}pyridazin-3-one ("A69");

6-(3,5-difluorophenyl)-2-{3-[6-(1-methylpiperidin-4-ylamino)pyridazin-3-yl]benzyl}pyridazin-3-one

"A70"

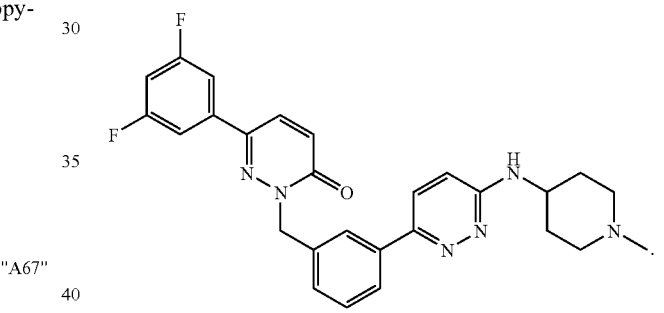

EXAMPLE 14

The preparation of ethyl 2-{3-[6-oxo-3-(3,4,5-trifluorophenyl)-6H-pyridazin-1-ylmethyl]phenyl}pyrimidine-5-carboxylate ("A29") is carried out analogously to the following scheme

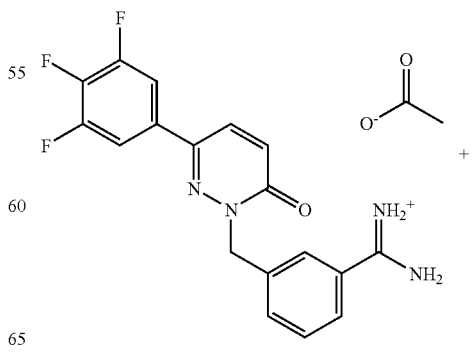

-continued

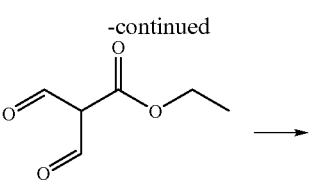

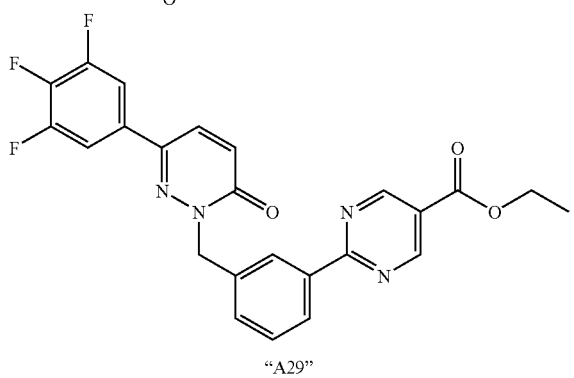

"A29"

4.7 g (11.23 mmol) of 3-[6-oxo-3-(3,4,5-trifluorophenyl)-6H-pyridazin-1-ylmethyl]benzamidinium acetate are suspended in 40 ml of pyridine, and 2.4 g (16.85 mmol) of ethyl 2-formyl-3-oxopropionate (prepared in accordance with S. H. Berz et al., Journal of Organic Chemistry 1982, 47, 2216) are added, and the mixture is stirred at 80° C. for 4 h. A further 500 mg (3.47 mmol) of ethyl 2-formyl-3-oxopropionate are subsequently added, and the mixture is stirred at 80° C. for 1 h. The reaction mixture is stirred into 400 ml of water, and the precipitate is filtered off with suction, washed a number of times with water and dried in a drying cabinet.

Yield: 4.43 g of "A29" (76%), Rt=3.58 min (method B), ESI 467.

The following compounds are obtained analogously
ethyl 2-{3-[3-(3,5-difluorophenyl)-6-oxo-6H-pyridazin-1-ylmethyl]-phenyl}pyrimidine-5-carboxylate ("A30")

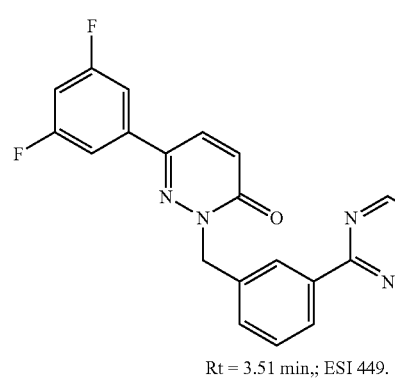

Rt = 3.51 min,; ESI 449.

Preparation of 6-(3,5-difluorophenyl)-2-[3-(5-hydroxymethylpyrimidin-2-yl)-benzyl]-2H-pyridazin-3-one ("A101")

1 g (2.43 mmol) of 2-{3-[3-(3,5-difluorophenyl)-6-oxo-6H-pyridazin-1-yl-methyl]phenyl}pyrimidine-5-carbaldehyde [preparation Example 7] is suspended in 15 mol of ethanol and 15 ml of THF. The reaction mixture is cooled to 5° C., 374 mg (9.89 mmol) of sodium borohydride are added, and the mixture is brought to room temperature over the course of 30 min. The reaction mixture is poured into a mixture of ice/water/1 N HCl (1:1:1). The precipitated product is filtered off with suction and dried in a drying cabinet.

Yield: 960 mg, white solid "A101", ESI 407.

EXAMPLE 15

The preparation of 2-{3-[6-oxo-3-(3,4,5-trifluorophenyl)-6H-pyridazin-1-yl-methyl]phenyl}pyrimidine-5-carboxylic acid ("A31") is carried out analogously to the following scheme

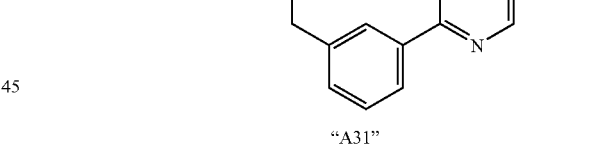

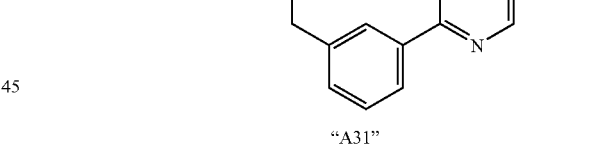

"A31"

3.4 g (7.29 mmol) of ethyl 2-{3-[6-oxo-3-(3,4,5-trifluorophenyl)-6H-pyridazin-1-ylmethyl]phenyl}pyrimidine-5-carboxylate are dissolved in 300 ml of THF and 30 ml of water, and 713 mg (29.2 mmol) of lithium hydroxide are added. The reaction mixture is refluxed for 4 h and cooled to room temperature, and the organic solvent is removed by distillation in a rotary evaporator. 300 ml of water and 30 ml of THF are added to the residue, and conc. HCl is slowly added dropwise to this solution with stirring until the reaction is strongly acidic. The precipitate formed is filtered off with suction, washed with copious water and dried in a vacuum drying cabinet.

Yield: 2.87 g of "A31", Rt=3.06 min (method B), ESI 439.

The following compound is obtained analogously
2-{3-[3-(3,5-difluorophenyl)-6-oxo-6H-pyridazin-1-ylmethyl]phenyl}-pyrimidine-5-carboxylic acid ("A32"), ESI 421.

EXAMPLE 16

The preparation of N-(2-dimethylaminoethyl)-2-{3-[6-oxo-3-(3,4,5-trifluorophenyl)-6H-pyridazin-1-ylmethyl]phenyl}pyrimidine-5-carboxamide ("A33") is carried out analogously to the following scheme

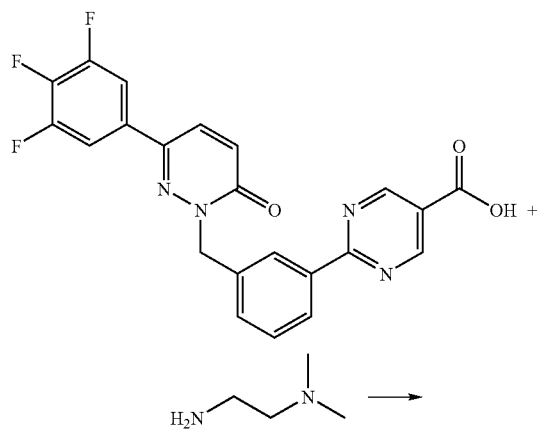

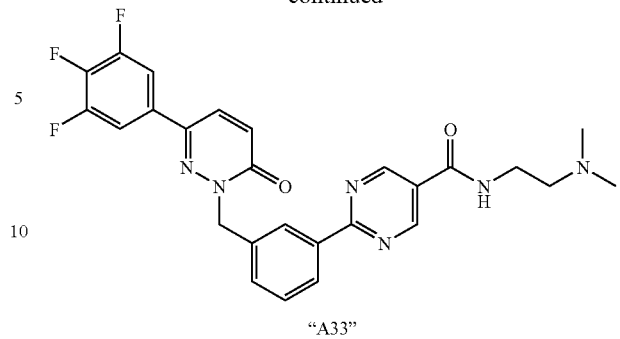

"A33"

150 mg (0.334 mmol) of 2-{3-[6-oxo-3-(3,4,5-trifluorophenyl)-6H-pyridazin-1-ylmethyl]phenyl}pyrimidine-5-carboxylic acid are dissolved in 2 ml of DMF, and 75 µl (0.67 mmol) of 4-methylmorpholine, 97 mg (0.50 mmol) of EDCl and 60 mg (0.43 mmol) of HOBt are added. 47 µl (0.43 mmol) of N,N-dimethylaminoethylenediamine are added, and the reaction mixture is stirred at room temperature for 18 h. The reaction solution is separated directly by means of preparative HPLC.

Yield: 124 mg of "A33" trifluoroacetate; Rt=2.63 (method B); ESI 509.

The following compounds are obtained analogously

| Compound No. | Name and/or structure | ESI [M + H]⁺ | HPLC (Rt in min) method |
|---|---|---|---|
| "A34" | 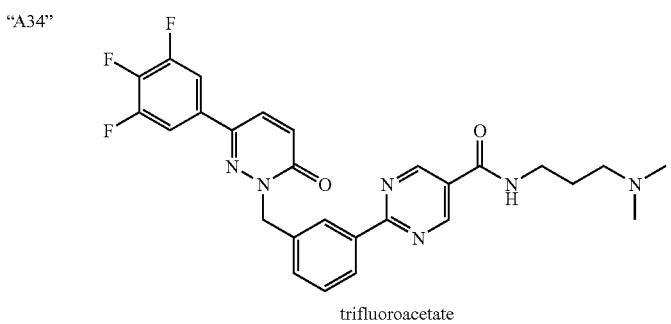 trifluoroacetate | 523 | 2.64 B |
| "A35" | 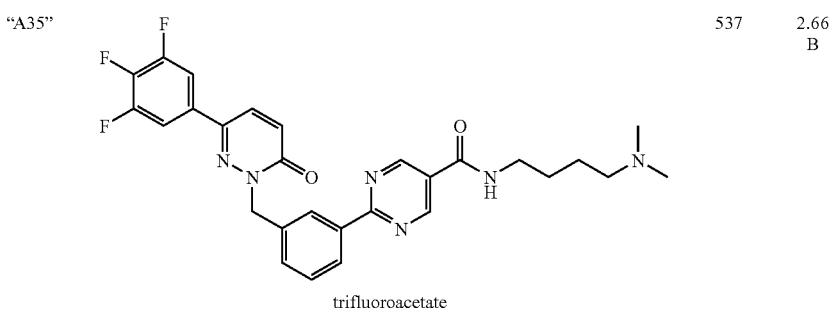 trifluoroacetate | 537 | 2.66 B |

-continued
| Compound No. | Name and/or structure | ESI [M + H]+ | HPLC (Rt in min) method |
|---|---|---|---|
| "A36" | 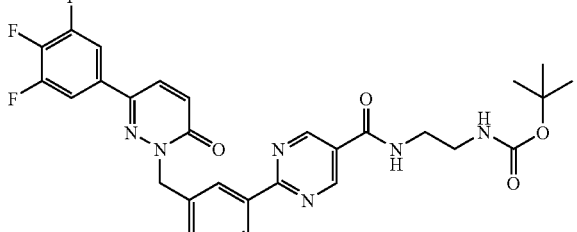 | 581 | 3.28 B |
| "A37" | 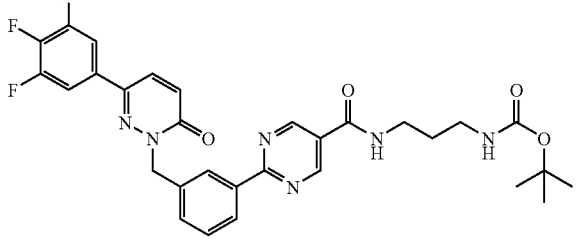 | 595 | 3.34 B |
| "A38" | 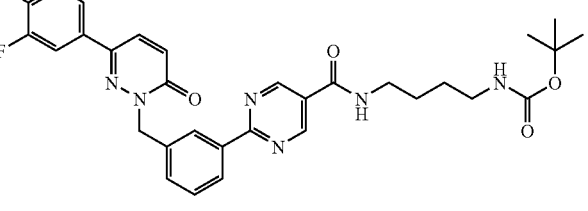 | 609 | 3.36 B |
| "A39" | 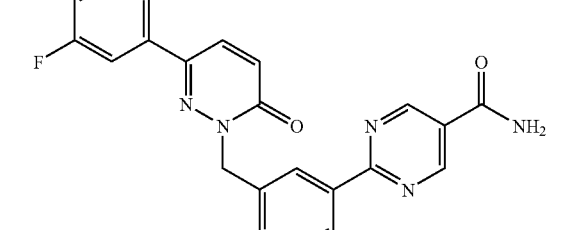 | 438 | 2.90 B |
| "A40" | 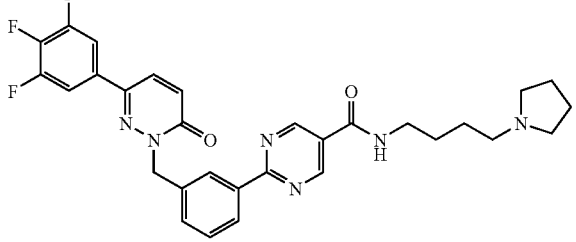<br>trifluoroacetate | 562 | 2.72 B |

| Compound No. | Name and/or structure | ESI [M + H]⁺ | HPLC (Rt in min) method |
|---|---|---|---|
| "A41" | (structure) trifluoroacetate | 521 | 2.63 B |
| "A42" | (structure) | 510 | 2.91 B |
| "A43" | (structure) | 621 | 3.48 B |
| "A44" | (structure) | 657 (M + Na) | 3.51 B |
| "A44a" | from "A44" using TFA/dioxane: (structure) trifluoroacetate | 535 | |

| Compound No. | Name and/or structure | ESI [M + H]+ | HPLC (Rt in min) method |
|---|---|---|---|
| "A45" | 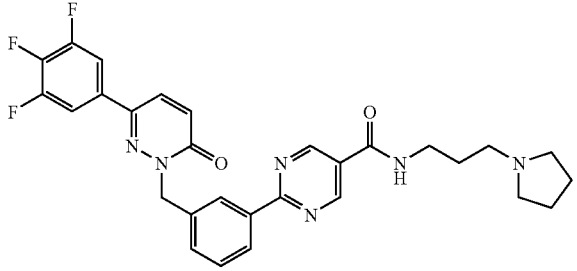 [SMILES: O=C(NCCCN1CCCC1)c1cnc(-c2cccc(Cn3nc(-c4cc(F)c(F)c(F)c4)ccc3=O)c2)nc1] trifluoroacetate | 549 | 2.68 B |
| "A46" | 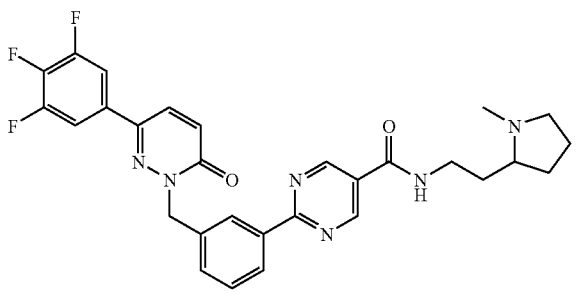 [SMILES: CN1CCCC1CCNC(=O)c1cnc(-c2cccc(Cn3nc(-c4cc(F)c(F)c(F)c4)ccc3=O)c2)nc1] trifluoroacetate | 549 | 2.68 B |
| "A47" | 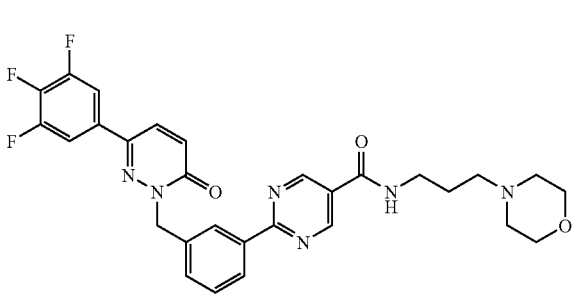 [SMILES: O=C(NCCCN1CCOCC1)c1cnc(-c2cccc(Cn3nc(-c4cc(F)c(F)c(F)c4)ccc3=O)c2)nc1] trifluoroacetate | 565 | 2.65 B |
| "A48" | 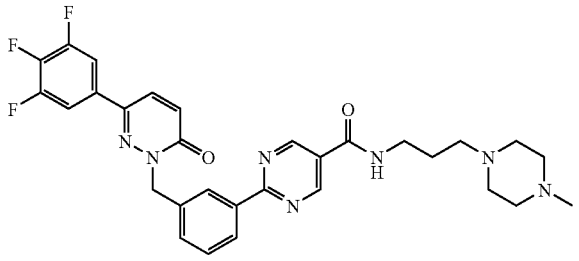 [SMILES: CN1CCN(CCCNC(=O)c2cnc(-c3cccc(Cn4nc(-c5cc(F)c(F)c(F)c5)ccc4=O)c3)nc2)CC1] trifluoroacetate | 578 | 2.50 B |
| "A49" | 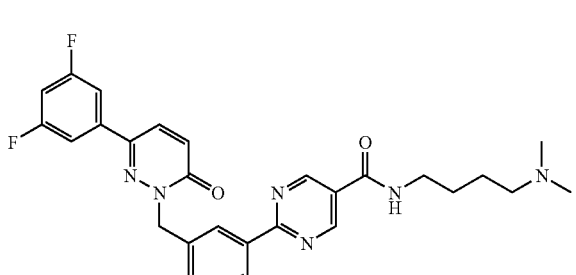 trifluoroacetate | 519 | 2.60 B |

| Compound No. | Name and/or structure | ESI [M + H]+ | HPLC (Rt in min) method |
|---|---|---|---|
| "A50" | 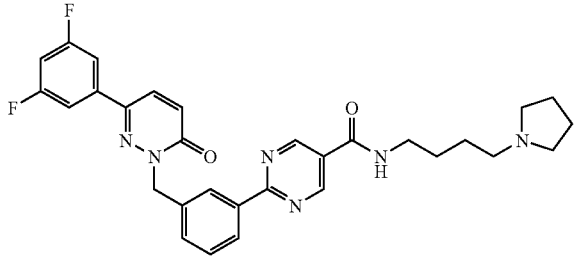 [SMILES: O=C(NCCCCN1CCCC1)c1cnc(-c2cccc(Cn3nc(-c4cc(F)cc(F)c4)ccc3=O)c2)nc1]<br>trifluoroacetate | 544 | 2.64 B |
| "A71" | 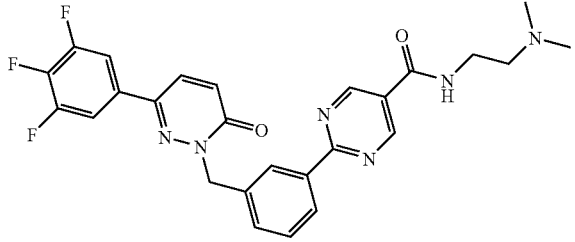 [SMILES: CN(C)CCNC(=O)c1cnc(-c2cccc(Cn3nc(-c4cc(F)c(F)c(F)c4)ccc3=O)c2)nc1]<br>trifluoroacetate | 509 | |
| "A72" | 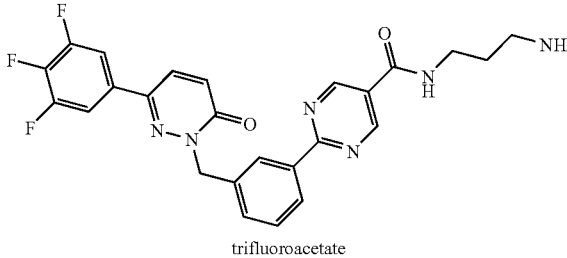<br>trifluoroacetate<br>(obtainable from Boc-protected precursor) | 495 | |
| "A73" | 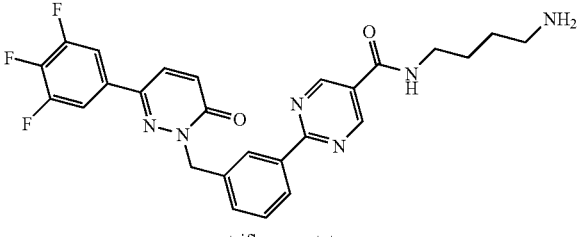<br>trifluoroacetate<br>(obtainable from Boc-protected precursor) | 509 | |
| "A74" | 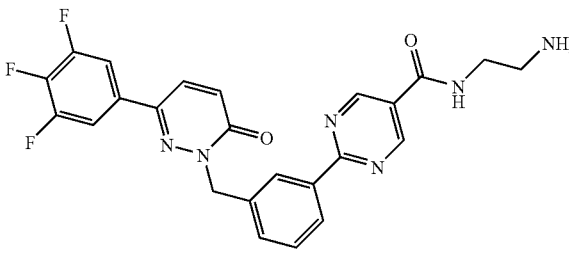<br>trifluoroacetate<br>(obtainable from Boc-protected precursor) | 481 | |

| Compound No. | Name and/or structure | ESI [M + H]+ | HPLC (Rt in min) method |
|---|---|---|---|
| "A84" | 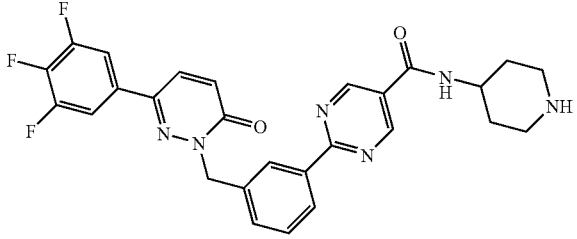 [SMILES: O=C(NC1CCNCC1)c1cnc(-c2cccc(Cn3nc(-c4cc(F)c(F)c(F)c4)ccc3=O)c2)nc1]<br>trifluoroacetate<br>(obtainable from Boc-protected precursor) | 521 | |
| "A90" | 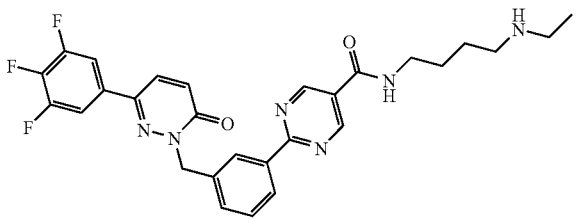 [SMILES: CCNCCCCNC(=O)c1cnc(-c2cccc(Cn3nc(-c4cc(F)c(F)c(F)c4)ccc3=O)c2)nc1]<br>trifluoroacetate<br>(obtainable from Boc-protected precursor) | 537 | |
| "A92" | 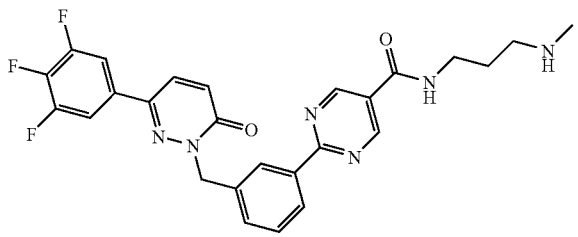<br>trifluoroacetate<br>(obtainable from Boc-protected precursor) | 509 | |

EXAMPLE 17

The preparation of N-[2-(1H-imidazol-4-yl)ethyl]-2-{3-[6-oxo-3-(3,4,5-trifluorophenyl)-6H-pyridazin-1-ylmethyl]phenyl}pyrimidine-5-carboxamide ("A51") is carried out analogously to the following scheme

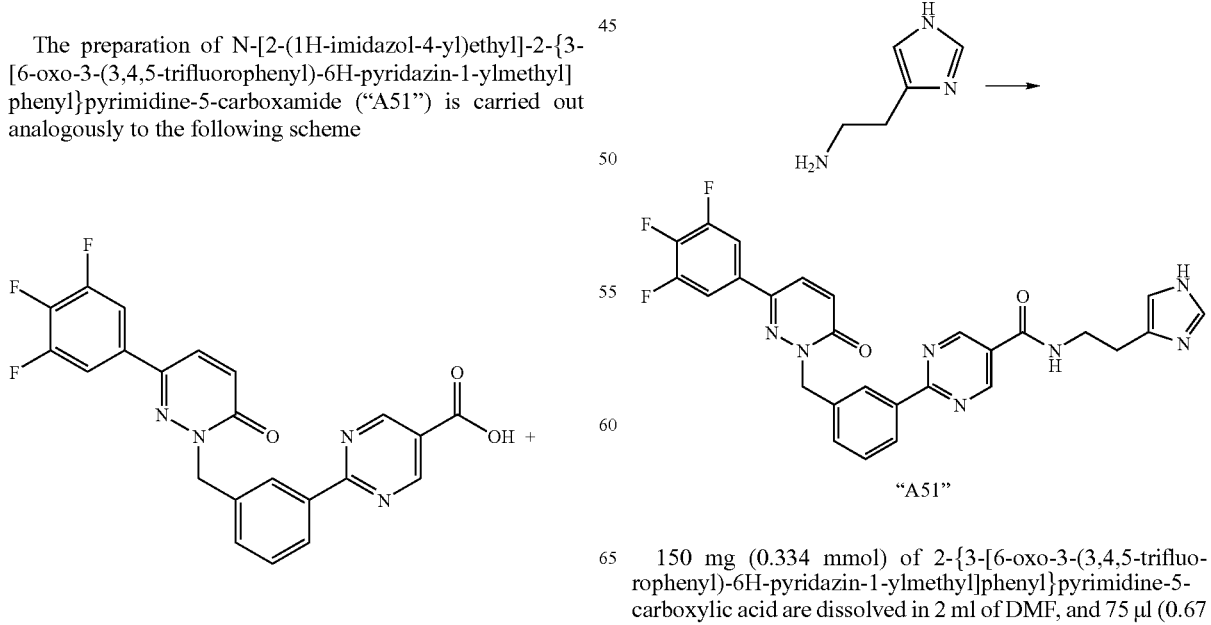

150 mg (0.334 mmol) of 2-{3-[6-oxo-3-(3,4,5-trifluorophenyl)-6H-pyridazin-1-ylmethyl]phenyl}pyrimidine-5-carboxylic acid are dissolved in 2 ml of DMF, and 75 µl (0.67 mmol) of 4-methylmorpholine, 97 mg (0.50 mmol) of EDCl and 60 mg (0.43 mmol) of HOBt are added. 51 mg (0.44 mmol) of histamine are added, and the reaction mixture is stirred at room temperature for 18 h. Water is added to the reaction mixture, and the resultant precipitate is filtered off with suction. Acetonitrile is added to the residue, which is again filtered off with suction, and the residue is dried in vacuo.

Yield: 127 mg of "A51", Rt=2.63 min (method B), ESI 532.

The following compounds are obtained analogously

| Compound No. | Name and/or structure | ESI [M + H]+ | HPLC (Rt in min) method |
|---|---|---|---|
| "A52" | | 547 | 2.85 B |
| "A53" | | 563 | 2.99 B |

EXAMPLE 18

The preparation of 2-[3-(5-chloropyrimidin-2-yl)benzyl]-6-(3,4,5-trifluorophenyl)-2H-pyridazin-3-one ("A54") is carried out analogously to the following scheme

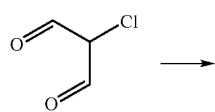

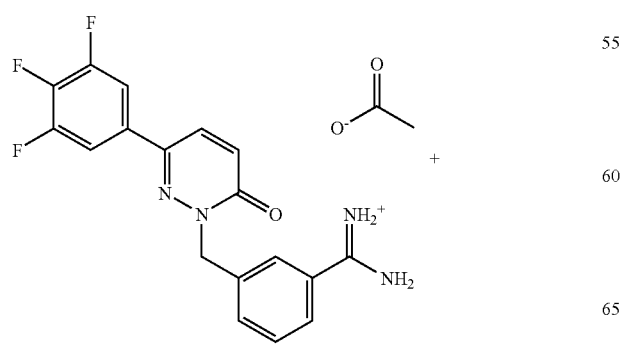

"A54"

250 mg (0.60 mmol) of 3-[6-oxo-3-(3,4,5-trifluorophenyl)-6H-pyridazin-1-ylmethyl]benzamidinium acetate are suspended in 3 ml of pyridine, 74 mg (0.66 mmol) of 2-chloromalonaldehyde are added, and the mixture is stirred at 90°

C. for 15 h. The reaction mixture is evaporated, and the residue is purified by means of preparative HPLC, giving "A54".

EXAMPLE 19

The preparation of 2-[3-(4-methylpyrimidin-2-yl)benzyl]-6-(3,4,5-trifluorophenyl)-2H-pyridazin-3-one ("A3") is carried out analogously to the following scheme

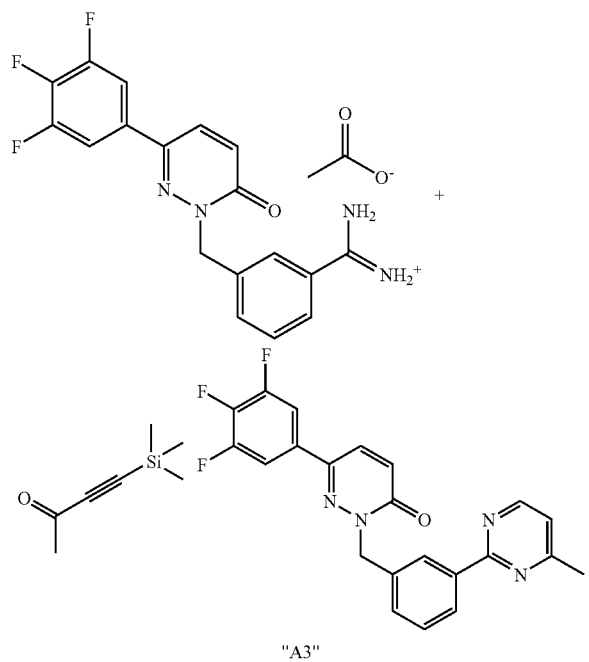

"A3"

150 mg (0.36 mmol) of 3-[6-oxo-3-(3,4,5-trifluorophenyl)-6H-pyridazin-1-ylmethyl]benzamidinium acetate and 99.5 mg (0.72 mmol) of potassium carbonate are suspended in 5 ml of acetonitrile, 42 mg (0.3 mmol) of 4-trimethylsilyl)-3-butyn-2-one are added, and the mixture is heated in a microwave reactor at 120° C. for 45 min (Emrys optimiser). The reaction mixture is filtered and evaporated, and the residue is purified by means of preparative HPLC.

Yield: 16 mg of "A3", white solid, Rt=3.38 min (method B), ESI-MS: 408.

EXAMPLE 20

The preparation of 2-(3-pyrimidin-2-ylbenzyl)-6-(3,4,5-trifluorophenyl)-2H-pyridazin-3-one ("A4") is carried out analogously to the following scheme

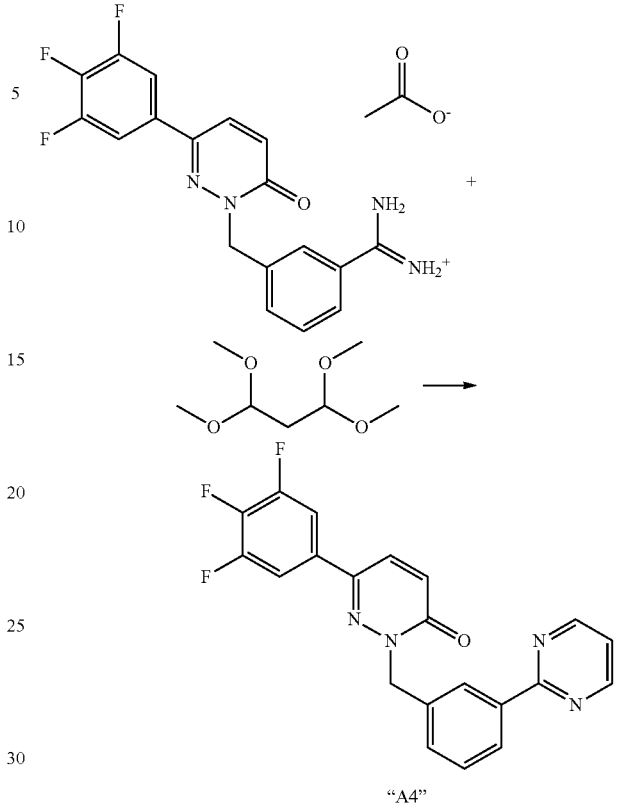

"A4"

150 mg (0.36 mmol) of 3-[6-oxo-3-(3,4,5-trifluorophenyl)-6H-pyridazin-1-ylmethyl]benzamidinium acetate and 1.1 ml (6.6 mmol) of 1,1,3,3-tetramethoxypropane are stirred at 175° C. for 1 h. The reaction mixture is purified directly by means of preparative HPLC.

Yield: 23 mg of "A4", white solid; Rt=3.28 min (method B); ESI-MS: 395.

EXAMPLE 21

The preparation of 4-{1-[3-(5-methylpyrimidin-2-yl)benzyl]-6-oxo-1,6-dihydropyridazin-3-yl}-N-(3-piperidin-1-ylpropyl)benzamide ("A55") is carried out analogously to the following scheme

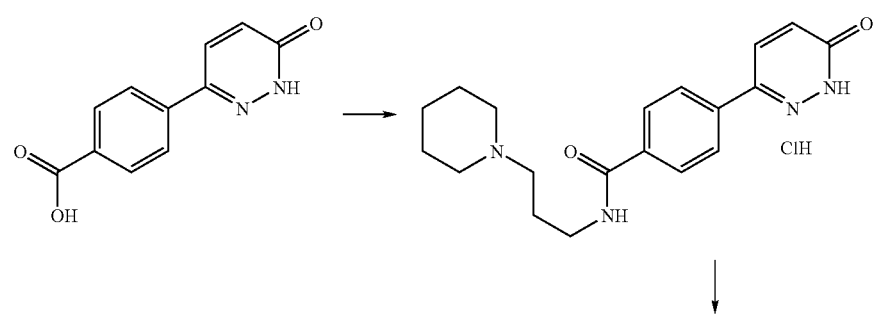

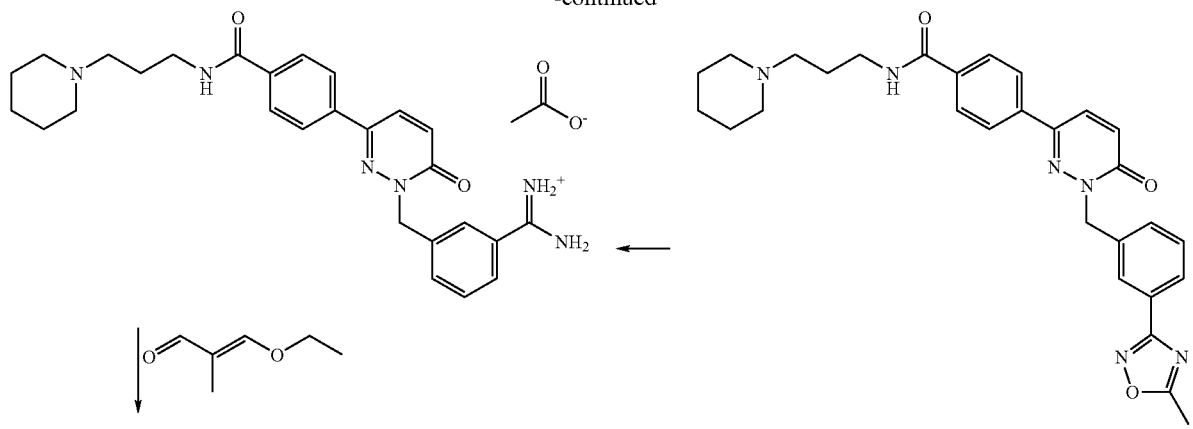

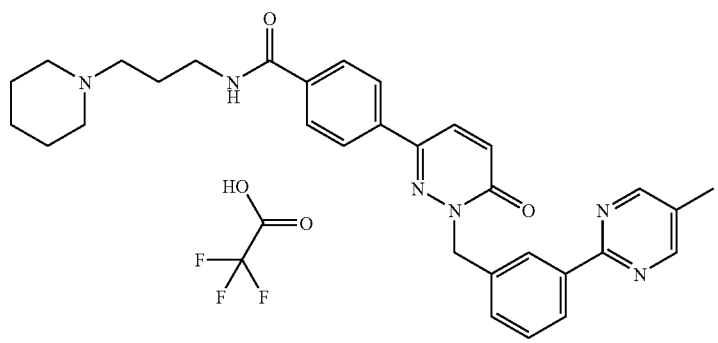

"A55"

1.5 g (6.94 mmol) of 4-(6-oxo-1,6-dihydropyridazin-3-yl) benzoic acid (preparation according to DE 10010422) are dissolved in 20 ml of DMF, 1.18 g (8.33 mmol) of 3-piperidinopropylamine, 1.56 ml (13.9 mmol) of 4-methylmorpholine, 2.7 g (13.9 mmol) of EDCl and 967 mg (6.94 mmol) of HOBt are added, and the mixture is stirred at room temperature for 18 h. The DMF is removed by distillation, and 2 M NaOH is added to the residue. The mixture is evaporated, and 100 ml of THF are added, the mixture is stirred for 1 h and filtered, 50 ml of ether are added, and 10 ml of 4 N HCl in dioxane are added. An oil forms in the process, the supernatant is decanted off, ether is again added, and the supernatant is decanted again. 30 ml of isopropanol are added to the oily residue. After 3 days, crystals form, which are filtered off with suction, washed with isopropanol and dried.

Yield: 500 mg of "A55", Rt=1.70 min, ESI 341.

EXAMPLE 22

The preparation of N-(2-{3-[3-(3,5-difluorophenyl)-6-oxo-6H-pyridazin-1-ylmethyl]phenyl}pyrimidin-5-yl)-2-dimethylaminoacetamide ("A85") is carried out analogously to the following scheme

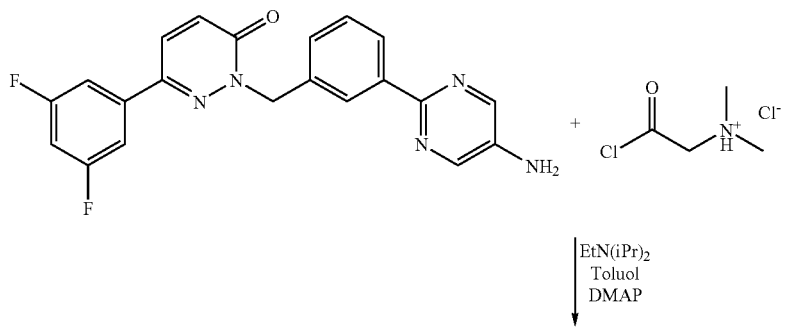

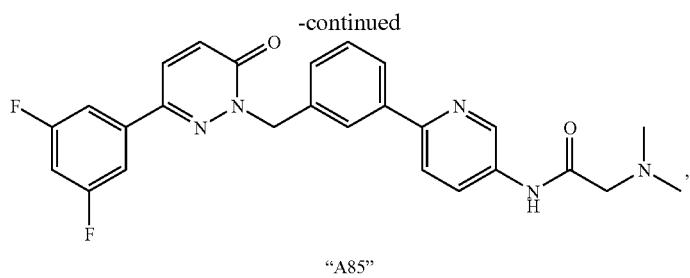

"A85"

trifluoroacetate, ESI 477.

The following compounds are obtained analogously

N-(2-{3-[3-(3,5-difluorophenyl)-6-oxo-6H-pyridazin-1-ylmethyl]-phenyl}pyrimidin-5-yl)-4-dimethylaminobutyramide hydrochloride

"A87"

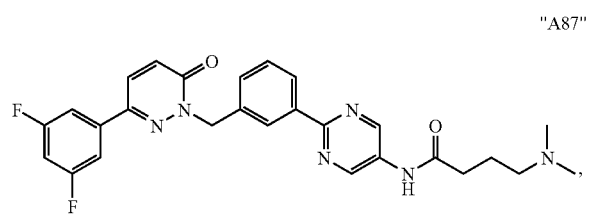

ESI 505;

N-(2-{3-[3-(3,5-difluorophenyl)-6-oxo-6H-pyridazin-1-ylmethyl]-phenyl}pyrimidin-5-yl)-3-dimethylaminopropionamide

"A95"

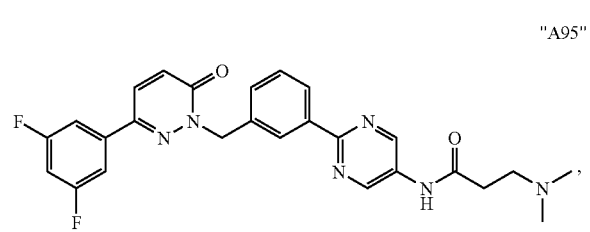

ESI 491.

EXAMPLE 23

Reaction of

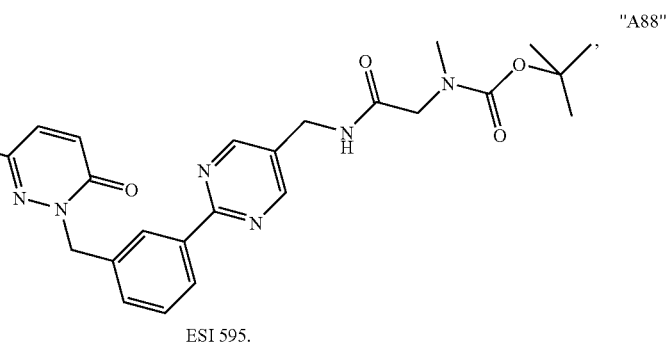

with Cl—CO—CH$_2$—N(CH$_3$)COO-tert-butyl under standard conditions and conventional work-up gives

"A88"

ESI 595.

The following compound is obtained analogously

"A89"

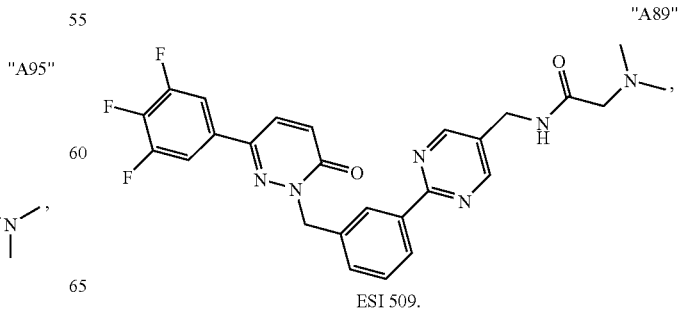

ESI 509.

EXAMPLE 24

The preparation of 2-{3-[6-oxo-3-(3,4,5-trifluorophenyl)-6H-pyridazin-1-ylmethyl]phenyl}pyrimidine-5-carbonitrile ("A77") and of 2-[3-(5-aminomethylpyrimidin-2-yl)benzyl]-6-(3,4,5-trifluorophenyl)-2H-pyridazin-3-one ("A93") is carried out analogously to the following scheme

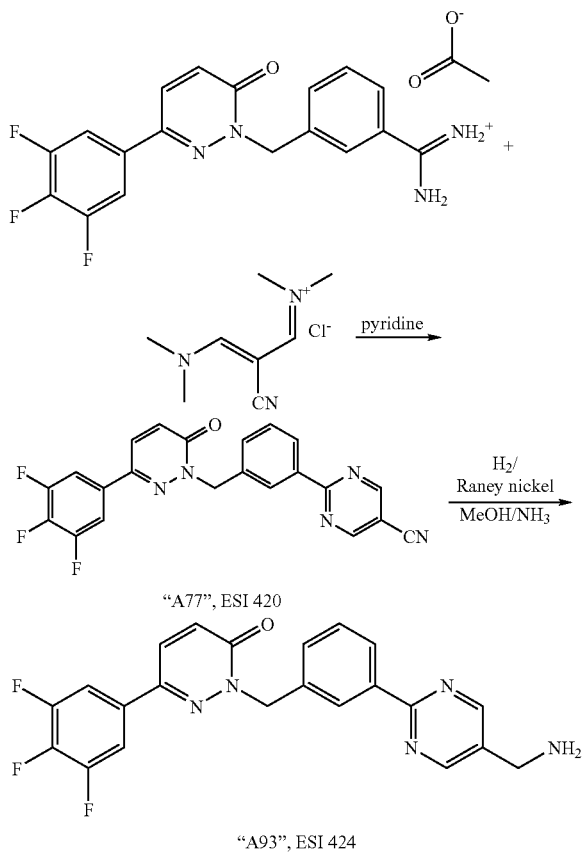

24.1 3.5 g (18.6 mmol) of 3-dimethylamino-2-cyano-2-propen-1-yl-idene)dimethylammonium chloride (prepared analogously to U.S. Pat. No. 3,853,946) are suspended in 60 ml of pyridine, and 7.8 g (18.6 mmol) of 3-[6-oxo-3-(3,4,5-trifluorophenyl)-6H-pyridazin-1-ylmethyl]benzamidinium acetate are added. The suspension is stirred at 100° C. for 4 hours. After cooling to room temperature, the mixture is stirred into 300 ml of water, and the crystals are filtered off with suction and washed with water. The solid is dried in a vacuum drying cabinet;

Yield: 6.14 g of "A77", beige crystals;
HPLC: Rt=3.34 min (method C); LC-MS: 420 (M+H).

24.2 2.9 g (6.9 mmol) of 2-{3-[6-oxo-3-(3,4,5-trifluorophenyl)-6H-pyridazin-1-ylmethyl]phenyl}pyrimidine-5-carbonitrile ("A77") are dissolved in 60 ml of THF and 60 ml of methanol, and 2 g of Raney nickel are added. The mixture is subsequently hydrogenated at atmospheric pressure under a hydrogen atmosphere for 6 h. The catalyst is filtered off with suction and washed with THF, and the filtrate is evaporated.

Yield: 2.9 g of "A93", pale-yellow solid; HPLC: 2.53 min (method C);
LC-MS: 424 (M+H).

EXAMPLE 25

The preparation of 6-(3,5-difluorophenyl)-2-[3-(6-oxo-1,6-dihydropyrimidin-2-yl)benzyl]-2H-pyridazin-3-one ("A80"), ESI 393, and of 6-(3,5-difluorophenyl)-2-{3-[4-(3-dimethylaminopropoxy)pyrimidin-2-yl]-benzyl}-2H-pyridazin-3-one ("A81") hydrochloride, ESI 478, is carried out analogously to the following scheme

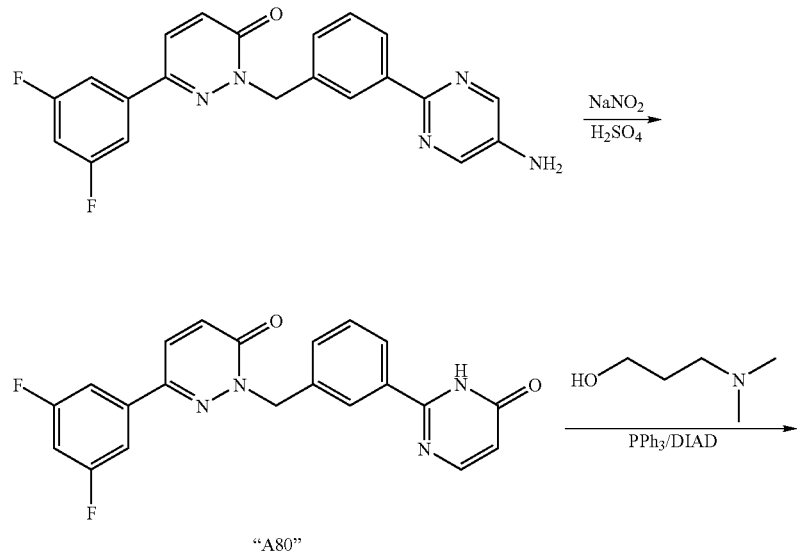

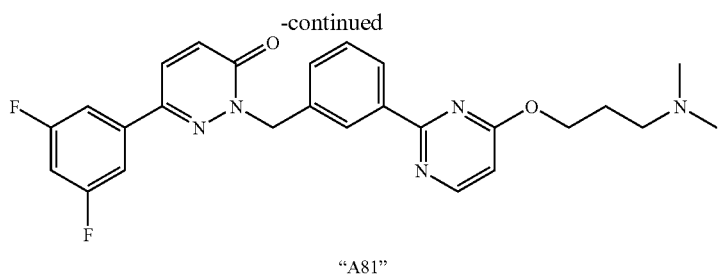

"A81"

EXAMPLE 26

The preparation of 2-(3-pyrimidin-5-ylbenzyl)-6-(3,4,5-trifluorophenyl)-2H-pyridazin-3-one ("A83"), ESI 395, is carried out analogously to the following scheme

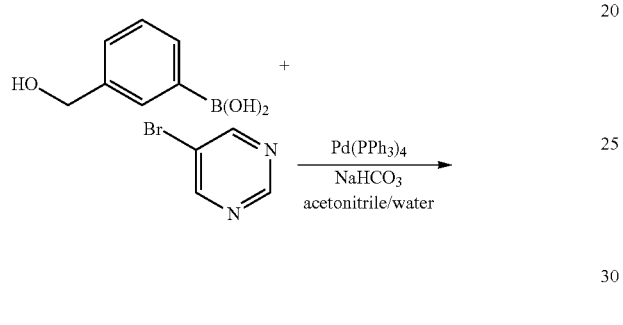

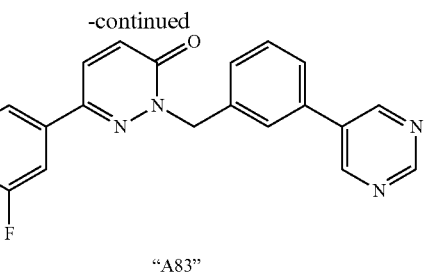

"A83"

The following compounds are obtained analogously

2-[3-(6-methylpyridin-3-yl)benzyl]-6-(3,4,5-trifluorophenyl)-2H-pyridazin-3-one ("A86"), ESI 408;

2-(3-pyridin-4-ylbenzyl)-6-(3,4,5-trifluorophenyl)-2H-pyridazin-3-one ("A94"), ESI 394;

The synthesis of "A83", "A86" and "A94" can also be carried out analogously to Example 4.

EXAMPLE 26a

The preparation of 2-[3-(5-methylpyrimidin-2-yl)benzyl]-6-(2H-pyrazol-3-yl)-2H-pyridazin-3-one ("A100"), ESI 345 is carried out analogously to Example 8.

EXAMPLE 27

The preparation of 3-(4-methylpiperazin-1-yl)-N-(2-{3-[6-oxo-3-(3,4,5-trifluorophenyl)-6H-pyridazin-1-ylmethyl]phenyl}pyrimidin-5-ylmethyl)-propionamide ("A96"), ESI 578, is carried out analogously to the following scheme

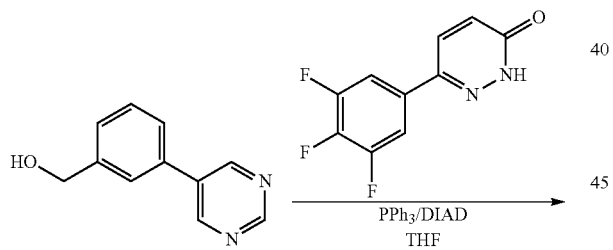

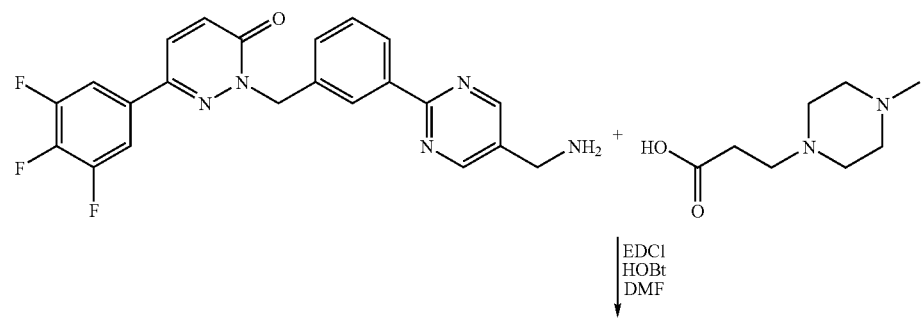

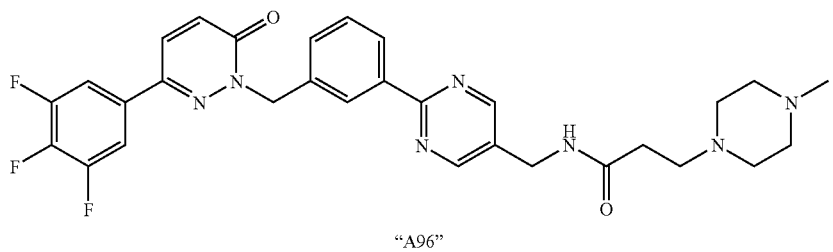

"A96"

169 mg (0.4 mmol) of 2-[3-(5-aminomethylpyrimidin-2-yl)benzyl]-6-(3,4,5-trifluorophenyl)-2H-pyridazin-3-one and 83 mg (0.48 mmol) of 3-(4-methylpiperazin-1-yl)propanoic acid are suspended in 2 ml of DMF, and 90 μl (0.8 mmol) of N-methylmorpholine, 116 mg (0.60 mmol) of EDCl and 72 mg (0.52 mmol) of HOBt are added, and the mixture is stirred at room temperature for 15 h. 10 ml of water are added to the reaction mixture, which is then extracted with ethyl acetate. The crude product is crystallised using ether.

Yield: 104 mg of "A96", beige solid; HPLC: Rt=2.49 min

LC-MS: 578 (M+H).

The following compounds are obtained analogously 2-(4-methylpiperazin-1-yl)-N-(2-{3-[6-oxo-3-(3,4,5-trifluorophenyl)-6H-pyridazin-1-ylmethyl]phenyl}pyrimidin-5-ylmethyl)acetamide, ESI 564,

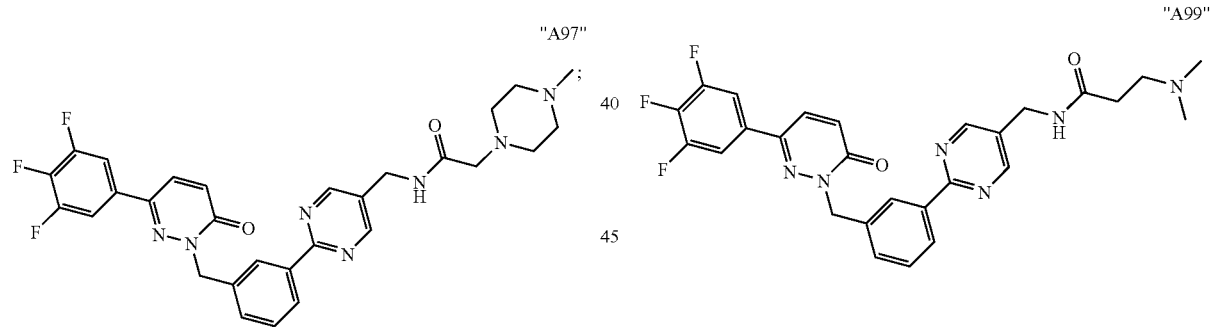

"A97"

2-methylamino-N-(2-{3-[6-oxo-3-(3,4,5-trifluorophenyl)-6H-pyridazin-1-ylmethyl]phenyl}pyrimidin-5-ylmethyl)acetamide, trifluoroacetate, ESI 495

"A98"

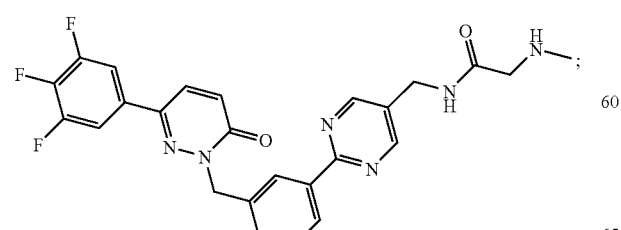

3-dimethylamino-N-(2-{3-[6-oxo-3-(3,4,5-trifluorophenyl)-6H-pyridazin-1-ylmethyl]phenyl}pyrimidin-5-ylmethyl)propionamide ("A99") trifluoroacetate, ESI 523,

"A99"

EXAMPLE 28

The preparation of 4-(2-{3-[3-(3,5-difluorophenyl)-6-oxo-6H-pyridazin-1-ylmethyl]phenyl}-pyrimidin-5-yl)morpholin-3-one ("A75") is carried out analogously to the following scheme

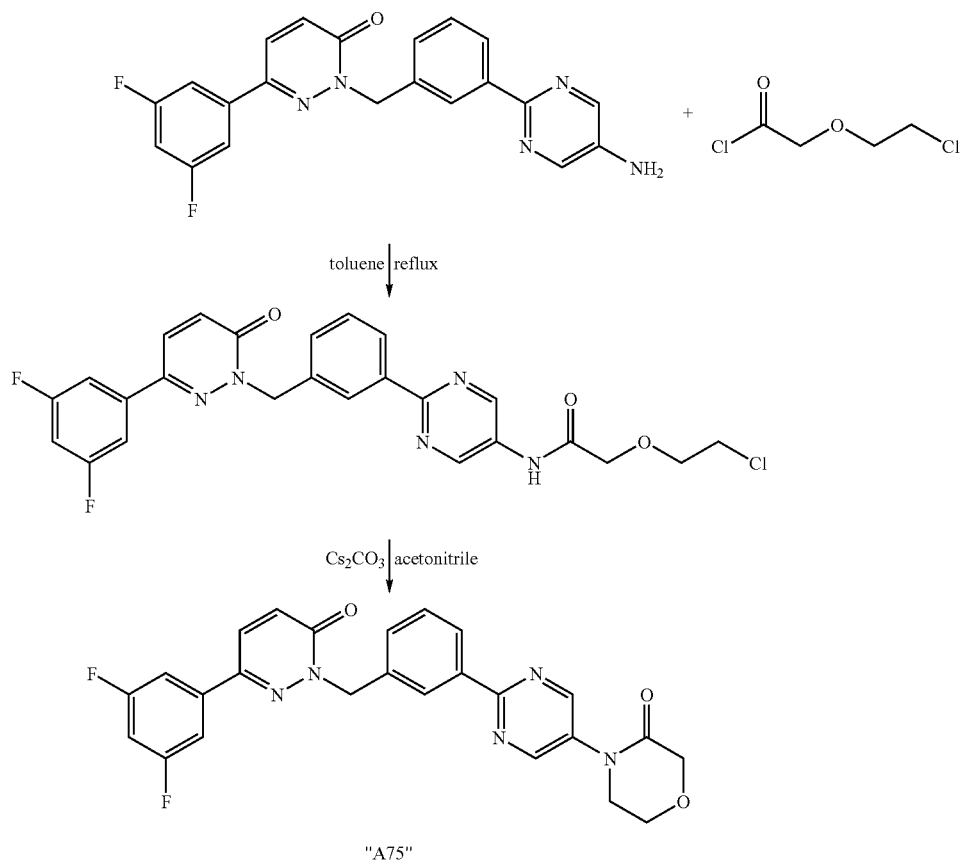
EXAMPLE 29
The preparation of 6-[4-(3-dimethylaminopropoxy)-3,5-difluorophenyl]-2-[3-(5-methylpyrimidin-2yl)benzyl]-2H-pyridazin-3-one ("A78") trifluoroacetate, ESI 492, is carried out analogously to the following scheme
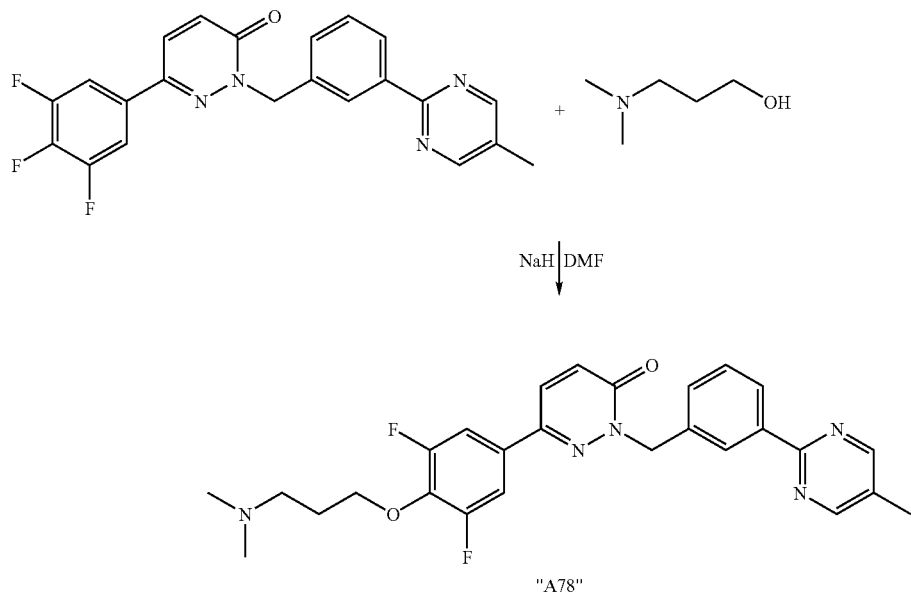

63 μl (0.54 mmol) of 3-dimethylaminopropan-1-ol is dissolved in 10 ml of DMF, and 22 mg (0.54 mmol) of sodium hydride in paraffin oil (60%) are added, and the mixture is stirred for 15 min. 200 mg (0.49 mmol) of 2-[3-(5-methylpyrimidin-2-yl)benzyl]-6-(3,4,5-trifluorophenyl)-2H-pyridazin-3-one are subsequently added. After 2 h at room temperature, the reaction is terminated by addition of 2 ml of 1 N HCl. The solution is evaporated and purified by means of preparative HPLC.

Yield: 9 mg of "A78", Rt=2.51 min (method C), LC-MS: 492 (M+H).

EXAMPLE 30

The following compounds are obtained analogously to Example 8

| Compound No. | Name and/or structure | ESI [M + H]+ | HPLC (Rt in min) method |
|---|---|---|---|
| "A112" | | 412 | |
| "A113" | | 359 | |

EXAMPLE 31

The following compounds are obtained analogously to Example 10

| Compound No. | Name and/or structure | ESI [M + H]+ | HPLC (Rt in min) method |
|---|---|---|---|
| "A114" | | 504 | |
| "A115" | | 504 | |
| "A116" | | 504 | |

-continued

| Compound No. | Name and/or structure | ESI [M + H]+ | HPLC (Rt in min) method |
|---|---|---|---|
| "A117" | | 451 | |
| "A118" | trifluoroacetate | 476 | |
| "A119" | 6-(3,5-difluorophenyl)-2-{3-[5-(8-methyl-8-aza-bicyclo[3.2.1]oct-3-yloxy)pyrimidin-2-yl]benzyl}-2H-pyridazin-3-one, trifluoroacetate | 516 | |
| "A120" | | 533 | |
| "A121" | 6-(3,5-difluorophenyl)-2-{3-[5-((S)-1-methylpyrrolidin-3-yloxy)pyrimidin-2-yl]benzyl}-2H-pyridazin-3-one, trifluoroacetate | 476 | |
| "A122" | 6-(3,5-difluorophenyl)-2-{3-[5-((R)-1-methylpyrrolidin-3-yloxy)pyrimidin-2-yl]benzyl}-2H-pyridazin-3-one, trifluoroacetate | 476 | |
| "A123" | | 432 | |

-continued

| Compound No. | Name and/or structure | ESI [M + H]⁺ | HPLC (Rt in min) method |
|---|---|---|---|
| "A124" | (structure: 6-(pyridin-4-yl)-2-{3-[5-(3-dimethylaminopropoxy)pyrimidin-2-yl]benzyl}-2H-pyridazin-3-one) | 443 | |
| "A125" | (structure: 6-(3-methoxyphenyl)-2-{3-[5-(3-dimethylaminopropoxy)pyrimidin-2-yl]benzyl}-2H-pyridazin-3-one) trifluoroacetate | 472 | |
| "A126" | (structure: 6-(3,5-difluorophenyl)-2-{3-[5-(2-(2-oxoimidazolidin-1-yl)ethoxy)pyrimidin-2-yl]benzyl}-2H-pyridazin-3-one) | 505 | |
| "A127" | 6-(3,5-difluorophenyl)-2-{3-[5-(2-pyrrolidin-1-yl-ethoxy)pyrimidin-2-yl]benzyl}-2H-pyridazin-3-one, hydrochloride | 490 | |
| "A128" | 6-(3,5-difluorophenyl)-2-{3-[5-(3-morpholin-4-yl-propoxy)pyrimidin-2-yl]benzyl}-2H-pyridazin-3-one, trifluoroacetate | 520 | |
| "A129" | (structure: 6-(3,5-difluorophenyl)-2-{3-[5-(3-diethylaminopropoxy)pyrimidin-2-yl]benzyl}-2H-pyridazin-3-one) trifluoroacetate | 506 | |
| "A130" | 6-(3,5-difluorophenyl)-2-{3-[5-(2-morpholin-4-yl-ethoxy)pyrimidin-2-yl]benzyl}-2H-pyridazin-3-one, hydrochloride | 506 | |
| "A131" | (structure: 6-(3,5-difluorophenyl)-2-{3-[5-((1-methylpiperidin-3-yl)oxy)pyrimidin-2-yl]benzyl}-2H-pyridazin-3-one) | 490 | |

EXAMPLE 32

The following compounds are obtained analogously to Example 10 with subsequent removal of Boc

| Compound No. | Name and/or structure | ESI [M + H]⁺ | HPLC (Rt in min) method |
|---|---|---|---|
| "A132" | 6-(3,5-difluorophenyl)-2-{3-[5-(4-methylamino-butoxy)pyrimidin-2-yl]benzyl}-2H-pyridazin-3-one, hydrochloride | 478 | |
| "A133" | 6-(3,5-difluorophenyl)-2-{3-[5-(3-methylamino-propoxy)pyrimidin-2-yl]benzyl}-2H-pyridazin-3-one, hydrochloride | 464 | |
| "A134" | 6-(3,5-difluorophenyl)-2-{3-[5-(pyrrolidin-3-yl-methoxy)pyrimidin-2-yl]benzyl}-2H-pyridazin-3-one, hydrochloride | 476 | |
| "A135" | 6-(3,5-difluorophenyl)-2-{3-[5-(3-ethylamino-propoxy)pyrimidin-2-yl]benzyl}-2H-pyridazin-3-one, hydrochloride | 478 | |
| "A136" | 2-{3-[5-(2-aminoethoxy)pyrimidin-2-yl]benzyl}-6-(3,5-difluorophenyl)-2H-pyridazin-3-one, hydrochloride | 436 | |
| "A137" | 6-(3,5-difluorophenyl)-2-{3-[5-(piperidin-3-yloxy)-pyrimidin-2-yl]benzyl}-2H-pyridazin-3-one, hydrochloride | 476 | |
| "A138" | 6-(3,5-difluorophenyl)-2-{3-[5-(piperidin-4-yl-methoxy)pyrimidin-2-yl]benzyl}-2H-pyridazin-3-one, hydrochloride | 490 | |
| "A139" | 6-(3,5-difluorophenyl)-2-{3-[5-(pyrrolidin-3-yloxy)-pyrimidin-2-yl]benzyl}-2H-pyridazin-3-one, trifluoroacetate | 462 | |
| "A140" | 6-(3,5-difluorophenyl)-2-{3-[5-((S)-pyrrolidin-3-yloxy)pyrimidin-2-yl]benzyl}-2H-pyridazin-3-one, trifluoroacetate | 462 | |
| "A141" | 6-(3,5-difluorophenyl)-2-{3-[5-((R)-pyrrolidin-3-yloxy)pyrimidin-2-yl]benzyl}-2H-pyridazin-3-one, trifluoroacetate | 462 | |
| "A142" | 2-{3-[5-(piperidin-4-yloxy)pyrimidin-2-yl]benzyl}-6-pyridin-4-yl-2H-pyridazin-3-one 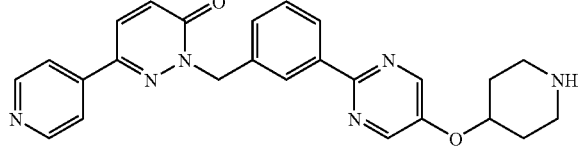 | 441 | |
| "A143" | 4-(6-oxo-1-{3-[5-(piperidin-4-yloxy)pyrimidin-2-yl]-benzyl}-1,6-dihydropyridazin-3-yl)benzonitrile 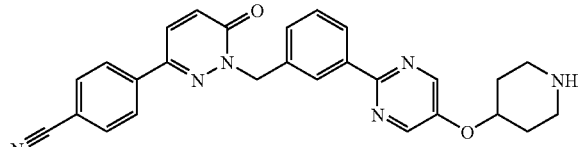 | 465 | |
| "A144" | 3-(6-oxo-1-{3-[5-(piperidin-4-yloxy)pyrimidin-2-yl]-benzyl}-1,6-dihydropyridazin-3-yl)benzonitrile | 465 | |
| "A145" | 6-(3,5-difluorophenyl)-2-{3-[5-(2-piperazin-1-yl-ethoxy)pyrimidin-2-yl]benzyl}-2H-pyridazin-3-one, trifluoroacetate | 505 | |
| "A146" | 6-(3,5-difluorophenyl)-2-{3-[5-(piperidin-4-yloxy)-pyrimidin-2-yl]benzyl}-2H-pyridazin-3-one | | |
| "A147" | 3-(6-oxo-1-{3-[5-(2-piperazin-1-ylethoxy)-pyrimidin-2-yl]benzyl}-1,6-dihydropyridazin-3-yl)-benzonitrile | 494 | |
| "A148" | 6-(3-fluorophenyl)-2-{3-[5-(piperidin-4-yl-methoxy)pyrimidin-2-yl]benzyl}-2H-pyridazin-3-one | 472 | |

EXAMPLE 33

The following compounds are obtained analogously to Example 12 with subsequent removal of Boc

| Compound No. | Name and/or structure | ESI [M + H]+ |
|---|---|---|
| "A149" | 2-{3-[5-(1-piperidin-4-yl-1H-pyrazol-4-yl)pyrimidin-2-yl]-benzyl}-6-(3,4,5-trifluorophenyl)-2H-pyridazin-3-one | 544 |
| "A150" | 3-(6-oxo-1-{3-[5-(1-piperidin-4-yl-1H-pyrazol-4-yl)-pyrimidin-2-yl]benzyl}-1,6-dihydropyridazin-3-yl)benzonitrile | 515 |
| "A151" | 6-(1-methyl-1H-pyrazol-4-yl)-2-{3-[5-(1-piperidin-4-yl-1H-pyrazol-4-yl)pyrimidin-2-yl]benzyl}-2H-pyridazin-3-one, trifluoroacetate | 494 |
| "A152" | 6-(3-methoxyphenyl)-2-{3-[5-(1-piperidin-4-yl-1H-pyrazol-4-yl)pyrimidin-2-yl]benzyl}-2H-pyridazin-3-one, trifluoroacetate | 520 |
| "A153" | 6-(3-fluorophenyl)-2-{3-[5-(1-piperidin-4-yl-1H-pyrazol-4-yl)pyrimidin-2-yl]benzyl}-2H-pyridazin-3-one | 508 |

| Compound No. | Name and/or structure | ESI [M + H]+ |
|---|---|---|
| "A154" | 6-(3,5-difluorophenyl)-2-{3-[5-(1H-pyrazol-4-yl)pyrimidin-2-yl]benzyl}-2H-pyridazin-3-one | 443 |
| "A155" | 6-(3,5-difluorophenyl)-2-(3-{5-[1-(2-methylaminoethyl)-1H-pyrazol-4-yl]pyrimidin-2-yl}benzyl)-2H-pyridazin-3-one, hydrochloride | 500 |
| "A156" | 6-(3-chlorophenyl)-2-{3-[5-(1-piperidin-4-yl-1H-pyrazol-4-yl)pyrimidin-2-yl]benzyl}-2H-pyridazin-3-one, hydrochloride | 524 |
| "A157" | [structure shown] hydrochloride | 508 |
| "A158" | 6-(3,5-difluorophenyl)-2-(3-{5-[1-(3-methylaminopropyl)-1H-pyrazol-4-yl]pyrimidin-2-yl}benzyl)-2H-pyridazin-3-one, hydrochloride | 514 |

| Compound No. | Name and/or structure | ESI [M + H]⁺ |
|---|---|---|
| "A159" | 3-[1-(3-{5-[1-(2-methylaminoethyl)-1H-pyrazol-4-yl]-pyrimidin-2-yl}benzyl)-6-oxo-1,6-dihydropyridazin-3-yl]-benzonitrile | 489 |

¹H-NMR (d₆-DMSO): δ [ppm] = 2.1 (bs, 1H), 2.35 (s, 3H), 2.97 (t, J = 6.2 Hz, 2H), 4.28 (t, J = 6.2 Hz, 2H), 5.53 (s, 2H), 7.23 (d, J = 9.8 Hz, 1H), 7.58 (m, 2 Hz, 2H), 7.79 (t, J = 8.0 Hz, 1H), 8.00 (dt, J₁ = 7.5 Hz, J₂ =1.2 Hz, 1H), 8.16 (s, 1H), 8.25 (d, J = 9.8 Hz, 1H), 8.32 (dt, J₁ = 7.5 Hz, J₂ = 1.2 Hz, 1H), 8.38 (dt, J₁ =6.5 Hz, J₂ = 1.8 Hz, 1H), 8.45 (t, J = 1.6 Hz, 1H), 8.46 (s, 1H), 8.53 (bs, 1H), 9.20 (s, 2H)

| Compound No. | Name and/or structure | ESI [M + H]⁺ |
|---|---|---|
| "A160" | 6-(3,5-difluorophenyl)-2-(3-{5-[1-(2-piperazin-1-ylethyl)-1H-pyrazol-4-yl]pyrimidin-2-yl}benzyl)-2H-pyridazin-3-one | 555 |
| "A161" | 3-(6-oxo-1-{3-[5-(1H-pyrazol-4-yl)pyrimidin-2-yl]benzyl}-1,6-dihydropyridazin-3-yl)benzonitrile | 432 |

¹H-NMR (d₆-DMSO): δ [ppm] = 5.48 (s, 2H), 7.18 (d, J = 10 Hz, 1H), 7.53 (t, J = 7.5 Hz, 1H), 7.55 (m, 1H), 7.73 (t, J = 7.8 Hz, 1H), 7.94 (dt, J₁ = 7.5 Hz, J₂ = 1.2 Hz, 1H), 8.15 (bs, 1H), 8.19 (d, J = 10 Hz, 1H), 8.27 (dt, J₁ = 7.5 Hz, J₂ = 1.2 Hz, 1H), 8.33 (dt, J₁ = 6.5 Hz, J₂ = 1.8 Hz, 1H), 8.39 (t, J = 1.6 Hz, 1H), 8.44 (bs, 1H), 8.48 (bs, 1H), 9.18 (s, 2H), 13.2 (bs, 1H)

| Compound No. | Name and/or structure | ESI [M + H]⁺ |
|---|---|---|
| "A162" | 3-[6-oxo-1-(3-{5-[1-(2-piperazin-1-ylethyl)-1H-pyrazol-4-yl]pyrimidin-2-yl}benzyl)-1,6-dihydropyridazin-3-yl]-benzonitrile | 544 |

EXAMPLE 34

The following compounds are obtained analogously to Example 16

| Compound No. | Name and/or structure | ESI [M + H]+ | HPLC (Rt in min) method |
|---|---|---|---|
| "A163" | N-(4-dimethylaminobutyl)-2-[3-(6-oxo-3-pyridin-4-yl-6H-pyridazin-1-ylmethyl)phenyl]pyrimidine-5-carboxamide, trifluoroacetate | 484 | |
| "A164" | N-(4-dimethylaminobutyl)-2-{3-[3-(4-cyanophenyl)-6-oxo-6H-pyridazin-1-ylmethyl]phenyl}pyrimidine-5-carboxamide, trifluoroacetate | 508 | |

EXAMPLE 35

The following compounds are obtained analogously to Example 27

| Compound No. | Name and/or structure | ESI [M + H]+ | HPLC (Rt in min) method B |
|---|---|---|---|
| "A165" | | 595 | 3.18 |

Compound "A98" is obtained therefrom by removal of Boc.

-continued

| Compound No. | Name and/or structure | ESI [M + H]+ | HPLC (Rt in min) method B |
|---|---|---|---|
| "A166" | ![structure] | 509 | 2.59 |
| "A167" | ![structure] | 631 (M + Na) | 3.22 |

Compound "A168", trifluoroacetate, ESI 509, is obtained therefrom by removal of Boc

[structure of A168]

EXAMPLE 36

The preparation of the compound 3-[6-oxo-1-(3-{5-[1-(2-pyrrolidin-1-yl-ethyl)-1H-pyrazol-4-yl]pyrimidin-2-yl}benzyl)-1,6-dihydropyridazin-3-yl]-benzonitrile ("A168") is carried out analogously to the following scheme

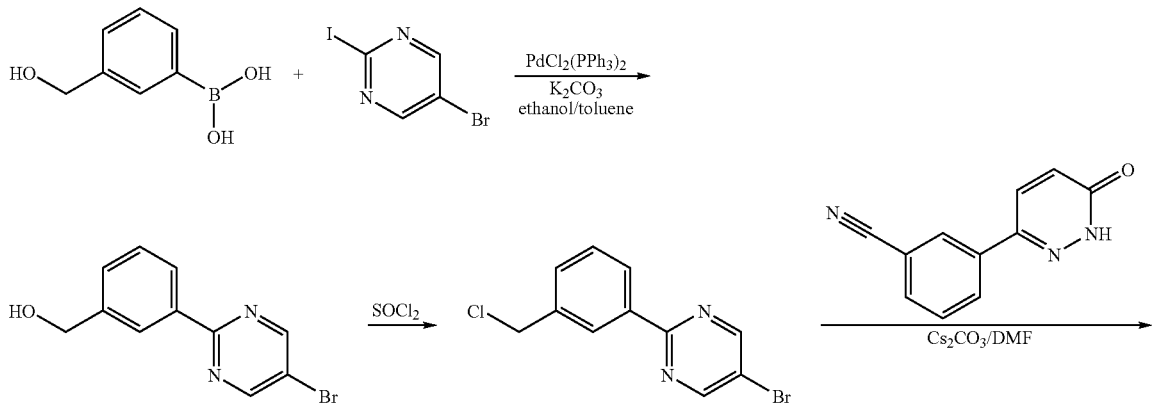

-continued

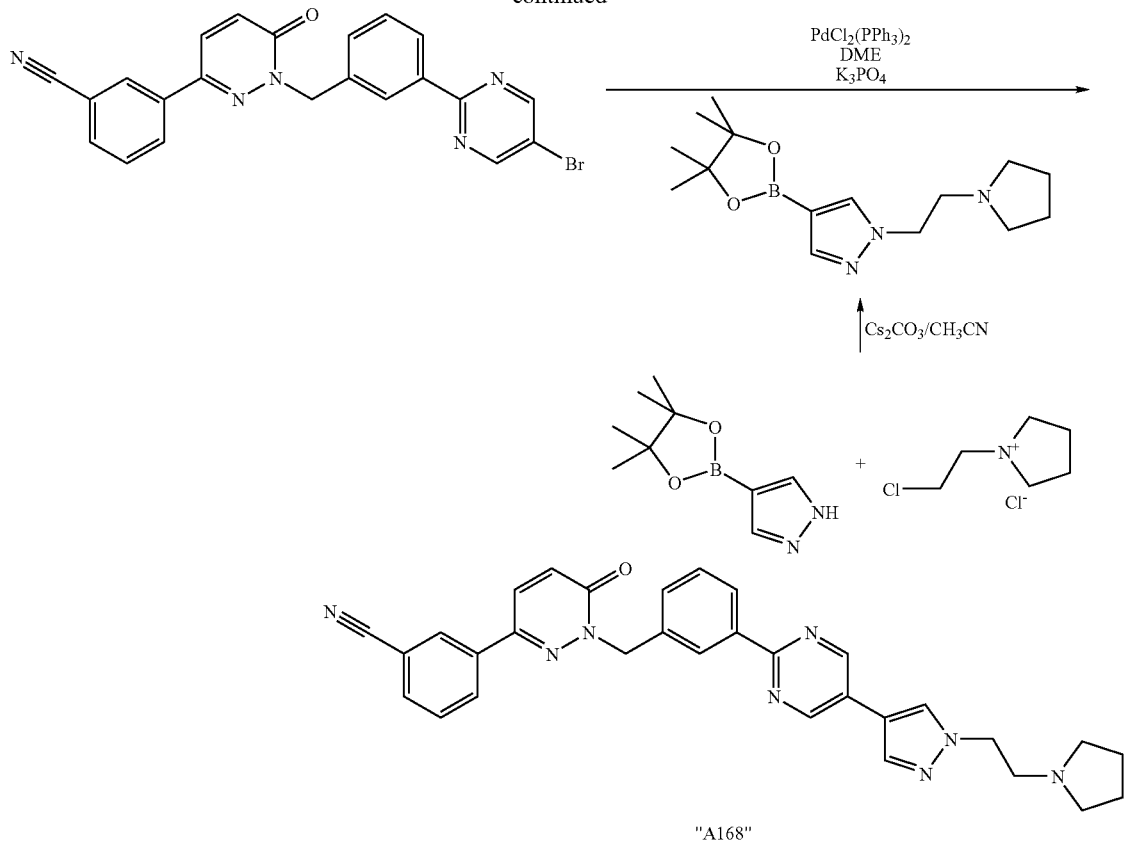

"A168"

36.1 A solution of 70.0 g (660 mmol) of sodium carbonate in 325 ml of water is added to a solution, kept under nitrogen, of 95.0 g (332 mmol) of 5-bromo-2-iodopyrimidine in 325 ml of toluene, and the mixture is heated to 80° C. 2.3 g (3.3 mmol) of bis(triphenylphosphine)palladium(II) chloride are added, and a solution of 50.0 g (329 mmol) of 3-(hydroxymethyl)-benzeneboronic acid in 650 ml of ethanol is subsequently added dropwise. The reaction mixture is stirred at 80° C. for 18 hours. The reaction mixture is cooled to room temperature and filtered. 1 l of ethyl acetate and 1 l of water are added to the filtrate. The organic phase is separated off, dried over sodium sulfate and evaporated. The residue is recrystallised from 2-propanol: [3-(5-bromopyrimidin-2-yl)phenyl]methanol as pale-yellow crystals; ESI 265,267.

36.2 116 g (438 mmol) of [3-(5-bromopyrimidin-2-yl)phenyl]methanol is added in portions with stirring to 159 ml (2.19 mol) of thionyl chloride held at 30° C. The reaction solution is stirred at room temperature for 18 hours. The reaction mixture is evaporated. The residue is taken up in toluene and re-evaporated. This procedure is repeated three times. The residue is recrystallised from toluene: 5-bromo-2-(3-chloromethylphenyl)pyrimidine as colourless crystals; m.p. 148° C.; ESI 283, 285, 286.

36.3 87.9 g (310 mmol) of 5-bromo-2-(3-chloromethylphenyl)pyrimidine and 111 g (341 mmol) of caesium carbonate are added to a suspension of 61.1 g (310 mmol) of 3-(6-oxo-1,6-dihydropyridazin-3-yl)benzonitrile in 600 ml of DMF, and the mixture is stirred at 40° C. for 24 hours. The reaction mixture is added to 600 ml of water. The resultant precipitate is filtered off with suction, washed with water and dried in vacuo: 3-{1-[3-(5-bromopyrimidin-2-yl)benzyl]-6-oxo-1,6-dihydropyridazin-3-yl}benzonitrile as beige crystals, ESI 444, 446.

36.4 A solution of 10.0 g (50.5 mmol) of pyrazole-4-boronic acid pinacol ester is dissolved in 100 ml of acetonitrile, and 17.5 g (101 mmol) of N-(2-chloroethyl)pyrrolidine hydrochloride and 49.4 g (152 mmol) of caesium carbonate are added. The resultant suspension is stirred at room temperature for 18 hours. The reaction mixture is filtered with suction and washed with acetonitrile The filtrate is evaporated and partitioned between ethyl acetate and saturated sodium chloride solution. The organic phase is dried over sodium sulfate and evaporated: 1-(2-pyrrolidin-1-ylethyl)-4-(4,4,5,5-tetramethyl-1,3,2-dioxaborolan-2-yl)-1H-pyrazole as pale-orange oil, which gradually crystallises;

$^1$H-NMR (d$_6$-DMSO): δ [ppm]=1.25 (s, 12H), 1.65 (m, 4H), 2.44 (m, 4H), 2.79 (t, J=6.8 Hz, 2H), 4.21 (t, J=6.8 Hz, 2H), 7.56 (s, 1H), 7.93 (s, 1H).

36.5 A suspension of 2.09 g (4.71 mmol) of 3-{1-[3-(5-bromopyrimidin-2-yl)benzyl]-6-oxo-1,6-dihydropyridazin-3-yl}benzonitrile, 1.73 g (5.18 mmol) of 1-(2-pyrrolidin-1-ylethyl)-4-(4,4,5,5-tetramethyl-1,3,2-dioxaborolan-2-yl)-1H-pyrazole (content 87%) and 2.00 g (9.42 mmol) of tripotassium phosphate trihydrate in 20 ml of 1,2-dimethoxyethane is heated to 85° C. under nitrogen. 264 mg (0.377 mmol) of bis(triphenylphosphine)-palladium(II) chloride and 79 μl (0.57 mmol) of triethylamine are then added, and the mixture is stirred at 85° C. for 18 hours. 30 ml of dichloromethane are added to the reaction mixture, which is then filtered through kieselguhr with suction. 100 ml of water, 20 ml of 2 N NaOH and 50 ml of dichloromethane are added to the filtrate. The organic phase is separated off, dried over sodium sulfate and evaporated. The residue is chromatographed on a silica gel column with dichloromethane/methanol: 3-[6-oxo-1-(3-{5-[1-(2-pyrrolidin-1-ylethyl)-1H-pyrazol-4-yl]pyrimidin-2-yl}benzyl)-1,6-dihydropyridazin-3-yl]benzonitrile as beige crystals; ESI 529;

¹H-NMR (d₆-DMSO): δ [ppm]=1.68 (m, 4H), 2.49 (m, 2H), 2.88 (m, 2H), 3.32 (m, 2H), 4.28 (t, J=6.8 Hz, 2H), 5.48 (s, 2H), 7.17 (d, J=10 Hz, 1H), 7.52 (t, J=7.3 Hz, 1 H), 7.55 (m, 1 H), 7.73 (t, J=7.8 Hz, 1 H), 7.94 (d, J=8 Hz, 1H), 8.09 (s, 1H), 8.19 (d, J=10 Hz, 1H), 8.26 (d, J=8 Hz, 1H), 8.33 (dt, J₁=7.2 Hz, J₂=1.8 Hz, 1H), 8.39 (t, J=1.8 Hz, 1 H), 8.43 (s, 1H), 8.48 (bs, 1H), 9.14 (s, 2H).

The following compounds are obtained analogously

| Compound No. | Name and/or structure | ESI [M + H]⁺ |
|---|---|---|
| "A169" | 6-(1-methyl-1H-pyrazol-4-yl)-2-(3-{5-[1-(2-pyrrolidin-1-ylethyl)-1H-pyrazol-4-yl]pyrimidin-2-yl}-benzyl)-2H-pyridazin-3-one 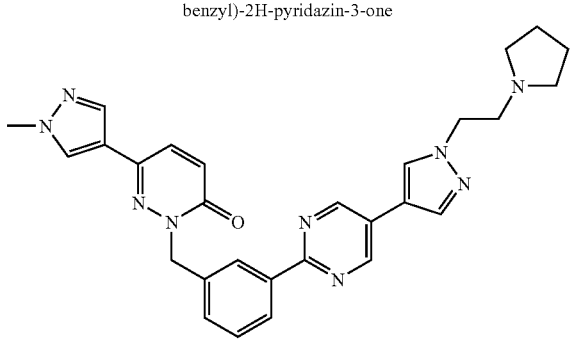 ¹H-NMR (d₆-DMSO): δ [ppm] = 1.68 (m, 4H), 2.50 (m, 2H), 2.88 (m, 2H), 3.31 (m, 2H), 3.88 (s, 3H), 4.28 (t, J = 6.8 Hz, 2H), 5.37 (s, 2H), 7.07 (d, J = 9.5 Hz, 1H), 7.50 (m, 2H), 7.83 (d, J = 9.5 Hz, 1H), 7.91 (s, 1H), 8.10 (s, 1H), 8.23 (s, 1H), 8.32 (d, J = 7.3 Hz, 1H), 8.38 (bs, 1H), 8.44 (s, 1H), 9.14 (s, 2H). | 508 |
| "A170" | 6-(3,5-difluorophenyl)-2-(3-{5-[1-(2-morpholin-4-yl-ethyl)-1H-pyrazol-4-yl]pyrimidin-2-yl}benzyl)-2H-pyridazin-3-one 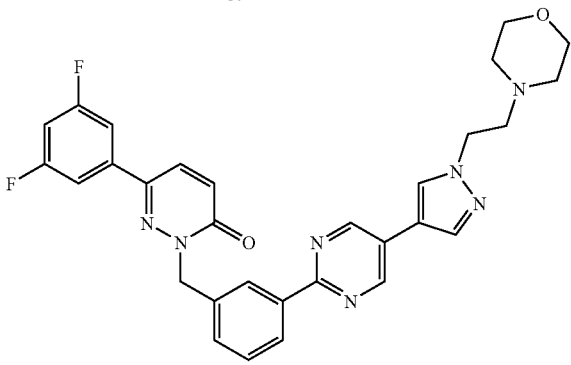 | 556 |
| "A171" | 6-(3,5-difluorophenyl)-2-(3-{5-[1-(2-dimethylamino-ethyl)-1H-pyrazol-4-yl]pyrimidin-2-yl}benzyl)-2H-pyridazin-3-one | 514 |
| "A172" | 6-(3,5-difluorophenyl)-2-(3-{5-[1-(3-dimethylamino-propyl)-1H-pyrazol-4-yl]pyrimidin-2-yl}benzyl)-2H-pyridazin-3-one | 528 |
| "A173" | 6-(3,5-difluorophenyl)-2-(3-{5-[1-(2-pyrrolidin-1-yl-ethyl)-1H-pyrazol-4-yl]pyrimidin-2-yl}benzyl)-2H-pyridazin-3-one | 540 |

-continued

| Compound No. | Name and/or structure | ESI [M + H]⁺ |
|---|---|---|
| "A174" | 3-[1-(3-{5-[1-(2-morpholin-4-ylethyl)-1H-pyrazol-4-yl]pyrimidin-2-yl}benzyl)-6-oxo-1,6-dihydropyridazin-3-yl]benzonitrile | 545 |

¹H-NMR (d₆-DMSO): δ [ppm] = 2.43 (m, 4H), 2.75 (t, J = 6.5 Hz, 2H), 3.56 (m, 4H), 4.29 (t, J = 6.5 Hz, 2H), 5.47 (s, 2H), 7.17 (d, J = 10 Hz, 1H), 7.53 (m, 2H), 7.72 (t, J = 7.8 Hz, 1H), 7.93 (dt, J₁ = 7.7, J₂ = 1.3 Hz, 1H), 8.09 (s, 1H), 8.18 (d, J = 10 Hz, 1H), 8.26 (d, J = 8 Hz, 1H), 8.32 (dt, J₁ = 7 Hz, J₂ = 1.5 Hz, 1H), 8.38 (t, J = 1.6 Hz, 1H), 8.42 (s, 1H), 8.47 (bs, 1H), 8.13 (s, 2H)

| | | |
|---|---|---|
| "A175" | 2-(3-{5-[1-(2-morpholin-4-ylethyl)-1H-pyrazol-4-yl]-pyrimidin-2-yl}benzyl)-6-pyridin-3-yl-2H-pyridazin-3-one, trifluoroacetate | 521 |
| "A176" | 6-(1-methyl-1H-pyrazol-4-yl)-2-(3-{5-[1-(2-morpholin-4-ylethyl)-1H-pyrazol-4-yl]pyrimidin-2-yl}benzyl)-2H-pyridazin-3-one, trifluoroacetate | 524 |
| "A177" | 2-(3-{5-[1-(2-morpholin-4-ylethyl)-1H-pyrazol-4-yl]-pyrimidin-2-yl}benzyl)-6-pyridin-4-yl-2H-pyridazin-3-one, trifluoroacetate | 521 |
| "A178" | 6-(4-methanesulfonylphenyl)-2-(3-{5-[1-(2-morpholin-4-ylethyl)-1H-pyrazol-4-yl]pyrimidin-2-yl}-benzyl)-2H-pyridazin-3-one, hydrochloride | 598 |
| "A179" | 6-pyridin-4-yl-2-(3-{5-[1-(2-pyrrolidin-1-ylethyl)-1H-pyrazol-4-yl]pyrimidin-2-yl}benzyl)-2H-pyridazin-3-one | 505 |

¹H-NMR (d₆-DMSO): δ [ppm] = 1.75 (b, 4H), 2.68 (b, 4H), 3.1 (b, 2H), 4.36 (b, 2H), 5.49 (s, 2H), 7.19 (d, J = 9.5 Hz, 1H), 7.54 (m, 2H), 7.91 (d, J = 6.5 Hz, 2H), 8.14 (bs, 1H), 8.18 (d, J = 9.5 Hz, 1H), 8.33 (dt, J₁ = 6.5 Hz, J₂ = 1.8 Hz, 1H), 8.46 (m, 2H), 8.72 (d, J = 6.5 Hz, 2H), 9.15 (s, 2H)

-continued

| Compound No. | Name and/or structure | ESI [M + H]+ |
| --- | --- | --- |
| "A180" | 4-[6-oxo-1-(3-{5-[1-(2-pyrrolidin-1-ylethyl)-1H-pyrazol-4-yl]pyrimidin-2-yl}benzyl)-1,6-dihydropyridazin-3-yl]-benzonitrile 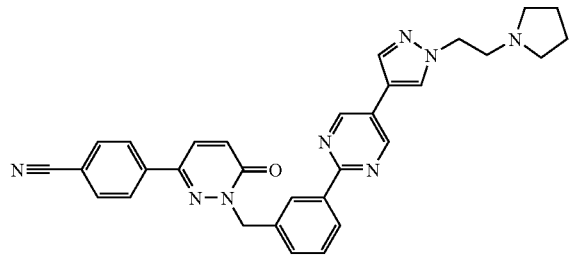 1H-NMR (d6-DMSO): δ [ppm] = 1.68 (m, 4H), 2.51 (m, 4H), 2.90 (m, 2H), 4.28 (m, 2H), 5.47 (s, 2H), 7.17 (d, J = 9.5 Hz, 1H), 7.52 (m, 2H), 7.98 (d, J = 9 Hz, 2H), 8.10 (s, 1H), 8.12 (d, J = 9 Hz, 2H), 8.17 (d, J = 9.5 Hz, 1H), 8.38 (dt, J1 =6.5 Hz, J2 =1.8 Hz, 1H), 8.44 (s, 1H), 8.45 (bs, 1H), 9.13 (s, 2H) | 529 |
| "A181" | 2-(3-{5-[1-(2-morpholin-4-ylethyl)-1H-pyrazol-4-yl]-pyrimidin-2-yl}benzyl)-6-pyridin-4-yl-2H-pyridazin-3-one | 521 |
| "A182" | 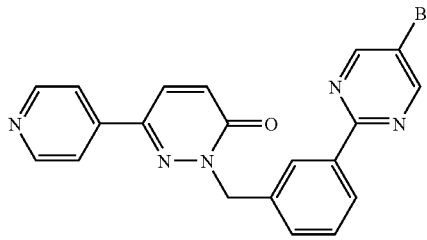 | 421 |
| "A183" | 6-(4-methanesulfonylphenyl)-2-(3-{5-[1-(2-morpholin-4-ylethyl)-1H-pyrazol-4-yl]pyrimidin-2-yl}benzyl)-2H-pyridazin-3-one | 598 |
| "A184" | 6-(5-methyloxazol-2-yl)-2-(3-{5-[1-(2-pyrrolidin-1-yl-ethyl)-1H-pyrazol-4-yl]pyrimidin-2-yl}benzyl)-2H-pyridazin-3-one 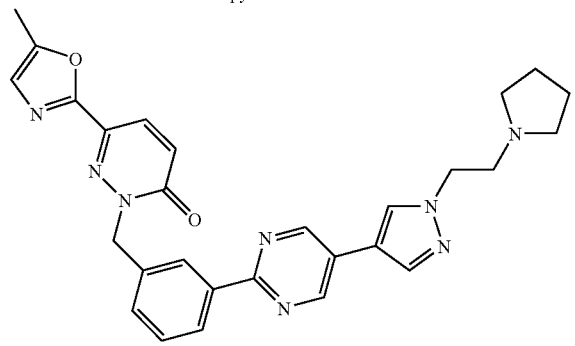 | 509 |
| "A185" | 6-(3-fluorophenyl)-2-(3-{5-[1-(2-pyrrolidin-1-ylethyl)-1H-pyrazol-4-yl]pyrimidin-2-yl}benzyl)-2H-pyridazin-3-one | 522 |

-continued
| Compound No. | Name and/or structure | ESI [M + H]+ |
|---|---|---|
| "A186" | 6-(1-propyl-1H-pyrazol-4-yl)-2-(3-{5-[1-(2-pyrrolidin-1-yl-ethyl)-1H-pyrazol-4-yl]pyrimidin-2-yl}benzyl)-2H-pyridazin-3-one 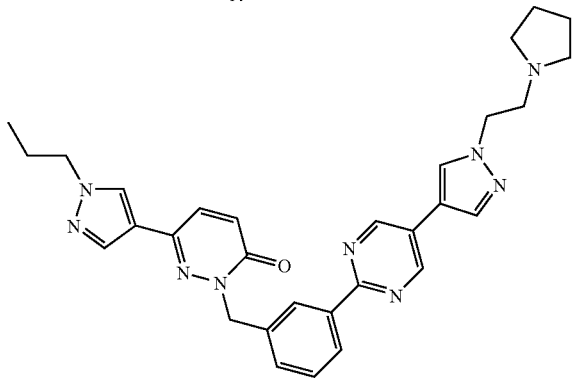 | 536 |
| "A187" | 2-(3-{5-[1-(2-pyrrolidin-1-ylethyl)-1H-pyrazol-4-yl]-pyrimidin-2-yl}benzyl)-6-thiophen-3-yl-2H-pyridazin-3-one 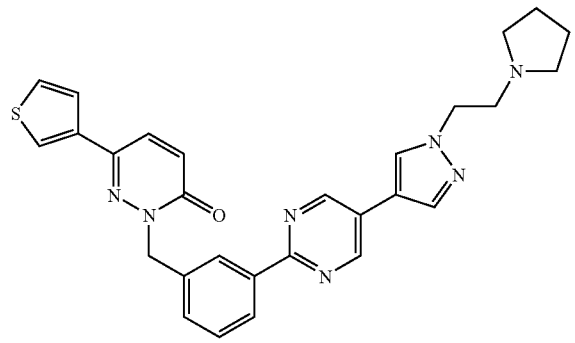 | 510 |
| "A188" | 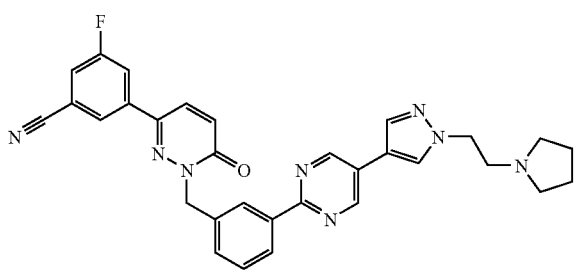 | |
| "A188a" | 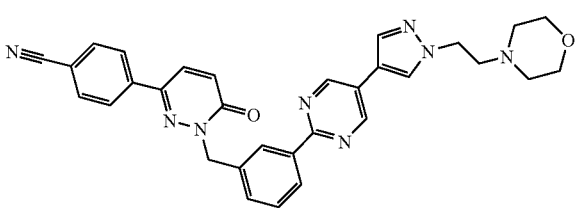 | |

EXAMPLE 37
The preparation of the compound 3-(1-{3-[5-(3-dimethylaminopropoxy)-pyrimidin-2-yl]benzyl}-6-oxo-1,6-dihydropyridazin-3-yl)benzonitrile ("A189") is carried out analogously to the following scheme
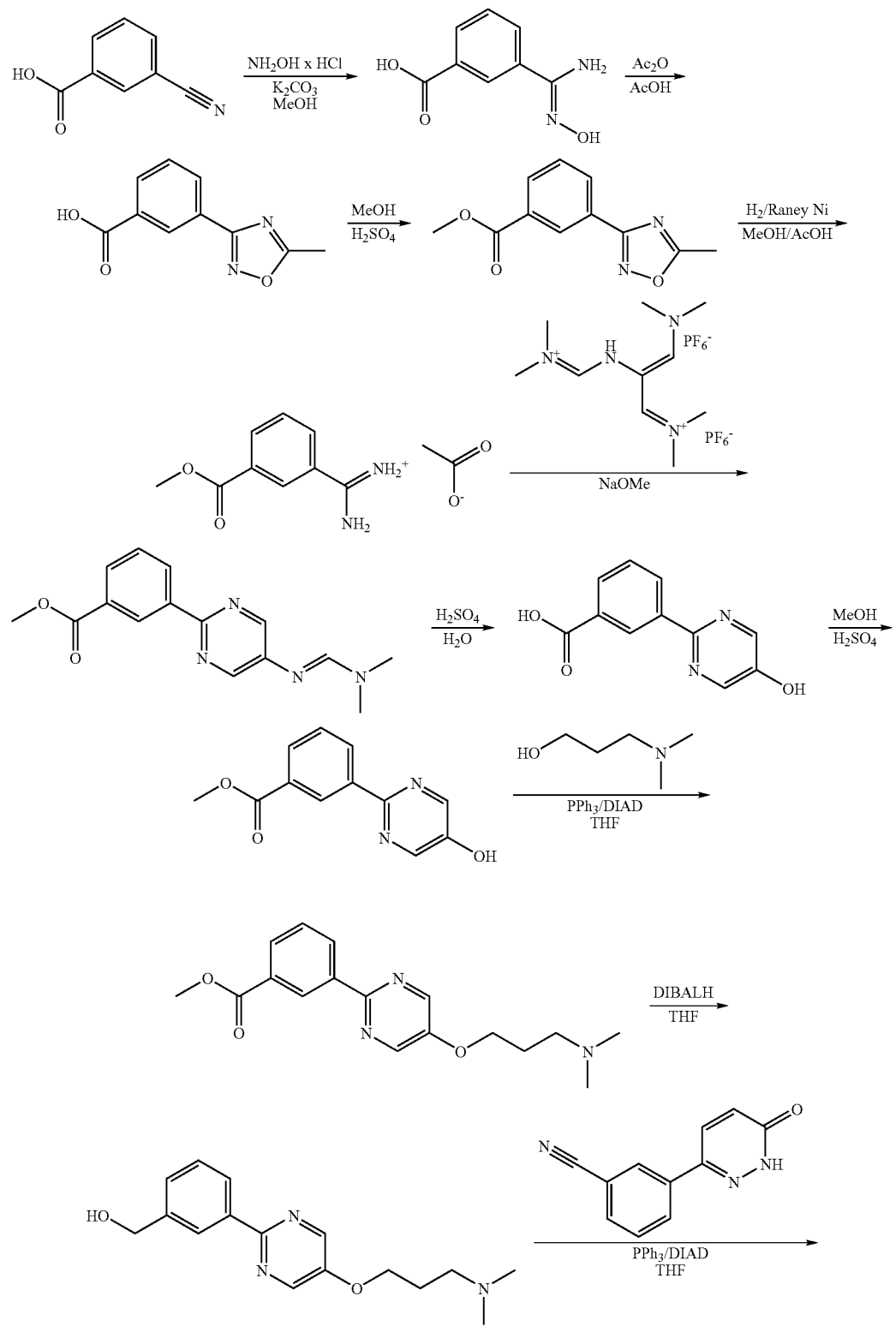

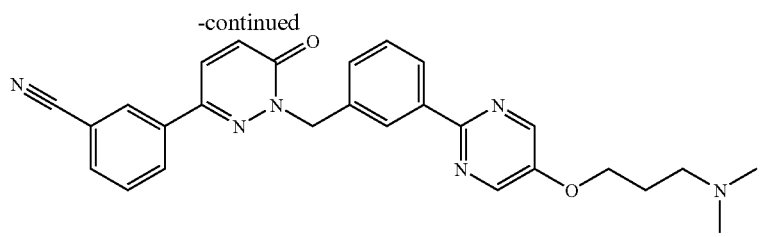

"A189"

37.1 1382 g (10.0 mol) of potassium carbonate are added in portions with stirring to a suspension, held at 30° C., of 500 g (3.40 mol) of 3-cyanobenzoic acid in 8 l of methanol. 695 g (10.0 mol) of hydroxylammonium chloride are subsequently added in small portions at an internal temperature of 40-45° C. The reaction mixture is then heated at the boil for 15 hours. The reaction mixture is evaporated in vacuo, and the residue is dissolved in water and acidified using 37% aqueous hydrochloric acid. The resultant precipitate is filtered off with suction, washed with water and dried in vacuo: 3-(N-hydroxycarbamimidoyl)benzoic acid as colourless crystals; ESI 181.

37.2 A mixture of 614 g (3.41 mol) of 3-(N-hydroxycarbamimidoyl)benzoic acid, 756 ml (8.0 mol) of acetic anhydride and 2 l of acetic acid is heated at a temperature of 118° C. for 14 hours. The reaction mixture is cooled to 6° C. and filtered with suction. The residue is taken up in 2 l of water, filtered off with suction and washed well with water. The residue is recrystallised from ethanol/water: 3-(5-methyl-1,2,4-oxadiazol-3-yl)benzoic acid as colourless crystals; m.p. 225° C.; ESI 205.

37.3 7.83 ml (147 mmol) of concentrated sulfuric acid are added to a suspension of 30.0 g (147 mmol) of 3-(5-methyl-1,2,4-oxadiazol-3-yl)benzoic acid in 150 ml of methanol, and the mixture is heated at the boil for 18 hours. The reaction mixture is cooled in an ice bath, water is added, and the solid is filtered off with suction and washed well with water: methyl 3-(5-methyl-1,2,4-oxadiazol-3-yl)benzoate as colourless crystals; ESI 219.

37.4 150 ml of acetic acid, 150 ml of water and 50 g of water-moist Raney nickel are added to a solution of 327 g (1.47 mol) of methyl 3-(5-methyl-1,2,4-oxadiazol-3-yl)benzoate in 3 l of methanol, and the mixture is hydrogenated at room temperature and atmospheric pressure for 18 hours. The catalyst is filtered off, and the filtrate is evaporated. The residue is taken up in tert-butyl methyl ether, heated to the boil and filtered off with suction. The residue is dried in vacuo: 3-methoxycarbonylbenzamidinium acetate as colourless crystals; ESI 179.

37.5 2.2 l of a freshly prepared 1.5 M sodium methoxide solution are added dropwise with stirring to a suspension of 259 g (1.09 mol) of 3-methoxycarbonylbenzamidinium acetate and 528 g (1.08 mol) of ({2-dimethylamino-1-[dimethylimmoniomethyl]vinylamino}methylene)dimethylammonium dihexafluorophosphate (prepared in accordance with C. B. Dousson et al., Synthesis 2005, 1817) in 1 l of methanol. The reaction mixture is then warmed to 60° C. over the course of 40 min and held at this temperature for 30 min. The reaction mixture is then cooled to room temperature, diluted with 10 l of dichloromethane and washed three times with 5 l of water each time. The organic phase is dried over sodium sulfate and evaporated. The residue is recrystallised from ethyl acetate: methyl 3-[5-(dimethylaminomethyleneamino)pyrimidin-2-yl]benzoate as beige crystals; m.p. 140° C., ESI 285

37.6 160 ml (2.88 mol) of concentrated sulfuric acid are added to a suspension of 103.5 g (364 mmol) of methyl 3-[5-(dimethylaminomethyleneamino)pyrimidin-2-yl]benzoate in 1.3 l of water, and the mixture is heated at the boil for 4 hours. The reaction mixture is cooled to room temperature, diluted with water and filtered with suction. The residue is washed with water and dried in vacuo: 3-(5-hydroxypyrimidin-2-yl)benzoic acid as brownish crystals; ESI 217.

37.7 32.7 ml (445 mmol) of thionyl chloride are added to a suspension of 88.0 g (366 mmol) of 3-(5-hydroxypyrimidin-2-yl)benzoic acid in 1.4 l of methanol, and the mixture is heated at 80° C. for 2 hours. 20 ml (276 mmol) of thionyl chloride are then added, and, after 2 hours, a further 10 ml (138 mmol) of thionyl chloride are then added. After each addition, the reaction mixture is stirred at 80° C. for 2 hours. The reaction mixture is concentrated in vacuo to a volume of about 300 ml. The resultant precipitate is filtered off and dried in vacuo: methyl 3-(5-hydroxypyrimidin-2-yl)benzoate as brownish crystals; ESI 231.

37.8 A solution, kept under nitrogen, of 6.1 g (26.5 mmol) of methyl 3-(5-hydroxypyrimidin-2-yl)benzoate, 10.5 g (39.8 mmol) of triphenylphosphine and 4.76 ml (39.8 mmol) of 3-(dimethylamino)-1-propanol in 200 ml of THF is cooled in an ice bath, and 8.21 ml (39.8 mmol) of diisopropyl azodicarboxylate are slowly added dropwise with stirring. After the reaction mixture has been stirred at room temperature for 2 hours, it is evaporated in vacuo. The residue is partitioned between dichloromethane and saturated aqueous potassium hydrogensulfate solution. The aqueous phase is separated off, adjusted to a pH of 12 using saturated aqueous sodium hydroxide solution and extracted twice with dichloromethane. The organic phase is dried over sodium sulfate and evaporated. The residue is chromatographed on a silica gel column with dichloromethane/methanol as eluent: methyl 3-[5-(3-dimethylaminopropoxy)pyrimidin-2-yl]benzoate as colourless crystals; ESI 316.

37.9 200 ml of a 1 M solution of diisobutylaluminium hydride in THF are added dropwise with stirring to a solution, kept under nitrogen, of 12.6 g (40.0 mmol) of methyl 3-[5-(3-dimethylaminopropoxy)pyrimidin-2-yl]benzoate in 200 ml of THF. After the mixture has been stirred at room temperature for 1 hour, 10 ml of a saturated aqueous sodium sulfate solution are added dropwise. The resultant precipitate is filtered off with suction and washed with dichloromethane. The filtrate is dried over sodium sulfate and evaporated. The residue is taken up in a mixture of diethyl ether and petroleum ether. The resultant precipitate is filtered off with suction, washed with petroleum ether and dried in vacuo: {3-[5-(3-dimethylaminopropoxy)-pyrimidin-2-yl]phenyl}methanol as colourless crystals; m.p. 95-97° C.; ESI 288.

37.10 3.16 g (18.0 mmol) of 3-(6-oxo-1,6-dihydropyridazin-3-yl)benzonitrile and 6.36 g (24.0 mmol) of triphenylphosphine are added to a solution of 5.06 g (17.6 mmol) of {3-[5-(3-dimethylaminopropoxy)pyrimidin-2-yl]

phenyl}methanol in 100 ml of THF. The resultant suspension is cooled in an ice bath, and 4.96 ml (24.0 mmol) of diisopropyl azodicarboxylate are slowly added dropwise. After the mixture has been stirred at room temperature for 1 hour, tert-butyl methyl ether and 1 N aqueous hydrochloric acid is added. The aqueous phase is separated off and washed three times with tert-butyl methyl ether. The aqueous phase is adjusted to a pH of 14 using 2 N sodium hydroxide solution and extracted twice with dichloromethane. The organic phase is dried over sodium sulfate and evaporated. The residue chromatographed on a silica gel column with dichloromethane/methanol: 3-(1-{3-[5-(3-dimethylaminopropoxy)pyrimidin-2-yl]benzyl}-6-oxo-1,6-dihydropyridazin-3-yl)benzonitrile as colourless crystals; m.p. 128° C.; ESI 467;

$^1$H-NMR (d$_6$-DMSO): δ [ppm]=1.89 (quintet, J=6.8 Hz, 2H), 2.15 (s, 6H), 2.37 (t, J=7 Hz, 2H), 4.21 (t, J=6.5 Hz, 2H), 5.44 (s, 2H), 7.16 (d, J=10 Hz, 1H), 7.48 (m, 2H), 7.72 (t, J=7.8 Hz, 1H), 7.92 (dt, J$_1$=7.5 Hz, J$_2$=1.2 Hz, 1H), 8.17 (d, J=10 Hz, 1H), 8.23 (m, 2H), 8.37 (t, J=1.6 Hz, 1H), 8.39 (bs, 1H), 8.63 (s, 2H).

The following compounds are obtained analogously "A114", "A24",

| Compound No. | Name and/or structure | ESI [M + H]$^+$ |
|---|---|---|
| "A190" | 2-{3-[5-(3-dimethylaminopropoxy)pyrimidin-2-yl]benzyl}-6-(1-methyl-1H-pyrazol-4-yl)-2H-pyridazin-3-one, trifluoroacetate | 446 |

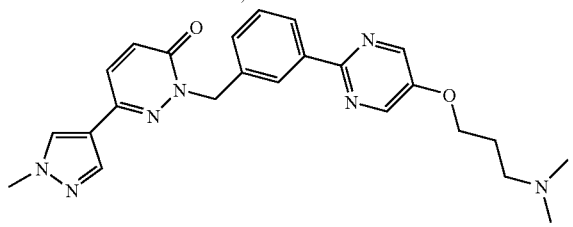

| "A191" | 2-{3-[5-(3-dimethylaminopropoxy)pyrimidin-2-yl]benzyl}-6-(3-fluorophenyl)-2H-pyridazin-3-one, hydrochloride | 460 |
| "A192" | 2-{3-[5-(3-dimethylaminopropoxy)pyrimidin-2-yl]benzyl}-6-thiazol-2-yl-2H-pyridazin-3-one, hydrochloride | 449 |
| "A193" | 2-{3-[5-(3-dimethylaminopropoxy)pyrimidin-2-yl]benzyl}-6-phenyl-2H-pyridazin-3-one, hydrochloride | 442 |
| "A194" | 4-(1-{3-[5-(3-dimethylaminopropoxy)pyrimidin-2-yl]benzyl}-6-oxo-1,6-dihydropyridazin-3-yl)benzonitrile, hydrochloride | 467 |
| "A195" | 2-{3-[5-(3-dimethylaminopropoxy)pyrimidin-2-yl]benzyl}-6-p-tolyl-2H-pyridazin-3-one | 456 |
| "A196" | 2-{3-[5-(3-dimethylaminopropoxy)pyrimidin-2-yl]benzyl}-6-(2H-pyrazol-3-yl)-2H-pyridazin-3-one, trifluoroacetate | 432 |
| "A197" | 6-(3,4-difluorophenyl)-2-{3-[5-(3-dimethylaminopropoxy)pyrimidin-2-yl]benzyl}-2H-pyridazin-3-one, hydrochloride | 478 |
| "A198" | 2-{3-[5-(3-dimethylaminopropoxy)pyrimidin-2-yl]benzyl}-6-(4-methanesulfonylphenyl)-2H-pyridazin-3-one, hydrochloride | 520 |
| "A199" | 2-{3-[5-(3-dimethylaminopropoxy)pyrimidin-2-yl]benzyl}-6-[4-(5-methyl-1,2,4-oxadiazol-3-yl)phenyl]-2H-pyridazin-3-one, hydrochloride | 524 |
| "A200" | 2-{3-[5-(3-dimethylaminopropoxy)pyrimidin-2-yl]benzyl}-6-pyridin-4-yl-2H-pyridazin-3-one, trifluoroacetate | 443 |
| "A201" | 6-(3-bromophenyl)-2-{3-[5-(3-dimethylaminopropoxy)pyrimidin-2-yl]benzyl}-2H-pyridazin-3-one, trifluoroacetate | 521 |
| "A202" | 2-{3-[5-(3-dimethylaminopropoxy)pyrimidin-2-yl]benzyl}-6-(3,4,5-trifluorophenyl)-2H-pyridazin-3-one | 496 |
| "A203" | 6-(3,5-dimethoxyphenyl)-2-{3-[5-(3-dimethylaminopropoxy)pyrimidin-2-yl]benzyl}-2H-pyridazin-3-one, trifluoroacetate | 502 |
| "A204" | 2-{3-[5-(3-dimethylaminopropoxy)pyrimidin-2-yl]benzyl}-6-(3-fluoro-4-methoxyphenyl)-2H-pyridazin-3-one, hydrochloride | 490 |
| "A205" | 2-{3-[5-(3-dimethylaminopropoxy)pyrimidin-2-yl]benzyl}-6-(4-methoxyphenyl)-2H-pyridazin-3-one, hydrochloride | 472 |
| "A206" | 2-{3-[5-(3-dimethylaminopropoxy)pyrimidin-2-yl]benzyl}-6-(3-trifluoromethylphenyl)-2H-pyridazin-3-one, hydrochloride | 510 |
| "A207" | 6-(3-chlorophenyl)-2-{3-[5-(3-dimethylaminopropoxy)pyrimidin-2-yl]benzyl}-2H-pyridazin-3-one | 476 |

-continued

| Compound No. | Name and/or structure | ESI [M + H]⁺ |
|---|---|---|
| "A208" | 2-{3-[5-(3-dimethylaminopropoxy)pyrimidin-2-yl]-benzyl}-6-pyridin-3-yl-2H-pyridazin-3-one | 443 |
| "A209" | 2-{3-[5-(3-dimethylaminopropoxy)pyrimidin-2-yl]-benzyl}-6-(1-methyl-1H-pyrazol-4-yl)-2H-pyridazin-3-one | 446 |
| "A210" | 6-(3-chloro-5-fluorophenyl)-2-{3-[5-(3-dimethylamino-propoxy)pyrimidin-2-yl]benzyl}-2H-pyridazin-3-one <br> ¹H-NMR (d₆-DMSO): δ [ppm] = 1.89 (quintet, J = 6.7 Hz, 2H), 2.16 (s, 6H), 2.38 (t, J = 7 Hz, 2H), 4.21 (t, J = 6.5 Hz, 2H), 5.44 (s, 2H), 7.14 (d, J = 10 Hz, 1H), 7.48 (m, 2H), 7.54 (dt, J₁ =8.5 Hz, J₂ = 2 Hz, 1H), 7.77 (dt, J₁ =10 Hz, J₂ =1.7 Hz, 1H), 7.85 (t, J = 1.6 Hz, 1H), 8.15 (d, J = 10 Hz, 1H), 8.23 (m, 1H), 8.37 (bs, 1H), 8.62 (s, 2H) | 494 |
| "A211" | 2-{3-[5-(3-dimethylaminopropoxy)pyrimidin-2-yl]-benzyl}-6-(4-fluoro-3-methoxyphenyl)-2H-pyridazin-3-one, hydrochloride | 490 |
| "A212" | 6-(4-chlorophenyl)-2-{3-[5-(3-dimethylaminopropoxy)-pyrimidin-2-yl]benzyl}-2H-pyridazin-3-one, trifluoroacetate | 476 |
| "A213" | 2-{3-[5-(3-dimethylaminopropoxy)pyrimidin-2-yl]-benzyl}-6-(4-fluorophenyl)-2H-pyridazin-3-one, trifluoroacetate | 460 |
| "A214" | 2-{3-[5-(3-dimethylaminopropoxy)pyrimidin-2-yl]-benzyl}-6-thiophen-2-yl-2H-pyridazin-3-one, trifluoroacetate | 448 |
| "A215" | N-[4-(1-{3-[5-(3-dimethylaminopropoxy)pyrimidin-2-yl]benzyl}-6-oxo-1,6-dihydropyridazin-3-yl)phenyl]-acetamide, trifluoroacetate | 499 |
| "A216" | 6-(3,4-dimethoxyphenyl)-2-{3-[5-(3-dimethylamino-propoxy)pyrimidin-2-yl]benzyl}-2H-pyridazin-3-one, trifluoroacetate | 502 |
| "A217" | 6-benzo-2,1,3-thiadiazol-5-yl-2-{3-[5-(3-dimethyl-aminopropoxy)pyrimidin-2-yl]benzyl}-2H-pyridazin-3-one | 500 |
| "A218" | 2-{3-[5-(3-dimethylaminopropoxy)pyrimidin-2-yl]-benzyl}-6-furan-3-yl-2H-pyridazin-3-one, trifluoro-acetate | 432 |
| "A219" | 2-{3-[5-(3-dimethylaminopropoxy)pyrimidin-2-yl]-benzyl}-6-(5-methyl-1,2,4-oxadiazol-3-yl)-2H-pyridazin-3-one, hydrochloride | 448 |
| "A220" | 4-(1-{3-[5-(1-methylpiperidin-4-yloxy)pyrimidin-2-yl]-benzyl}-6-oxo-1,6-dihydropyridazin-3-yl)benzonitrile | 479 |
| "A221" | 3-(1-{3-[5-(1-methylpiperidin-4-yloxy)pyrimidin-2-yl]-benzyl}-6-oxo-1,6-dihydropyridazin-3-yl)benzonitrile, hydrochloride | 479 |
| "A222" | 3-(1-{3-[5-(2-morpholin-4-ylethoxy)pyrimidin-2-yl]-benzyl}-6-oxo-1,6-dihydropyridazin-3-yl)benzonitrile | 495 |
| "A223" | 2-{3-[5-(1-methylpiperidin-4-yloxy)pyrimidin-2-yl]-benzyl}-6-pyridin-4-yl-2H-pyridazin-3-one | 455 |
| "A224" | 6-(4-methanesulfonylphenyl)-2-{3-[5-(1-methyl piperidin-4-yloxy)pyrimidin-2-yl]benzyl}-2H-pyridazin-3-one, trifluoroacetate | 532 |

| Compound No. | Name and/or structure | ESI [M + H]+ |
|---|---|---|
| "A225" | methyl 5-(1-{3-[5-(1-methylpiperidin-4-yloxy)pyrimidin-2-yl]benzyl}-6-oxo-1,6-dihydropyridazin-3-yl)thiophene-2-carboxylate, trifluoroacetate | 518 |
| "A226" | 2-{3-[5-(1-methylpiperidin-4-yloxy)pyrimidin-2-yl]-benzyl}-6-(1-methyl-1H-pyrazol-4-yl)-2H-pyridazin-3-one<br>$^1$H-NMR (d$_6$-DMSO): δ [ppm] = 1.70 (m, 2H), 2.00 (m, 2H), 2.22 (s, 3H), 2.24 (m, 2H), 2.66 (m, 2H), 3.88 (s, 3H), 4.62 (m, 1H), 5.34 (s, 2H), 7.06 (d, J = 9.5 Hz, 1H), 7.44 (dt, J$_1$ =7.3 Hz, J$_2$ =1.5 Hz, 1H), 7.48 (t, J = 7.5 Hz, 1H), 7.81 (d, J = 9.5 Hz, 1H), 7.90 (s, 1H), 8.22 (m, 2H), 8.25 (s, 1H), 8.28 (bs, 1H), 8.65 (s, 2H) | 458 |
| "A227" | 2-{3-[5-(3-dimethylaminopropoxy)pyrimidin-2-yl]-benzyl}-6-(5-oxo-4,5-dihydro-1,2,4-oxadiazol-3-yl)-2H-pyridazin-3-one, trifluoroacetate | 450 |
| "A228" | 2-{3-[5-(3-dimethylaminopropoxy)pyrimidin-2-yl]-benzyl}-6-piperazin-1-yl-2H-pyridazin-3-one, trifluoroacetate<br>[preparation proceeds via Boc-protected compound and subsequent removal of the Boc group] | 450 |

EXAMPLE 38

The preparation of the compounds
6-(1-methyl-1H-pyrazol-4-yl)-2-{3-[5-(2-morpholin-4-ylethoxy)pyrimidin-2-yl]benzyl}-2H-pyridazin-3-one ("A229"),
2-[3-(5-bromopyrimidin-2-yl)benzyl]-6-(1-methyl-1H-pyrazol-4-yl)-2H-pyridazin-3-one ("A230") and
2-[3-(5-hydroxypyrimidin-2-yl)benzyl]-6-(1-methyl-1H-pyrazol-4-yl)-2H-pyridazin-3-one ("A231")
is carried out analogously to the following scheme

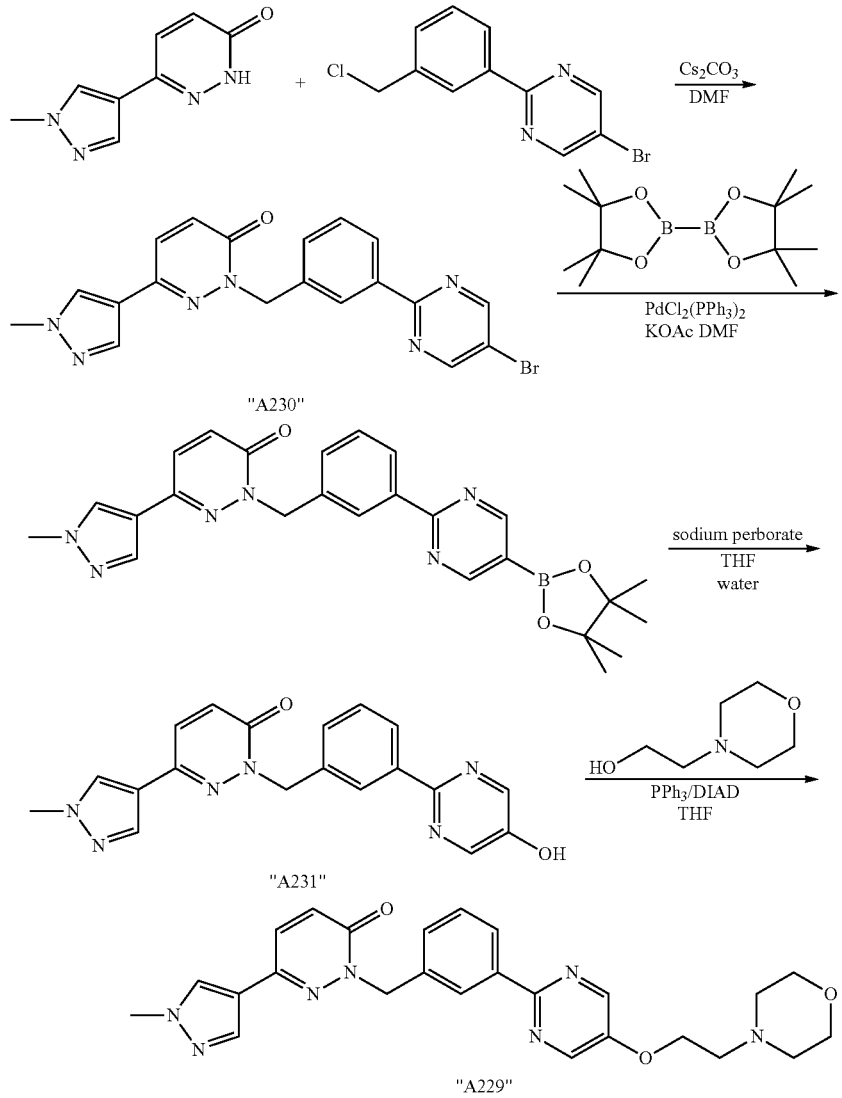

38.1 12.4 g (43.6 mmol) of 5-bromo-2-(3-chloromethylphenyl)pyrimidine and 14.2 g (43.6 mmol) of caesium carbonate are added to a suspension of 7.68 g (43.6 mmol) of 6-(1-methyl-1H-pyrazol-4-yl)-2H-pyridazin-3-one in 90 ml of DMF, and the mixture is stirred at room temperature for 24 hours. The reaction mixture is added to 400 ml of water. The resultant precipitate is filtered off with suction, washed with water and dried in vacuo; 2-[3-(5-bromopyrimidin-2-yl)benzyl]-6-(1-methyl-1H-pyrazol-4-yl)-2H-pyridazin-3-one as yellow-brown crystals; m.p. 184° C.; ESI 423, 425.

38.2 10.9 g (42.9 g) of bis(pinacolato)diboron and 9.72 g (99.0 mmol) of potassium acetate are added to a suspension of 14.0 g (33.0 mmol) of 2-[3-(5-bromopyrimidin-2-yl)benzyl]-6-(1-methyl-1H-pyrazol-4-yl)-2H-pyridazin-3-one in 65 ml of DMF, and the mixture is heated to 70° C. under nitrogen. After the mixture has been stirred at this temperature for 15 minutes, 695 mg (0.99 mmol) of bis(triphenylphosphine)palladium(II) chloride are added, and the reaction mixture is stirred at 70° C. under nitrogen for 18 hours. The reaction mixture is allowed to cool to room temperature, water and dichloromethane are added, the mixture is filtered through kieselguhr, and the organic phase is separated off. The organic phase is dried over sodium sulfate and evaporated, and the residue is recrystallised from 2-propanol: 6-(1-methyl-1H-pyrazol-4-yl)-2-{3-[5-(4,4,5,5-tetramethyl-1,3,2-dioxaborolan-2-yl)pyrimidin-2-yl]benzyl}-2H-pyridazin-3-one as grey crystals; m.p. 204° C.;

$^1$H-NMR (d$_6$-DMSO): δ [ppm]=1.34 (s, 12H), 3.87 (s, 3H), 5.35 (s, 2H), 7.05 (d, J=9.6 Hz, 1H), 7.52 (m, 2H), 7.80 (d, J=9.6 Hz, 1H), 7.89 (s, 1H), 8.21 (s, 1H), 8.35 (m, 1H), 8.45 (bs, 1 H), 9.01 (s, 2H).

38.3 8.50 g (85.1 mmol) of sodium perborate are added in portions with ice cooling to a suspension of 13.4 g (28.4 mmol) of 6-(1-methyl-1H-pyrazol-4-yl)-2-{3-[5-(4,4,5,5-tetramethyl-1,3,2-dioxaborolan-2-yl)pyrimidin-2-yl]-benzyl}-2H-pyridazin-3-one in 55 ml of THF and 55 ml of water, and the mixture is stirred at room temperature for 2 hours. The reaction mixture is filtered through kieselguhr with suction. The filtrate is concentrated in vacuo to about half the original volume and adjusted to a pH of 1 using 2 N hydrochloric acid. The resultant precipitate is filtered off with suction, washed with water and dried in vacuo: 2-[3-(5-hydroxypyrimidin-2-yl)-benzyl]-6-(1-methyl-1H-pyrazol-4-yl)-2H-pyridazin-3-one as pale-beige crystals; m.p. 239° C.; ESI 361.

38.4 394 mg (1.50 mmol) of triphenylphosphine and 242 μl (2.00 mmol) of 4-(2-hydroxyethyl)morpholine are added successively to a suspension of 360 mg (1.00 mmol) of 2-[3-(5-hydroxypyrimidin-2-yl)-benzyl]-6-(1-methyl-1H-pyrazol-4-yl)-2H-pyridazin-3-one in 2 ml of THF. 294 μl (1.50 mmol) of diisopropyl azodicarboxylate are then slowly added dropwise with ice cooling. The resultant solution is stirred at room temperature for 18 hours. The reaction mixture is evaporated in vacuo, and the oily residue is dissolved in 2-propanol. The solid formed after some time is filtered off with suction, washed with 2-propanol and tert-butyl methyl ether and dried in vacuo: 6-(1-methyl-1H-pyrazol-4-yl)-2-{3-[5-(2-morpholin-4-ylethoxy)pyrimidin-2-yl]benzyl}-2H-pyridazin-3-one ("A229") as colourless crystals; m.p. 134° C.; ESI 474;

$^1$H-NMR (d$_6$-DMSO): δ [ppm]=2.48 (m, 4H), 2.73 (t, J=5.5 Hz, 2H), 3.57 (m, 4H), 3.87 (s, 3H), 4.30 (t, J=5.5 Hz, 2H), 5.33 (s, 2H), 7.05 (d, J=9.5 Hz, 1H), 7.43 (dt, J$_1$=7.3 Hz, J$_2$=1.5 Hz, 1H), 7.47 (t, J=7.5 Hz, 1H), 7.80 (d, J=9.5 Hz, 1H), 7.89 (s, 1 H), 8.21 (s, 1H), 8.22 (dt, J$_1$=7.5 Hz, J$_2$=1.5 Hz, 1H), 8.28 (bs, 1H), 8.64 (s, 2H).

The p-toluenesulfonate and the phosphate are obtained from "A229" by salt formation.

The following compounds are obtained analogously

| Compound No. | Name and/or structure | ESI [M + H]$^+$ |
| --- | --- | --- |
| ("A232") | 6-(1-methyl-1H-pyrazol-4-yl)-2-{3-[5-(2-morpholin-4-yl-ethoxy)pyrimidin-2-yl]benzyl}-2H-pyridazin-3-one, hydrochloride (from "A229") | 474 |
| ("A233") | 2-{3-[5-(1-methylpiperidin-4-ylmethoxy)pyrimidin-2-yl]-benzyl}-6-(1-methyl-1H-pyrazol-4-yl)-2H-pyridazin-3-one, hydrochloride (from "A237") | 472 |
| ("A234") | 2-{3-[5-(1-methylpiperidin-4-ylmethoxy)pyrimidin-2-yl]-benzyl}-6-(1-methyl-1H-pyrazol-4-yl)-2H-pyridazin-3-one, trifluoroacetate (from "A237") | 472 |
| "A235" | 6-(3-fluorophenyl)-2-{3-[5-(2-morpholin-4-ylethoxy)-pyrimidin-2-yl]benzyl}-2H-pyridazin-3-one | 488 |
| "A236" | 6-(1-methyl-1H-pyrazol-4-yl)-2-{3-[5-(2-morpholin-4-yl-ethoxy)pyrimidin-2-yl]benzyl}-2H-pyridazin-3-one, dihydrochloride (from "A229") | 474 |
| "A237" | 2-{3-[5-(1-methylpiperidin-4-ylmethoxy)pyrimidin-2-yl]-benzyl}-6-(1-methyl-1H-pyrazol-4-yl)-2H-pyridazin-3-one | 472 |
| "A238" | 2-{3-[5-(1-methylpiperidin-4-yloxy)pyrimidin-2-yl]benzyl}-6-(1-methyl-1H-pyrazol-4-yl)-2H-pyridazin-3-one, formate | 458 |
| "A239" | 2-[3-(5-methoxypyrimidin-2-yl)benzyl]-6-(1-methyl-1H-pyrazol-4-yl)-2H-pyridazin-3-one | 375 |
| "A240" | 2-{3-[5-(3-methoxypropoxy)pyrimidin-2-yl]benzyl}-6-(1-methyl-1H-pyrazol-4-yl)-2H-pyridazin-3-one | 433 |
| "A241" | 2-{3-[5-(2-methoxyethoxy)pyrimidin-2-yl]benzyl}-6-(1-methyl-1H-pyrazol-4-yl)-2H-pyridazin-3-one | 419 |
| "A242" | 2-{3-[5-(2-morpholin-4-ylethoxy)pyrimidin-2-yl]benzyl}-6-(1-propyl-1H-pyrazol-4-yl)-2H-pyridazin-3-one | 502 |
| "A243" | 2-(3-{5-[2-(4-methylpiperazin-1-yl)ethoxy]pyrimidin-2-yl}-benzyl)-6-(1-methyl-1H-pyrazol-4-yl)-2H-pyridazin-3-one | 487 |
| "A244" | 2-(3-{5-[2-(4-methyl-3-oxopiperazin-1-yl)ethoxy]-pyrimidin-2-yl}benzyl)-6-(1-methyl-1H-pyrazol-4-yl)-2H-pyridazin-3-one | 501 |
| "A245" | 6-(1-methyl-1H-pyrazol-4-yl)-2-{3-[5-(3-morpholin-4-yl-propoxy)pyrimidin-2-yl]benzyl}-2H-pyridazin-3-one, trifluoroacetate | 488 |

-continued

| Compound No. | Name and/or structure | ESI [M + H]+ |
|---|---|---|
| "A246" | 6-(1-methyl-1H-pyrazol-4-yl)-2-{3-[5-(2-morpholin-4-yl-propoxy)pyrimidin-2-yl]benzyl}-2H-pyridazin-3-one, trifluoroacetate | 488 |
| "A247" | 2-{3-[5-(1-methyl-2-morpholin-4-ylethoxy)pyrimidin-2-yl]-benzyl}-6-(1-methyl-1H-pyrazol-4-yl)-2H-pyridazin-3-one, trifluoroacetate | 488 |
| "A248" | 2-{3-[5-(2-dimethylaminoethoxy)pyrimidin-2-yl]benzyl}-6-(1-methyl-1H-pyrazol-4-yl)-2H-pyridazin-3-one | 432 |
| "A305" | | 445 |
| "A306" | 2-{3-[5-(1-azabicyclo[2.2.2]oct-3-yloxy)pyrimidin-2-yl]-benzyl}-6-(1-methyl-1H-pyrazol-4-yl)-2H-pyridazin-3-one | 470 |
| "A307" | trifluoroacetate | 514 |
| "A310" | trifluoroacetate | 509 |
| "A312" | trifluoroacetate | 507 |

| Compound No. | Name and/or structure | ESI [M + H]+ |
|---|---|---|
| "A314" | 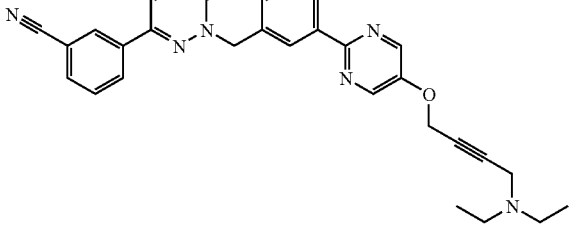
trifluoroacetate | 505 |

EXAMPLE 39

Alternative preparation of "A229"

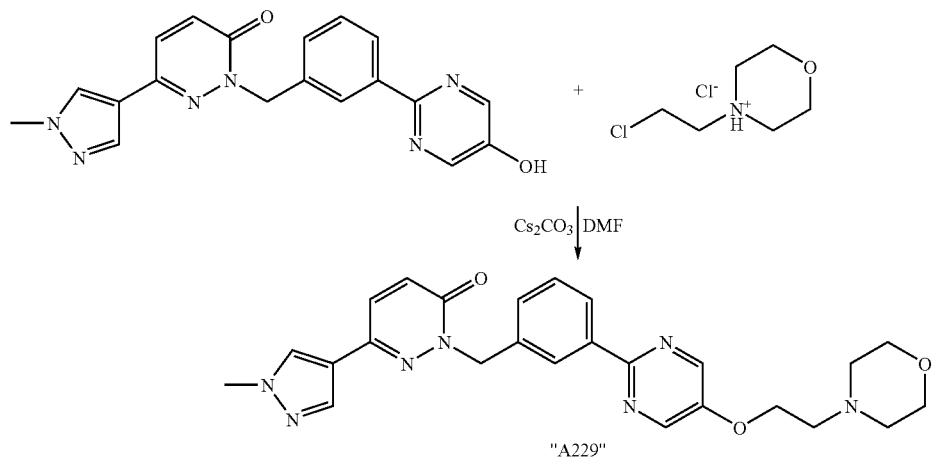

A suspension of 360 mg (1.00 mmol) of 2-[3-(5-hydroxy-pyrimidin-2-yl)-benzyl]-6-(1-methyl-1H-pyrazol-4-yl)-2H-pyridazin-3-one, 195 mg (1.05 mmol) of N-(2-chloroethyl) morpholinium chloride and 521 mg (1.60 mmol) of caesium carbonate in 2 ml of DMF is heated to 80° C. with stirring and stirred at this temperature for 6 hours. The reaction mixture is allowed to cool, and 50 ml of water are added. The resultant precipitate is filtered off with suction, washed with water and dried in vacuo: 6-(1-methyl-1H-pyrazol-4-yl)-2-{3-[5-(2-morpholin-4-ylethoxy)pyrimidin-2-yl]benzyl}-2H-pyridazin-3-one as colourless crystals.

The following compounds are obtained analogously

| Compound No. | Name and/or structure | ESI [M + H]+ |
|---|---|---|
| "A249" | 2-{3-[5-(2-methyl-3-morpholin-4-ylpropoxy)pyrimidin-2-yl]benzyl}-6-(1-methyl-1H-pyrazol-4-yl)-2H-pyridazin-3-one<br>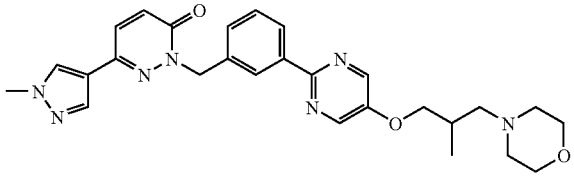 | 502 |
| "A250" | 6-(1-methyl-1H-pyrazol-4-yl)-2-{3-[5-(2-pyrrolidin-1-yl-ethoxy)pyrimidin-2-yl]benzyl}-2H-pyridazin-3-one | 458 |
| "A251" | 2-[3-(5-ethoxypyrimidin-2-yl)benzyl]-6-(1-methyl-1H-pyrazol-4-yl)-2H-pyridazin-3-one | 389 |

-continued

| Compound No. | Name and/or structure | ESI [M + H]+ |
|---|---|---|
| "A252" | 6-(1-methyl-1H-pyrazol-4-yl)-2-{3-[5-(2-morpholin-4-yl-2-oxoethoxy)pyrimidin-2-yl]benzyl}-2H-pyridazin-3-one | 488 |
| "A253" | 6-(3-chlorophenyl)-2-{3-[5-(2-morpholin-4-ylethoxy)-pyrimidin-2-yl]benzyl}-2H-pyridazin-3-one | 504 |
| "A254" | | |
| "A255" | | |
| "A256" | | |
| "A304" | | 418 |

EXAMPLE 40

The preparation of the compound 3-(1-{3-[5-(1-methylpiperidin-4-yl-methoxy)pyrimidin-2-yl]benzyl}-6-oxo-1,6-dihydropyridazin-3-yl)benzonitrile ("A257") is carried out analogously to the following scheme

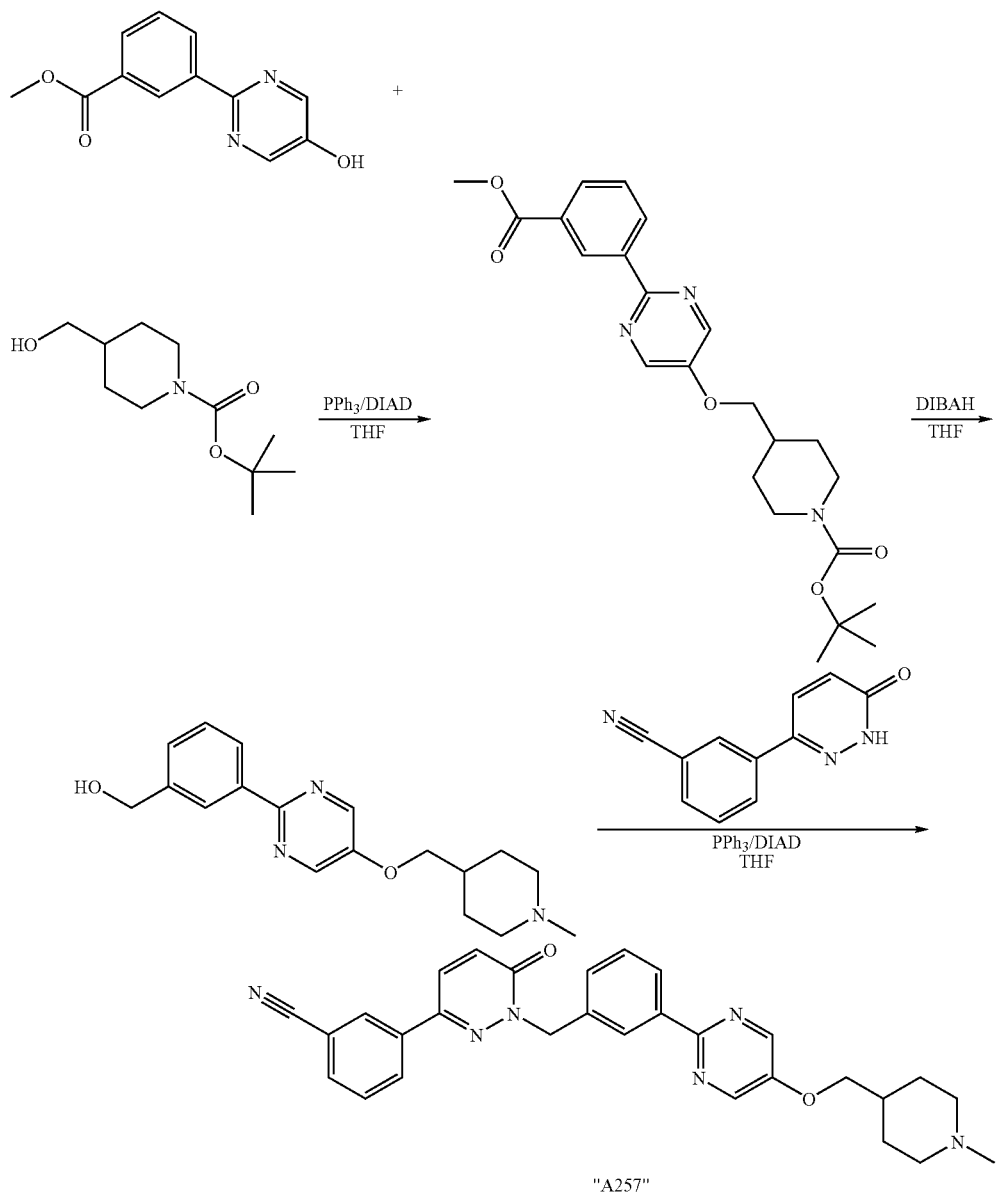

"A257"

40.1 17.7 g (67.8 mmol) of triphenylphosphine are added to a suspension of 13.0 g (56.5 mmol) of methyl 3-(5-hydroxypyrimidin-2-yl)benzoate and 13.4 g (62.1 mmol) of N-Boc-piperidinemethanol in 115 ml of THF, and the mixture is cooled to 5° C. 13.3 ml (67.8 mmol) of diisopropyl azodicarboxylate are added dropwise over the course of 45 minutes with stirring to the suspension held at this temperature. The reaction mixture is stirred at room temperature for 1 hour. A further 22.2 g (84.7 mmol) of triphenylphosphine and 16.6 ml (84.7 mmol) of diisopropyl azodicarboxylate are subsequently added. The reaction mixture is stirred at room temperature for 18 hours and evaporated in vacuo. The resultant solid is filtered off with suction, washed with diethyl ether and chromatographed on a silica gel column with dichloromethane/methanol as eluent: tert-butyl 4-[2-(3-methoxycarbonylphenyl)pyrimidin-5-yloxymethyl]piperidine-1-carboxylate as lemon-yellow crystals;
m.p. 166° C.; ESI 428.

40.2 25 ml (25 mmol) of a 1 M solution of diisobutylaluminium hydride in THF are added dropwise under nitrogen to a suspension of 1.71 g (3.99 mmol) of tert-butyl 4-[2-(3-methoxycarbonylphenyl)pyrimidin-5-yloxymethyl]piperidine-1-carboxylate in 20 ml of THF. The reaction mixture is stirred at room temperature for 1 hour, and 1 ml of a saturated sodium sulfate solution is added. The resultant precipitate is filtered off with suction and washed with THF and hot 2-propanol. The filtrate is evaporated and recrystallised from tert-butyl methyl ether: {3-[5-(1-methylpiperidin-4-ylmethoxy)pyrimidin-2-yl]phenyl}methanol as beige crystals; m.p. 175° C.; ESI 314.

40.3 264 mg (1.30 mmol) of 3-(6-oxo-1,6-dihydropyridazin-3-yl)-benzonitrile and 397 mg (1.5 mmol) of triphenylphosphine are added successively to a solution of 313 mg (1.00 mmol) of {3-[5-(1-methylpiperidin-4-ylmethoxy)pyrimidin-2-yl]phenyl}methanol in 2 ml of THF. The reaction mixture is cooled in an ice bath, and 294 µl (1.5 mmol) of diisopropyl azodicarboxylate are added dropwise with stirring. The reaction mixture is stirred at room temperature for 18 hours and evaporated. The residue is chromatographed on a silica gel column with dichloromethane/methanol. The product-containing fractions are combined and evaporated, and the residue is digested with tert-butyl methyl ether, filtered off with suction and dried in vacuo: 3-(1-{3-[5-(1-methylpiperidin-4-ylmethoxy)pyrimidin-2-yl]benzyl}-6-oxo-1,6-dihydropyridazin-3-yl)benzonitrile as colourless crystals; m.p. 177° C.; ESI 493;

$^1$H-NMR ($d_6$-DMSO): δ [ppm]=1.33 (m, 2H), 1.75 (m, 3H), 1.89 (m, 2H), 2.17 (s, 3H), 2.80 (m, 2H), 4.05 (d, J=6.1 Hz, 2H), 5.45 (s, 2H), 7.16 (d, J=10 Hz, 1H), 7.49 (m, 2H), 7.73 (t, J=7.8 Hz, 1H), 7.93 (d, J=7.8 Hz, 1H), 8.17 (d, J=10 Hz, 1H), 8.24 (m, 2H), 8.38 (m, 2H), 8.64 (s, 2H).

The hemisulfate, citrate, tartrate, sulfate, succinate and hydrochloride are obtained from "A257" by salt formation.

EXAMPLE 41

The preparation of the compounds
2-[3-(5-bromopyridin-2-yl)benzyl]-6-(3,5-difluorophenyl)-2H-pyridazin-3-one ("A258") and
6-(3,5-difluorophenyl)-2-{3-[5-(1-piperidin-4-yl-1H-pyrazol-4-yl)pyridin-2-yl]benzyl}-2H-pyridazin-3-one ("A259")
is carried out analogously to the following scheme

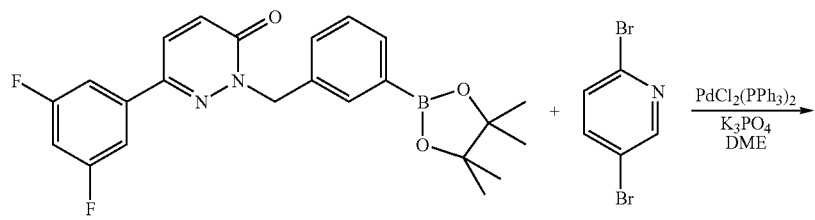

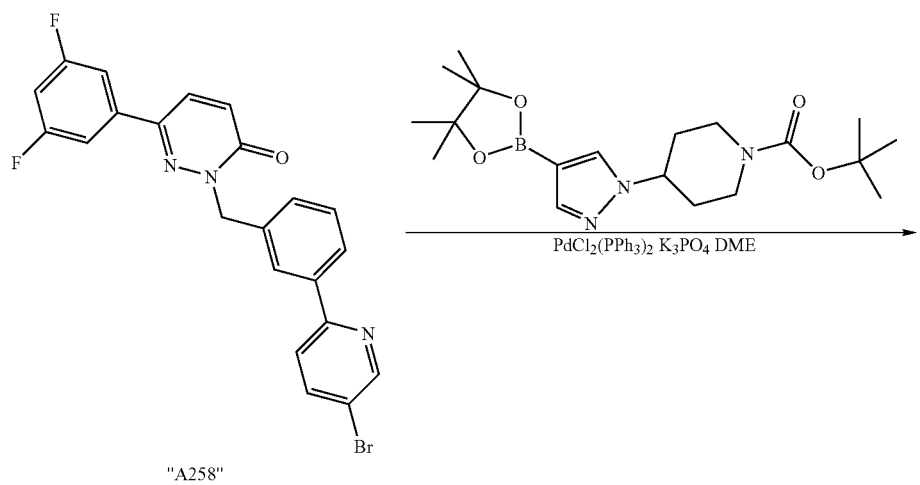

"A258"

-continued

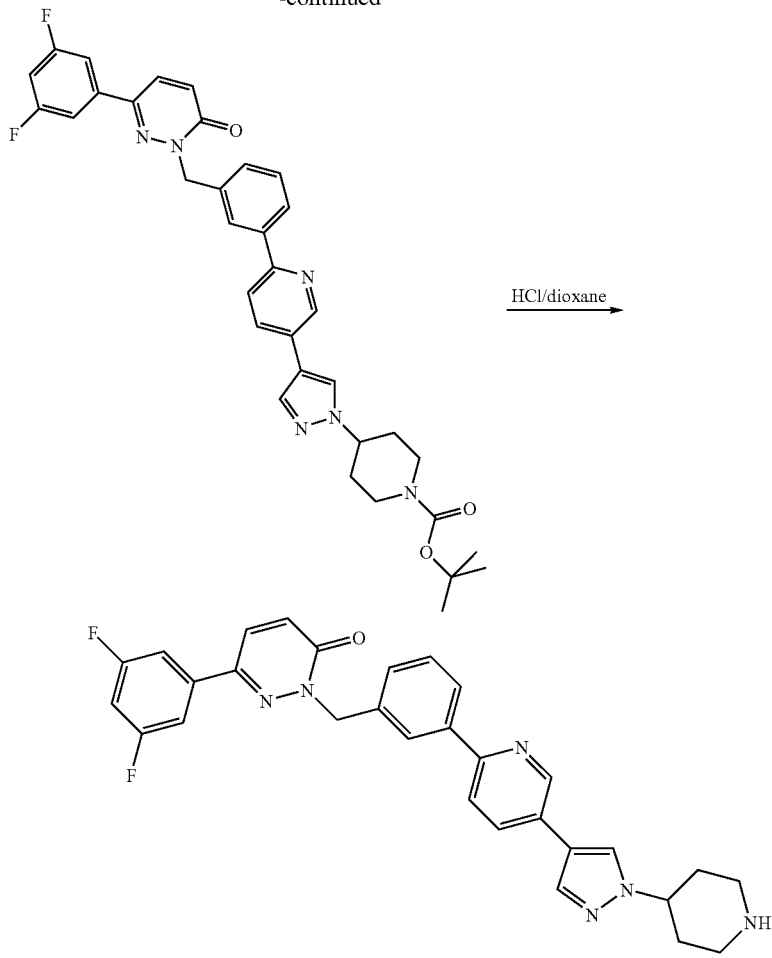

"A259"

41.1 A suspension of 695 mg (1.64 mmol) of 6-(3,5-difluorophenyl)-2-[3-(4,4,5,5-tetramethyl-1,3,2-dioxaborolan-2-yl)benzyl]-2H-pyridazin-3-one (preparation see Example 11), 427 mg (1.80 mmol) of 2,5-dibromopyridine and 695 mg (3.28 mmol) of tripotassium phosphate trihydrate in 10 ml of 1,2-dimethoxyethane is heated to 80° C. under nitrogen. 92 mg (0.13 mmol) of bis(triphenylphosphine)palladium(II) chloride are then added, and the reaction mixture is stirred at 80° C. for 18 hours. The reaction mixture is allowed to cool, and water is added. The resultant precipitate is filtered off with suction, washed with water and dried: 2-[3-(5-bromopyridin-2-yl)-benzyl]-6-(3,5-difluorophenyl)-2H-pyridazin-3-one as yellowish crystals; ESI 453, 455.

41.2 A suspension of 333 mg (0.732 mmol) of 2-[3-(5-bromopyridin-2-yl)benzyl]-6-(3,5-difluorophenyl)-2H-pyridazin-3-one, 304 mg (0.805 mmol) of tert-butyl 4-[4-(4,4,5,5-tetramethyl-1,3,2-dioxaborolan-2-yl)pyrazol-1-yl]-piperidine-1-carboxylate and 311 mg (1.46 mmol) of tripotassium phosphate trihydrate in 2 ml of 1,2-dimethoxyethane is heated to 80° C. under nitrogen. 43 mg (0.06 mmol) of bis(triphenylphosphine)palladium(II) chloride are then added, and the reaction mixture is stirred at 80° C. for 2 hours. The reaction mixture is allowed to cool, and water is added. The resultant precipitate is filtered off with suction and washed with water. The residue is recrystallised from 2-propanol: tert-butyl 4-[4-(6-{3-[3-(3,5-difluorophenyl)-6-oxo-6H-pyridazin-1-ylmethyl]phenyl}pyridin-3-yl)pyrazol-1-yl]piperidine-1-carboxylate as grey crystals; ESI 625.

41.3 5 ml of 4 N HCl in dioxane are added to 347 mg (0.556 mmol) of tert-butyl 4-[4-(6-{3-[3-(3,5-difluorophenyl)-6-oxo-6H-pyridazin-1-yl-methyl]phenyl}pyridin-3-yl)pyrazol-1-yl]piperidine-1-carboxylate. The resultant precipitate is filtered off and dissolved in a mixture of 2 N sodium hydroxide solution and dichloromethane. The organic phase is separated off, dried over sodium sulfate and evaporated. The residue is recrystallised from 2-propanol: 6-(3,5-difluorophenyl)-2-{3-[5-(1-piperidin-4-yl-1H-pyrazol-4-yl)pyridin-2-yl]benzyl}-2H-pyridazin-3-one as pale-yellow crystals; ESI 525;

$^1$H-NMR (d$_6$-DMSO): δ [ppm]=1.82 (m, 2H), 2.00 (m, 2H), 2.07 (bs, 1H), 2.61 (m, 2H), 3.06 (m, 2H), 4.22 (m, 1H), 5.45 (s, 2H), 7.15 (d, J=9.5 Hz, 1H), 7.35 (m, 1H), 7.42 (d, J=7.5 Hz, 1H), 7.48 (t, J=7.8 Hz, 1H), 7.67 (m, 2H), 7.93 (d, J=8 Hz, 1H), 8.02 (m, 2H), 8.06 (d, J=8 Hz, 1H), 8.15 (d, J=9.5 Hz, 1H), 8.19 (bs, 1H), 8.39 (s, 1H), 8.93 (bs, 1H).

EXAMPLE 42

The preparation of the compounds
3-(1-{3-[5-(3-dimethylaminopropoxy)pyrimidin-2-yl]benzyl}-6-oxo-1,6-dihydropyridazin-3-yl)benzamide ("A260") and of "A261"
is carried out analogously to the following scheme

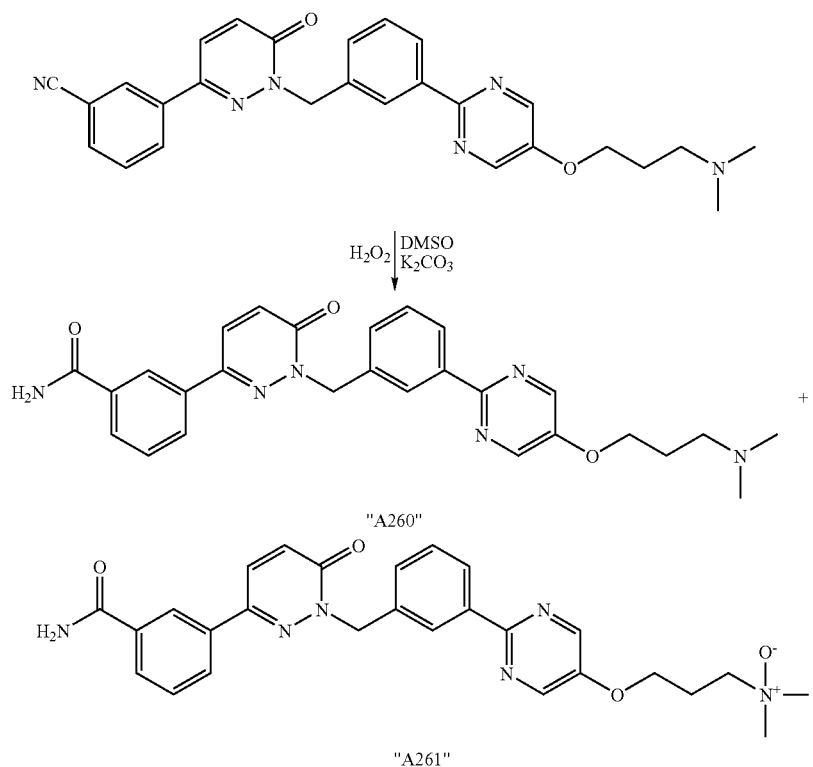

EXAMPLE 43

The preparation of the compounds

3-{1-[3-(5-bromopyrimidin-2-yl)benzyl]-6-oxo-1,6-dihydropyridazin-3-yl}-benzonitrile ("A262"), 3-{1-[3-(5-hydroxypyrimidin-2-yl)benzyl]-6-oxo-1,6-dihydropyridazin-3-yl}-benzonitrile ("A263"), 3-(6-oxo-1-{3-[5-(piperidin-4-ylmethoxy)pyrimidin-2-yl]benzyl}-1,6-dihydropyridazin-3-yl)benzonitrile ("A264"), tert-butyl 4-(2-{3-[3-(3-cyanophenyl)-6-oxo-6H-pyridazin-1-ylmethyl]-phenyl}pyrimidin-5-yloxymethyl)piperidine-1-carboxylate ("A265") and the alternative synthesis of "A257"

are carried out analogously to the following scheme

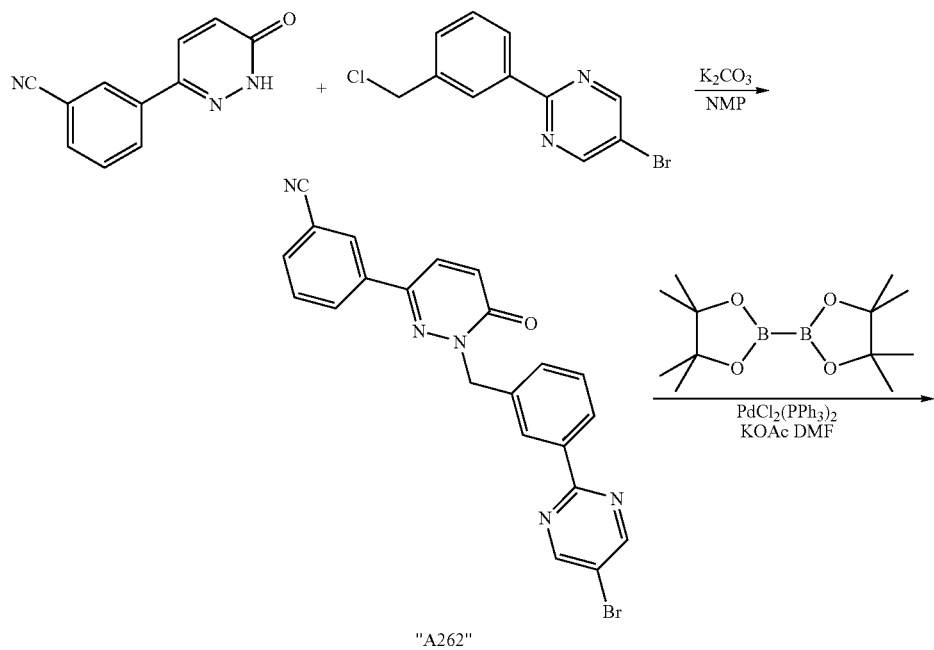

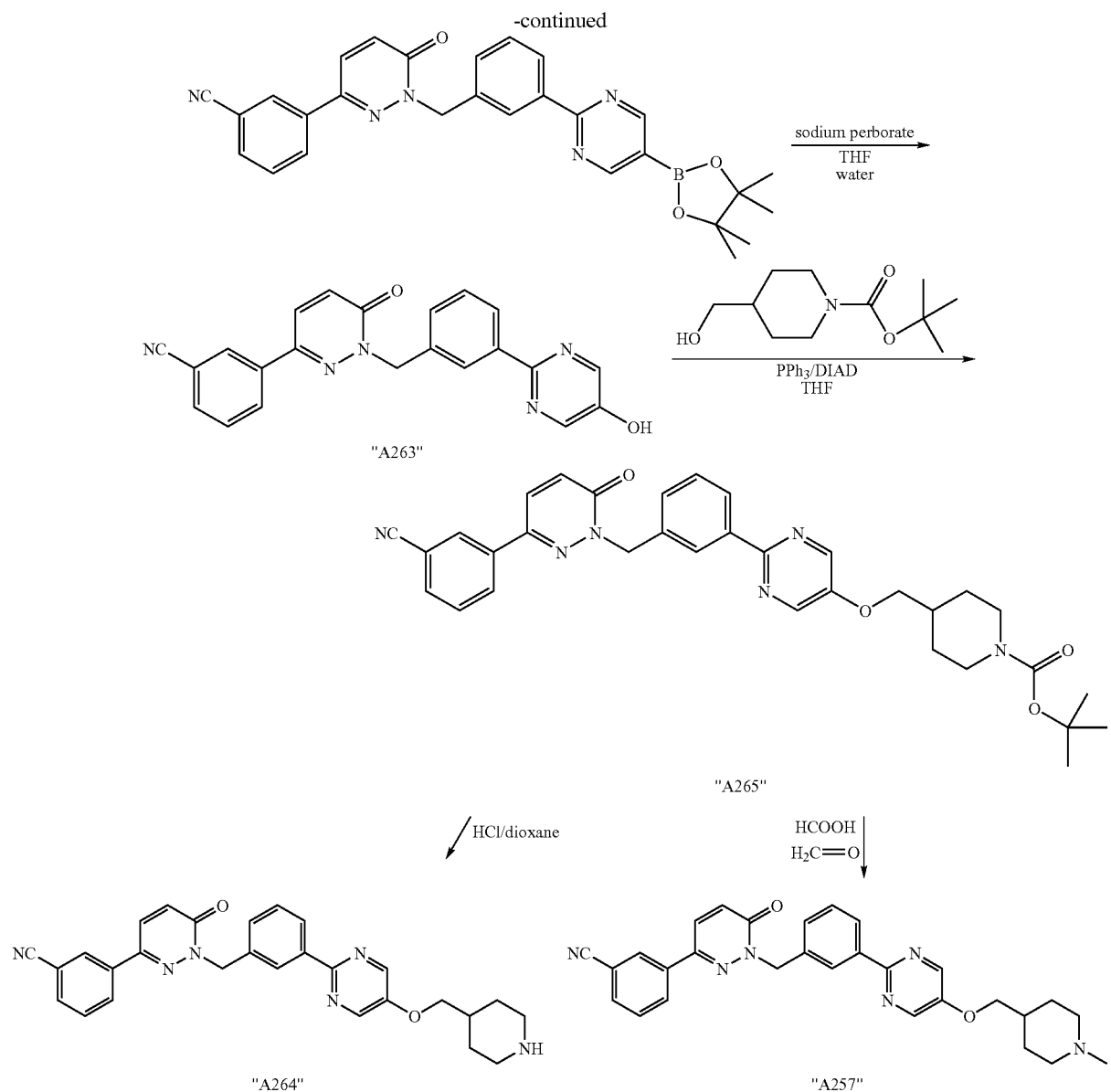

43.1 6.00 g (21 mmol) of 5-bromo-2-(3-chloromethylphenyl)pyrimidine and 2.76 g (341 mmol) of potassium carbonate are added to a suspension of 4.15 g (20 mmol) of 3-(6-oxo-1,6-dihydropyridazin-3-yl)benzonitrile in 40 ml of 1-methyl-2-pyrrolidone, and the mixture is stirred at 80° C. for 18 hours. The reaction mixture is added to 200 ml of water. The resultant precipitate is filtered off with suction, washed with water and dried in vacuo: 3-{1-[3-(5-bromopyrimidin-2-yl)benzyl]-6-oxo-1,6-dihydropyridazin-3-yl}-benzonitrile ("A262") as beige crystals, ESI 444, 446.

43.2 11.8 g (47 mmol) of bis(pinacolato)diboron and 11.9 g (122 mmol) of potassium acetate are added to a solution of 18.0 g (41.0 mmol) of 3-{1-[3-(5-bromopyrimidin-2-yl)benzyl]-6-oxo-1,6-dihydropyridazin-3-yl}benzonitrile in 85 ml of DMF, and the mixture is heated to 80° C. under nitrogen. After the mixture has been stirred at this temperature for 15 minutes, 273 mg (1.22 mmol) of palladium(II) acetate are added, and the reaction mixture is stirred at 80° C. under nitrogen for 2 hours. The reaction mixture is allowed to cool to room temperature, water and dichloromethane are added, the mixture is filtered through kieselguhr, and the organic phase is separated off. The organic phase is dried over sodium sulfate and evaporated: 3-(6-oxo-1-{3-[5-(4,4,5,5-tetramethyl-1,3,2-dioxaborolan-2-yl)pyrimidin-2-yl]benzyl}-1,6-dihydropyridazin-3-yl)benzonitrile as grey solid, which is employed in the subsequent reaction without further purification.

43.3 4.93 g (49.4 mmol) of sodium perborate are added in portions with ice cooling to a suspension of 5.33 g (10.9 mmol) of 3-(6-oxo-1-{3-[5-(4,4,5,5-tetramethyl-1,3,2-dioxaborolan-2-yl)pyrimidin-2-yl]benzyl}-1,6-dihydropyridazin-3-yl)benzonitrile in 35 ml of THF and 35 ml of water, and the mixture is stirred at room temperature for 2 hours. 300 ml of dichloromethane and 100 ml of saturated ammonium chloride solution are added to the reaction mixture. The organic phase is separated off, dried over sodium sulfate and evaporated. The residue is recrystallised from methanol:

3-{1-[3-(5-hydroxypyrimidin-2-yl)benzyl]-6-oxo-1,6-dihydropyridazin-3-yl}benzonitrile ("A263") as brownish solid; m.p. 248° C.; ESI 382.

43.4 15.6 g (68.8 mmol) of N-Boc-4-piperidinemethanol and 19.1 g (72.1 mmol) of triphenylphosphine are added successively to a suspension of 25 g (65.6 mmol) of 3-{1-[3-(5-hydroxypyrimidin-2-yl)benzyl]-6-oxo-1,6-dihydropyridazin-3-yl}benzonitrile in 250 ml of THF. 14.9 ml (72.1 mmol) of diisopropyl azodicarboxylate are then slowly added dropwise with ice cooling. The resultant solution is stirred at room temperature for a further 2 hours. 750 ml of 2-propanol and 13.1 ml of a 0.5 M solution of potassium hydroxide in ethanol are added to the reaction mixture. The resultant precipitate is filtered off with suction, washed with diethyl ether and dried in vacuo: tert-butyl 4-(2-{3-[3-(3-cyanophenyl)-6-oxo-6H-pyridazin-1-yl-methyl]phenyl}pyrimidin-5-yloxymethyl)piperidine-1-carboxylate ("A265") as colourless crystals; m.p. 178° C.; ESI 579.

43.5 A solution of 1.22 g (2.10 mmol) of tert-butyl 4-(2-{3-[3-(3-cyanophenyl)-6-oxo-6H-pyridazin-1-ylmethyl]phenyl}pyrimidin-5-yloxymethyl)-piperidine-1-carboxylate in 12 ml of a 4 N solution of hydrogen chloride in dioxane is stirred at room temperature for 16 h, during which an insoluble precipitate forms. The supernatant solution is decanted off. Dichloromethane and a saturated sodium hydrogencarbonate solution are added to the residue. The organic phase is separated off, dried over sodium sulfate and evaporated in vacuo. The residue is chromatographed on a silica gel column with dichloromethane/methanol: 3-(6-oxo-1-{3-[5-(piperidin-4-yl-methoxy)pyrimidin-2-yl]benzyl}-1,6-dihydropyridazin-3-yl)benzonitrile ("A264") as colourless crystals; ESI 479.

43.6 6.60 ml of 35% aqueous formaldehyde solution are added to a solution of 16.0 g (28.0 mmol) of tert-butyl 4-(2-{3-[3-(3-cyanophenyl)-6-oxo-6H-pyridazin-1-ylmethyl]phenyl}pyrimidin-5-yloxymethyl)piperidine-1-carboxylate in 80 ml of formic acid, and the mixture is stirred at a temperature of 110° C. for 2 hours. 300 ml of water are added to the reaction mixture, which is then concentrated in vacuo to a volume of 150 ml. The mixture is extracted with 200 ml of dichloromethane. The organic phase is washed with sodium hydrogencarbonate solution, dried over sodium sulfate and evaporated. The residue is recrystallised from 2-propanol: 3-(1-{3-[5-(1-methylpiperidin-4-ylmethoxy)pyrimidin-2-yl]benzyl}-6-oxo-1,6-dihydropyridazin-3-yl)benzonitrile ("A257") as colourless crystals; m.p. 177° C., ESI 493.

The following compounds are obtained analogously

| Compound No. | Name and/or structure | ESI [M + H]$^+$ |
|---|---|---|
| "A266" | 6-(1-methyl-1H-pyrazol-4-yl)-2-{3-[5-(piperidin-4-yloxy)-pyrimidin-2-yl]benzyl}-2H-pyridazin-3-one | 444 |
| "A267" | 6-(1-methyl-1H-pyrazol-4-yl)-2-{3-[5-(piperidin-4-yl-methoxy)pyrimidin-2-yl]benzyl}-2H-pyridazin-3-one | 458 |
| "A268" | 3-(1-{3-[5-(3-methylaminopropoxy)pyrimidin-2-yl]-benzyl}-6-oxo-1,6-dihydropyridazin-3-yl)benzonitrile, hydrochloride | 453 |
| "A269" | 3-[1-(3-{5-[2-(4-methyl-3-oxopiperazin-1-yl)ethoxy]-pyrimidin-2-yl}benzyl)-6-oxo-1,6-dihydropyridazin-3-yl]-benzonitrile | 522 |
| "A270" | 3-[1-(3-{5-[2-(4-methylpiperazin-1-yl)ethoxy]pyrimidin-2-yl}benzyl)-6-oxo-1,6-dihydropyridazin-3-yl]-benzonitrile | 508 |
| "A271" | 3-(1-{3-[5-(2-methoxyethoxy)pyrimidin-2-yl]benzyl}-6-oxo-1,6-dihydropyridazin-3-yl)benzonitrile | 440 |
| "A272" | 3-(1-{3-[5-(3-methoxypropoxy)pyrimidin-2-yl]benzyl}-6-oxo-1,6-dihydropyridazin-3-yl)benzonitrile | 454 |
| "A273" | 6-(3-fluorophenyl)-2-{3-[5-(1-methylpiperidin-4-yl-methoxy)pyrimidin-2-yl]benzyl}-2H-pyridazin-3-one | 486 |
| "A274" | 2-{3-[5-(1-methylpiperidin-4-yloxy)pyrimidin-2-yl]-benzyl}-6-(1-propyl-1H-pyrazol-4-yl)-2H-pyridazin-3-one<br>$^1$H-NMR (d$_6$-DMSO): δ [ppm] = 0.83 (t, J = 7.4 Hz, 3H), 1.69 (m, 2H), 1.80 (sextet, J = 7.2 Hz, 2H), 1.98 (m, 2H), 2.20 (s, 3H), 2.22 (m, 2H), 2.63 (m, 2H), 4.09 (t, J = 6.8 Hz, 2H), 4.60 (m, 1H), 5.34 (s, 2H), 7.05 (d, J = 9.5 Hz, 1H), 7.43 (dt, J$_1$ = 7.3 Hz, J$_2$ = 1.5 Hz, 1H), 7.47 (t, J = 7.5 Hz, 1H), 7.82 (d, J = 9.5 Hz, 1H), 7.90 (s, 1H), 8.21 (dt, J$_1$ = 7.5 Hz, J$_2$ = 1.5 Hz, 1H), 8.25 (s, 1H), 8.28 (bs, 1H), 8.64 (s, 2H) | 486 |
| "A275" | 6-(3-chlorophenyl)-2-{3-[5-(1-methylpiperidin-4-yl-methoxy)pyrimidin-2-yl]benzyl}-2H-pyridazin-3-one | 503 |

-continued

| Compound No. | Name and/or structure | ESI+ [M + H]+ |
|---|---|---|
| "A276" | (structure: 3-fluoro-5-cyanophenyl-pyridazinone-benzyl-pyrimidine-O-methyl-(1-methylpiperidin-4-yl)) | |
| "A276a" | (structure: 1-ethylpyrazole-pyridazinone-benzyl-pyrimidine-O-(1-methylpiperidin-4-yl)) | |

EXAMPLE 44

44.1 Preparation of 5-(1-{3-[5-(1-methylpiperidin-4-yloxy)pyrimidin-2-yl]benzyl}-6-oxo-1,6-dihydropyridazin-3-yl)thiophene-2-carboxylic acid ("A277")

2 g (3.85 mmol) of methyl 5-(1-{3-[5-(1-methylpiperidin-4-yloxy)pyrimidin-2-yl]benzyl}-6-oxo-1,6-dihydropyridazin-3-yl)thiophene-2-carboxylate ("A225") are dissolved in 50 ml of THF and 5 ml of water, and 283 mg (11.6 mmol) of lithium hydroxide are added. The solution is stirred at room temperature for 15 h. The reaction mixture is evaporated, and the residue is dissolved in 200 ml of water and extracted with 200 ml of ethyl acetate by shaking. The aqueous phase is washed with 2×200 ml of ethyl acetate. The organic phase is discarded, and the aqueous phase is adjusted to pH 7-8 using 1 N HCl and extracted with 2×300 ml of ethyl acetate. The organic phase is dried over sodium sulfate and evaporated to dryness;

yield: 1.2 g of "A277"; HPLC: Rt=2.27 min; LC-MS: 504 (M+H).

44.2 Preparation of 5-(1-{3-[5-(1-methylpiperidin-4-yloxy)pyrimidin-2-yl]-benzyl}-6-oxo-1,6-dihydropyridazin-3-yl)thiophene-2-carboxamide ("A278")

150 mg (0.30 mmol) of 5-(1-{3-[5-(1-methylpiperidin-4-yloxy)pyrimidin-2-yl]-benzyl}-6-oxo-1,6-dihydropyridazin-3-yl)thiophene-2-carboxylic acid ("A277") are suspended in 2 ml of DMF, and 1 ml (5.9 mmol) of 10% ammonia solution in THF, 67 µl (0.60 mmol) of N-methylmorpholine, 115 mg (0.60 mmol) of EDCl and 41 mg (0.30 mmol) of HOBt are added, and the mixture is stirred at room temperature for 15 h. The reaction mixture is evaporated and purified by means of preparative HPLC; yield: 10 mg of "A278" trifluoroacetate, white solid; HPLC: Rt=2.15 min; LC-MS: 503 (M+H).

44.3 Preparation of N-methyl-5-(1-{3-[5-(1-methylpiperidin-4-yloxy)-pyrimidin-2-yl]benzyl}-6-oxo-1,6-dihydropyridazin-3-yl)thiophene-2-carboxamide ("A279")

150 mg (0.30 mmol) of 5-(1-{3-[5-(1-methylpiperidin-4-yloxy)pyrimidin-2-yl]-benzyl}-6-oxo-1,6-dihydropyridazin-3-yl)thiophene-2-carboxylic acid ("A277") are suspended in 2 ml of DMF, and 205 mg (2.98 mmol) of methylamine hydrochloride, 67 µl (0.60 mmol) of N-methylmorpholine, 115 mg (0.60 mmol) of EDCl, 41 mg (0.30 mmol) of HOBt and 1.01 ml (5.96 mmol) of N-ethyldiisopropylamine are added, and the mixture is stirred at room temperature for 15 h. A further 205 mg (2.98 mmol) of methylamine hydrochloride, 67 µl (0.60 mmol) of N-methylmorpholine, 115 mg (0.60 mmol) of EDCl, 41 mg (0.30 mmol) of HOBt and 1.01 ml (5.96 mmol) of N-ethyldiisopropylamine are added, and the mixture is stirred at room temperature for 15 h. The reaction mixture is evaporated, and the residue is purified by means of preparative HPLC; yield: 99 mg of "A279" trifluoroacetate, white solid; HPLC: Rt=2.22 min; LC-MS: 517 (M+H).

EXAMPLE 45

Preparation of 2-{3-[5-(3-dimethylaminopropoxy)pyrimidin-2-yl]benzyl}-6-(5-oxo-4,5-dihydro-1,2,4-oxadiazol-3-yl)-2H-pyridazin-3-one ("A227")

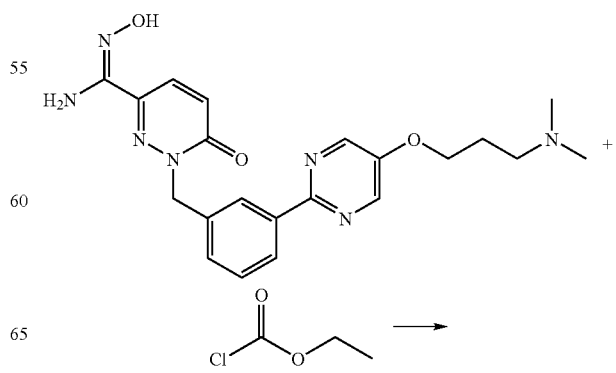

-continued

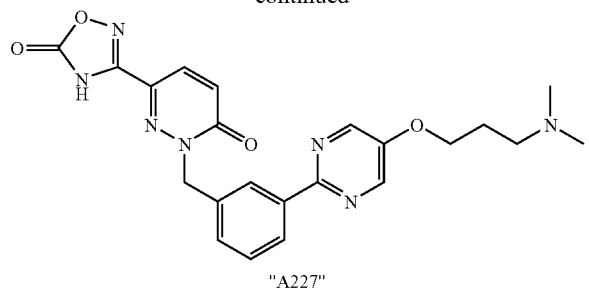

"A227"

500 mg (1.18 mmol) of 1-{3-[5-(3-dimethylaminopropoxy)pyrimidin-2-yl]-benzyl}-N-hydroxy-6-oxo-1,6-dihydropyridazine-3-carboxamidine are dissolved in 15 ml of DMF, and 286 µl (3.54 mmol) of pyridine are added. 124 µl (1.30 mmol) of ethyl chloroformate are subsequently added with stirring, and the solution is stirred at 80° C. for 15 and subsequently at 100° C. for 72 h. The reaction mixture is evaporated, and the residue is purified by means of preparative HPLC; yield: 21.2 mg of "A227" trifluoroacetate; HPLC: Rt=2.07 min; LC-MS: 450 (M+H).

EXAMPLE 46

Preparation of 2-[3-(5-aminopyrazin-2-yl)benzyl]-6-(3,5-difluorophenyl)-2H-pyridazin-3-one ("A280")

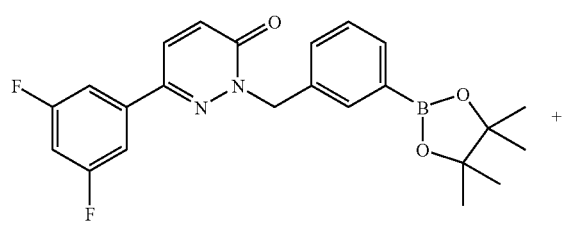

+

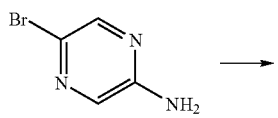

→

-continued

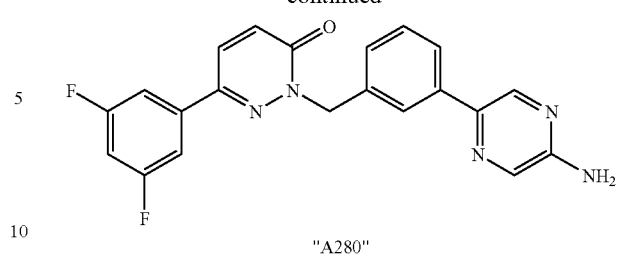

"A280"

5 ml of water and 5 ml of acetonitrile are added to 150 mg (0.35 mmol) of 6-(3,5-difluorophenyl)-2-[3-(4,4,5,5-tetramethyl-1,3,2-dioxaborolan-2-yl)-benzyl]-2H-pyridazin-3-one, 63 mg (0.35 mmol) of 5-bromopyrazin-2-yl-amine and 167 mg (1.99 mmol) of sodium hydrogencarbonate, and the mixture is degassed a number of times. Under an argon atmosphere, 20 mg (0.017 mmol) of tetrakis(triphenylphosphine)palladium(0) are added, and the mixture is subsequently heated at 80° C. for 15 h with stirring. A further 20 mg (0.017 mmol) of tetrakis(triphenylphosphine)palladium(0) are subsequently added, and the mixture is stirred at 80° C. for a further 24 h. The hot suspension is filtered. The filtrate is concentrated to half. After cooling to room temperature, the resultant precipitate is filtered off with suction and washed with a little water. The residue is purified by means of preparative HPLC; yield: 21 mg of "A280"; HPLC: Rt=2.68 min (method C); LC-MS: 392 (M+H).

The following compounds are obtained analogously

| Compound No. | Name and/or structure | ESI [M + H]+ |
|---|---|---|
| "A281" | 6-(3,5-difluorophenyl)-2-[3-(6-methylpyridazin-3-yl)-benzyl]-2H-pyridazin-3-one | 391 |
| "A282" | 2-[3-(6-aminopyridazin-3-yl)benzyl]-6-(3,5-difluoro-phenyl)-2H-pyridazin-3-one | 392 |

EXAMPLE 47

Preparation of methyl (E)-3-(2-{3-[6-oxo-3-(3,4,5-trifluorophenyl)-6H-pyridazin-1-ylmethyl]phenyl}pyrimidin-5-yl)acrylate ("A283")

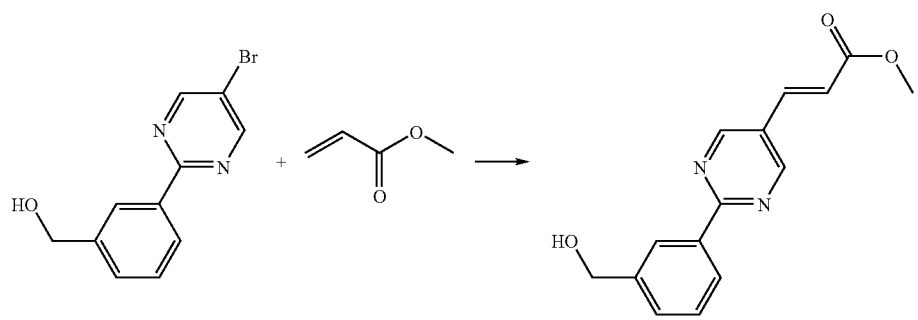

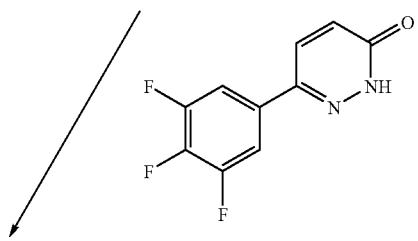

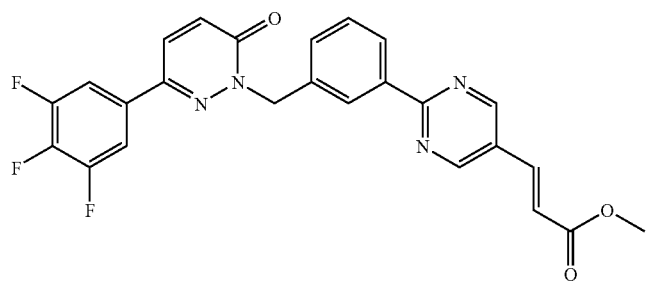

"A283"

47.1 100 mg (0.38 mmol) of [3-(5-bromopyrimidin-2-yl)phenyl]methanol and 51 µl (0.56 mmol) of methyl acrylate are suspended in 2 ml of DMF, and 20 mg (0.075 mmol) of triphenylphosphine, 222 mg (2.26 mmol) of potassium acetate and 157 mg (0.57 mmol) of tetra-n-butylammonium chloride are added. The reaction mixture is degassed and flushed with argon, and 17 mg (0.075 mmol) of palladium(II) acetate are added under an argon atmosphere. The mixture is heated at 80° C. for 2 h. After cooling, water is added, during which a pale-grey precipitate forms. This is filtered off with suction, washed with water and dried in vacuo. The product is reacted further without further purification; yield: 111 mg: HPLC: Rt=2.42 min (method C); LC-MS: 271 (M+H).

47.2 90 mg (0.4 mmol) of 6-(3,4,5-trifluorophenyl)-2H-pyridazin-3-one and 111 mg (0.41 mmol) of methyl (E)-3-[2-(3-hydroxymethylphenyl)-pyrimidin-5-yl]acrylate are suspended in 3 ml of THF with 200 mg (0.6 mmol) of polymer-bound triphenylphosphine (about 3 mmol of triphenylphosphine per g), and the mixture is shaken at room temperature for 30 min. The mixture is cooled to 0° C., and 95 µl (0.6 mmol) of diethyl azodicarboxylate are added. The reaction mixture is shaken at room temperature for 24 h. The reaction mixture is purified by means of preparative HPLC; yield: 7 mg of "A283"; HPLC: Rt=3.41 min (method C); LC-MS: 479 (M+H).

EXAMPLE 48

Preparation of 2-{3-[5-((E)-3-aminopropenyl)pyrimidin-2-yl]benzyl}-6-(3,4,5-trifluorophenyl)-2H-pyridazin-3-one ("A284")

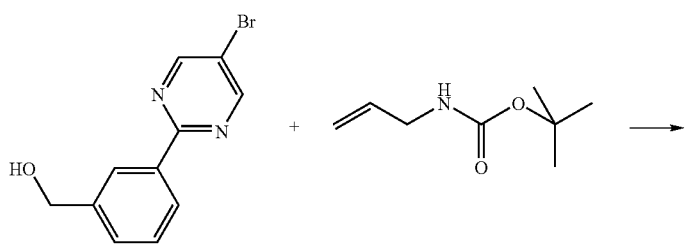

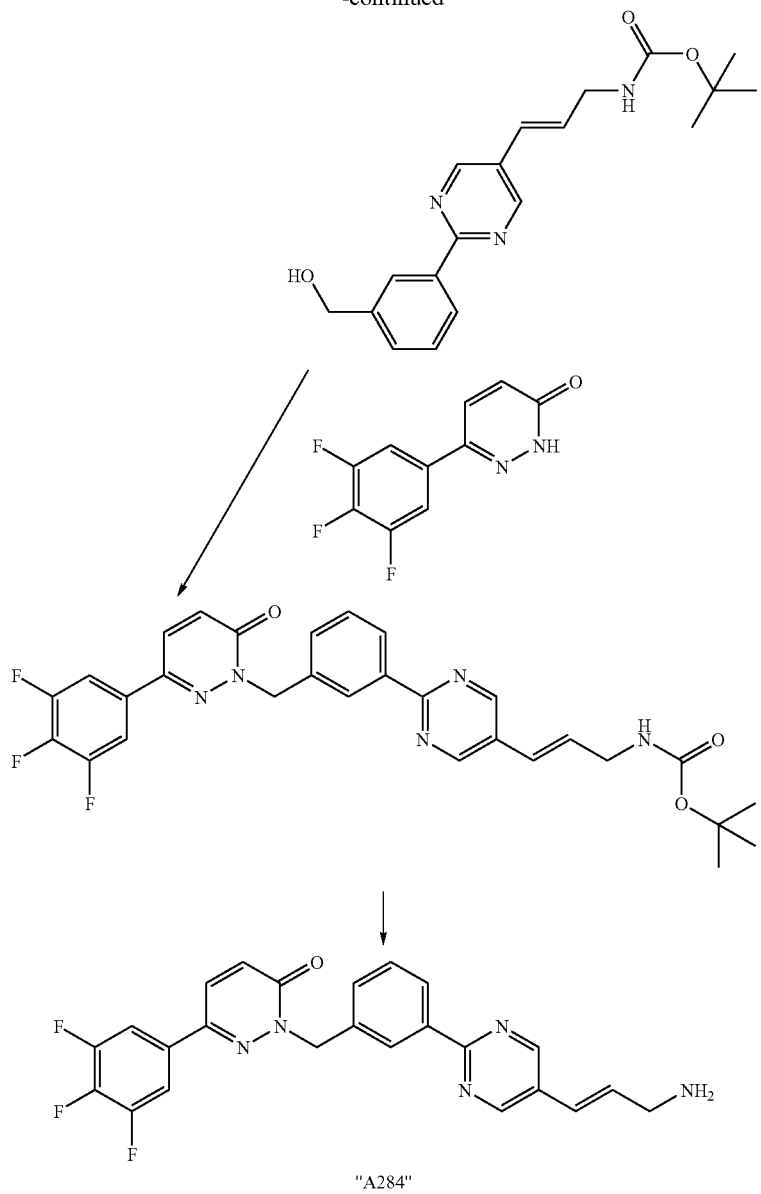

"A284"

48.1 812 mg (3.06 mmol) of [3-(5-bromopyrimidin-2-yl) phenyl]methanol and 722 mg (4.59 mmol) of tert-butyl N-allylcarbamate are suspended in 16 ml of DMF, and 160 mg (0.61 mmol) of triphenylphosphine, 1.8 g (4.6 mmol) of potassium acetate and 1.28 g (4.59 mmol) of tetra-n-butylammonium chloride are added. The reaction mixture is degassed and flushed with argon, and 137 mg (0.0.61 mmol) of palladium(II) acetate are added under an argon atmosphere. The mixture is heated at 80° C. for 2 h. After cooling, the mixture is filtered through kieselguhr with suction, and the filtrate is added to water and extracted with 2×100 ml of ethyl acetate, dried over sodium sulfate and evaporated. The product was reacted further without further purification; yield: 380 mg; HPLC: Rt=2.66 min (method C); LC-MS: 342 (M+H).

48.2 66 mg (0.29 mmol) of 6-(3,4,5-trifluorophenyl)-2H-pyridazin-3-one and 142 mg (0.29 mmol) of tert-butyl {(E)-3-[2-(3-hydroxymethylphenyl)-pyrimidin-5-yl] allyl}carbamate are suspended in 3 ml of THF with 145 mg (0.44 mmol) of polymer-bound triphenylphosphine (about 3 mmol of triphenylphosphine per g), and the mixture is shaken at room temperature for 30 min. The mixture is cooled to 0° C., and 69 µl (0.44 mmol) of diethyl azodicarboxylate are added. The reaction mixture is shaken at room temperature for 24 h. The reaction mixture is purified by means of preparative HPLC: yield: 28 mg; HPLC: Rt=3.50 min (method C); LC-MS: 550 (M+H).

48.3 28 mg (0.051 mmol) of tert-butyl [(Z)-3-(2-{3-[6-oxo-3-(3,4,5-trifluorophenyl)-6H-pyridazin-1-ylmethyl] phenyl}pyrimidin-5-yl)allyl]carbamate are dissolved in 4 ml of dichloromethane, and 79 µl (1.02 mmol) of trifluoroacetic acid are added. The reaction mixture is stirred at room temperature for 15 h and evaporated. The residue is purified by means of preparative HPLC; yield: 11 mg of "A284" trifluoroacetate; HPLC: Rt=2.64 min (method C); LC-MS: 450 (M+H).

EXAMPLE 49

Preparation of 2-{3-[5-(3-aminopropyl)pyrimidin-2-yl]benzyl}-6-(3,4,5-trifluorophenyl)-2H-pyridazin-3-one ("A285")

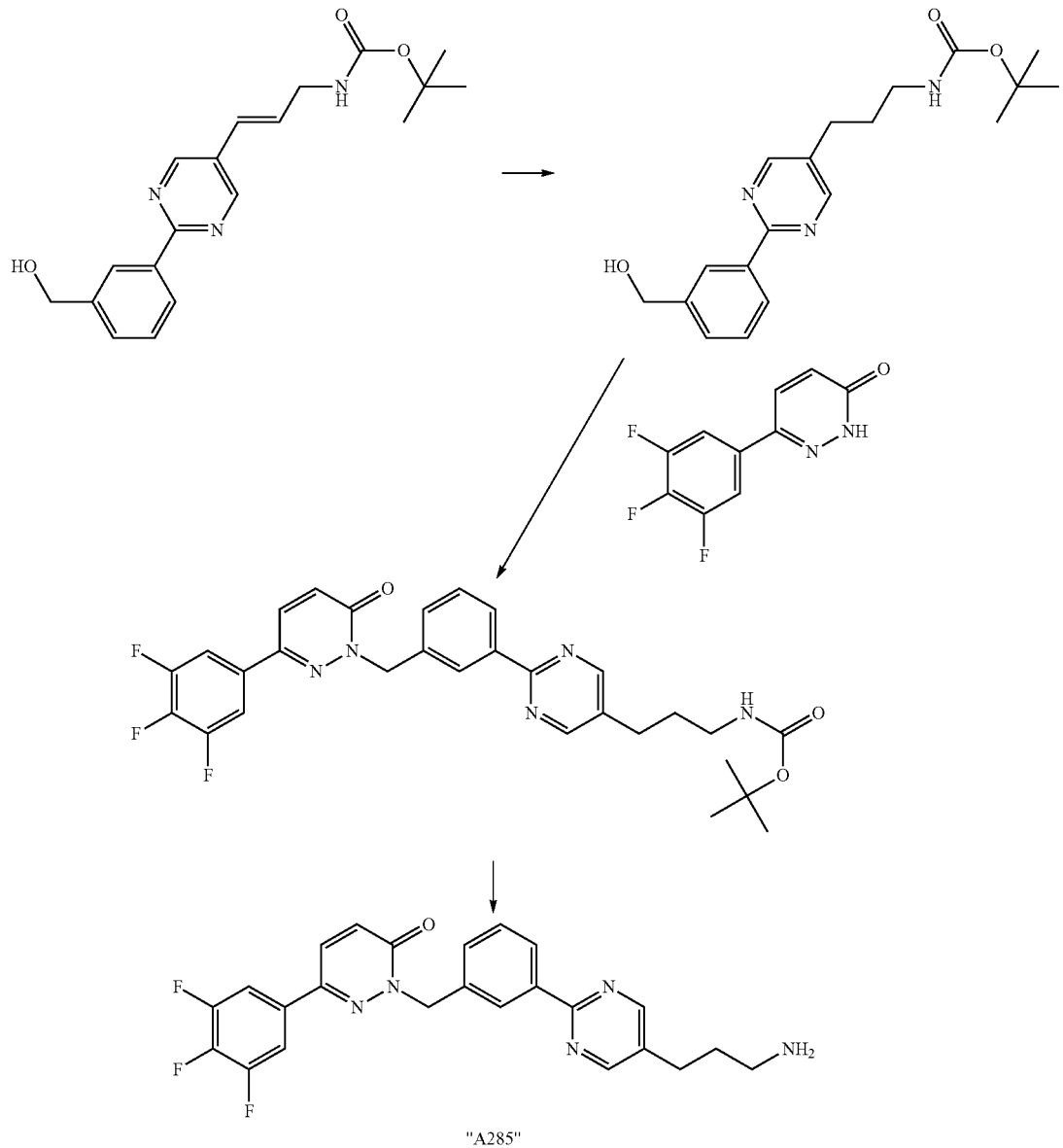

"A285"

49.1 280 mg (0.82 mmol) of tert-butyl {(E)-3-[2-(3-hydroxymethyl-phenyl)pyrimidin-5-yl]allyl}carbamate are dissolved in 10 ml of THF and shaken with 300 mg of platinum on activated carbon (5%, contains 56% of water) under a hydrogen atmosphere at room temperature for 17 h. The catalyst is filtered off with suction, and the filtrate is evaporated to dryness; yield: 289 mg; HPLC: Rt=2.60 min (method C) LC-MS: 344 (M+H).

49.2 195 mg (0.86 mmol) of 6-(3,4,5-trifluorophenyl)-2H-pyridazin-3-one and 369 mg (0.86 mmol) of tert-butyl {3-[2-(3-hydroxymethylphenyl)pyrimidin-5-yl]propyl}carbamate are suspended in 10 ml of THF with 430 mg (1.29 mmol) of polymer-bound triphenylphosphine (about 3 mmol of triphenylphosphine per g) and shaken at room temperature for 30 min. The mixture is cooled to 0° C., and 297 mg (0.1.29 mmol) of di-tert-butyl azodicarboxylate are added. The reaction mixture is shaken at room temperature for 24 h. A further 430 mg (1.29 mmol) of polymer-bound triphenylphosphine (about 3 mmol of triphenylphosphine per g) and 297 mg (1.29 mmol) of di-tert-butyl azodicarboxylate are added, and the reaction mixture is shaken at room temperature for 24 h. The reaction mixture is filtered, the residue is evaporated and the residue is purified by means of preparative HPLC; yield: 333 mg; HPLC: Rt=3.45 min; LC-MS: 552 (M+H).

49.3 70 mg (0.127 mmol) of tert-butyl [3-(2-{3-[6-oxo-3-(3,4,5-trifluorophenyl)-6H-pyridazin-1-ylmethyl]phenyl}pyrimidin-5-yl)propyl]carbamate are dissolved in 3 ml of dichloromethane, and 195 µl (2.54 mmol) of trifluoroacetic acid are added. The reaction mixture is stirred at room temperature for 15 h and evaporated. The residue is digested with diethyl ether and dried in vacuo; yield: 74 mg of "A285"; HPLC: Rt=2.63 min (method C); LC-MS: 452 (M+H).

EXAMPLE 50

Preparation of 2-{3-[5-(4-methylpiperazin-1-yl)pyrimidin-2-yl]benzyl}-6-(1-methyl-1H-pyrazol-4-yl)-2H-pyridazin-3-one ("A286")

50.1 Preparation of methyl 3-(5-aminopyrimidin-2-yl)benzoate

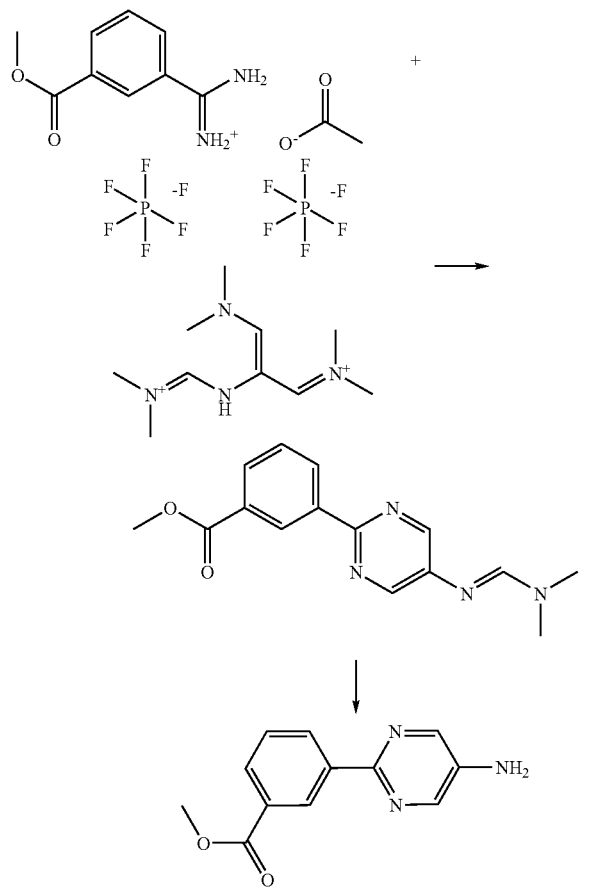

65.4 g (274 mmol) of methyl 3-carbamimidoylbenzoate is suspended in 800 ml of methanol, and 134 g (274 mmol) of ({2-dimethylamino-1-[dimethylimmoniomethyl]vinylamino}methylene)dimethylammonium dihexafluorophosphate are added. 102 ml (548 mmol) of 30% sodium methoxide solution in methanol is added dropwise to this suspension. A solution forms. This is stirred at an internal temperature of 60° C. for 1 hour. After cooling to room temperature, a further 20 ml of 30% sodium methoxide solution in methanol are added dropwise, and the mixture is stirred at 60° C. for 1 hour. After cooling to room temperature, the resultant precipitate is filtered off with suction, and the residue is suspended in 1 l of water and stirred at room temperature for 30 min. The precipitate is filtered off with suction and dried at 80° C. in a vacuum drying cabinet; yield: 68.5 g; HPLC: Rt=2.03 min (method C); LC-MS: 285 $(_{M+H})$.

10.2 g (35.9 mmol) of methyl 3-[5-(dimethylaminomethyleneamino)pyrimidin-2-yl]benzoate are suspended in 1 l of methanol. 5.3 ml (107.3 mmol) of fuming sulfuric acid are added dropwise with gentle cooling (about 5-10° C.) (note, highly exothermic reaction). When the addition is complete, the mixture is stirred firstly at RT for 30 min and subsequently at an oil-bath temperature of 88°. The reaction is monitored by means of HPLC. After 20 h, the clear, dark-yellow solution is evaporated to dryness. The residue is dissolved in 600 ml of ethyl acetate and washed with 2×150 ml of 1 N NaOH and 2×1 N HCl, dried over sodium sulfate and evaporated; yield: 3 g; HPLC: Rt=2.17 min (method C); LC-MS: 300 (M+H).

50.2 Preparation of {3-[5-(4-methylpiperazin-1yl)pyrimidin-2-yl]-phenyl}methanol

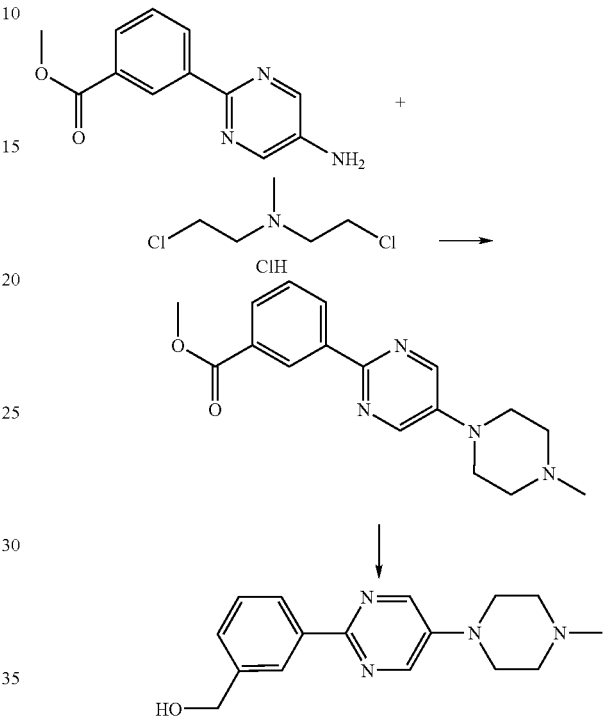

2.5 g (10.9 mmol) of methyl 3-(5-aminopyrimidin-2-yl)benzoate are dissolved in 10 ml of NMP, and 2.59 g (18.5 mmol) of potassium carbonate and 3.6 g (18.5 mmol) of bis(2-chloroethyl)ethylamine hydrochloride are added. The suspension is stirred at 120° C. for 15 h under an argon atmosphere. The mixture is subsequently stirred at 140° C. for a further 12 h. After cooling to room temperature, the reaction mixture is stirred into 150 ml of water. The resultant precipitate is filtered off through kieselguhr with suction and discarded. The filtrate is adjusted to pH=14 using 32% NaOH. The slightly cloudy solution is extracted with 2×200 ml of ethyl acetate. The combined organic phases are washed with saturated sodium chloride solution, dried over sodium sulfate and evaporated to dryness and dried in vacuo. The product is reacted further without further purification; yield: 860 mg; HPLC: Rt=2.11 min (method C); LC-MS: 313 (M+H).

860 mg (2.75 mmol) of methyl 3-[5-(4-methylpiperazin-1-yl)pyrimidin-2-yl]-benzoate are dissolved in 16 ml of THF, and 13.8 ml (13.8 mmol) of 1 M diisobutylaluminium hydride in THF are added dropwise at room temperature, and the reaction mixture is stirred at room temperature for 1 h. A further 13.8 ml (13.8 mmol) of 1 M diisobutylaluminium hydride in THF are added dropwise, and the reaction mixture is stirred at room temperature for 1 h. 3 ml of saturated sodium sulfate solution are added to the reaction mixture with ice cooling. Dichloromethane is added to the gelatinous mixture, which is then stirred for 30 min and filtered. The filtrate is dried over sodium sulfate and evaporated.

Yield: 300 mg, yellow solid. The product is reacted further without further purification; HPLC: 1.68 min (method C); LC-MS: 285 (M+H).

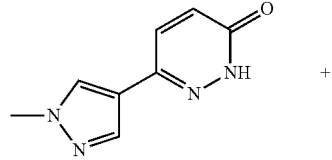

+

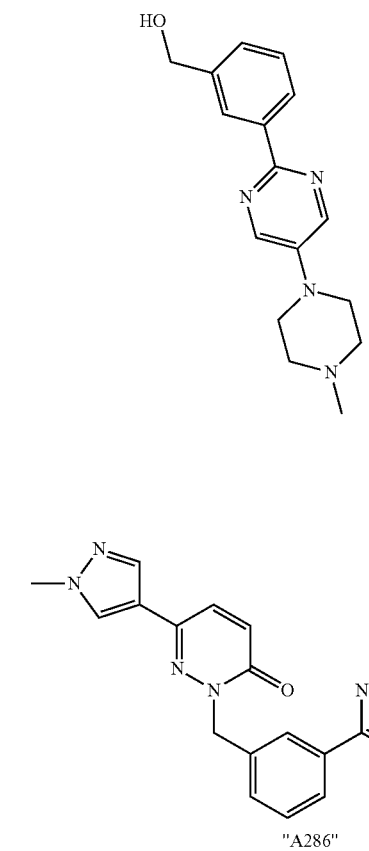

71 mg (0.40 mmol) of 6-(1-methyl-1H-pyrazol-4-yl)-2H-pyridazin-3-one and 163 mg (0.40 mmol) of {3-[5-(4-methylpiperazin-1-yl)pyrimidin-2-yl]phenyl}-methanol are suspended in 3 ml of THF and 1 ml of DMF with 200 mg (0.60 mmol) of polymer-bound triphenylphosphine (about 3 mmol of triphenylphosphine per g) and shaken at room temperature for 30 min. 139 mg (0.60 mmol) of di-tert-butyl azodicarboxylate are added. The reaction mixture is shaken at room temperature for 1 h. A further 200 mg (0.6 mmol) of polymer-bound triphenylphosphine (about 3 mmol of triphenylphosphine per g) and 139 mg (0.60 mmol) of di-tert-butyl azodicarboxylate are added, and the reaction mixture is shaken at room temperature for 2 h. The reaction mixture is filtered, the residue is evaporated, and the residue is purified by means of preparative HPLC; yield: 18 mg of "A286"; HPLC: Rt=2.08 min (method C); LC-MS: 443 (M+H).

EXAMPLE 51

Preparation of 3-(1-{3-[5-(4-methylpiperazin-1-yl)pyrimidin-2-yl]benzyl}-6-oxo-1,6-dihydropyridazin-3-yl)benzonitrile ("A287")

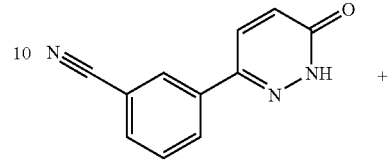

+

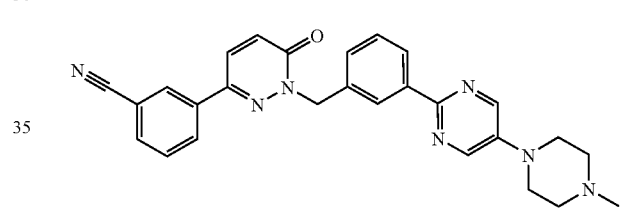

149 mg (0.76 mmol) of 3-(6-oxo-1,6-dihydropyridazin-3-yl)benzonitrile and 256 mg (0.76 mmol) of {3-[5-(4-methylpiperazin-1-yl)pyrimidin-2-yl]phenyl}-methanol are suspended in 5 ml of DMF with 378 mg (1.13 mmol) of polymer-bound triphenylphosphine (about 3 mmol of triphenylphosphine per g) and shaken at room temperature for 30 min. 266 mg (1.134 mmol) of di-tert-butyl azodicarboxylate are added. The reaction mixture is shaken at room temperature for 2 h. A further 378 mg (1.13 mmol) of polymer-bound triphenylphosphine (about 3 mmol of triphenylphosphine per g) and 266 mg (1.134 mmol) of di-tert-butyl azodicarboxylate are added, and the reaction mixture is shaken at room temperature for 2 h. The reaction mixture is filtered, the filtrate is evaporated, and the residue is purified by means of column chromatography on silica gel; yield: 59 mg of "A287"; HPLC: Rt=2.38 min (method C); LC-MS: 464 (M+H).

EXAMPLE 52

Preparation of 3-{6-oxo-1-[3-(5-piperazin-1-ylpyrimidin-2-yl)benzyl]-1,6-dihydropyridazin-3-yl}benzonitrile ("A288")

52.1 Preparation of tert-butyl 4-[2-(3-hydroxymethylphenyl)pyrimidin-5-yl]piperazine-1-carboxylate

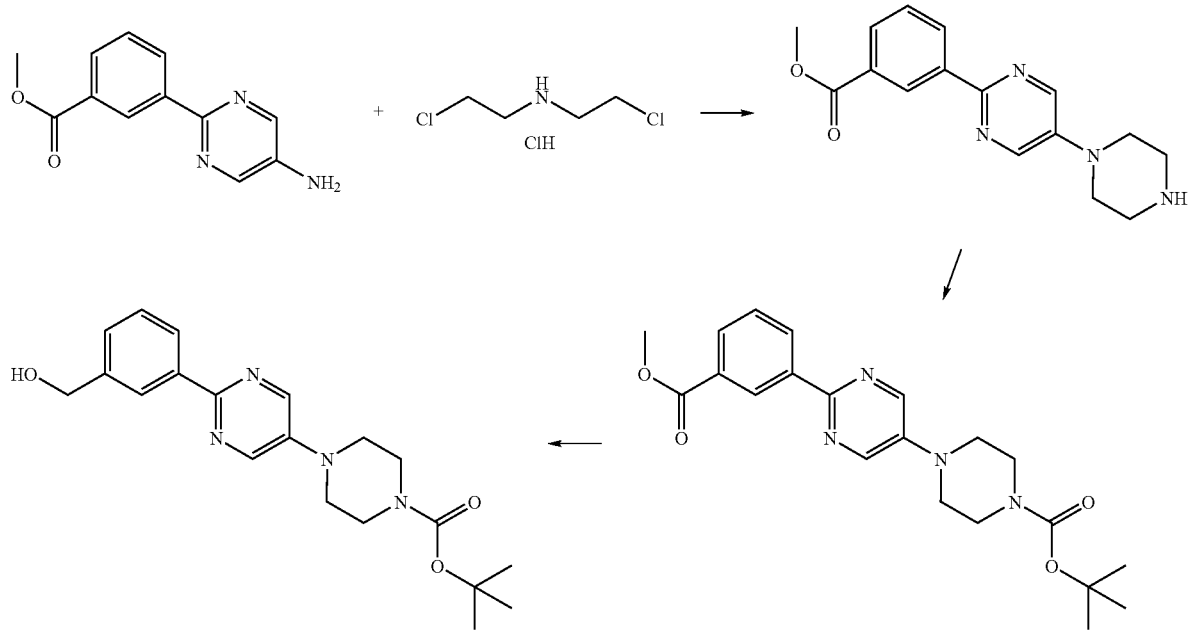

3.2 g (13.95 mmol) of methyl 3-(5-aminopyrimidin-2-yl)benzoate are dissolved in 80 ml of NMP, and 4.73 g (25.96 mmol) of bis(2-chloroethyl)ammonium chloride and 3.13 g (23.73 mmol) of potassium carbonate are added. The suspension is stirred at 130° C. for 7 days under an argon atmosphere. The reaction mixture is filtered, and the filtrate is stirred into 1 l of diethyl ether. An oily residue deposits in the process. The organic phase is separated off and discarded. 500 ml of ethyl acetate and 200 ml of saturated sodium hydrogencarbonate solution are added to the residue, the organic phase is separated off, and the aqueous phase is extracted again with 500 ml of ethyl acetate. The organic phases are combined, dried over sodium sulfate and evaporated. The residue is reacted further without further work-up; yield: 2.4 g; HPLC: Rt=2.07 min (method C); LC-MS: 299 (M+H).

2.4 g (5.4 mmol) of methyl 3-(5-piperazin-1-ylpyrimidin-2-yl)benzoate is dissolved in 15 ml of DMF, 2.98 g (21.6 mmol) of potassium carbonate and 1.5 ml (7.0 mmol) of di-tert-butyl dicarbonate are added, and the mixture is stirred at room temperature for 30 min. The reaction mixture is filtered, and the filtrate is evaporated. The residue is taken up in 200 ml of ethyl acetate and 50 ml of saturated sodium hydrogencarbonate solution. The organic phase is separated off and washed with 50 ml of 1 N HCl, dried over sodium sulfate and evaporated. The product is reacted further without further purification; yield: 1.1 g; HPLC: 3.18 min (method C); LC-MS: 399 (M+H).

862 mg (2.16 mmol) of tert-butyl 4-[2-(3-methoxycarbonylphenyl)pyrimidin-5-yl]piperazine-1-carboxylate are dissolved in 15 ml of THF, and 10.8 ml (10.8 mmol) of 1 M diisobutylaluminium hydride in THF are added at room temperature. The reaction mixture is stirred at room temperature for 1 h. 3 ml of sat. sodium sulfate solution are added to the reaction mixture with ice cooling. 30 ml of dichloromethane and 5 ml of methanol are added to the gelatinous mixture, which is then stirred for 10 min and filtered through kieselguhr with suction. The filtrate is dried over sodium sulfate and evaporated. The residue is dissolved in dichloromethane and filtered, and the filtrate is evaporated. The product is reacted further without further purification; yield: 677 mg; HPLC: 2.66 min (method C); LC-MS: 371 (M+H).

52.2

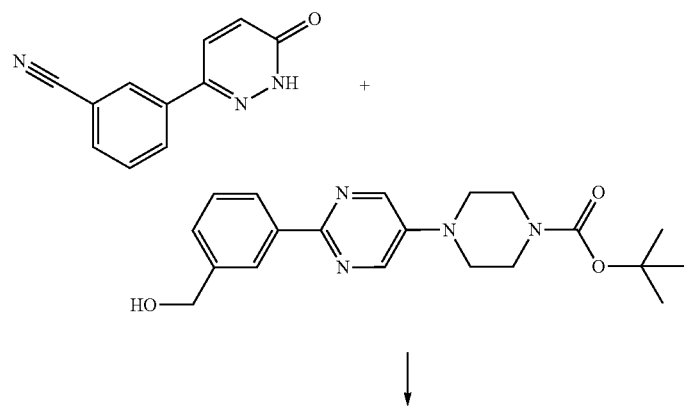

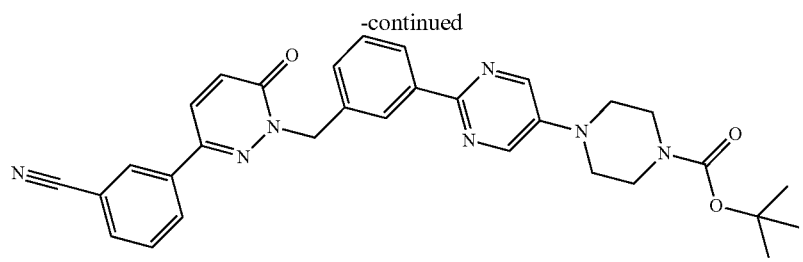

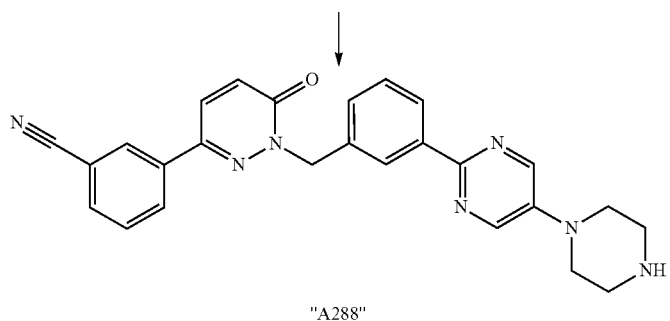

"A288"

94 mg (0.48 mmol) of 3-(6-oxo-1,6-dihydropyridazin-3-yl)benzonitrile and 177 mg (0.48 mmol) of tert-butyl 4-[2-(3-hydroxymethylphenyl)pyrimidin-5-yl]piperazine-1-carboxylate are suspended in 4 ml of THF and 1 ml of DMF with 240 mg (0.72 mmol) of polymer-bound triphenylphosphine (about 3 mmol of triphenylphosphine per g) and shaken at room temperature for 30 min. 168 mg (0.72 mmol) of di-tert-butyl azodicarboxylate are added. The reaction mixture is filtered, the filtrate is evaporated, and the residue is purified by means of column chromatography on silica gel; yield: 143 mg; HPLC: Rt=3.24 min (method C); LC-MS: 550 (M+H).

143 mg (0.26 mmol of tert-butyl 4-(2-{3-[3-(3-cyanophenyl)-6-oxo-6H-pyridazin-1-ylmethyl]phenyl}pyrimidin-5-yl)piperazine-1-carbamate are dissolved in 6 ml of acetonitrile, and 6 ml of 4 M HCl in dioxane are added. The reaction mixture is stirred at room temperature for 1 h and evaporated. The residue is taken up in water and ethyl acetate, and the water phase is adjusted to pH 12 using NaOH and extracted with ethyl acetate and dichloromethane. The organic phases are combined, dried over sodium sulfate and purified by means of column chromatography.

Yield: 117 mg of "A288" HPLC: Rt=2.36 min (method C); LC-MS: 450 (M+H).

Preparation of a Precursor for the Preparation of "A289" and "A290"

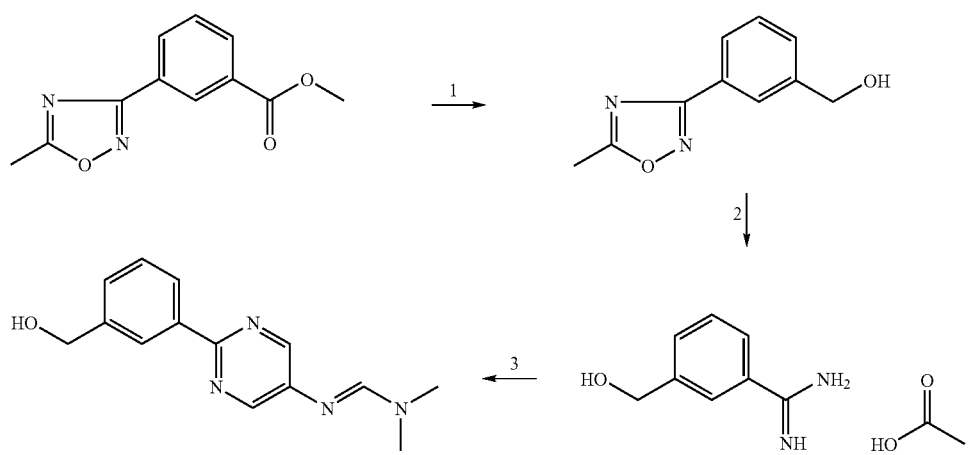

1. Preparation of [3-(5-methyl-1,2,4-oxadiazol-3-yl)phenyl]methanol 3.46 g of methyl 3-(5-methyl-1,2,4-oxadiazol-3-yl)benzoate (15.86 mmol) are dissolved in 50 ml of abs. THF in a 250 ml three-necked flask, and 0.691 g of LiBH4 (31.71 mmol) is subsequently introduced in portions with stirring at 0° C. under a nitrogen atmosphere, and the mixture is stirred without cooling for a further 20 h. For work-up, the reaction mixture is adjusted to pH 7 by slow dropwise addition of 1 N HCl with stirring, diluted with 100 ml of water and extracted 3× with 50 ml of dichloromethane. The combined organic phases are washed 1× 100 ml of water, dried over sodium sulfate and evaporated to dryness in a rotary evaporator. The purification is carried out by chromatography (50 g of silica gel/DCM+0-1% of MeOH). The product is crystallised from diethyl ether/petroleum ether; m.p. 57-58° C.

2. Preparation of 3-hydroxymethylbenzamidinium acetate 40 g of Raney nickel (water-wet) are added to 124.84 g of [3-(5-methyl-1,2,4-oxadiazol-3-yl)phenyl]methanol (569.39 mmol) in a mixture of 1300 ml of methanol, 100 ml of glacial acetic acid and 100 ml of water, and the mixture is hydrogenated at room temperature and atmospheric pressure until 14.7 l of hydrogen have been taken up (45 h). For work-up, the catalyst is filtered off, and the solution which remains is evaporated to dryness, and the residue is boiled up in methyl tert-butyl ether and filtered off. The crystals are dried overnight in vacuo.

3. Preparation of N'-[2-(3-hydroxymethylphenyl)pyrimidin-5-yl]-N,N-dimethylformamidine 716 mg of 3-hydroxymethylbenzamidinium acetate (3.41 mmol) and 1.66 g of ({2-dimethylamino-1-[dimethylimmoniomethyl]vinylamino}methylene)-dimethylammonium dihexafluorophosphate (amino-reduction precursor) (3.41 mmol) were suspended in 15 ml of abs. methanol in an $N_2$-flushed 100 ml three-necked flask with $CaCl_2$ protection, and a freshly prepared solution of 0.235 g of Na in 5 ml of abs. methanol is added dropwise with stirring. The reaction mixture is stirred at 60° C. for 30 min, during which a clear solution forms. For work-up, the reaction batch is diluted with 50 ml of dichloromethane, washed 2× with 20 ml of water, evaporated to dryness and purified by chromatography (silica gel DCM+0-5% of MeOH); m.p. 105-6° C.

EXAMPLE 53

Preparation of 6-(4-methanesulfonylphenyl)-2-[3-(5-piperazin-1-yl-pyrimidin-2-yl)benzyl]-2H-pyridazin-3-one ("A289")

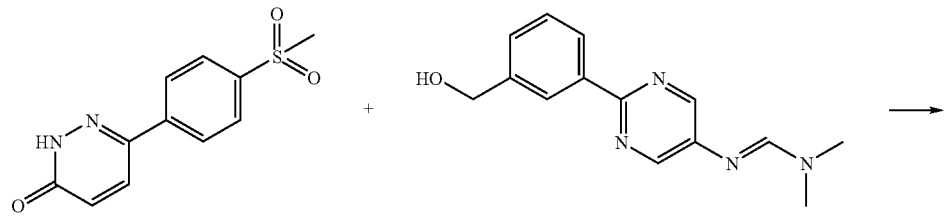

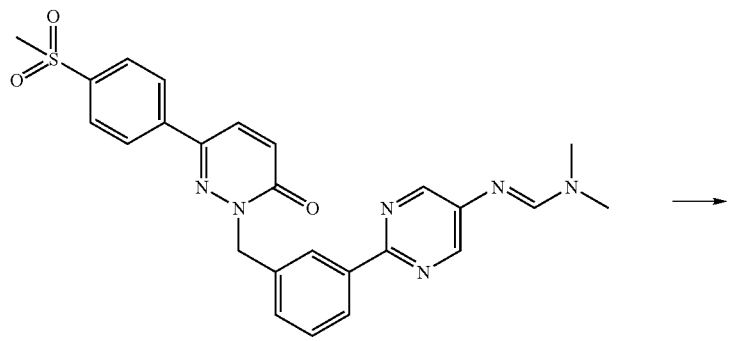

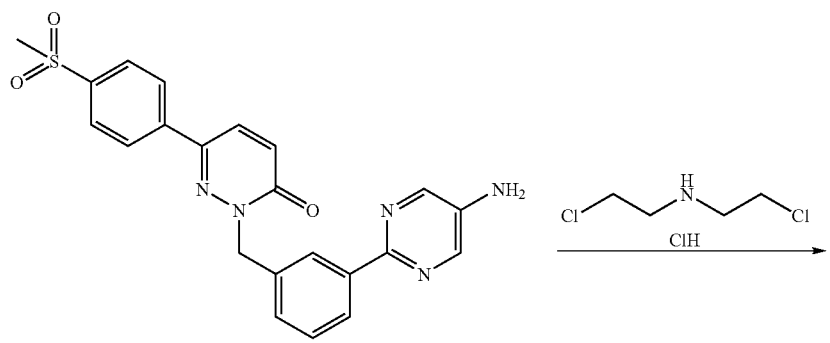

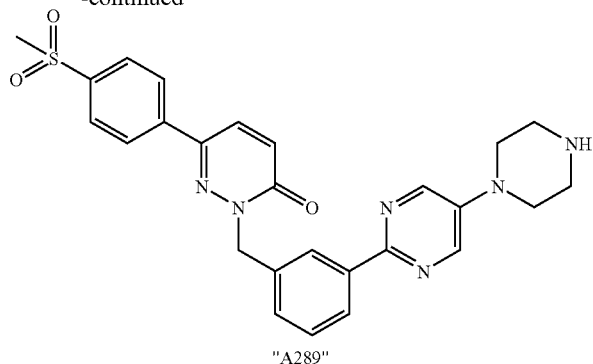

"A289"

53.1 1.95 g (7.8 mmol) of 6-(4-methanesulfonylphenyl)-2H-pyridazin-3-one and 2 g (7.8 mmol) of N'-[2-(3-hydroxymethylphenyl)pyrimidin-5-yl]-N,N-dimethylformamidine are suspended in 50 ml of THF and 15 ml of DMF with 3.9 g (11.7 mmol) of polymer-bound triphenylphosphine (about 3 mmol of triphenylphosphine per g) and shaken at room temperature for 30 min. 2.75 g (11.7 mmol) of di-tert-butyl azodicarboxylate are added.

The reaction mixture is shaken at room temperature for 15 h. A further 2.6 g (7.8 mmol) of polymer-bound triphenylphosphine (about 3 mmol of triphenylphosphine per g) and 1.80 g (7.8 mmol) of di-tert-butyl azodicarboxylate are added. The reaction mixture is shaken at room temperature for 15 h. The reaction mixture is filtered, and the filtrate is evaporated. 1 N HCl (100 ml) is added to the oily residue, which is then extracted with ethyl acetate (100 ml). The acidic water phase is washed again with ethyl acetate and then adjusted to pH7 using solid sodium hydrogencarbonate. The mixture is extracted 2× with ethyl acetate. The organic phase is evaporated, and the residue is dried in vacuo; yield: 1 g; HPLC: Rt=2.19 min (method C); LC-MS: 489 (M+H).

53.2 1.7 g (3.48 mmol) of N'-(2-{3-[3-(4-methanesulfonylphenyl)-6-oxo-6H-pyridazin-1-ylmethyl]phenyl}pyrimidin-5-yl)-N,N-dimethylformamidine are dissolved in 30 ml of dioxane and 30 ml of water, and 1.68 g (12.2 mmol) of potassium carbonate are added. The reaction mixture is refluxed for 15 h. After cooling to room temperature, the reaction mixture is concentrated to about 30 ml, and the resultant precipitate is filtered off with suction, washed with water and dried in vacuo.

Yield: 1.5 g HPLC: 2.30 min (method C); LC-MS: 434 (M+H).

53.3 1.4 g (3.23 mmol) of 2-[3-(5-aminopyrimidin-2-yl)benzyl]-6-(4-methanesulfonylphenyl)-2H-pyridazin-3-one are dissolved in 30 ml of NMP, and 1.59 g (8.72 mmol) of bis(2-chloroethyl)ethylamine hydrochloride and 1.22 g (8.72 mmol) of potassium carbonate are added. The suspension is stirred at 130° C. for 5 days under an argon atmosphere. The reaction mixture is filtered, and the filtrate is stirred into 200 ml of diethyl ether. An oily residue deposits in the process. The residue is purified by means of column chromatography on silica gel. The resultant product is purified by means of preparative HPLC; yield: 41 mg of "A289" trifluoroacetate; HPLC: Rt=2.19 min (method C); LC-MS: 503 (M+H).

EXAMPLE 54

Preparation of 4-{1-[3-(5-aminopyrimidin-2-yl)benzyl]-6-oxo-1,6-dihydro-pyridazin-3-yl}benzonitrile ("A290")

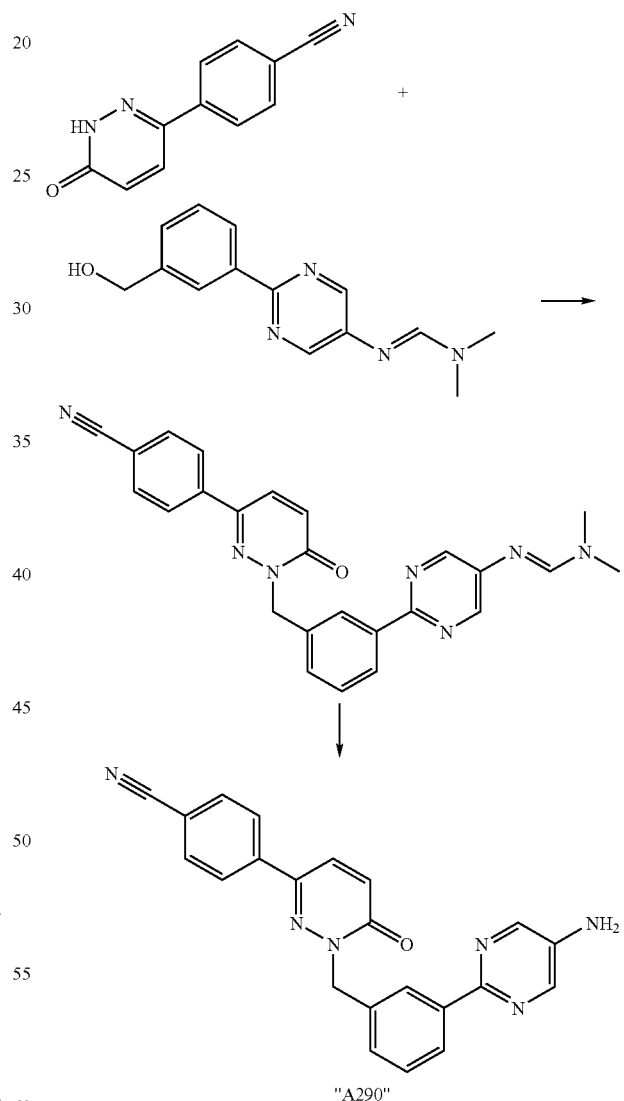

"A290"

54.1 1.5 g (7.8 mmol) of 6-(4-cyanophenyl)-2H-pyridazin-3-one and 2 g (7.8 mmol) of N'-[2-(3-hydroxymethylphenyl)pyrimidin-5-yl]-N,N-dimethylformamidine are suspended in 50 ml of THF and 15 ml of DMF with 3.9 g (11.7 mmol) of polymer-bound triphenylphosphine (about 3 mmol of triphenylphosphine per g) and shaken at room temperature for 30 min. 2.75 g (11.7 mmol) of di-tert-butyl azodicarboxylate are added. The reaction mixture is shaken at room temperature for 15 h. A further 2.6 g (7.8 mmol) of polymer-bound triphenylphosphine (about 3 mmol of triphenylphosphine per g) and 1.80 g (7.8 mmol) of di-tert-butyl azodicarboxylate are added. The reaction mixture is shaken at room temperature for 15 h. The reaction mixture is filtered, and the filtrate is evaporated. 1 N HCl (100 ml) is added to the oily residue, which is then extracted with ethyl acetate (100 ml). The acidic water phase is washed again with ethyl acetate and then adjusted to pH7 using solid sodium hydrogencarbonate. The mixture is extracted 2× with ethyl acetate. The organic phase is evaporated, and the residue is dried in vacuo; yield: 1.2 g; HPLC: Rt=1.59 min (method C); LC-MS: 436 (M+H).

54.2 1.2 g (3.48 mmol) of N'-(2-{3-[3-(4-cyanophenyl)-6-oxo-6H-pyridazin-1-ylmethyl]phenyl}pyrimidin-5-yl)-N,N-dimethylformamidine are dissolved in 50 ml of dioxane and 50 ml of water, and 1.2 g (8.7 mmol) of potassium carbonate off with suction, washed with water and dried in vacuo. The residue is purified by means of column chromatography on silica gel; yield: 145 mg of "A290"; HPLC: 2.49 min (method C); LC-MS: 381 (M+H).

The compound 3-{1-[3-(5-aminopyrimidin-2-yl)benzyl]-6-oxo-1,6-dihydropyridazin-3-yl}benzonitrile ("A291"); ESI 381, is obtained analogously.

EXAMPLE 55

Preparation of
6-(1-methyl-1H-pyrazol-4-yl)-2-[3-(5-piperazin-1-ylpyrimidin-2-yl)benzyl]-2H-pyridazin-3-one ("A292") and
2-[3-(5-aminopyrimidin-2-yl)benzyl]-6-(1-methyl-1H-pyrazol-4-yl)-2H-pyridazin-3-one ("A293")

55.1 Preparation of N,N-dimethyl-N'-(2-{3-[3-(1-methyl-1H-pyrazol-4-yl)-6-oxo-6H-pyridazin-1-ylmethyl]phenyl}pyrimidin-5-yl)formamidine

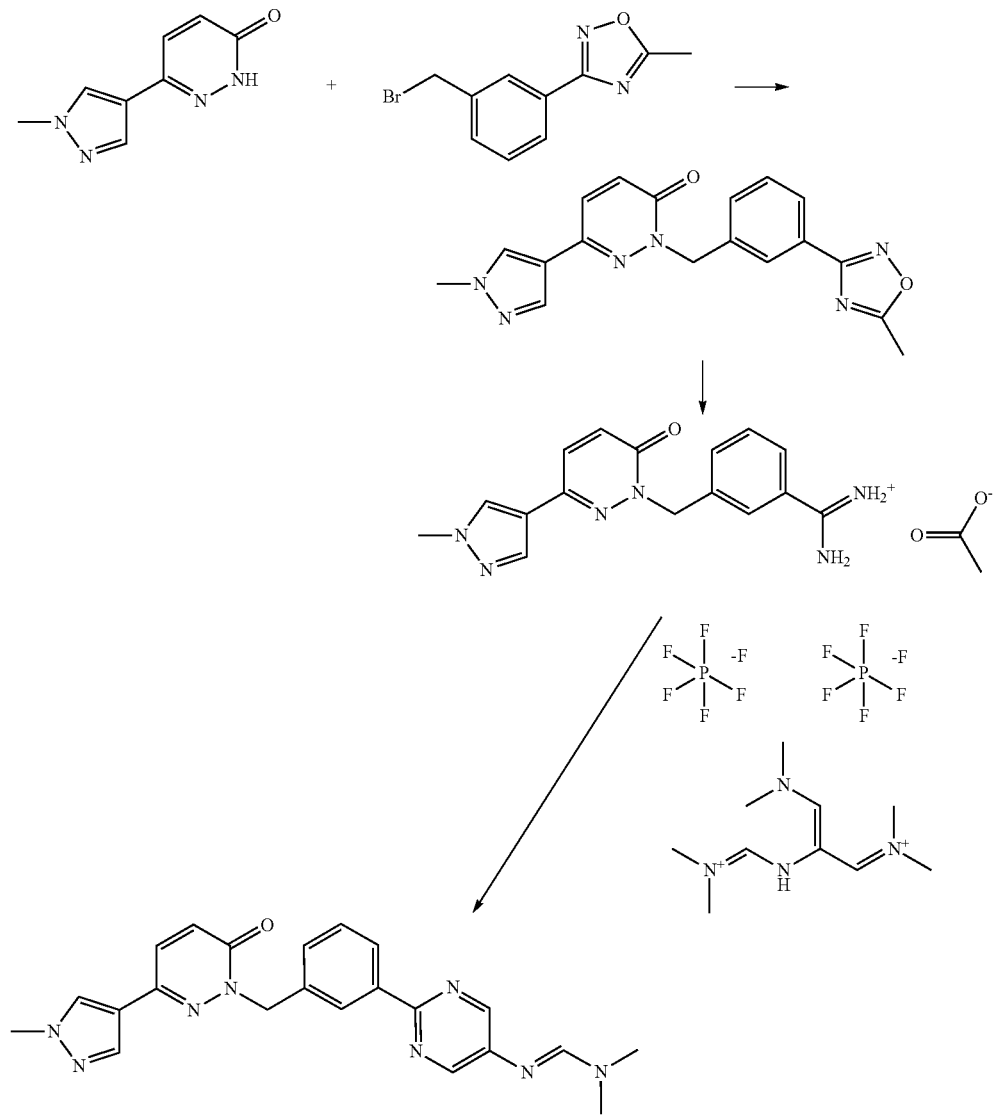

are added. The reaction mixture is refluxed for 15 h. After cooling to room temperature, the reaction mixture is concentrated to about 30 ml, and the resultant precipitate is filtered 3.33 g (24.1 mmol) of potassium carbonate are added to a solution of 1.7 g (4.8 mmol) of 6-(1-methyl-1H-pyrazol-4-yl)-2H-pyridazin-3-one and 1.22 g (4.8 mmol) of 3-(3-bromomethylphenyl)-5-methyl-1,2,4-oxadiazole (prepared by the method of W. W. K. R. Mederski et al, Tetrahedron 55, 1999, 12757-12770) in 50 ml of DMF, and the resultant suspension is stirred at room temperature for 5 days. Water is added to the reaction mixture, which is then extracted with ethyl acetate. The organic phase is washed with water, dried over sodium sulfate and evaporated. Isopropanol is added to the residue, and the mixture is stirred for 15 min and filtered, and the residue is rinsed with isopropanol and diethyl ether and dried in vacuo.

Yield: 740 mg; HPLC: Rt=2.42 min (method C); LC-MS: 349 (M+H).

2 ml of acetic acid, 2 ml of water and 6 g of Raney nickel are added to a solution of 6.77 g (19.4 mmol) of 6-(1-methyl-1H-pyrazol-4-yl)-2-[3-(5-methyl-1,2,4-oxadiazol-3-yl)benzyl]-2H-pyridazin-3-one in 300 ml of methanol, and the mixture is hydrogenated at room temperature and under a hydrogen atmosphere for 2 days. The reaction mixture is filtered, and the filtrate is evaporated and dried in vacuo. The product was reacted further without further purification; yield: 6 g; HPLC: 1.74 min (method C); LC-MS: 309 (M+H).

A suspension of 7.5 g (20.4 mmol) of 3-[6-oxo-3-(1-methyl-1H-pyrazol-4-yl)-6H-pyridazin-1-ylmethyl]benzamidinium acetate and 9.94 g (20.4 mmol) of ({2-dimethylamino-1-[dimethylimmoniomethyl]vinylamino}methylene)dimethylammonium dihexafluorophosphate are dissolved in 70 ml of methanol, and 7.6 ml (40.7 mmol) of 30% sodium methoxide solution in methanol are added dropwise. The reaction mixture is slowly warmed to 60° C. and stirred at this temperature for 60 minutes. After the mixture has been cooled to room temperature, a further 5.6 ml (30.0 mmol) of 30% sodium methoxide solution in methanol are added dropwise, and the mixture is stirred at 60° C. for 2 h. After cooling, the solvent is removed by distillation, and water is added to the residue. The aqueous phase is decanted off, ethyl acetate is added to the residue, and the mixture is stirred at room temperature for 15 min. The precipitate is filtered off with suction, washed with ethyl acetate and dried in vacuo; yield: 6.8 g of beige solid; HPLC: 2.05 min (method C); LC-MS: 415 (M+H).

55.2

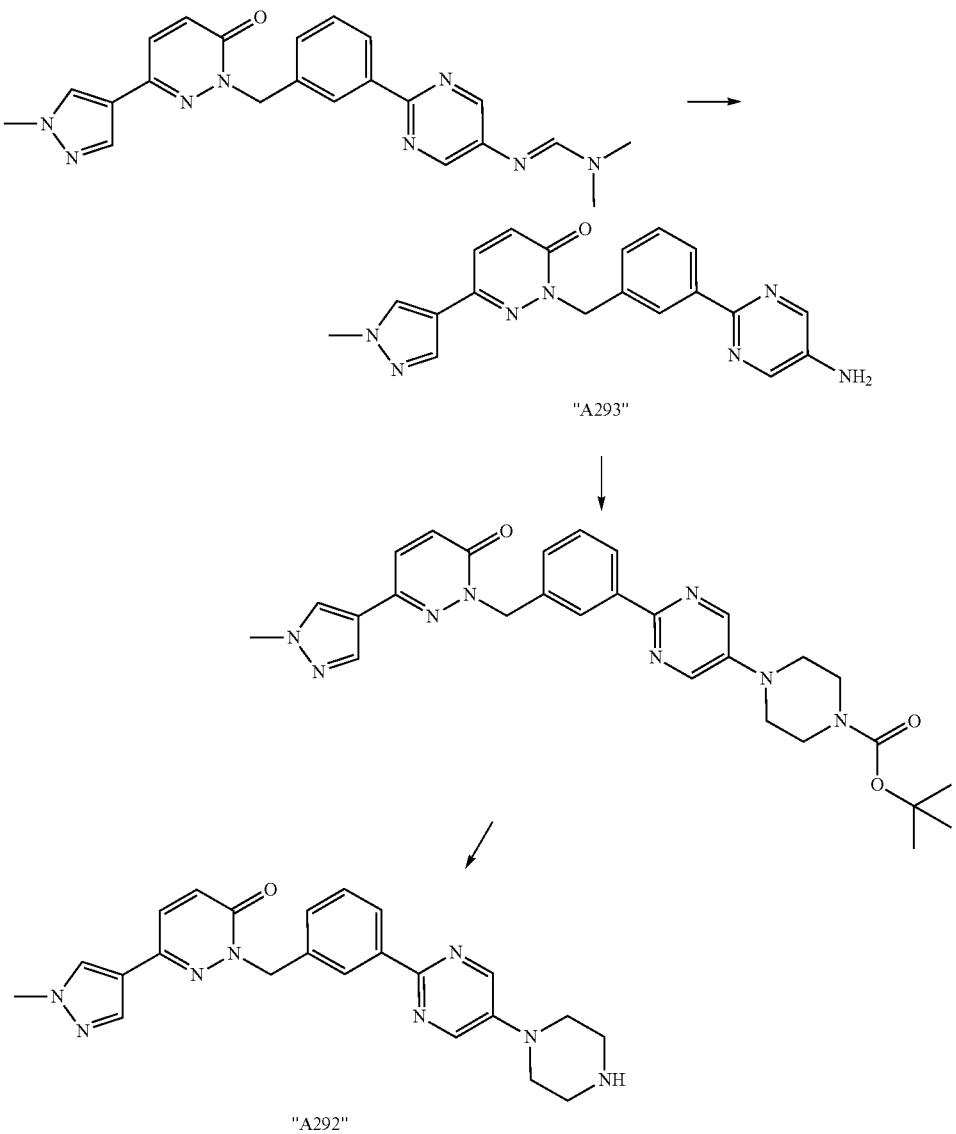

130 ml of dioxane and 5 g (11.4 mmol) of N,N-dimethyl-N'-(2-{3-[3-(1-methyl-1H-pyrazol-4-yl)-6-oxo-6H-pyridazin-1-ylmethyl]phenyl}pyrimidin-5-yl)formamidine are added to a solution of 5.5 g (40 mmol) of potassium carbonate in 130 ml of water. The reaction mixture is heated at the boil for 15 h and subsequently cooled to room temperature. The dioxane is removed by distillation, and the resultant precipitate is filtered off with suction, washed with water and dried in vacuo; yield: 3.6 g of "A293"; HPLC: 2.11 min (method C); LC-MS: 360 (M+H).

1.4 g (7.5 mmol) of bis(2-chloroethyl)methylammonium chloride are added to a solution, kept under nitrogen, of 1 g (2.78 mmol) of 2-[3-(5-amino-pyrimidin-2-yl)benzyl]-6-(1-methyl-1H-pyrazol-4-yl)-2H-pyridazin-3-one ("A293") in 25 ml of 1-methylpyrrolidone, and the reaction mixture is heated at 130° C. for 5 days. The reaction mixture is cooled and filtered, and the filtrate is added to 200 ml of diethyl ether. An oily residue deposits, to which 100 ml of saturated sodium hydrogencarbonate solution are added, and the mixture is extracted with 3×150 ml of dichloromethane. The organic phases are dried over sodium sulfate and evaporated. 300 mg of this residue are dissolved in 5 ml of DMF, and 387 mg of potassium carbonate and 195 µl (0.91 mmol) of di-tert-butyl dicarbonate are added, and the mixture is stirred at room temperature for 1 h. The reaction mixture is filtered, and the filtrate is evaporated. The residue is suspended in dichloromethane and washed with saturated sodium hydrogencarbonate. The organic phase is dried over sodium sulfate and subsequently evaporated. The residue is purified by means of column chromatography on silica gel; yield: 36 mg; HPLC: 2.89 min (method C); LC-MS: 529 (M+H).

90 mg (0.17 mmol) of tert-butyl 4-(2-{3-[3-(1-methyl-1H-pyrazol-4-yl)-6-oxo-6H-pyridazin-1-ylmethyl]phenyl}pyrimidin-5-yl)piperazine-1-carboxylate are dissolved in 10 ml of dioxane, and 1 ml of 4 N HCl in dioxane is added. The reaction mixture is stirred at room temperature for 15 h and subsequently evaporated to dryness; yield: 80 mg of "A292" hydrochloride; HPLC: 2.05 min (method C); LC-MS: 429 (M+H).

EXAMPLE 56

Alternative preparation of 3-{1-[3-(5-hydroxypyrimidin-2-yl)benzyl]-6-oxo-1,6-dihydropyridazin-3-yl}benzonitrile ("A263")

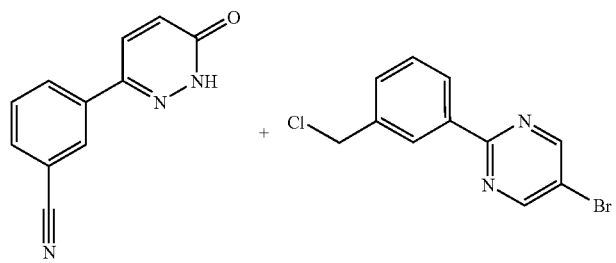

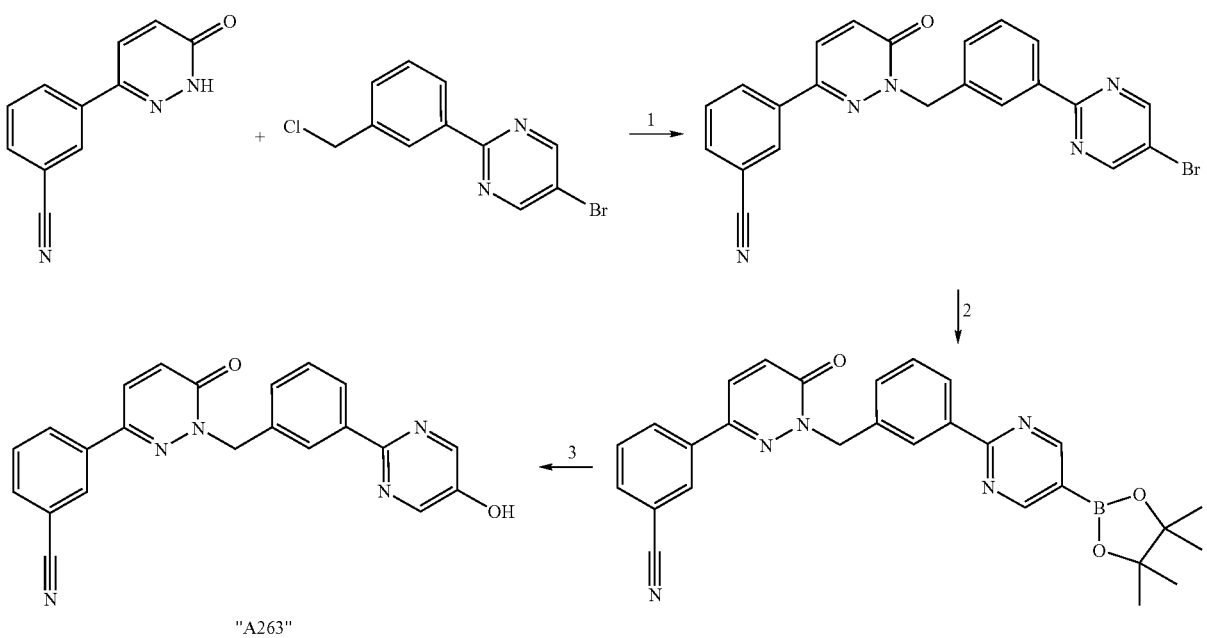

1. Preparation of 3-{1-[3-(5-bromopyrimidin-2-yl)benzyl]-6-oxo-1,6-dihydropyridazin-3-yl}benzonitrile 61.13 g of 3-cyanophenylpyridazinone (0.31 mol) and 87.9 g of 5-bromo-2-(3-chloromethylphenyl)pyrimidine (0.31 mol) are dissolved in 610 ml of DMF under an inert-gas atmosphere in a 1000 ml one-necked flask, and 111.11 g of caesium carbonate (0.34 mol) are subsequently added. The reaction mixture is stirred at 40° C. for 72 h. For work-up, the mixture is diluted with 600 ml of water with stirring, and the resultant precipitate is washed with copious water and a little methanol and chromatographed over 1 kg of silica gel. The product fractions are combined and evaporated to dryness in a rotary evaporator, and the product is slurried with a little methanol, filtered off with suction and dried at 70° C. in vacuo; m.p. 178-9° C.

2. Preparation of 3-(6-oxo-1-{3-[5-(4,4,5,5-tetramethyl-1,3,2-dioxaborolan-2-yl)pyrimidin-2-yl]benzyl}-1,6-dihydropyridazin-3-yl)benzonitrile 35.57 g of 3-{1-[3-(5-bromopyrimidin-2-yl)benzyl]-6-oxo-1,6-dihydropyridazin-3-yl}benzonitrile (0.08 mol), 26.43 g of bis(pinacolato)diboron (0.104 mol) and 23.75 g of potassium acetate (0.240 mol) are suspended in 165 ml of abs. DMF under an N₂ atmosphere in a 500 ml three-necked flask and heated at 70° C. with stirring, 1.686 g of (PPh₃)₂PdCl₂ (2.4 mmol) are subsequently added, and the reaction batch is stirred at 70° C. for 6 h, during which a dark-brown solution forms. For work-up, the reaction mixture is diluted with 600 ml of water with stirring at RT, and the resultant precipitate is filtered off with suction. The resultant precipitate is taken up in 500 ml of dichloromethane, shaken 2× with 200 ml of water, dried over sodium sulfate and evaporated to dryness. The residue is slurried in 200 ml of acetone, filtered off with suction and washed with a little acetone, m.p. 203-5° C.

3. Preparation of 3-{1-[3-(5-hydroxypyrimidin-2-yl)benzyl]-6-oxo-1,6-dihydropyridazin-3-yl}benzonitrile ("A263")

50.46 g of 3-(6-oxo-1-{3-[5-(4,4,5,5-tetramethyl-1,3,2-dioxaborolan-2-yl)-pyrimidin-2-yl]benzyl}-1,6-dihydropyridazin-3-yl)benzonitrile (102.7 mmol) and 33.81 g of sodium perborate tetrahydrate (339 mmol) are mixed in a mixture of 220 ml of THF and 220 ml of water in a 1000 ml one-necked flask and stirred at room temperature for 2 h, during which a pale precipitate deposits. The reaction mixture is diluted with 800 ml of dichloromethane, shaken with 500 ml of saturated aqueous ammonium chloride solution, dried over sodium sulfate and evaporated to dryness in a rotary evaporator. The residue is slurried in methanol, filtered off with suction and washed with diethyl ether, m.p. 245-8° C.

EXAMPLE 57

Preparation of 2-{3-[5-(2-hydroxyethoxy)pyrimidin-2-yl]benzyl}-6-(1-methyl-1H-pyrazol-4-yl)-2H-pyridazin-3-one ("A294")

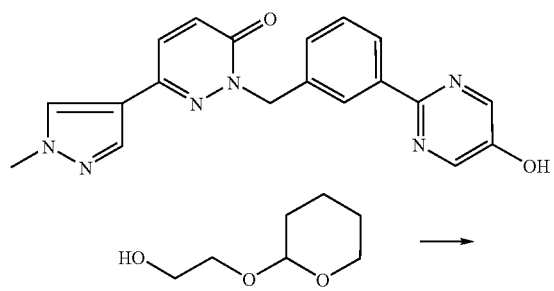

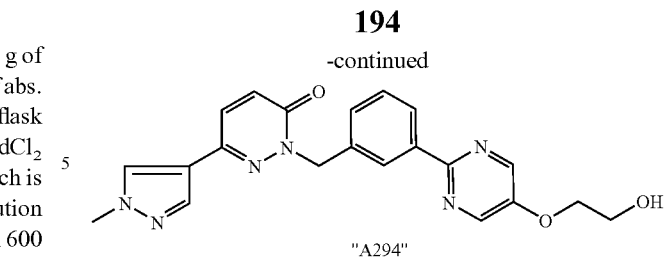
"A294"

252 mg of 2-[3-(5-hydroxypyrimidin-2-yl)benzyl]-6-(1-methyl-1H-pyrazol-4-yl)-2H-pyridazin-3-one (0.7 mmol) are suspended in abs. THF under a protective-gas atmosphere in a 25 ml three-necked flask, 0.19 ml of 2-(tetrahydropyran-2-yloxy)ethanol (1.4 mmol) and 367 mg of triphenylphosphine (1.4 mmol) are added, and the mixture is stirred at RT for 30 min. 275 µl of diisopropyl azodicarboxylate (1.4 mmol) are subsequently added dropwise, and the reaction mixture is stirred at RT for a further 2 h. For work-up, the reaction mixture is diluted with 20 ml of dichloromethane, washed with 10 ml of water, dried over sodium sulfate, evaporated to dryness and purified by chromatography. (silica gel: MTB ether→DCM→DCM:30% of MeOH). The THP-protected product is stirred at RT for 20 h in 5 ml of 4 N HCl in dioxane. The reaction solution is evaporated to dryness and crystallised from methanol/diethyl ether, giving "A294"; ESI 405; m.p. 182-3° C.

The following compounds are obtained analogously

| Compound No. | Name and/or structure | ESI [M + H]⁺ |
| --- | --- | --- |
| "A295" | 3-(1-{3-[5-(3-hydroxypropoxy)pyrimidin-2-yl]benzyl}-6-oxo-1,6-dihydropyridazin-3-yl)benzonitrile | 440 |
| "A296" | 3-(1-{3-[5-(2-hydroxyethoxy)pyrimidin-2-yl]benzyl}-6-oxo-1,6-dihydropyridazin-3-yl)benzonitrile | 426 |
| "A297" | 2-{3-[5-(3-hydroxypropoxy)pyrimidin-2-yl]benzyl}-6-(1-methyl-1H-pyrazol-4-yl)-2H-pyridazin-3-one | 419 |

EXAMPLE 58

Preparation of 1-{3-[5-(3-dimethylaminopropoxy)pyrimidin-2-yl]phenyl}-ethanol (precursor of "A298")

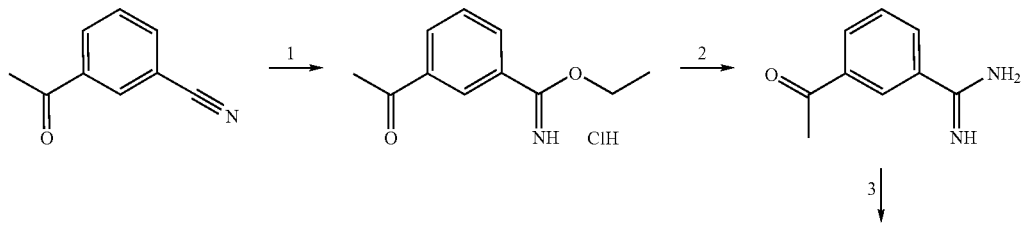

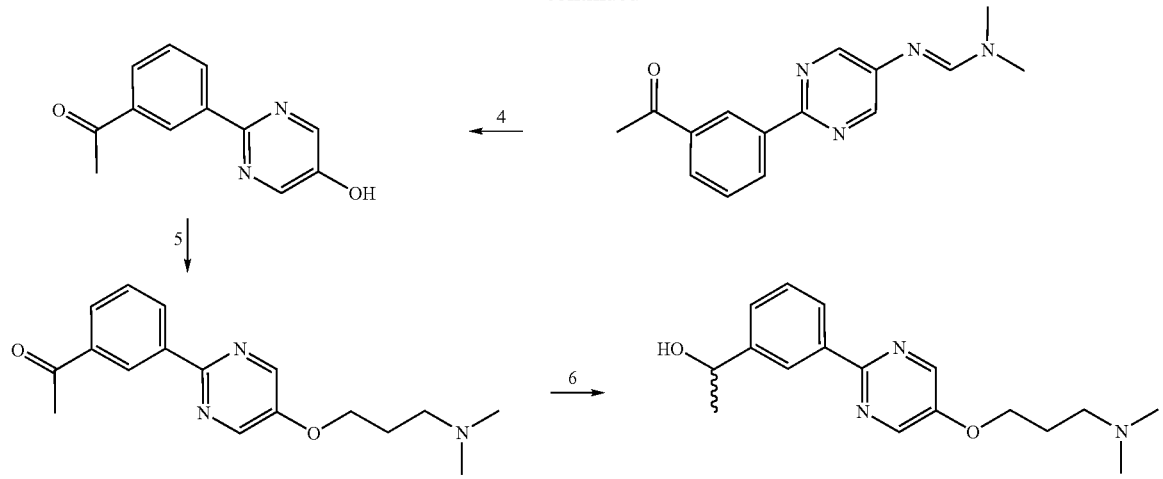

1. Preparation of ethyl 3-acetylbenzimidinate 30 g of 3-cyanacetophenone (207 mmol) are suspended in 170 ml of a 10% solution of HCl in diethyl ether in a 500 ml one-necked flask and cooled to 0° C., and 18.68 ml of abs. ethanol are added. The reaction mixture is stirred at RT for 14 days. For work-up, the reaction mixture is diluted with 500 ml of diethyl ether, the precipitate is filtered off with suction and rinsed with copious diethyl ether, and the residue is dried at 50° C. in a vacuum drying cabinet; m.p. 122-4° C.

2. Preparation of 3-acetylbenzamidine 17.453 g of ethyl 3-acetylbenzimidinate are suspended in 190 ml of abs. ethanol in a 1000 ml one-necked flask, and 190 ml of a 10% solution of ammonia in ethanol are subsequently added, and the reaction batch is refluxed for 3 h. The reaction batch is evaporated to dryness in a rotary evaporator and employed in crude form in the next step; LC-MS: 0.886 min/M+H$^+$: 163.2 g/mol.

3. Preparation of N'-[2-(3-acetylphenyl)pyrimidin-5-yl]-N,N-dimethylformamidine 16.18 g of 3-acetylbenzamidine (content 77%) (76.62 mmol) and 37.41 g of ({2-dimethylamino-1-[dimethylimmoniomethyl]vinylamino}methylene)dimethylammonium dihexafluorophosphate (amino-reduction precursor) (76.62 mmol) are suspended in 200 ml of abs. methanol in an N$_2$-flushed 1000 ml three-necked flask with CaCl$_2$ protection, and a freshly prepared 1.5 M sodium methoxide solution in methanol is added dropwise with stirring. The reaction mixture is stirred at 60° C. for 30 min, during which a clear solution forms. For work-up, about 90% of the methanol are removed in a rotary evaporator, and the remaining residue is diluted with 300 ml of dichloromethane, washed 2× with 100 ml of water, dried over sodium sulfate and evaporated to dryness. The purification is carried out by chromatography (silica gel DCM +1-5% of MeOH). The product fractions are combined, evaporated to dryness and stirred with i-PrOH; m.p. 146-8° C.

4. Preparation of 1-[3-(5-hydroxypyrimidin-2-yl)phenyl]ethanone 5.10 g of N'-[2-(3-acetylphenyl)pyrimidin-5-yl]-N,N-dimethylformamidine (19 mmol) are suspended in 65 ml of water in a 250 ml one-necked flask provided with magnetic stirrer and condenser, 8.44 ml of 95-97% sulfuric acid (152 mmol) are added, and the mixture is stirred at a bath temperature of 130° C. for 2 h. The mixture is diluted with ice-water, during which a dark-brown resin deposits. The aqueous solution is decanted off and extracted with dichloromethane. The combined dichloromethane phases are dried, filtered and evaporated to dryness, and the residue is triturated with ether, filtered off with suction and dried (=K1). The deposited dark-brown resin is extracted by stirring with tetrahydrofuran, filtered off with suction, the crystals are discarded, and the mother liquor is evaporated to dryness (=R1). The aqueous phase from the dichloromethane extraction is evaporated to dryness, the residue is extracted by stirring 2× with tetrahydrofuran, and the combined decanted-off solutions are diluted with dichloromethane, dried, filtered and evaporated to dryness (=R2). R1 and R2 are combined, adsorbed on silica gel and purified by chromatography (silica gel/dichloromethane+0-5% of methanol). The chromatography residue is triturated with ether, filtered off with suction, washed with ether and dried (=K2).

K1 and K2 are combined; m.p. 199-200° C.

5. Preparation of 1-{3-[5-(3-dimethylaminopropoxy)pyrimidin-2-yl]-phenyl}ethanone 2.4 g of 1-[3-(5-hydroxypyrimidin-2-yl)phenyl]ethanone (11.2 mmol) are suspended in 40 ml of abs. THF in an N$_2$-flushed apparatus with CaCl$_2$ protection, 1.576 ml of 3-(dimethylamino)-1-propanol (13.44 mmol) and 5.602 g of polymer-bound triphenylphosphine (16.81 mmol) are added, and the mixture is stirred at RT for 30 min. 3.87 g of di-tert-butyl azodicarboxylate (16.81 mmol) are added with ice/H$_2$O cooling and stirring, and the mixture is stirred at RT for a further 2 h. For work-up, the polymer is removed by filtration and rinsed with copious dichloromethane, and the filtrate is extracted 1× with water and 2× with aqueous 1 N HCl. The combined HCl extracts are rendered alkaline using NaOH and extracted 3× with 50 ml of dichloromethane. The dichloromethane extracts are combined, dried over sodium sulfate, evaporated to dryness and crystallised from petroleum ether 40-60; m.p. 61-2° C.

6. Preparation of 1-{3-[5-(3-dimethylaminopropoxy)pyrimidin-2-yl]-phenyl}ethanol 3.114 g of 1-{3-[5-(3-dimethylaminopropoxy)pyrimidin-2-yl]phenyl}ethanone (10.4 mmol) are dissolved in 30 ml of abs. ethanol in a 100 ml one-necked flask, and 0.394 g of sodium borohydride (10.4 mmol) is subsequently added in portions with ice/water cooling and stirring, and the reaction batch is stirred at RT for a further 20 h. For work-up, the reaction mixture is diluted with 50 ml of dichloromethane and shaken 2× against water, and the dichloromethane phase is evaporated to dryness and purified by chromatography (silica gel/DCM/MeOH 9:1);

HPLC: RT: 2.40 min;
LC-MS: 1.330 min/M+H$^+$: 302.2 g/mol.

EXAMPLE 59

Preparation of 3-[1-(1-{3-[5-(3-dimethylaminopropoxy)pyrimidin-2-yl]-phenyl}ethyl)-6-oxo-1,6-dihydropyridazin-3-yl]benzonitrile ("A298")

197 mg of 3-cyanophenylpyridazinone (1.00 mmol) is suspended in a mixture of 5 ml of abs. THF and 1 ml of abs. DMF in an N$_2$-flushed apparatus with CaCl$_2$ protection, 301 mg of 1-{3-[5-(3-dimethylaminopropoxy)-pyrimidin-2-yl]phenyl}ethanol (1.00 mmol) and 500 mg of polymer-bound triphenylphosphine (1.5 mmol) are added, the mixture is stirred at RT for 30 min, 345 mg of di-tert-butyl azodicarboxylate (1.5 mmol) are subsequently added with ice/H$_2$O cooling and stirring, and the mixture is stirred at RT for a further 2 h. For work-up, the reaction mixture is diluted with 10 ml of methanol, and the polymer is removed by filtration. The residue is washed with dichloromethane, and the combined filtrate is evaporated to dryness in a rotary evaporator and purified by chromatography (silica gel: DCM+0-30% of MeOHF), giving "A298", m.p. 105-7° C.

The following compounds are obtained analogously

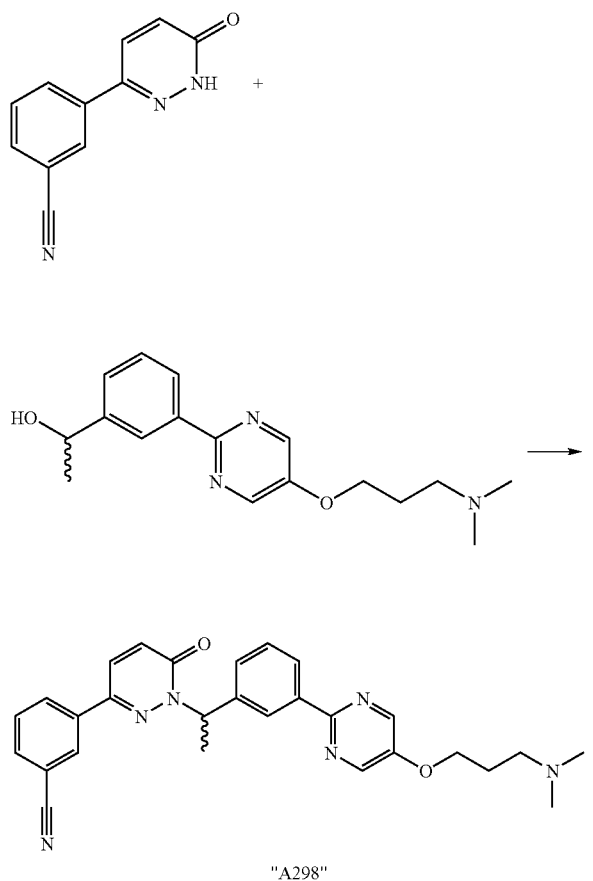

"A298"

| Compound No. | Name and/or structure | ESI [M + H]$^+$ |
|---|---|---|
| "A299" | 6-(3,5-difluorophenyl)-2-(1-{3-[5-(3-dimethylamino-propoxy)pyrimidin-2-yl]phenyl}ethyl)-2H-pyridazin-3-one | 492 |
| "A300" | 6-(3,5-difluorophenyl)-2-((R)-1-{3-[5-(3-dimethylamino-propoxy)pyrimidin-2-yl]phenyl}ethyl)-2H-pyridazin-3-one, hydrochloride | 492 |
| "A301" | 6-(3,5-difluorophenyl)-2-((S)-1-{3-[5-(3-dimethylamino-propoxy)pyrimidin-2-yl]phenyl}ethyl)-2H-pyridazin-3-one, hydrochloride | 492 |

EXAMPLE 60

Preparation of 3-(1-{3-[5-(1-methyl-1-oxypiperidin-4-ylmethoxy)-pyrimidin-2-yl]benzyl}-6-oxo-1,6-dihydropyridazin-3-yl)benzonitrile ("A302")

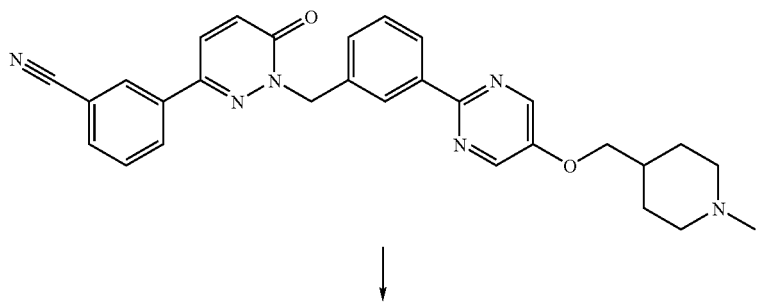

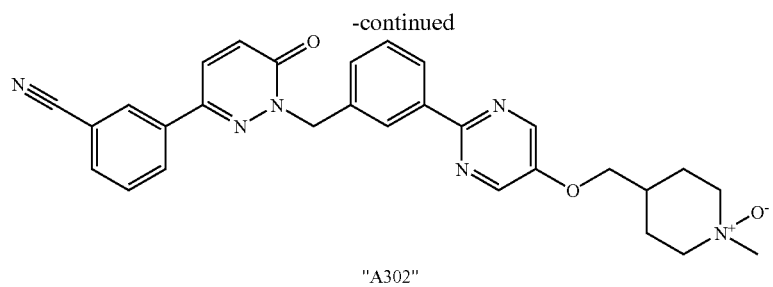

"A302"

100 mg of 3-(1-{3-[5-(1-methylpiperidin-4-ylmethoxy)pyrimidin-2-yl]benzyl}-6-oxo-1,6-dihydropyridazin-3-yl)benzonitrile (0.203 mmol) are suspended in 5 ml of water and 5 ml of acetonitrile in a reaction vial provided with a magnetic stirrer, 100 µl of perhydrol (0.979 mmol) are added, and the mixture is stirred at RT for 24 h. The mixture is then poured into water and extracted with dichloromethane, and the combined dichloromethane phases are dried, filtered and evaporated to dryness. The residue is adsorbed on silica gel and chromatographed (dichloromethane+0-50% of methanol). The chromatography residue is freeze-dried; ESI 509; m.p. 85° C. (decomposition).

EXAMPLE 61

Preparation of 3-(1-{3-[5-(1-formylpiperidin-4-ylmethoxy)pyrimidin-2-yl]-benzyl}-6-oxo-1,6-dihydropyridazin-3-yl)benzonitrile, ESI 409:

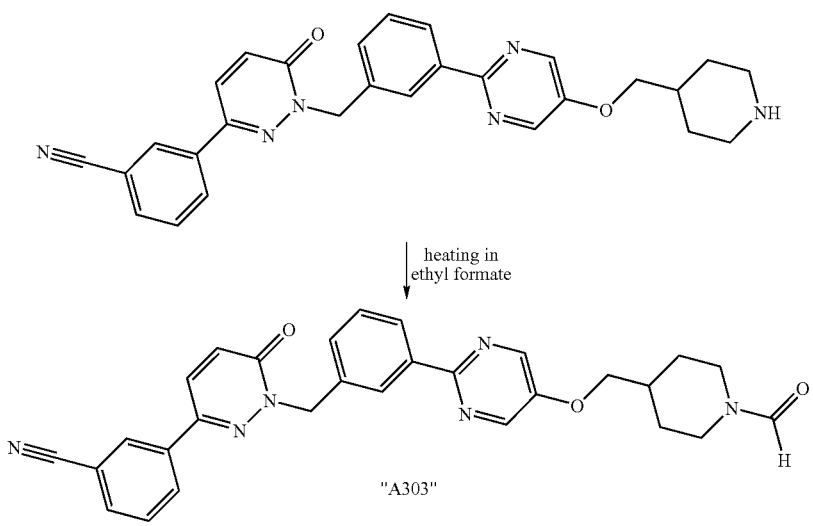

"A303"

EXAMPLE 62

Reaction of 3-(6-oxo-1-{3-[5-(piperidin-4-ylmethoxy)pyrimidin-2-yl]-benzyl}-1,6-dihydropyridazin-3-yl)benzonitrile with dimethylaminoethyl chloride hydrochloride and caesium carbonate in DMF followed by chromatographic separation gives ("A308")

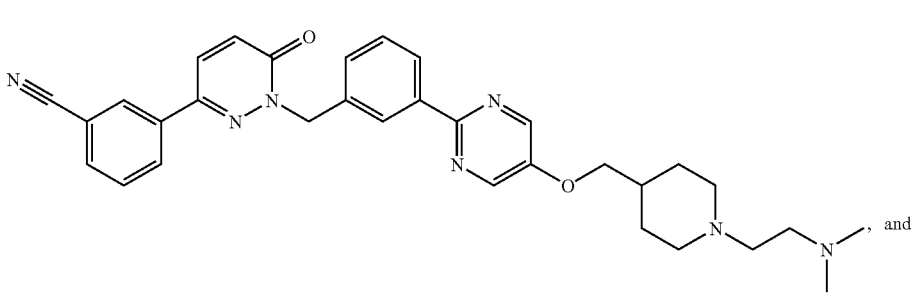

, and

ESI 550;

("A309")

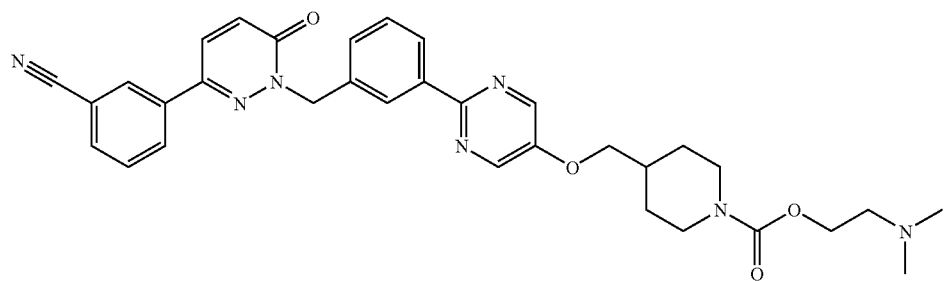

trifluoroacetate, ESI 594.

EXAMPLE 63

Reaction of 3-(6-oxo-1-{3-[5-(piperidin-4-ylmethoxy)pyrimidin-2-yl]-benzyl}-1,6-dihydropyridazin-3-yl)benzonitrile with beta-bromoethyl methyl ether and caesium carbonate in DMF gives the compound ("A311")

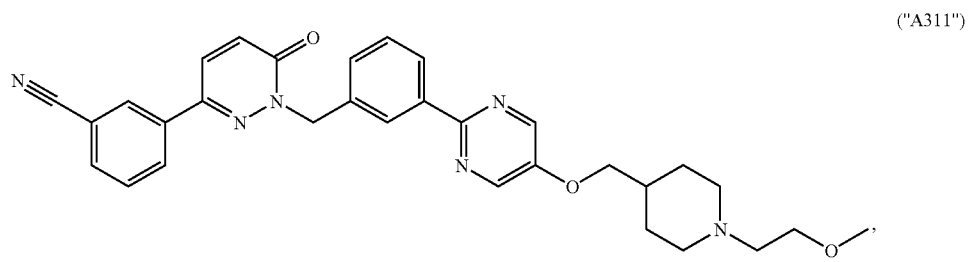

trifluoroacetate, ESI 537.

EXAMPLE 64

Reaction of 3-(6-oxo-1-{3-[5-(piperidin-4-ylmethoxy)pyrimidin-2-yl]-benzyl}-1,6-dihydropyridazin-3-yl)benzonitrile with bromoethane and caesium carbonate in DMF gives the compound ("A313")

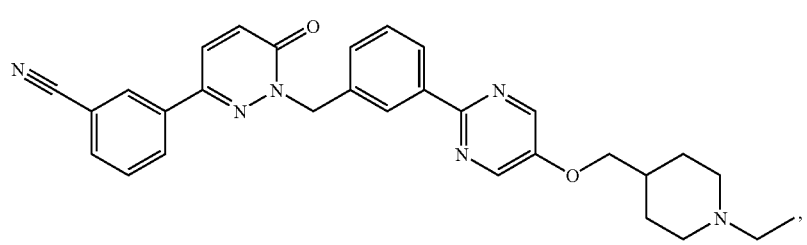

trifluoroacetate, ESI 507.

Pharmacological Data

TABLE 1

Met kinase inhibition of some representative compounds of the formula I

| Compound No. | IC$_{50}$ (cell assay) | IC$_{50}$ (enzyme assay) |
|---|---|---|
| "A1" | A | A |
| "A2" | A | A |
| "A6" |   | A |
| "A8" |   | A |
| "A9" | A |   |
| "A13" | B |   |
| "A14" | A |   |
| "A15" | A |   |
| "A16" | A |   |
| "A17" | A |   |
| "A18" | A |   |
| "A19" | A |   |
| "A20" | A |   |
| "A22" | A |   |
| "A23" | A |   |
| "A25" | A |   |
| "A26" | A |   |
| "A35" | A |   |
| "A57" | A |   |
| "A63" | A |   |
| "A64" | A |   |
| "A66" | A |   |
| "A79" | A |   |
| "A102" | A |   |
| "A168" | A |   |
| "A169" | A |   |
| "A189" | A |   |
| "A209" | A |   |
| "A226" | A |   |
| "A229" | A |   |
| "A237" | A |   |
| "A257" | A |   |
| "A287" | A |   |
| "A288" | A |   |

IC$_{50}$:
1 nM-1 μM = A
1 μM-10 μM = B
>10 μM = C

The compounds shown in Table I are particularly preferred compounds according to the invention.

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2 H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A compound of formula I

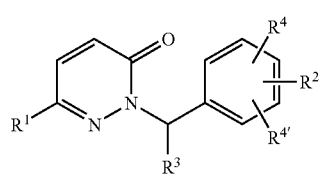

in which
R$^1$ denotes Ar or Het,
R$^2$ denotes pyrimidinyl, which is unsubstituted or mono-, di- or trisubstituted by Hal, A, [C(R$^3$)$_2$]$_n$OR$^3$, N=CR$^3$N(R$^3$)$_2$, SR$^3$, NO$_2$, CN, COOR$^3$, CON(R$^3$)$_2$, NR$^3$COA, NR$^3$SO$_2$A, SO$_2$N(R$^3$)$_2$, S(O)$_m$A, [C(R$^3$)$_2$]$_n$N(R$^3$)$_2$, [C(R$^3$)$_2$]$_n$Het, O[C(R$^3$)$_2$]$_p$OR$^3$, O[C(R$^3$)$_2$]$_n$N(R$^3$)$_2$, O[C(R$^3$)$_2$]$_n$C≡C[C(R$^3$)$_2$]$_n$N(R$^3$)$_2$, O[C(R$^3$)$_2$]$_n$N$^+$O$^{31}$(R$^3$)$_2$, O[C(R$^3$)$_2$]$_n$Het, S[C(R$^3$)$_2$]$_n$N(R$^3$)$_2$, S[C(R$^3$)$_2$]$_n$Het, NR$^3$[C(R$^3$)$_2$]$_n$N(R$^3$)$_2$, NR$^3$[C(R$^3$)$_2$]$_n$Het, NHCON(R$^3$)$_2$, NHCONH[C(R$^3$)$_2$]$_n$N(R$^3$)$_2$, NHCONH[C(R$^3$)$_2$]$_n$Het, [C(R$^3$)$_2$]$_n$NHCO[C(R$^3$)$_2$]$_n$N(R$^3$)$_2$, [C(R$^3$)$_2$]$_n$NHCO[C(R$^3$)$_2$]$_n$Het, CON(R$^3$)$_2$, CONR$^3$[C(R$^3$)$_2$]$_n$N(R$^3$)$_2$, CONR$^3$[C(R$^3$)$_2$]$_n$NR$^3$COOA, CONR$^3$[C(R$^3$)$_2$]$_n$OR$^3$, CONR$^3$[C(R$^3$)$_2$]$_n$Het, COHet, COA, CH=CH—COOR$^3$, CH=CH—N(R$^3$)$_2$ and/or =O, R$^3$ denotes H or A, R$^4$, R$^{4'}$ each, independently of one another, denote H, Hal, A, OR$^3$, CN, COOR$^3$, CON(R$^3$)$_2$, NR$^3$COA, NR$^3$SO$_2$A, SO$_2$N(R$^3$)$_2$ or S(O)$_m$A, Ar denotes phenyl, naphthyl or biphenyl, each of which is unsubstituted or mono-, di- or trisubstituted by Hal, A, [C(R$^3$)$_2$]$_n$OR$^3$, [C(R$^3$)$_2$]$_n$N(R$^3$)$_2$, SR$^3$, NO$_2$, CN, COOR$^3$, CON(R$^3$)$_2$, NR$^3$COA, NR$^3$SO$_2$A, SO$_2$N(R$^3$)$_2$, S(O)$_m$A, CO-Het, Het, O[C(R$^3$)$_2$]$_n$N(R$^3$)$_2$, O[C(R$^3$)$_2$]$_n$Het, NHCOOA, NHCON(R$^3$)$_2$, NHCOO[C(R$^3$)$_2$]$_n$N(R$^3$)$_2$, NHCOO[C(R$^3$)$_2$]$_n$Het, NHCONH[C(R$^3$)$_2$]$_n$N(R$^3$)$_2$, NHCONH[C(R$^3$)$_2$]$_n$Het, OCONH[C(R$^3$)$_2$]$_n$N(R$^3$)$_2$, OCONH[C(R$^3$)$_2$]$_n$Het, CONR$^3$[C(R$^3$)$_2$]$_n$N(R$^3$)$_2$, CONR$^3$[C(R$^3$)$_2$]$_n$Het and/or COA, Het denotes a mono-, bi- or tricyclic saturated, unsaturated or aromatic heterocycle having 1 to 4 N, O and/or S atoms, which is unsubstituted or mono-, di-, tri-, tetra- or penta- substituted by Hal, A, [C(R$^3$)$_2$]$_n$OR$^3$, [C(R$^3$)$_2$]$_n$N(R$^3$)$_2$, SR$^3$, NO$_2$, CN, COOR$^3$, CON(R$^3$)$_2$, NR$^3$COA, NR$^3$SO$_2$A, SO$_2$N(R$^3$)$_2$, S(O)$_m$A, CO-Het$^1$, [C(R$^3$)$_2$]$_n$Het$^1$, O[C(R$^3$)$_2$]$_n$N(R$^3$)$_2$, O[C(R$^3$)$_2$]$_n$Het$^1$, NHCOOA, NHCON(R$^3$)$_2$, NHCOO[C(R$^3$)$_2$]$_n$N(R$^3$)$_2$, NHCOO[C(R$^3$)$_2$]$_n$Het$^1$, NHCONH[C(R$^3$)$_2$]$_n$N(R$^3$)$_2$, NHCONH[C(R$^3$)$_2$]$_n$Het$^1$, OCONH[C(R$^3$)$_2$]$_n$N(R$^3$)$_2$, OCONH[C(R$^3$)$_2$]$_n$Het$^1$, CO-Het$^1$, CHO, COA, =S, =NH, =NA and/or =O, and where a ring nitrogen is optionally oxidized, Het$^1$ denotes a monocyclic saturated heterocycle having 1 to 2 N and/or O atoms, which is unsubstituted or mono- or disubstituted by A, OA, OH, Hal and/or =O, A denotes unbranched or branched alkyl having 1-10 C atoms, in which 1-7 H atoms are optionally replaced by F and/or in which one or two non-adjacent CH$_2$ groups are optionally replaced by O, NH, S, SO, SO$_2$ and/or by CH=CH groups, or cyclic alkyl having 3-7 C atoms, Hal denotes F, Cl, Br or I, m denotes 0, 1 or 2, n denotes 0, 1, 2, 3 or 4, and p denotes 1, 2, 3 or 4, or a pharmaceutically acceptable solvate, salt, tautomer or stereoisomer thereof.

2. A compound according to claim 1, in which

R$^2$ denotes pyrimidines, which is monosubstituted by Hal, A, [C(R$^3$)$_2$]$_n$OR$^3$, N=CR$^3$N(R$^3$)$_2$, CN, COOR$^3$, [C(R$^3$)$_2$]$_n$N(R$^3$)$_2$, [C(R$^3$)$_2$]$_n$Het, O[C(R$^3$)$_2$]$_p$OR$^3$, O[C(R$^3$)$_2$]$_n$N(R$^3$)$_2$, O[C(R$^3$)$_2$]$_n$C≡C[C(R$^3$)$_2$]$_n$N(R$^3$)$_2$, O[C(R$^3$)$_2$]$_n$N$^+$O$^-$(R$^3$)$_2$, O[C(R$^3$)$_2$]$_n$Het, NR$^3$[C(R$^3$)$_2$]$_n$N(R$^3$)$_2$, NR$^3$[C(R$^3$)$_2$]$_n$Het, [C(R$^3$)$_2$]$_n$NHCO[C(R$^3$)$_2$]$_n$N(R$^3$)$_2$, [C(R$^3$)$_2$]$_n$NHCO[C(R$^3$)$_2$]$_n$Het, CONR$^3$[C(R$^3$)$_2$]$_n$N(R$^3$)$_2$, CONR$^3$[C(R$^3$)$_2$]$_n$NR$^3$COOA, CONR$^3$[C(R$^3$)$_2$]$_n$OR$^3$, CONR$^3$[C(R$^3$)$_2$]$_n$Het, COHet, CH=CH—COOR$^3$, CH=CH—N(R$^3$)$_2$ and/or =O, or a pharmaceutically acceptable solvate, salt, tautomer or stereoisomer thereof.

3. A compound according to claim 1, in which

Ar denotes phenyl, naphthyl or biphenyl, each of which is unsubstituted or mono-, di- or trisubstituted by A, Hal, CN, S(O)$_m$A, NR$^3$COA, CON(R$^3$)$_2$, O[C(R$^3$)$_2$]$_n$N(R$^3$)$_2$, [C(R$^3$)$_2$]$_n$OR$^3$, CONR$^3$[C(R$^3$)$_2$]$_n$N(R$^3$)$_2$ and/or CONR$^3$[C(R$^3$)$_2$]$_n$Het, or a pharmaceutically acceptable solvate, salt, tautomer or stereoisomer thereof.

4. A compound according to claim 1, in which

R$^4$, R$^{4'}$ denote H, or a pharmaceutically acceptable solvate, salt, tautomer or stereoisomer thereof.

5. A compound according to claim 1, in which

Het denotes a mono-, bi- or tricyclic saturated, unsaturated or aromatic heterocycle having 1 to 4 N, O and/or S atoms, which is unsubstituted or mono-, di-, tri-, tetra- or penta- substituted by A, CHO, COOR$^3$, CON(R$^3$)$_2$, [C(R$^3$)$_2$]$_n$Het$^1$, [C(R$^3$)$_2$]$_n$OR$^3$, [C(R$^3$)$_2$]$_n$N(R$^3$)$_2$, O[C(R$^3$)$_2$]$_n$Het$^1$ and/or =O, and where a ring nitrogen is optionally oxidized, or a pharmaceutically acceptable solvate, salt, tautomer or stereoisomer thereof.

6. A compound according to claim 1, in which

Het$^1$ denotes a monocyclic saturated heterocycle having 1 to 2 N and/or O atoms, which is unsubstituted or mono- or disubstituted by A and/or =O, or a pharmaceutically acceptable solvate, salt, tautomer or stereoisomer thereof.

7. A compound according to claim 1, in which

A denotes unbranched or branched alkyl having 1-8 C atoms, in which 1-7 H atoms are optionally replaced by F, or a pharmaceutically acceptable solvate, salt, tautomer or stereoisomer thereof.

8. A compound according to claim 1, in which

R$^1$ denotes Ar or benzo-2,1,3-thiadiazolyl, or a pharmaceutically acceptable solvate, salt, tautomer or stereoisomer thereof.

9. A compound according to claim 1, in which

R$^3$ denotes H, methyl, ethyl or propyl, or a pharmaceutically acceptable solvate, salt, tautomer or stereoisomer thereof.

10. A compound according to claim 1, in which

R$^2$ denotes pyrimidinyl, which is unsubstituted or mono-, di- or trisubstituted by Hal, A, [C(R$^3$)$_2$]$_n$OR$^3$, N=CR$^3$N(R$^3$)$_2$, CN, COOR$^3$, [C(R$^3$)$_2$]$_n$N(R$^3$)$_2$, [C(R$^3$)$_2$]$_n$Het, O[C(R$^3$)$_2$]$_p$OR$^3$, O[C(R$^3$)$_2$]$_n$N(R$^3$)$_2$, O[C(R$^3$)$_2$]$_n$C≡C[C(R$^3$)$_2$]$_n$N(R$^3$)$_2$, O[C(R$^3$)$_2$]$_n$N$^+$O$^{3-}$(R$^3$)$_2$, O[C(R$^3$)$_2$]$_n$Het, NR$^3$[C(R$^3$)$_2$]$_n$N(R$^3$)$_2$, NR$^3$[C(R$^3$)$_2$]$_n$Het, [C(R$^3$)$_2$]$_n$NHCO[C(R$^3$)$_2$]$_n$N(R$^3$)$_2$, [C(R$^3$)$_2$]$_n$NHCO[C(R$^3$)$_2$]$_n$Het, CONR$^3$[C(R$^3$)$_2$]$_n$N(R$^3$)$_2$, CONR$^3$[C(R$^3$)$_2$]$_n$NR$^3$COOA, CONR$^3$[C(R$^3$)$_2$]$_n$OR$^3$, CONR$^3$[C(R$^3$)$_2$]$_n$Het, COHet, CH=CH—COOR$^3$, CH=CH—N(R$^3$)$_2$ and/or =O, or a pharmaceutically acceptable solvate, salt, tautomer or stereoisomer thereof.

11. A compound according to claim 1, in which

Het denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, azabicyclo[3.2.1]octyl, azabicyclo[2.2.2]octyl, imidazolidinyl, azepanyl or benzo-2,1,3-thiadiazolyl, each of which is unsubstituted or mono-, di-, tri-, tetra- or penta- substituted by A, CHO, COOR$^3$, CON(R$^3$)$_2$, [C(R$^3$)$_2$]$_n$Het$^1$, [C(R$^3$)$_2$]$_n$OR$^3$, [C(R$^3$)$_2$]$_n$N(R$^3$)$_2$, O[C(R$^3$)$_2$]$_n$Het$^1$ and/or =O, and where a ring nitrogen is optionally oxidized, or a pharmaceutically acceptable solvate, salt, tautomer or stereoisomer thereof.

12. A compound according to claim 1, in which
Het¹ denotes pyrrolidine, piperidine, piperazine or morpholine, each of which is unsubstituted or mono- or disubstituted by A and/or =O,
or a pharmaceutically acceptable solvate, salt, tautomer or stereoisomer thereof.

13. A compound according to claim 1, in which
$R^1$ denotes Ar or Het,
$R^2$ denotes pyrimidinyl, which is unsubstituted or mono-, di- or trisubstituted by Hal, A, $[C(R^3)_2]_nOR^3$, $N=CR^3N(R^3)_2$, CN, $COOR^3$, $[C(R^3)_2]_nN(R^3)_2$, $[C(R^3)_2]_n$Het, $O[C(R^3)_2]_pOR^3$, $O[C(R^3)_2]_nN(R^3)_2$, $O[C(R^3)_2]_nC\equiv C[C(R^3)_2]_nN(R^3)_2$, $O[C(R^3)_2]_nN^+O^{31}(R^3)_2$, $O[C(R^3)_2]_n$Het, $NR^3[C(R^3)_2]_nN(R^3)_2$, $NR^3[C(R^3)_2]_n$Het, $[C(R^3)_2]_nNHCO[C(R^3)_2]_nN(R^3)_2$, $[C(R^3)_2]_nNHCO[C(R^3)_2]_n$Het, $CONR^3[C(R^3)_2]_nN(R^3)_2$, $CONR^3[C(R^3)_2]_nNR^3COOA$, $CONR^3[C(R^3)_2]_nOR^3$, $CONR^3[C(R^3)_2]_n$Het, COHet, $CH=CH-COOR^3$, $CH=CH-N(R^3)_2$ and/or =O,
$R^3$ denotes H, methyl, ethyl or propyl,
$R^4$, $R^{4'}$ denote H,
Ar denotes phenyl, naphthyl or biphenyl, each of which is unsubstituted or mono-, di- or trisubstituted by A, Hal, CN, $S(O)_mA$, $NR^3COA$, $CON(R^3)_2$, $O[C(R^3)_2]_nN(R^3)_2$, $[C(R^3)_2]_nOR^3$, $CONR^3[C(R^3)_2]_nN(R^3)_2$ and/or $CONR^3[C(R^3)_2]_n$Het,
Het denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, azabicyclo[3.2.1]octyl, azabicyclo[2.2.2]octyl, imidazolidinyl, azepanyl or benzo-2,1,3-thiadiazolyl, each of which is unsubstituted or mono-, di-, tri-, tetra- or penta- substituted by A, CHO, $COOR^3$, $CON(R^3)_2$, $[C(R^3)_2]_n$Het¹, $[C(R^3)_2]_nOR^3$, $[C(R^3)_2]_nN(R^3)_2$, $O[C(R^3)_2]_n$Het¹ and/or =O,
and where a ring nitrogen is optionally oxidized,
Het¹ denotes pyrrolidine, piperidine, piperazine or morpholine, each of which is unsubstituted or mono- or disubstituted by A and/or =O,
A denotes unbranched or branched alkyl having 1-8 C atoms, in which 1-7 H atoms are optionally replaced by F,
Hal denotes F, Cl, Br or I,
m denotes 0, 1 or 2,
n denotes 0, 1, 2, 3 or 4, and
p denotes 1, 2, 3 or 4,
or a pharmaceutically acceptable solvate, salt, tautomer or stereoisomer thereof.

14. A process for preparing a compound of formula I according to claim 1 or a pharmaceutically acceptable solvate, salt, tautomer or stereoisomer thereof, comprising
reacting a compound of formula II

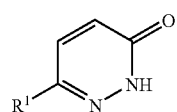

in which $R^1$ has the meaning indicated for the compound of formula I, with a compound of formula III

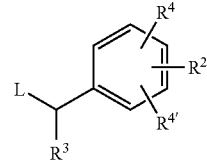

in which $R^2$, $R^3$, $R^4$ and $R^{4'}$ have the meanings indicated for the compound of formula I and
L denotes Cl, Br, I or a free or reactively functionally modified OH group,
and/or
converting a base or acid compound of formula I into one of its salts.

15. A pharmaceutical composition, comprising at least one compound of formula I according to claim 1 or a pharmaceutically acceptable solvate, salt, tautomer or stereoisomer thereof, and one or more pharmaceutically acceptable excipients and/or adjuvants.

16. A pharmaceutical composition according to claim 15, further comprising at least one further pharmaceutically active ingredient.

17. A kit, comprising separate packs of
(a) a compound of formula I according to claim 1 or a pharmaceutically acceptable solvate, salt, tautomer or stereoisomer thereof,
and
(b) a further pharmaceutically active ingredient.

18. A process for preparing a compound of formula I according to claim 1 or a pharmaceutically acceptable salt, tautomer or stereoisomer thereof, comprising
reacting a compound of formula II

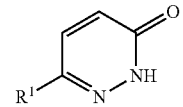

in which $R^1$ has the meaning indicated for the compound of formula I,
with a compound of formula III

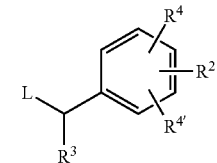

in which $R^2$, $R^3$, $R^4$ and $R^{4'}$ have the meanings indicated for the compound of formula I and
L denotes Cl, Br, I or a free or reactively functionally modified OH group.

19. A compound according to claim 1, wherein $R^2$ is pyrimidinyl, which is monosubstituted by Hal, A, $[C(R^3)_2]_nOR^3$, $N=CR^3N(R^3)_2$, $SR^3$, $NO_2$, CN, $COOR^3$, $CON(R^3)_2$, $NR^3COA$, $NR^3SO_2A$, $SO_2N(R^3)_2$, $S(O)_mA$, $[C(R^3)_2]_nN(R^3)_2$, $[C(R^3)_2]_n$Het, $O[C(R^3_2]_pOR^3$, $O[C(R^3)_2]_nN(R^3)_2$, O[C(R³)₂]ₙC≡C[C(R³)₂]ₙN(R³)₂, O[C(R³)₂]ₙN⁺O⁻(R³)₂, O[C(R³)₂]ₙHet, S[C(R³)₂]ₙN(R³)₂S[C(R³)₂]ₙHet, NR³[C(R³)₂]ₙN(R³)₂, NR³[C(R³)₂]ₙHet, NHCON(R³)₂, NHCONH[C(R³)₂]ₙN(R³)₂, NHCONH[C(R³)₂]ₙHet, [C(R³)₂]ₙNHCO[C(R³)₂]ₙN(R³)₂, [C(R³)₂]ₙNHCO[C(R³)₂]ₙHet, CON(R³)₂, CONR³[C(R³)₂]ₙN(R³)₂, CONR³[C(R³)₂]ₙNR³COOA, CONR³[C(R³)₂]ₙOR³, CONR³[C(R³)₂]ₙHet, COHet, COA, CH=CH—COOR³, CH=CH—N(R³)₂ and/or =O.

20. A compound, which is one of the following compounds

| No. | Name and/or structure |
|---|---|
| "A1" | 2-[3-(5-methylpyrimidin-2-yl)benzyl]-6-(3,4,5-trifluorophenyl)-2H-pyridazin-3-one |
| "A2" | 6-(3,5-difluorophenyl)-2-[3-(5-methylpyrimidin-2-yl)benzyl]-2H-pyridazin-3-one |
| "A3" | 2-[3-(4-methylpyrimidin-2-yl)benzyl]-6-(3,4,5-trifluorophenyl)-2H-pyridazin-3-one |
| "A4" | 2-(3-pyrimidin-2-ylbenzyl)-6-(3,4,5-trifluorophenyl)-2H-pyridazin-3-one |
| "A13" | 6-(3,5-difluorophenyl)-2-[3-(4-piperazin-1-ylpyrimidin-2-yl)benzyl]-2H-pyridazin-3-one |
| "A14" | 6-(3,5-difluorophenyl)-2-{3-[5-(4-methylpiperazin-1-ylmethyl)pyrimidin-2-yl]benzyl}-2H-pyridazin-3-one |
| "A15" | 3-{1-[3-(5-methylpyrimidin-2-yl)benzyl]-6-oxo-1,6-dihydropyridazin-3-yl}benzonitrile |
| "A16" | N'-(2-[3-(3,5-difluorophenyl)-6-oxo-6H-pyridazin-1-ylmethyl]-phenyl}pyrimidin-5-yl)-N,N-dimethylformamidine |
| "A17" | 2-[3-(5-aminopyrimidin-2-yl)benzyl]-6-(3,5-difluorophenyl)-2H-pyridazin-3-one |
| "A18" | 6-(3,5-difluorophenyl)-2-{3-[5-(4-methylpiperazin-1-yl)pyrimidin-2-yl]benzyl}-2H-pyridazin-3-one |
| "A19" | 6-(3,5-difluorophenyl)-2-[3-(5-piperazin-1-ylpyrimidin-2-yl)benzyl]-2H-pyridazin-3-one |
| "A20" | 2-{3-[5-(4-methylpiperazin-1-yl)pyrimidin-2-yl]benzyl}-6-(3,4,5-trifluorophenyl)-2H-pyridazin-3-one |
| "A21" | 6-(3,5-difluorophenyl)-2-[3-(5-hydroxypyrimidin-2-yl)benzyl]-2H-pyridazin-3-one |
| "A22" | 6-(3,5-difluorophenyl)-2-{3-[5-(3-dimethylaminopropoxy)-pyrimidin-2-yl]benzyl}-2H-pyridazin-3-one |
| "A23" | 6-(3,5-difluorophenyl)-2-{3-[5-(1-methylpiperidin-4-yloxy)-pyrimidin-2-yl]benzyl}-2H-pyridazin-3-one |
| |  |
| "A25" | 2-[3-(5-bromopyrimidin-2-yl)benzyl]-6-(3,5-difluorophenyl)-2H-pyridazin-3-one |
| "A26" | 6-(3,5-difluorophenyl)-2-{3-[5-(1-methyl-1H-pyrazol-4-yl)-pyrimidin-2-yl]benzyl}-2H-pyridazin-3-one |
| "A29" | ethyl 2-{3-[6-oxo-3-(3,4,5-trifluorophenyl)-6H-pyridazin-1-ylmethyl]phenyl}pyrimidine-5-carboxylate |
| "A30" | ethyl 2-{3-[3-(3,5-difluorophenyl)-6-oxo-6H-pyridazin-1-ylmethyl]phenyl}pyrimidine-5-carboxylate |
| |  |
| "A31" | 2-{3-[6-oxo-3-(3,4,5-trifluorophenyl)-6H-pyridazin-1-ylmethyl]-phenyl}pyrimidine-5-carboxylic acid |
| "A32" | 2-{3-[3-(3,5-difluorophenyl)-6-oxo-6H-pyridazin-1-ylmethyl]-phenyl}pyrimidine-5-carboxylic acid |
| "A33" | N-(2-dimethylaminoethyl)-2-{3-[6-oxo-3-(3,4,5-trifluorophenyl)-6H-pyridazin-1-ylmethyl]phenyl}pyrimidine-5-carboxamide |

-continued

| No. | Name and/or structure |
|---|---|
| "A34" | |
| "A35" | |
| "A36" | |
| "A37" | |
| "A38" | |

| No. | Name and/or structure |
|---|---|
| "A39" | 3-(3,4,5-trifluorophenyl)-pyridazin-6(1H)-one linked via N-CH2 to 3-(pyrimidin-2-yl)phenyl with 5-carboxamide (CONH2) |
| "A40" | Same core as A39; pyrimidine-5-carboxamide N-linked to (CH2)4-pyrrolidin-1-yl |
| "A41" | Same core; pyrimidine-5-carbonyl linked to 4-methylpiperazin-1-yl |
| "A42" | Same core; pyrimidine-5-carboxamide N-linked to (CH2)4-OH |
| "A43" | Same core; pyrimidine-5-carboxamide N-linked to 1-Boc-piperidin-4-yl |

| No. | Name and/or structure |
|---|---|
| "A44" | [structure] |
| "A44a" | [structure] |
| "A45" | [structure] |
| "A46" | [structure] |
| "A47" | [structure] |

-continued

| No. | Name and/or structure |
|---|---|
| "A48" | [structure: 3,4,5-trifluorophenyl-pyridazinone-CH2-phenyl-pyrimidine-C(O)NH-(CH2)3-N-methylpiperazine] |
| "A49" | [structure: 3,5-difluorophenyl-pyridazinone-CH2-phenyl-pyrimidine-C(O)NH-(CH2)4-N(CH3)2] |
| "A50" | [structure: 3,5-difluorophenyl-pyridazinone-CH2-phenyl-pyrimidine-C(O)NH-(CH2)4-pyrrolidine] |
| "A51" | N-[2-(1H-imidazol-4-yl)ethyl]-2-{3-[6-oxo-3-(3,4,5-trifluorophenyl)-6H-pyridazin-1-ylmethyl]phenyl}pyrimidine-5-carboxamide |
| "A52" | [structure: 3,4,5-trifluorophenyl-pyridazinone-CH2-phenyl-pyrimidine-C(O)NH-(CH2)3-1,2,4-triazole] |
| "A53" | [structure: 3,4,5-trifluorophenyl-pyridazinone-CH2-phenyl-pyrimidine-C(O)NH-(CH2)3-2-oxopyrrolidine] |
| "A54" | 2-[3-(5-chloropyrimidin-2-yl)benzyl]-6-(3,4,5-trifluorophenyl)-2H-pyridazin-3-one |
| "A55" | 4-{1-[3-(5-methylpyrimidin-2-yl)benzyl]-6-oxo-1,6-dihydropyridazin-3-yl}-N-(3-piperidin-1-ylpropyl)benzamide |
| "A56" | 6-(3,5-difluorophenyl)-2-{3-[5-(3-pyrrolidin-1-ylpropoxy)-pyrimidin-2-yl]benzyl}-2H-pyridazin-3-one |

-continued

| No. | Name and/or structure |
|---|---|
| "A57" | 6-(3,5-difluorophenyl)-2-(3-{5-[2-(4-methylpiperazin-1-yl)-ethoxy]pyrimidin-2-yl}benzyl)-2H-pyridazin-3-one |
| "A58" | 6-(3,5-difluorophenyl)-2-[3-(5-dimethylaminomethylpyrimidin-2-yl)benzyl]-2H-pyridazin-3-one |
| "A59" | 6-(3,5-difluorophenyl)-2-{3-[4-(methylpiperidin-4-yl-amino)pyrimidin-2-yl]benzyl}-2H-pyridazin-3-one |
| "A60" | 2-{3-[5-(3-dimethylaminopropoxy)pyrimidin-2-yl]benzyl}-6-(3,4,5-trifluorophenyl)-2H-pyridazin-3-one |
| "A63" | |
| "A64" | 2-{3-[5-(2-dimethylaminoethoxy)pyrimidin-2-yl]benzyl}-6-(3,5-difluorophenyl)-2H-pyridazin-3-one |
| "A65" | 2-{3-[5-(piperazin-1-yl)pyrimidin-2-yl]benzyl}-6-(3,4,5-trifluoro-phenyl)-2H-pyridazin-3-one |
| "A66" | 6-(3,5-difluorophenyl)-2-{3-[5-(1-methylpiperidin-4-ylmethoxy)-pyrimidin-2-yl]benzyl}-2H-pyridazin-3-one |
| "A71" | |
| "A72" | |

-continued

| No. | Name and/or structure |
|---|---|
| "A73" | (structure) |
| "A74" | (structure) |
| "A75" | 4-(2-{3-[3-(3,5-difluorophenyl)-6-oxo-6H-pyridazin-1-ylmethyl]-phenyl}pynmidin-5-yl)morpholin-3-one<br>(structure) |
| "A76" | N'-(2-{3-[3-(3,4,5-trifluorophenyl)-6-oxo-6H-pyridazin-1-yl-methyl]phenyl}pyrimidin-5-yl)-N,N-dimethylformamidine |
| "A77" | 2-{3-[6-oxo-3-(3,4,5-trifluorophenyl)-6H-pyridazin-1-ylmethyl]-phenyl}pyrimidine-5-carbonitrile<br>(structure) |
| "A78" | 6-[4-(3-dimethylaminopropoxy)-3,5-difluorophenyl]-2-[3-(5-methylpyrimidin-2-yl)benzyl]-2H-pyridazin-3-one<br>(structure) |
| "A79" | 6-benzo-1,2,5-thiadiazol-5-yl-2-[3-(5-methylpyrimidin-2-yl)-benzyl]-2H-pyridazin-3-one<br>(structure) |

-continued

| No. | Name and/or structure |
|---|---|
| "A80" | 6-(3,5-difluorophenyl)-2-[3-(6-oxo-1,6-dihydropyrimidin-2-yl)-benzyl]-2H-pyridazin-3-one |
| "A81" | 6-(3,5-difluorophenyl)-2-{3-[4-(3-dimethylaminopropoxy)-pyrimidin-2-yl]benzyl}-2H-pyridazin-3-one |
| "A82" | 2-[3-(5-aminopyrimidin-2-yl)benzyl]-6-(3,4,5-trifluorophenyl)-2H-pyridazin-3-one |
| "A83" | 2-(3-pyrimidin-5-ylbenzyl)-6-(3,4,5-trifluorophenyl)-2H-pyridazin-3-one |
| "A84" | *structure* |
| "A85" | N-(2-{3-[3-(3,5-difluorophenyl)-6-oxo-6H-pyridazin-1-ylmethyl]-phenyl}pyrimidin-5-yl)-2-dimethylaminoacetamide |
| "A87" | N-(2-{3-[3-(3,5-difluorophenyl)-6-oxo-6H-pyridazin-1-ylmethyl]-phenyl}pyrimidin-5-yl)-4-dimethylaminobutyramide |
| "A88" | *structure* |
| "A89" | *structure* |
| "A90" | *structure* |

| No. | Name and/or structure |
|---|---|
| "A92" | 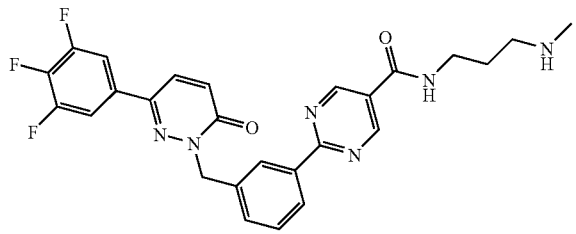 [SMILES: CNCCCNC(=O)c1cnc(-c2cccc(Cn3nc(-c4cc(F)c(F)c(F)c4)ccc3=O)c2)nc1] |
| "A93" | 2-[3-(5-aminomethylpyrimidin-2-yl)benzyl]-6-(3,4,5-trifluoro-phenyl)-2H-pyridazin-3-one |
| "A95" | N-(2-{3-[3-(3,5-difluorophenyl)-6-oxo-6H-pyridazin-1-ylmethyl]-phenyl}pyrimidin-5-yl)-3-dimethylaminopropionamide 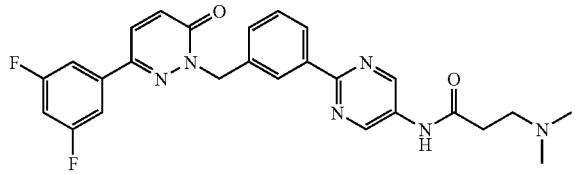 [SMILES: CN(C)CCC(=O)Nc1cnc(-c2cccc(Cn3nc(-c4cc(F)cc(F)c4)ccc3=O)c2)nc1] |
| "A96" | 3-(4-methylpiperazin-1-yl)-N-(2-{3-[6-oxo-3-(3,4,5-trifluoro-phenyl)-6H-pyridazin-1-ylmethyl]phenyl}pyrimidin-5-ylmethyl)-propionamide 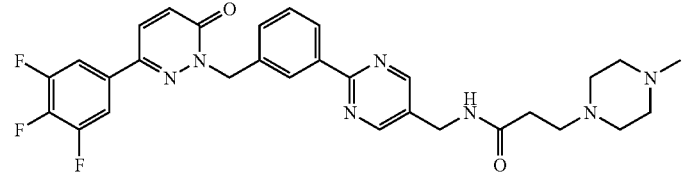 [SMILES: CN1CCN(CCC(=O)NCc2cnc(-c3cccc(Cn4nc(-c5cc(F)c(F)c(F)c5)ccc4=O)c3)nc2)CC1] |
| "A97" | 2-(4-methylpiperazin-1-yl)-N-(2-{3-[6-oxo-3-(3,4,5-trifluoro-phenyl)-6H-pyridazin-1-ylmethyl]phenyl}pyrimidin-5-yl-methyl)acetamide 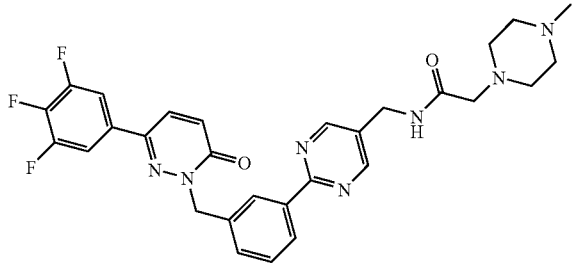 [SMILES: CN1CCN(CC(=O)NCc2cnc(-c3cccc(Cn4nc(-c5cc(F)c(F)c(F)c5)ccc4=O)c3)nc2)CC1] |
| "A98" | 2-methylamino-N-(2-{3-[6-oxo-3-(3,4,5-trifluorophenyl)-6H-pyridazin-1-ylmethyl]phenyl}pyrimidin-5-ylmethyl)acetamide 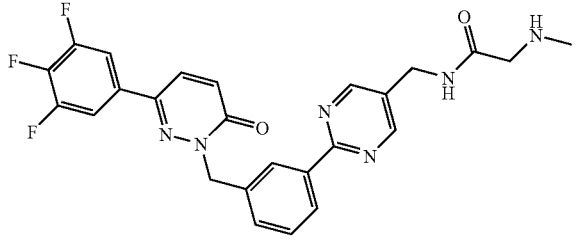 [SMILES: CNCC(=O)NCc1cnc(-c2cccc(Cn3nc(-c4cc(F)c(F)c(F)c4)ccc3=O)c2)nc1] |

-continued

| No. | Name and/or structure |
|---|---|
| "A99" | 3-dimethylamino-N-(2-{3-[6-oxo-3-(3,4,5-trifluorophenyl)-6H-pyridazin-1-ylmethyl]phenyl}pyrimidin-5-ylmethyl)propionamide 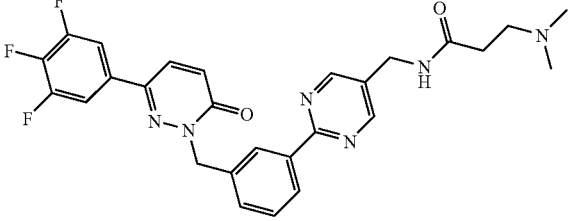 |
| "A100" | 2-[3-(5-methylpyrimidin-2-yl)benzyl]-6-(2H-pyrazol-3-yl)-2H-pyridazin-3-one |
| "A101" | 6-(3,5-difluorophenyl)-2-[3-(5-hydroxymethylpyrimidin-2-yl)-benzyl]-2H-pyridazin-3-one |
| "A102" | 6-(3,5-difluorophenyl)-2-{3-[5-(piperidin-4-yloxy)pyrimidin-2-yl]-benzyl}-2H-pyridazin-3-one |
| "A103" | 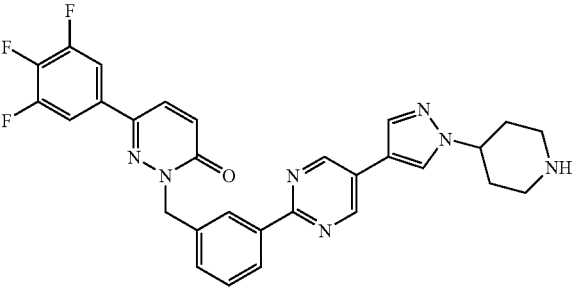 [SMILES: O=c1ccc(-c2cc(F)c(F)c(F)c2)nn1Cc1cccc(-c2ncc(-c3cnn(C4CCNCC4)c3)cn2)c1] |
| "A104" | 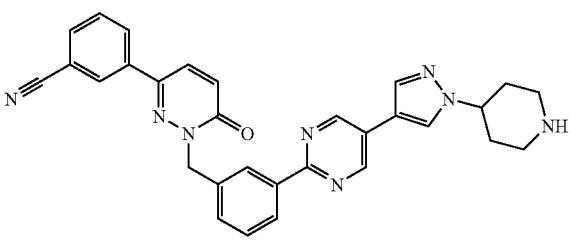 [SMILES: N#Cc1cccc(-c2ccc(=O)n(Cc3cccc(-c4ncc(-c5cnn(C6CCNCC6)c5)cn4)c3)n2)c1] |
| "A105" | 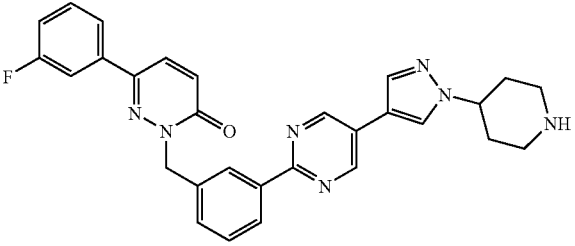 [SMILES: O=c1ccc(-c2cccc(F)c2)nn1Cc1cccc(-c2ncc(-c3cnn(C4CCNCC4)c3)cn2)c1] |
| "A106" | 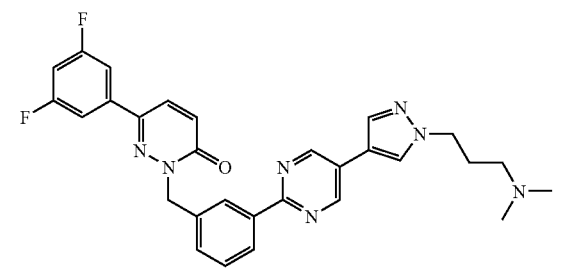 [SMILES: CN(C)CCCn1cc(-c2cnc(-c3cccc(Cn4nc(-c5cc(F)cc(F)c5)ccc4=O)c3)nc2)cn1] |

| No. | Name and/or structure |
|---|---|
| "A107" | 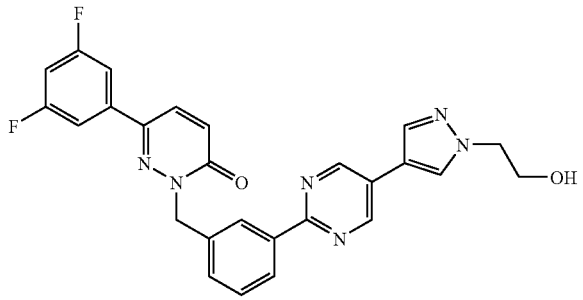 [SMILES: O=c1ccc(-c2cc(F)cc(F)c2)nn1Cc1cccc(-c2ncc(-c3cnn(CCO)c3)cn2)c1] |
| "A108" | 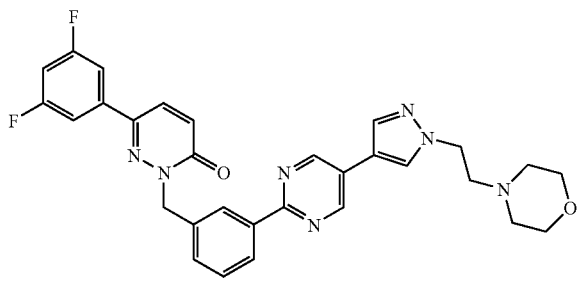 [SMILES: O=c1ccc(-c2cc(F)cc(F)c2)nn1Cc1cccc(-c2ncc(-c3cnn(CCN4CCOCC4)c3)cn2)c1] |
| "A109" | 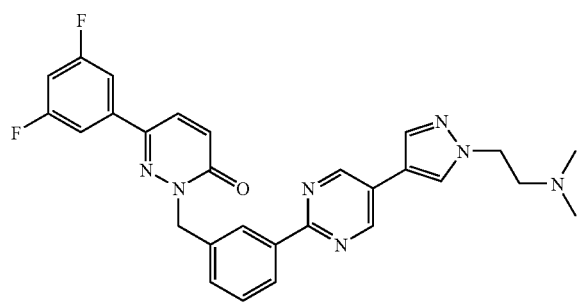 [SMILES: CN(C)CCn1cc(-c2cnc(-c3cccc(Cn4nc(-c5cc(F)cc(F)c5)ccc4=O)c3)nc2)cn1] |
| "A110" | 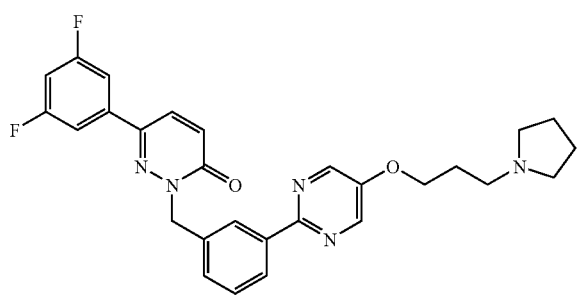 [SMILES: O=c1ccc(-c2cc(F)cc(F)c2)nn1Cc1cccc(-c2ncc(OCCCN3CCCC3)cn2)c1] |
| "A111" | 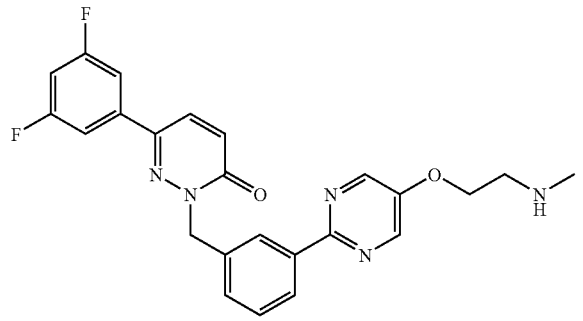 [SMILES: CNCCOc1cnc(-c2cccc(Cn3nc(-c4cc(F)cc(F)c4)ccc3=O)c2)nc1] |

| No. | Name and/or structure |
|---|---|
| "A112" | |
| "A113" | |
| "A114" | |
| "A115" | |
| "A116" | |
| "A117" | |
| "A118" | |
| "A119" | 6-(3,5-difluorophenyl)-2-{3-[5-(8-methyl-8-azabicyclo[3.2.1]oct-3-yloxy)pyrimidin-2-yl]benzyl}-2H-pyridazin-3-one |

-continued

| No. | Name and/or structure |
|---|---|
| "A120" | |
| "A121" | 6-(3,5-difluorophenyl)-2-{3-[5-((S)-1-methylpyrrolidin-3-yloxy)-pyrimidin-2-yl]benzyl}-2H-pyridazin-3-one, |
| "A122" | 6-(3,5-difluorophenyl)-2-{3-[5-((R)-1-methylpyrrolidin-3-yloxy)-pyrimidin-2-yl]benzyl}-2H-pyridazin-3-one, |
| "A123" | |
| "A124" | |
| "A125" | |
| "A126" | |
| "A127" | 6-(3,5-difluorophenyl)-2-{3-[5-(2-pyrrolidin-1-ylethoxy)-pyrimidin-2-yl]benzyl}-2H-pyridazin-3-one |
| "A128" | 6-(3,5-difluorophenyl)-2-{3-[5-(3-morpholin-4-ylpropoxy)-pyrimidin-2-yl]benzyl}-2H-pyridazin-3-one |

| No. | Name and/or structure |
|---|---|
| "A129" | (structure: 6-(3,5-difluorophenyl)-2-{3-[5-(3-diethylaminopropoxy)pyrimidin-2-yl]benzyl}-2H-pyridazin-3-one) |
| "A130" | 6-(3,5-difluorophenyl)-2-{3-[5-(2-morpholin-4-ylethoxy)-pyrimidin-2-yl]benzyl}-2H-pyridazin-3-one, hydrochloride |
| "A131" | (structure: 6-(3,5-difluorophenyl)-2-{3-[5-(1-methylpiperidin-3-yloxy)pyrimidin-2-yl]benzyl}-2H-pyridazin-3-one) |
| "A132" | 6-(3,5-difluorophenyl)-2-{3-[5-(4-methylaminobutoxy)pyrimidin-2-yl]benzyl}-2H-pyridazin-3-one |
| "A133" | 6-(3,5-difluorophenyl)-2-{3-[5-(3-methylaminopropoxy)-pyrimidin-2-yl]benzyl}-2H-pyridazin-3-one |
| "A134" | 6-(3,5-difluorophenyl)-2-{3-[5-(pyrrolidin-3-ylmethoxy)-pyrimidin-2-yl]benzyl}-2H-pyridazin-3-one |
| "A135" | 6-(3,5-difluorophenyl)-2-{3-[5-(3-ethylaminopropoxy)pyrimidin-2-yl]benzyl}-2H-pyridazin-3-one |
| "A136" | 2-{3-[5-(2-aminoethoxy)pyrimidin-2-yl]benzyl}-6-(3,5-difluoro-phenyl)-2H-pyridazin-3-one |
| "A137" | 6-(3,5-difluorophenyl)-2-{3-[5-(piperidin-3-yloxy)pyrimidin-2-yl]-benzyl}-2H-pyridazin-3-one |
| "A138" | 6-(3,5-difluorophenyl)-2-{3-[5-(piperidin-4-ylmethoxy)pyrimidin-2-yl]benzyl}-2H-pyridazin-3-one |
| "A139" | 6-(3,5-difluorophenyl)-2-{3-[5-(pyrrolidin-3-yloxy)pyrimidin-2-yl]benzyl}-2H-pyridazin-3-one |
| "A140" | 6-(3,5-difluorophenyl)-2-{3-[5-((S)-pyrrolidin-3-yloxy)pyrimidin-2-yl]benzyl}-2H-pyridazin-3-one |
| "A141" | 6-(3,5-difluorophenyl)-2-{3-[5-((R)-pyrrolidin-3-yloxy)pyrimidin-2-yl]benzyl}-2H-pyridazin-3-one |
| "A142" | 2-{3-[5-(piperidin-4-yloxy)pyrimidin-2-yl]benzyl}-6-pyridin-4-yl-2H-pyridazin-3-one |
|  | (structure) |
| "A143" | 4-(6-oxo-1-{3-[5-(piperidin-4-yloxy)pyrimidin-2-yl]benzyl}-1,6-dihydropyridazin-3-yl)benzonitrile |
|  | (structure) |
| "A144" | 3-(6-oxo-1-{3-[5-(piperidin-4-yloxy)pyrimidin-2-yl]benzyl}-1,6-dihydropyridazin-3-yl)benzonitrile |
| "A145" | 6-(3,5-difluorophenyl)-2-{3-[5-(2-piperazin-1-ylethoxy)pyrimidin-2-yl]benzyl}-2H-pyridazin-3-one |
| "A146" | 6-(3,5-difluorophenyl)-2-{3-[5-(piperidin-4-yloxy)pyrimidin-2-yl]-benzyl}-2H-pyridazin-3-one |
| "A147" | 3-(6-oxo-1-{3-[5-(2-piperazin-1-ylethoxy)pyrimidin-2-yl]benzyl}-1,6-dihydropyridazin-3-yl)benzonitrile |
| "A148" | 6-(3-fluorophenyl)-2-{3-[5-(piperidin-4-ylmethoxy)pyrimidin-2-yl]benzyl}-2H-pyridazin-3-one |

| No. | Name and/or structure |
|---|---|
| "A149" | 2-{3-[5-(1-piperidin-4-yl-1H-pyrazol-4-yl)pyrimidin-2-yl]benzyl}-6-(3,4,5-trifluorophenyl)-2H-pyridazin-3-one |
| "A150" | 3-(6-oxo-1-{3-[5-(1-piperidin-4-yl-1H-pyrazol-4-yl)pyrimidin-2-yl]benzyl}-1,6-dihydropyridazin-3-yl)benzonitrile |
| "A151" | 6-(1-methyl-1H-pyrazol-4-yl)-2-{3-[5-(1-piperidin-4-yl-1H-pyrazol-4-yl)pyrimidin-2-yl]benzyl}-2H-pyridazin-3-one |
| "A152" | 6-(3-methoxyphenyl)-2-{3-[5-(1-piperidin-4-yl-1H-pyrazol-4-yl)-pyrimidin-2-yl]benzyl}-2H-pyridazin-3-one |
| "A153" | 6-(3-fluorophenyl)-2-{3-[5-(1-piperidin-4-yl-1H-pyrazol-4-yl)-pyrimidin-2-yl]benzyl}-2H-pyridazin-3-one |
| "A154" | 6-(3,5-difluorophenyl)-2-{3-[5-(1H-pyrazol-4-yl)pyrimidin-2-yl]-benzyl}-2H-pyridazin-3-one |

| No. | Name and/or structure |
|---|---|
| "A155" | 6-(3,5-difluorophenyl)-2-(3-{5-[1-(2-methylaminoethyl)-1H-pyrazol-4-yl]pyrimidin-2-yl}benzyl)-2H-pyridazin-3-one, 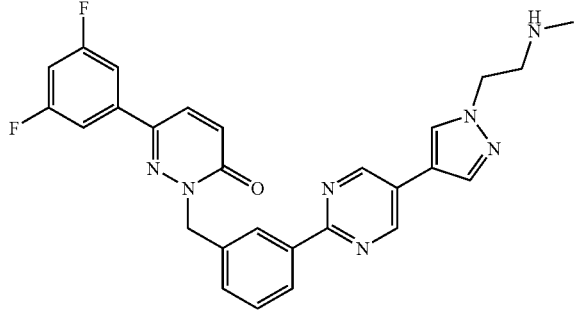 [SMILES: CNCCn1cc(-c2cnc(-c3cccc(Cn4nc(-c5cc(F)cc(F)c5)ccc4=O)c3)nc2)cn1] |
| "A156" | 6-(3-chlorophenyl)-2-{3-[5-(1-piperidin-4-yl-1H-pyrazol-4-yl)-pyrimidin-2-yl]benzyl}-2H-pyridazin-3-one 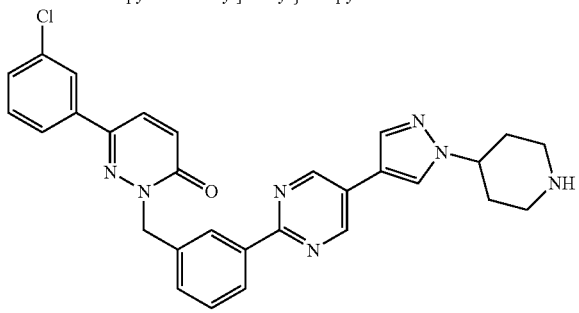 |
| "A157" | 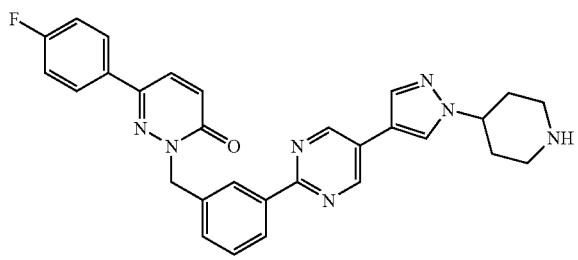 [SMILES: O=c1ccc(-c2ccc(F)cc2)nn1Cc1cccc(-c2ncc(-c3cnn(C4CCNCC4)c3)cn2)c1] |
| "A158" | 6-(3,5-difluorophenyl)-2-(3-{5-[1-(3-methylaminopropyl)-1H-pyrazol-4-yl]pyrimidin-2-yl}benzyl)-2H-pyridazin-3-one 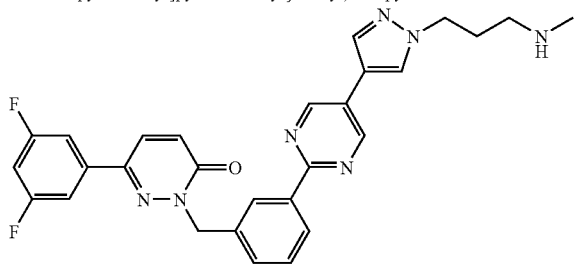 |

-continued

| No. | Name and/or structure |
|---|---|
| "A159" | 3-[1-(3-{5-[1-(2-methylaminoethyl)-1H-pyrazol-4-yl]pyrimidin-2-yl}benzyl)-6-oxo-1,6-dihydropyridazin-3-yl]benzonitrile 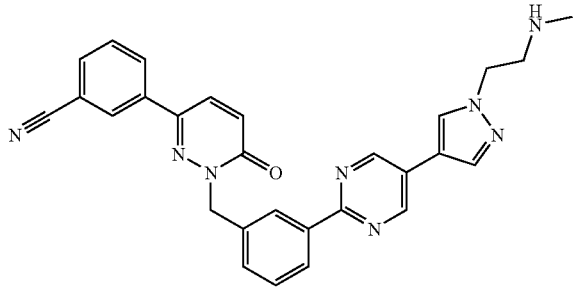 [SMILES: CNCCn1cc(-c2cnc(-c3cccc(Cn4nc(-c5cccc(C#N)c5)ccc4=O)c3)nc2)cn1] |
| "A160" | 6-(3,5-difluorophenyl)-2-(3-{5-[1-(2-piperazin-1-ylethyl)-1H-pyrazol-4-yl]pyrimidin-2-yl}benzyl)-2H-pyridazin-3-one 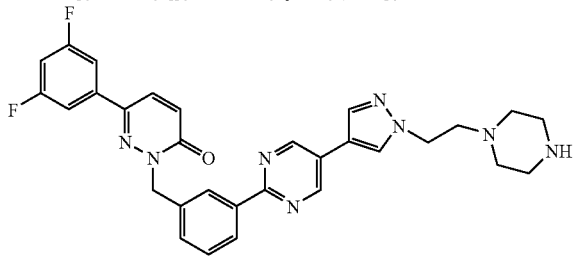 |
| "A161" | 3-(6-oxo-1-{3-[5-(1H-pyrazol-4-yl)pyrimidin-2-yl]benzyl}-1,6-dihydropyridazin-3-yl)benzonitrile 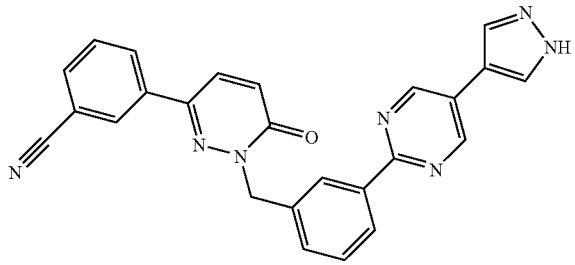 [SMILES: N#Cc1cccc(-c2ccc(=O)n(Cc3cccc(-c4ncc(-c5cn[nH]c5)cn4)c3)n2)c1] |
| "A162" | 3-[6-oxo-1-(3-{5-[1-(2-piperazin-1-ylethyl)-1H-pyrazol-4-yl]-pyrimidin-2-yl}benzyl)-1,6-dihydropyridazin-3-yl]benzonitrile 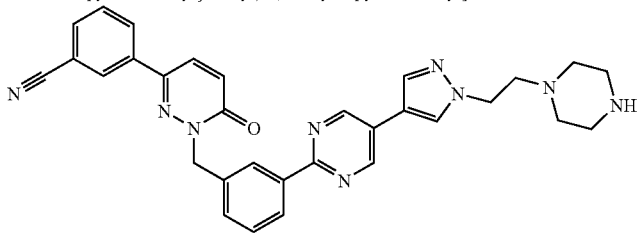 |
| "A163" | N-(4-dimethylaminobutyl)-2-[3-(6-oxo-3-pyridin-4-yl-6H-pyridazin-1-ylmethyl)phenyl]pyrimidine-5-carboxamide 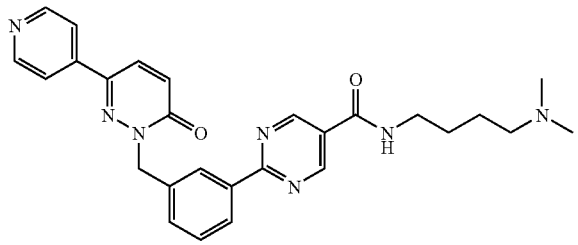 [SMILES: CN(C)CCCCNC(=O)c1cnc(-c2cccc(Cn3nc(-c4ccncc4)ccc3=O)c2)nc1] |

| No. | Name and/or structure |
|---|---|
| "A164" | N-(4-dimethylaminobutyl)-2-{3-[3-(4-cyanophenyl)-6-oxo-6H-pyridazin-1-ylmethyl]phenyl}pyrimidine-5-carboxamide 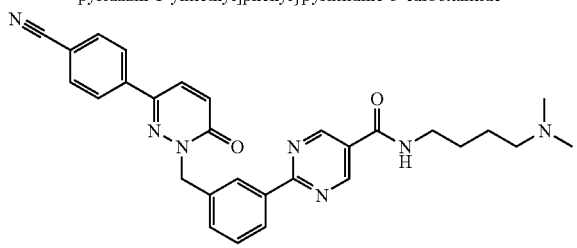 |
| "A165" | 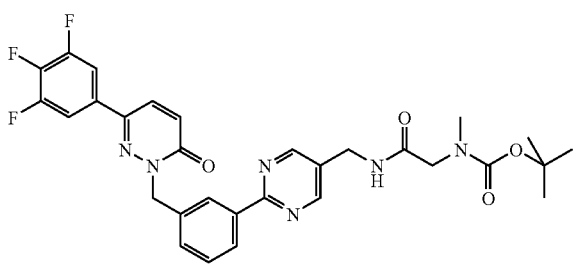 [SMILES: CN(CC(=O)NCc1cnc(-c2cccc(Cn3nc(-c4cc(F)c(F)c(F)c4)ccc3=O)c2)nc1)C(=O)OC(C)(C)C] |
| "A166" | 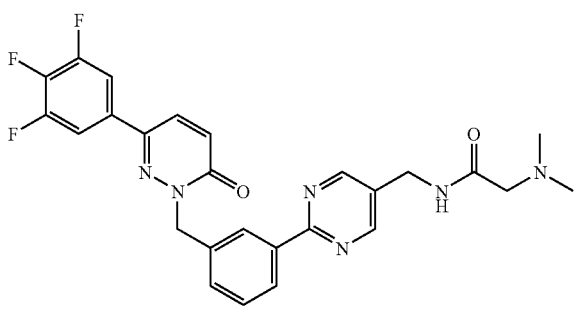 [SMILES: CN(C)CC(=O)NCc1cnc(-c2cccc(Cn3nc(-c4cc(F)c(F)c(F)c4)ccc3=O)c2)nc1] |
| "A167" | 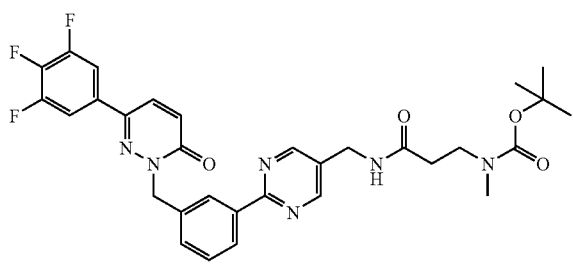 [SMILES: CN(CCC(=O)NCc1cnc(-c2cccc(Cn3nc(-c4cc(F)c(F)c(F)c4)ccc3=O)c2)nc1)C(=O)OC(C)(C)C] |
| "A168" | 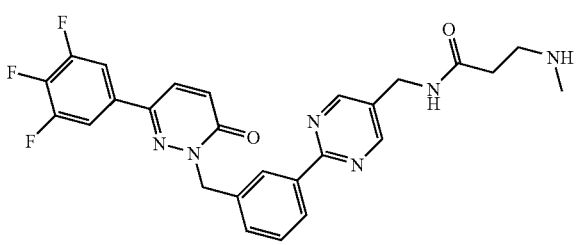 [SMILES: CNCCC(=O)NCc1cnc(-c2cccc(Cn3nc(-c4cc(F)c(F)c(F)c4)ccc3=O)c2)nc1] |

-continued

| No. | Name and/or structure |
|---|---|
| "A169" | 6-(1-methyl-1H-pyrazol-4-yl)-2-(3-{5-[1-(2-pyrrolidin-1-ylethyl)-1H-pyrazol-4-yl]pyrimidin-2-yl}benzyl)-2H-pyridazin-3-one |

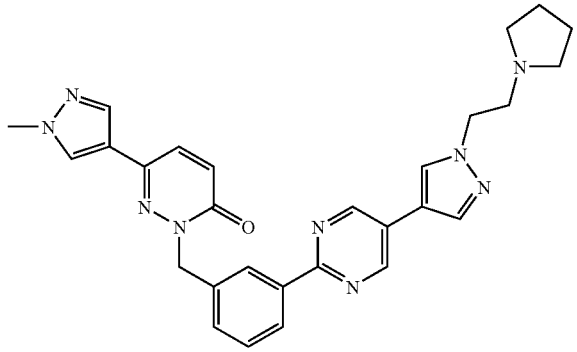 [SMILES: Cn1cc(-c2ccc(=O)n(Cc3cccc(-c4ncc(-c5cnn(CCN6CCCC6)c5)cn4)c3)n2)cn1]

| | |
|---|---|
| "A170" | 6-(3,5-difluorophenyl)-2-(3-{5-[1-(2-morpholin-4-ylethyl)-1H-pyrazol-4-yl]pyrimidin-2-yl}benzyl)-2H-pyridazin-3-one |

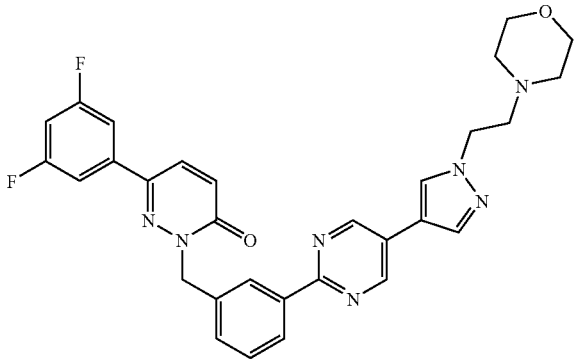 [SMILES: O=c1ccc(-c2cc(F)cc(F)c2)nn1Cc1cccc(-c2ncc(-c3cnn(CCN4CCOCC4)c3)cn2)c1]

| | |
|---|---|
| "A171" | 6-(3,5-difluorophenyl)-2-(3-{5-[1-(2-dimethylaminoethyl)-1H-pyrazol-4-yl]pyrimidin-2-yl}benzyl)-2H-pyridazin-3-one |

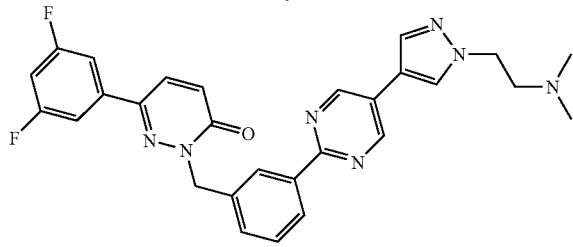

| | |
|---|---|
| "A172" | 6-(3,5-difluorophenyl)-2-(3-{5-[1-(3-dimethylaminopropyl)-1H-pyrazol-4-yl]pyrimidin-2-yl}benzyl)-2H-pyridazin-3-one |
| "A173" | 6-(3,5-difluorophenyl)-2-(3-{5-[1-(2-pyrrolidin-1-ylethyl)-1H-pyrazol-4-yl]pyrimidin-2-yl}benzyl)-2H-pyridazin-3-one |
| "A174" | 3-[1-(3-{5-[1-(2-morpholin-4-ylethyl)-1H-pyrazol-4-yl]pyrimidin-2-yl}benzyl)-6-oxo-1,6-dihydropyridazin-3-yl]benzonitrile |

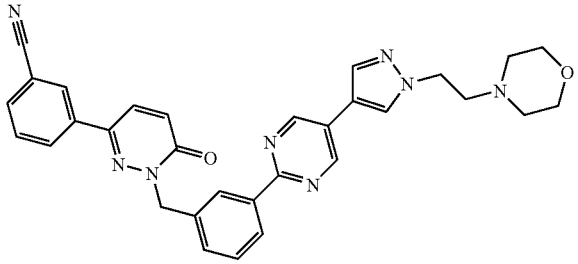 [SMILES: N#Cc1cccc(-c2ccc(=O)n(Cc3cccc(-c4ncc(-c5cnn(CCN6CCOCC6)c5)cn4)c3)n2)c1]

-continued

| No. | Name and/or structure |
|---|---|
| "A175" | 2-(3-{5-[1-(2-morpholin-4-ylethyl)-1H-pyrazol-4-yl]pyrimidin-2-yl}benzyl)-6-pyridin-3-yl-2H-pyridazin-3-one |

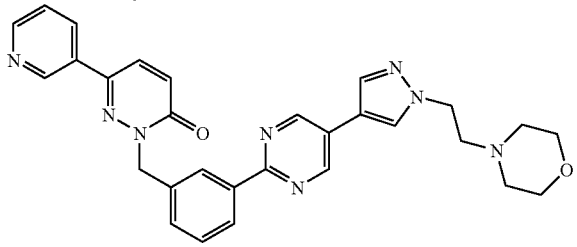

| | |
|---|---|
| "A176" | 6-(1-methyl-1H-pyrazol-4-yl)-2-(3-{5-[1-(2-morpholin-4-ylethyl)-1H-pyrazol-4-yl]pyrimidin-2-yl}benzyl)-2H-pyridazin-3-one |

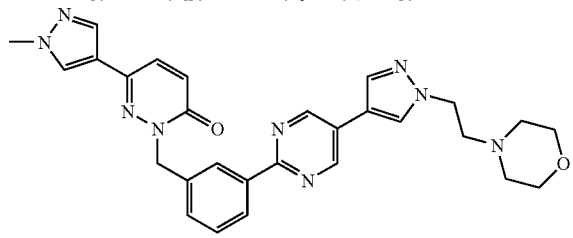

| | |
|---|---|
| "A177" | 2-(3-{5-[1-(2-morpholin-4-ylethyl)-1H-pyrazol-4-yl]pyrimidin-2-yl}benzyl)-6-pyridin-4-yl-2H-pyridazin-3-one |
| "A178" | 6-(4-methanesulfonylphenyl)-2-(3-{5-[1-(2-morpholin-4-ylethyl)-1H-pyrazol-4-yl]pyrimidin-2-yl}benzyl)-2H-pyridazin-3-one |
| "A179" | 6-pyridin-4-yl-2-(3-{5-[1-(2-pyrrolidin-1-ylethyl)-1H-pyrazol-4-yl]pyrimidin-2-yl}benzyl)-2H-pyridazin-3-one |
| "A180" | 4-[6-oxo-1-(3-{5-[1-(2-pyrrolidin-1-ylethyl)-1H-pyrazol-4-yl]-pyrimidin-2-yl}benzyl)-1,6-dihydropyridazin-3-yl]benzonitrile |

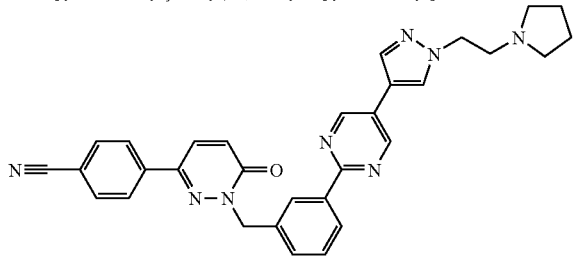

| | |
|---|---|
| "A181" | 2-(3-{5-[1-(2-morpholin-4-ylethyl)-1H-pyrazol-4-yl]pyrimidin-2-yl}benzyl)-6-pyridin-4-yl-2H-pyridazin-3-one |
| "A182" | |

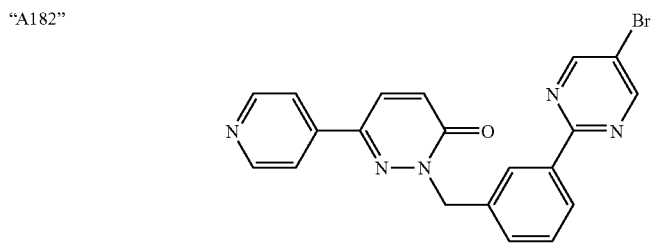

| | |
|---|---|
| "A183" | 6-(4-methanesulfonylphenyl)-2-(3-{5-[1-(2-morpholin-4-ylethyl)-1H-pyrazol-4-yl]pyrimidin-2-yl}benzyl)-2H-pyridazin-3-one |

| No. | Name and/or structure |
|---|---|
| "A184" | 6-(5-methyloxazol-2-yl)-2-(3-{5-[1-(2-pyrrolidin-1-ylethyl)-1H-pyrazol-4-yl]pyrimidin-2-yl}benzyl)-2H-pyridazin-3-one |

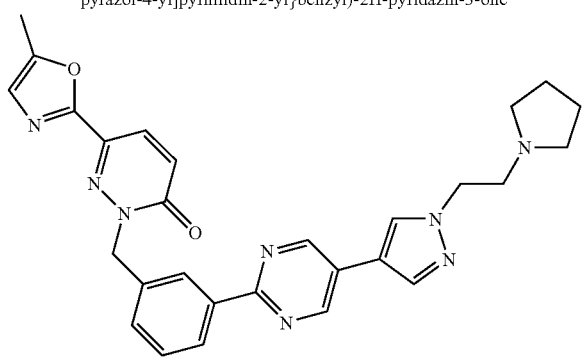

| | |
|---|---|
| "A185" | 6-(3-fluorophenyl)-2-(3-{5-[1-(2-pyrrolidin-1-ylethyl)-1H-pyrazol-4-yl]pyrimidin-2-yl}benzyl)-2H-pyridazin-3-one |
| "A186" | 6-(1-propyl-1H-pyrazol-4-yl)-2-(3-{5-[1-(2-pyrrolidin-1-ylethyl)-1H-pyrazol-4-yl]pyrimidin-2-yl}benzyl)-2H-pyridazin-3-one |

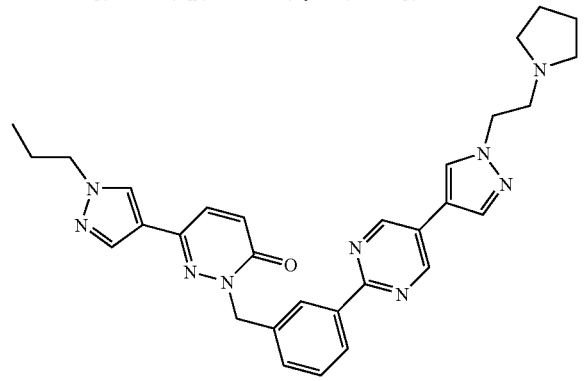 [SMILES: CCCn1cc(-c2ccc(=O)n(Cc3cccc(-c4ncc(-c5cnn(CCN6CCCC6)c5)cn4)c3)n2)cn1]

| | |
|---|---|
| "A187" | 2-(3-{5-[1-(2-pyrrolidin-1-ylethyl)-1H-pyrazol-4-yl]pyrimidin-2-yl}benzyl)-6-thiophen-3-yl-2H-pyridazin-3-one |

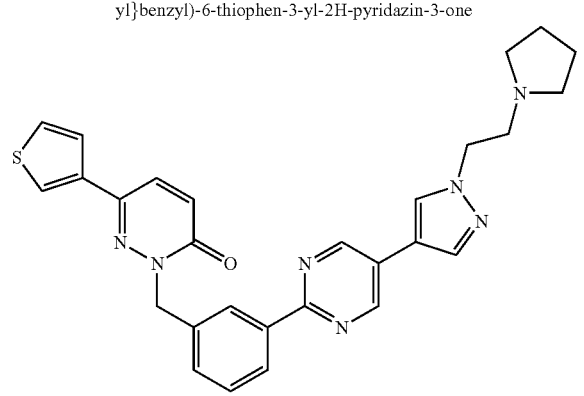

| | |
|---|---|
| "A188" | |

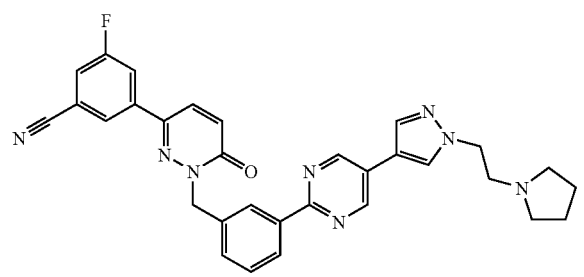 [SMILES: N#Cc1cc(F)cc(-c2ccc(=O)n(Cc3cccc(-c4ncc(-c5cnn(CCN6CCCC6)c5)cn4)c3)n2)c1]

-continued

| No. | Name and/or structure |
|---|---|
| "A188a" | [structure] |
| "A189" | 3-(1-{3-[5-(3-dimethylaminopropoxy)pyrimidin-2-yl]benzyl}-6-oxo-1,6-dihydropyridazin-3-yl)benzonitrile |
| "A190" | 2-{3-[5-(3-dimethylaminopropoxy)pyrimidin-2-yl]benzyl}-6-(1-methyl-1H-pyrazol-4-yl)-2H-pyridazin-3-one [structure] |
| "A191" | 2-{3-[5-(3-dimethylaminopropoxy)pyrimidin-2-yl]benzyl}-6-(3-fluorophenyl)-2H-pyridazin-3-one |
| "A192" | 2-{3-[5-(3-dimethylaminopropoxy)pyrimidin-2-yl]benzyl}-6-thiazol-2-yl-2H-pyridazin-3-one |
| "A193" | 2-{3-[5-(3-dimethylaminopropoxy)pyrimidin-2-yl]benzyl}-6-phenyl-2H-pyridazin-3-one |
| "A194" | 4-(1-{3-[5-(3-dimethylaminopropoxy)pyrimidin-2-yl]benzyl}-6-oxo-1,6-dihydropyridazin-3-yl)benzonitrile |
| "A195" | 2-{3-[5-(3-dimethylaminopropoxy)pyrimidin-2-yl]benzyl}-6-p-tolyl-2H-pyridazin-3-one |
| "A196" | 2-{3-[5-(3-dimethylaminopropoxy)pyrimidin-2-yl]benzyl}-6-(2H-pyrazol-3-yl)-2H-pyridazin-3-one |
| "A197" | 6-(3,4-difluorophenyl)-2-{3-[5-(3-dimethylaminopropoxy)-pyrimidin-2-yl]benzyl}-2H-pyridazin-3-one |
| "A198" | 2-{3-[5-(3-dimethylaminopropoxy)pyrimidin-2-yl]benzyl}-6-(4-methanesulfonylphenyl)-2H-pyridazin-3-one |
| "A199" | 2-{3-[5-(3-dimethylaminopropoxy)pyrimidin-2-yl]benzyl}-6-[4-(5-methyl-1,2,4-oxadiazol-3-yl)phenyl]-2H-pyridazin-3-one |
| "A200" | 2-{3-[5-(3-dimethylaminopropoxy)pyrimidin-2-yl]benzyl}-6-pyridin-4-yl-2H-pyridazin-3-one |
| "A201" | 6-(3-bromophenyl)-2-{3-[5-(3-dimethylaminopropoxy)pyrimidin-2-yl]benzyl}-2H-pyridazin-3-one |
| "A202" | 2-{3-[5-(3-dimethylaminopropoxy)pyrimidin-2-yl]benzyl}-6-(3,4,5-trifluorophenyl)-2H-pyridazin-3-one |
| "A203" | 6-(3,5-dimethoxyphenyl)-2-{3-[5-(3-dimethylaminopropoxy)-pyrimidin-2-yl]benzyl}-2H-pyridazin-3-one |
| "A204" | 2-{3-[5-(3-dimethylaminopropoxy)pyrimidin-2-yl]benzyl}-6-(3-fluoro-4-methoxyphenyl)-2H-pyridazin-3-one |
| "A205" | 2-{3-[5-(3-dimethylaminopropoxy)pyrimidin-2-yl]benzyl}-6-(4-methoxyphenyl)-2H-pyridazin-3-one |
| "A206" | 2-{3-[5-(3-dimethylaminopropoxy)pyrimidin-2-yl]benzyl}-6-(3-trifluoromethylphenyl)-2H-pyridazin-3-one, |
| "A207" | 6-(3-chlorophenyl)-2-{3-[5-(3-dimethylaminopropoxy)pyrimidin-2-yl]benzyl}-2H-pyridazin-3-one |
| "A208" | 2-{3-[5-(3-dimethylaminopropoxy)pyrimidin-2-yl]benzyl}-6-pyridin-3-yl-2H-pyridazin-3-one |
| "A209" | 2-{3-[5-(3-dimethylaminopropoxy)pyrimidin-2-yl]benzyl}-6-(1-methyl-1H-pyrazol-4-yl)-2H-pyridazin-3-one |
| "A210" | 6-(3-chloro-5-fluorophenyl)-2-{3-[5-(3-dimethylaminopropoxy)-pyrimidin-2-yl]benzyl}-2H-pyridazin-3-one |
| "A211" | 2-{3-[5-(3-dimethylaminopropoxy)pyrimidin-2-yl]benzyl}-6-(4-fluoro-3-methoxyphenyl)-2H-pyridazin-3-one |
| "A212" | 6-(4-chlorophenyl)-2-{3-[5-(3-dimethylaminopropoxy)pyrimidin-2-yl]benzyl}-2H-pyridazin-3-one |
| "A213" | 2-{3-[5-(3-dimethylaminopropoxy)pyrimidin-2-yl]benzyl}-6-(4-fluorophenyl)-2H-pyridazin-3-one |
| "A214" | 2-{3-[5-(3-dimethylaminopropoxy)pyrimidin-2-yl]benzyl}-6-thiophen-2-yl-2H-pyridazin-3-one |

-continued

| No. | Name and/or structure |
|---|---|
| "A215" | N-[4-(1-{3-[5-(3-dimethylaminopropoxy)pyrimidin-2-yl]benzyl}-6-oxo-1,6-dihydropyridazin-3-yl)phenyl]acetamide |
| "A216" | 6-(3,4-dimethoxyphenyl)-2-{3-[5-(3-dimethylaminopropoxy)-pyrimidin-2-yl]benzyl}-2H-pyridazin-3-one |
| "A217" | 6-benzo-1,2,5-thiadiazol-5-yl-2-{3-[5-(3-dimethylaminopropoxy)-pyrimidin-2-yl]benzyl}-2H-pyridazin-3-one |
| "A218" | 2-{3-[5-(3-dimethylaminopropoxy)pyrimidin-2-yl]benzyl}-6-turan-3-yl-2H-pyridazin-3-one |
| "A219" | 2-{3-[5-(3-dimethylaminopropoxy)pyrimidin-2-yl]benzyl}-6-(5-methyl-1,2,4-oxadiazol-3-yl)-2H-pyridazin-3-one |
| "A220" | 4-(1-{3-[5-(1-methylpiperidin-4-yloxy)pyrimidin-2-yl]benzyl}-6-oxo-1,6-dihydropyridazin-3-yl)benzonitrile |
| "A221" | 3-(1-{3-[5-(1-methylpiperidin-4-yloxy)pyrimidin-2-yl]benzyl}-6-oxo-1,6-dihydropyridazin-3-yl)benzonitrile |
| "A222" | 3-(1-{3-[5-(2-morpholin-4-ylethoxy)pyrimidin-2-yl]benzyl}-6-oxo-1,6-dihydropyridazin-3-yl)benzonitrile |
| "A223" | 2-{3-[5-(1-methylpiperidin-4-yloxy)pyrimidin-2-yl]benzyl}-6-pyridin-4-yl-2H-pyridazin-3-one |
| "A224" | 6-(4-methanesulfonylphenyl)-2-{3-[5-(1-methylpiperidin-4-yloxy)-pyrimidin-2-yl]benzyl}-2H-pyridazin-3-one |
| "A225" | methyl 5-(1-{3-[5-(1-methylpiperidin-4-yloxy)pyrimidin-2-yl]-benzyl}-6-oxo-1,6-dihydropyridazin-3-yl)thiophene-2-carboxylate |
| "A226" | 2-{3-[5-(1-methylpiperidin-4-yloxy)pyrimidin-2-yl]benzyl}-6-(1-methyl-1H-pyrazol-4-yl)-2H-pyridazin-3-one |
| "A227" | 2-{3-[5-(3-dimethylaminopropoxy)pyrimidin-2-yl]benzyl}-6-(5-oxo-4,5-dihydro-1,2,4-oxadiazol-3-yl)-2H-pyridazin-3-one |

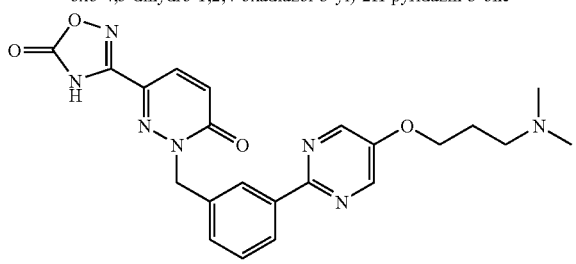

-continued

| No. | Name and/or structure |
|---|---|
| "A228" | 2-{3-[5-(3-dimethylaminopropoxy)pyrimidin-2-yl]benzyl}-6-piperazin-1-yl-2H-pyridazin-3-one |
| "A229" | 6-(1-methyl-1H-pyrazol-4-yl)-2-{3-[5-(2-morpholin-4-ylethoxy)-pyrimidin-2-yl]benzyl}-2H-pyridazin-3-one |
| "A230" | 2-[3-(5-bromopyrimidin-2-yl)benzyl]-6-(1-methyl-1H-pyrazol-4-yl)-2H-pyridazin-3-one |
| "A231" | 2-[3-(5-hydroxypyrimidin-2-yl)benzyl]-6-(1-methyl-1H-pyrazol-4-yl)-2H-pyridazin-3-one |
| "A235" | 6-(3-fluorophenyl)-2-{3-[5-(2-morpholin-4-ylethoxy)pyrimidin-2-yl]benzyl}-2H-pyridazin-3-one |
| "A237" | 2-{3-[5-(1-methylpiperidin-4-ylmethoxy)pyrimidin-2-yl]benzyl}-6-(1-methyl-1H-pyrazol-4-yl)-2H-pyridazin-3-one |
| "A238" | 2-{3-[5-(1-methylpiperidin-4-yloxy)pyrimidin-2-yl]benzyl}-6-(1-methyl-1H-pyrazol-4-yl)-2H-pyridazin-3-one |
| "A239" | 2-[3-(5-methoxypyrimidin-2-yl)benzyl]-6-(1-methyl-1H-pyrazol-4-yl)-2H-pyridazin-3-one |
| "A240" | 2-{3-[5-(3-methoxypropoxy)pyrimidin-2-yl]benzyl}-6-(1-methyl-1H-pyrazol-4-yl)-2H-pyridazin-3-one |
| "A241" | 2-{3-[5-(2-methoxyethoxy)pyrimidin-2-yl]benzyl}-6-(1-methyl-1H-pyrazol-4-yl)-2H-pyridazin-3-one |
| "A242" | 2-{3-[5-(2-morpholin-4-ylethoxy)pyrimidin-2-yl]benzyl}-6-(1-propyl-1H-pyrazol-4-yl)-2H-pyridazin-3-one |
| "A243" | 2-(3-{5-[2-(4-methylpiperazin-1-yl)ethoxy]pyrimidin-2-yl}-benzyl)-6-(1-methyl-1H-pyrazol-4-yl)-2H-pyridazin-3-one |
| "A244" | 2-(3-{5-[2-(4-methyl-3-oxopiperazin-1-yl)ethoxy]pyrimidin-2-yl}-benzyl)-6-(1-methyl-1H-pyrazol-4-yl)-2H-pyridazin-3-one |
| "A245" | 6-(1-methyl-1H-pyrazol-4-yl)-2-{3-[5-(3-morpholin-4-ylpropoxy)-pyrimidin-2-yl]benzyl}-2H-pyridazin-3-one |
| "A246" | 6-(1-methyl-1H-pyrazol-4-yl)-2-{3-[5-(2-morpholin-4-ylpropoxy)-pyrimidin-2-yl]benzyl}-2H-pyridazin-3-one |
| "A247" | 2-{3-[5-(1-methyl-2-morpholin-4-ylethoxy)pyrimidin-2-yl]-benzyl}-6-(1-methyl-1H-pyrazol-4-yl)-2H-pyridazin-3-one |
| "A248" | 2-{3-[5-(2-dimethylaminoethoxy)pyrimidin-2-yl]benzyl}-6-(1-methyl-1H-pyrazol-4-yl)-2H-pyridazin-3-one |

| No. | Name and/or structure |
|---|---|
| "A249" | 2-{3-[5-(2-methyl-3-morpholin-4-ylpropoxy)pyrimidin-2-yl]-benzyl}-6-(1-methyl-1H-pyrazol-4-yl)-2H-pyridazin-3-one |
| "A250" | 6-(1-methyl-1H-pyrazol-4-yl)-2-{3-[5-(2-pyrrolidin-1-ylethoxy)-pyrimidin-2-yl]benzyl}-2H-pyridazin-3-one |
| "A251" | 2-[3-(5-ethoxypyrimidin-2-yl)benzyl]-6-(1-methyl-1H-pyrazol-4-yl)-2H-pyridazin-3-one |
| "A252" | 6-(1-methyl-1H-pyrazol-4-yl)-2-{3-[5-(2-morpholin-4-yl-2-oxo-ethoxy)pyrimidin-2-yl]benzyl}-2H-pyridazin-3-one |
| "A253" | 6-(3-chlorophenyl)-2-{3-[5-(2-morpholin-4-ylethoxy)pyrimidin-2-yl]benzyl}-2H-pyridazin-3-one |
| "A254" | |
| "A255" | |
| "A256" | |
| "A257" | 3-(1-{3-[5-(1-methylpiperidin-4-ylmethoxy)pyrimidin-2-yl]-benzyl}-6-oxo-1,6-dihydropyridazin-3-yl)benzonitrile |
| "A260" | 3-(1-{3-[5-(3-dimethylaminopropoxy)pyrimidin-2-yl]benzyl}-6-oxo-1,6-dihydropyridazin-3-yl)benzamide |

-continued

| No. | Name and/or structure |
|---|---|
| "A261" | 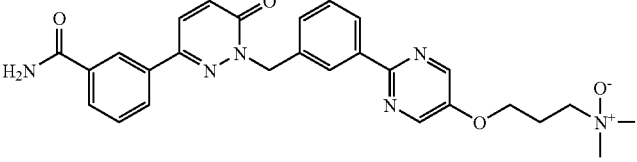 |
| "A262" | 3-{1-[3-(5-bromopyrimidin-2-yl)benzyl]-6-oxo-1,6-dihydro-pyridazin-3-yl}benzonitrile |
| "A263" | 3-{1-[3-(5-hydroxypyrimidin-2-yl)benzyl]-6-oxo-1,6-dihydro-pyridazin-3-yl}benzonitrile |
| "A264" | 3-(6-oxo-1-{3-[5-(piperidin-4-ylmethoxy)pyrimidin-2-yl]benzyl}-1,6-dihydropyridazin-3-yl)benzonitrile |
| "A265" | tert-butyl 4-(2-{3-[3-(3-cyanophenyl)-6-oxo-6H-pyridazin-1-ylmethyl]phenyl}pyrimidin-5-yloxymethyl)piperidine-1-carboxylate |
| "A266" | 6-(1-methyl-1H-pyrazol-4-yl)-2-{3-[5-(piperidin-4-yloxy)-pyrimidin-2-yl]benzyl}-2H-pyridazin-3-one |
| "A267" | 6-(1-methyl-1H-pyrazol-4-yl)-2-{3-[5-(piperidin-4-ylmethoxy)-pyrimidin-2-yl]benzyl}-2H-pyridazin-3-one |
| "A268" | 3-(1-{3-[5-(3-methylaminopropoxy)pyrimidin-2-yl]benzyl}-6-oxo-1,6-dihydropyridazin-3-yl)benzonitrile |
| | 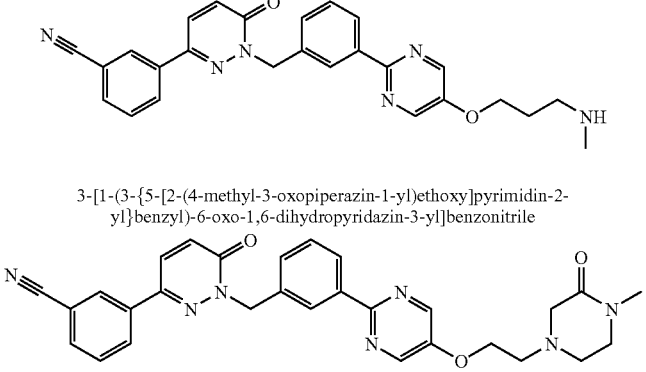 |
| "A269" | 3-[1-(3-{5-[2-(4-methyl-3-oxopiperazin-1-yl)ethoxy]pyrimidin-2-yl}benzyl)-6-oxo-1,6-dihydropyridazin-3-yl]benzonitrile |
| | 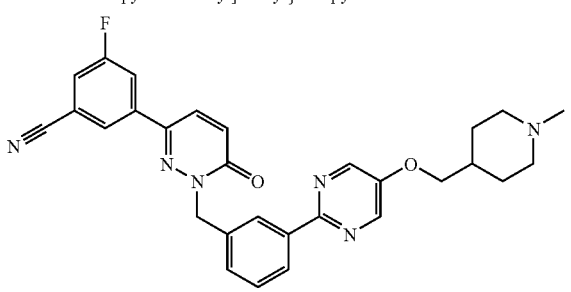 |
| "A270" | 3-[1-(3-{5-[2-(4-methylpiperazin-1-yl)ethoxy]pyrimidin-2-yl}-benzyl)-6-oxo-1,6-dihydropyridazin-3-yl]benzonitrile |
| "A271" | 3-(1-{3-[5-(2-methoxyethoxy)pyrimidin-2-yl]benzyl}-6-oxo-1,6-dihydropyridazin-3-yl)benzonitrile |
| "A272" | 3-(1-{3-[5-(3-methoxypropoxy)pyrimidin-2-yl]benzyl}-6-oxo-1,6-dihydropyridazin-3-yl)benzonitrile |
| "A273" | 6-(3-fluorophenyl)-2-{3-[5-(1-methylpiperidin-4-ylmethoxy)-pyrimidin-2-yl]benzyl}-2H-pyridazin-3-one |
| "A274" | 2-{3-[5-(1-methylpiperidin-4-yloxy)pyrimidin-2-yl]benzyl}-6-(1-propyl-1H-pyrazol-4-yl)-2H-pyridazin-3-one |
| "A275" | 6-(3-chlorophenyl)-2-{3-[5-(1-methylpiperidin-4-ylmethoxy)-pyrimidin-2-yl]benzyl}-2H-pyridazin-3-one |
| "A276" | |

| No. | Name and/or structure |
|---|---|
| "A276a" | *(structure shown)* |
| "A277" | 5-(1-{3-[5-(1-methylpiperidin-4-yloxy)pyrimidin-2-yl]benzyl}-6-oxo-1,6-dihydropyridazin-3-yl)thiophene-2-carboxylic acid |
| "A278" | 5-(1-{3-[5-(1-methylpiperidin-4-yloxy)pyrimidin-2-yl]benzyl}-6-oxo-1,6-dihydropyridazin-3-yl)thiophene-2-carboxamide |
| "A279" | N-methyl-5-(1-{3-[5-(1-methylpiperidin-4-yloxy)pyrimidin-2-yl]-benzyl}-6-oxo-1,6-dihydropyridazin-3-yl)thiophene-2-carboxamide |
| "A283" | methyl (E)-3-(2-{3-[6-oxo-3-(3,4,5-trifluorophenyl)-6H-pyridazin-1-ylmethyl]phenyl}pyrimidin-5-yl)acrylate |
| "A284" | 2-{3-[5-((E)-3-aminopropenyl)pyrimidin-2-yl]benzyl}-6-(3,4,5-trifluorophenyl)-2H-pyridazin-3-one |
| "A285" | 2-{3-[5-(3-aminopropyl)pyrimidin-2-yl]benzyl}-6-(3,4,5-trifluorophenyl)-2H-pyridazin-3-one |
| "A286" | 2-{3-[5-(4-methylpiperazin-1-yl)pyrimidin-2-yl]benzyl}-6-(1-methyl-1H-pyrazol-4-yl)-2H-pyridazin-3-one |
| "A287" | 3-(1-{3-[5-(4-methylpiperazin-1-yl)pyrimidin-2-yl]benzyl}-6-oxo-1,6-dihydropyridazin-3-yl)benzonitrile |
| "A288" | 3-{6-oxo-1-[3-(5-piperazin-1-ylpyrimidin-2-yl)benzyl]-1,6-dihydropyridazin-3-yl}benzonitrile |
| "A289" | 6-(4-methanesulfonylphenyl)-2-[3-(5-piperazin-1-ylpyrimidin-2-yl)benzyl]-2H-pyridazin-3-one |
| "A290" | 4-{1-[3-(5-aminopyrimidin-2-yl)benzyl]-6-oxo-1,6-dihydro-pyridazin-3-yl}benzonitrile |
| "A291" | 3-{1-[3-(5-aminopyrimidin-2-yl)benzyl]-6-oxo-1,6-dihydro-pyridazin-3-yl}benzonitrile |
| "A292" | 6-(1-methyl-1H-pyrazol-4-yl)-2-[3-(5-piperazin-1-ylpyrimidin-2-yl)benzyl]-2H-pyridazin-3-one |
| "A293" | 2-[3-(5-aminopyrimidin-2-yl)benzyl]-6-(1-methyl-1H-pyrazol-4-yl)-2H-pyridazin-3-one |
| "A294" | 2-{3-[5-(2-hydroxyethoxy)pyrimidin-2-yl]benzyl}-6-(1-methyl-1H-pyrazol-4-yl)-2H-pyridazin-3-one |
| "A295" | 3-(1-{3-[5-(3-hydroxypropoxy)pyrimidin-2-yl]benzyl}-6-oxo-1,6-dihydropyridazin-3-yl)benzonitrile |
| "A296" | 3-(1-{3-[5-(2-hydroxyethoxy)pyrimidin-2-yl]benzyl}-6-oxo-1,6-dihydropyridazin-3-yl)benzonitrile |
| "A297" | 2-{3-[5-(3-hydroxypropoxy)pyrimidin-2-yl]benzyl}-6-(1-methyl-1H-pyrazol-4-yl)-2H-pyridazin-3-one |
| "A298" | 3-[1-(1-{3-[5-(3-dimethylaminopropoxy)pyrimidin-2-yl]phenyl}-ethyl)-6-oxo-1,6-dihydropyridazin-3-yl]benzonitrile |
| "A299" | 6-(3,5-difluorophenyl)-2-(1-{3-[5-(3-dimethylaminopropoxy)-pyrimidin-2-yl]phenyl}ethyl)-2H-pyridazin-3-one |
| "A300" | 6-(3,5-difluorophenyl)-2-((R)-1-{3-[5-(3-dimethylaminopropoxy)-pyrimidin-2-yl]phenyl}ethyl)-2H-pyridazin-3-one |
| "A301" | 6-(3,5-difluorophenyl)-2-((S)-1-{3-[5-(3-dimethylaminopropoxy)-pyrimidin-2-yl]phenyl}ethyl)-2H-pyridazin-3-one |
| "A302" | 3-(1-{3-[5-(1-methyl-1-oxypiperidin-4-ylmethoxy)pyrimidin-2-yl]-benzyl}-6-oxo-1,6-dihydropyridazin-3-yl)benzonitrile |
| "A303" | 3-(1-{3-[5-(1-formylpiperidin-4-ylmethoxy)pyrimidin-2-yl]-benzyl}-6-oxo-1,6-dihydropyridazin-3-yl)benzonitrile |
| "A304" | *(structure shown)* |

-continued
| No. | Name and/or structure |
|---|---|
| "A305" | 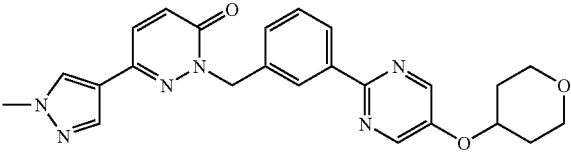 [SMILES: Cn1cc(-c2ccc(=O)n(Cc3cccc(-c4ncc(OC5CCOCC5)cn4)c3)n2)cn1] |
| "A306" | 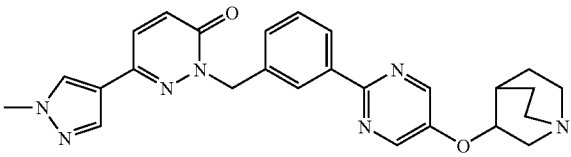 [SMILES: Cn1cc(-c2ccc(=O)n(Cc3cccc(-c4ncc(OC5CN6CCC5CC6)cn4)c3)n2)cn1] |
| "A307" | 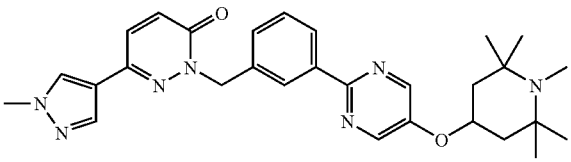 |
| "A308" | 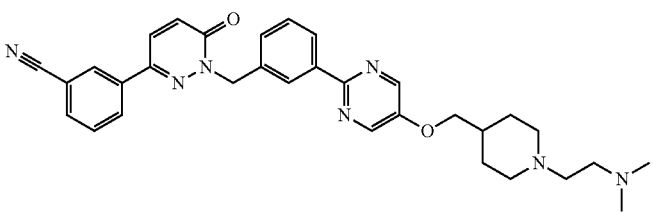 [SMILES: CN(C)CCN1CCC(COc2cnc(-c3cccc(Cn4nc(-c5cccc(C#N)c5)ccc4=O)c3)nc2)CC1] |
| "A309" | 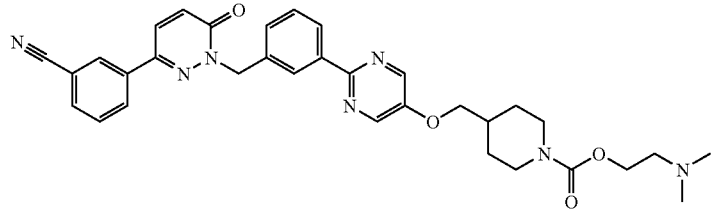 [SMILES: CN(C)CCOC(=O)N1CCC(COc2cnc(-c3cccc(Cn4nc(-c5cccc(C#N)c5)ccc4=O)c3)nc2)CC1] |
| "A310" | 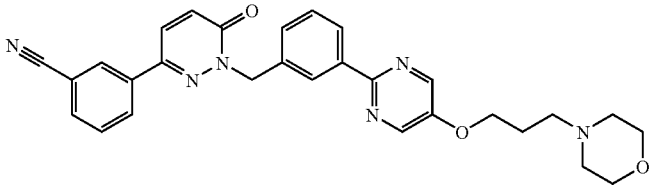 [SMILES: N#Cc1cccc(-c2ccc(=O)n(Cc3cccc(-c4ncc(OCCCN5CCOCC5)cn4)c3)n2)c1] |
| "A311" | 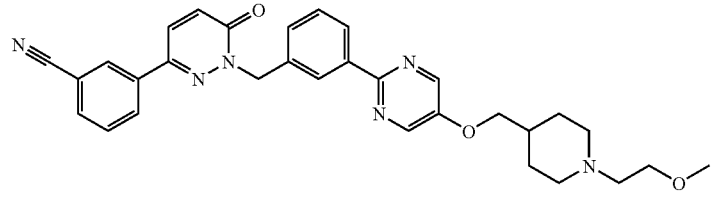 [SMILES: COCCN1CCC(COc2cnc(-c3cccc(Cn4nc(-c5cccc(C#N)c5)ccc4=O)c3)nc2)CC1] |
| "A312" | 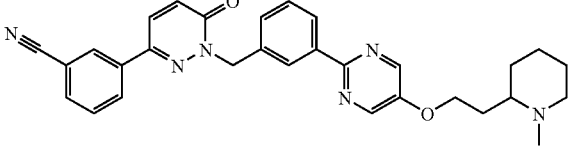 |

| No. | Name and/or structure |
|---|---|
| "A313" | 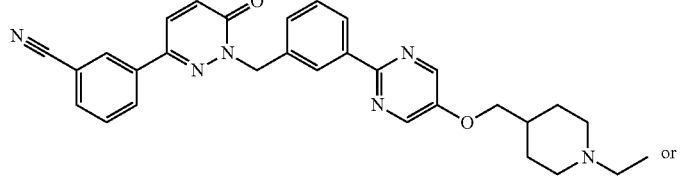 or |
| "A314" | 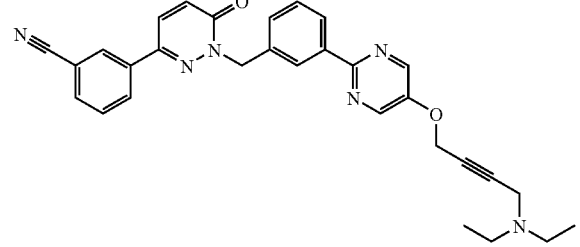 | or a pharmaceutically acceptable solvate, salt, tautomer or stereoisomer thereof.

21. A compound, which is one of the following compounds

| No. | Name and/or structure |
|---|---|
| "A23" | 6-(3,5-difluorophenyl)-2-{3-[5-(1-methylpiperidin-4-yloxy)-pyrimidin-2-yl]benzyl}-2H-pyridazin-3-one<br />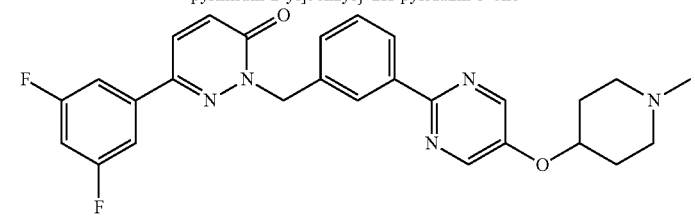 |
| "A30" | ethyl 2-{3-[3-(3,5-difluorophenyl)-6-oxo-6H-pyridazin-1-yl-methyl]phenyl}pyrimidine-5-carboxylate<br />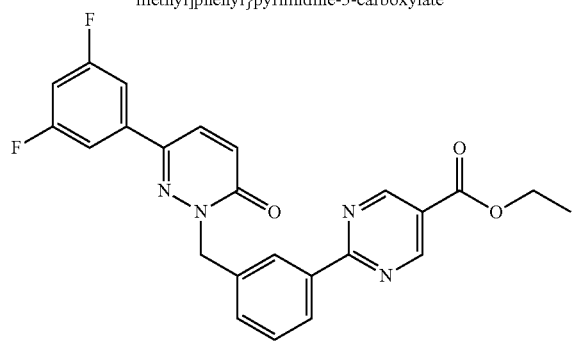 |

| No. | Name and/or structure |
|---|---|
| "A34" | 3-[3,4,5-trifluorophenyl]-pyridazin-6-one linked via N-CH2 to phenyl-pyrimidine-C(O)NH-(CH2)3-N(CH3)2 |
| "A35" | 3-[3,4,5-trifluorophenyl]-pyridazin-6-one linked via N-CH2 to phenyl-pyrimidine-C(O)NH-(CH2)4-N(CH3)2 |
| "A36" | 3-[3,4,5-trifluorophenyl]-pyridazin-6-one linked via N-CH2 to phenyl-pyrimidine-C(O)NH-(CH2)2-NH-C(O)O-C(CH3)3 |
| "A37" | 3-[3,4,5-trifluorophenyl]-pyridazin-6-one linked via N-CH2 to phenyl-pyrimidine-C(O)NH-(CH2)3-NH-C(O)O-C(CH3)3 |

-continued
| No. | Name and/or structure |
|---|---|
| "A38" | 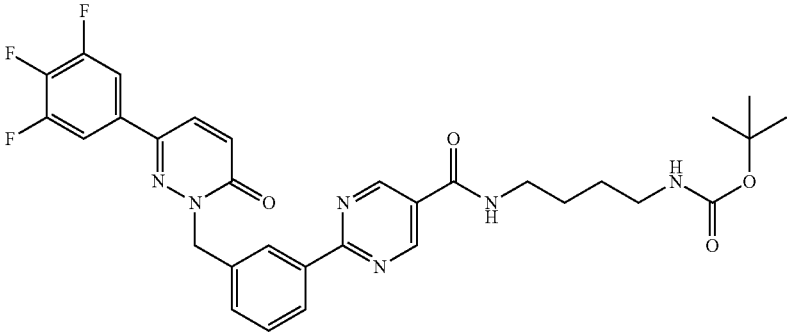 [SMILES: CC(C)(C)OC(=O)NCCCCNC(=O)c1cnc(-c2cccc(Cn3nc(-c4cc(F)c(F)c(F)c4)ccc3=O)c2)nc1] |
| "A39" | 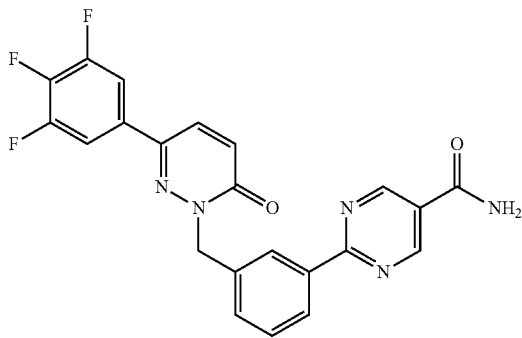 [SMILES: NC(=O)c1cnc(-c2cccc(Cn3nc(-c4cc(F)c(F)c(F)c4)ccc3=O)c2)nc1] |
| "A40" | 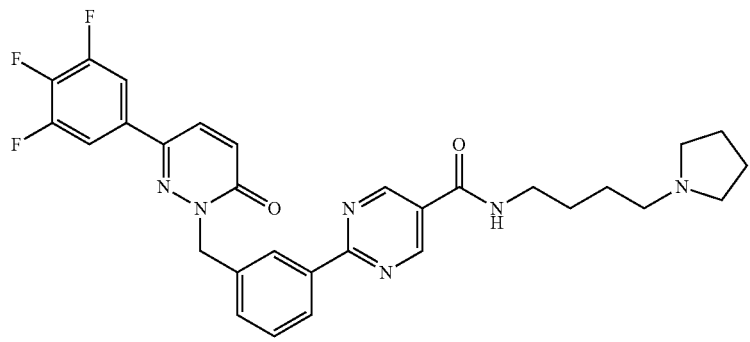 [SMILES: O=C(NCCCCN1CCCC1)c1cnc(-c2cccc(Cn3nc(-c4cc(F)c(F)c(F)c4)ccc3=O)c2)nc1] |
| "A41" | 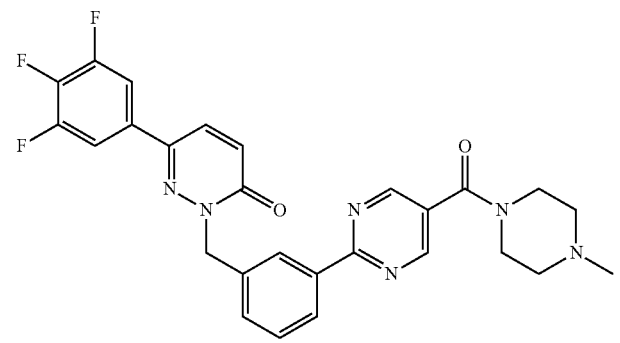 [SMILES: CN1CCN(C(=O)c2cnc(-c3cccc(Cn4nc(-c5cc(F)c(F)c(F)c5)ccc4=O)c3)nc2)CC1] |

| No. | Name and/or structure |
|---|---|
| "A42" | 3-(3,4,5-trifluorophenyl)-pyridazin-6(1H)-one linked via CH2 to 3-phenyl-pyrimidine-5-carboxamide with N-(4-hydroxybutyl) |
| "A43" | 3-(3,4,5-trifluorophenyl)-pyridazin-6(1H)-one linked via CH2 to 3-phenyl-pyrimidine-5-carboxamide with N-(1-Boc-piperidin-4-yl) |
| "A44" | 3-(3,4,5-trifluorophenyl)-pyridazin-6(1H)-one linked via CH2 to 3-phenyl-pyrimidine-5-carboxamide with N-((1-Boc-piperidin-4-yl)methyl) |
| "A44a" | 3-(3,4,5-trifluorophenyl)-pyridazin-6(1H)-one linked via CH2 to 3-phenyl-pyrimidine-5-carboxamide with N-(piperidin-4-ylmethyl) |

-continued
| No. | Name and/or structure |
|---|---|
| "A45" | 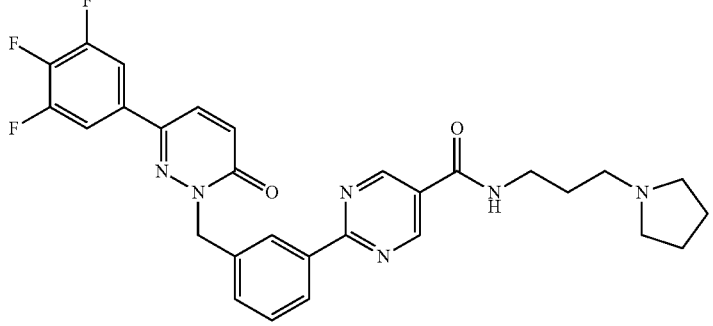 |
| "A46" | 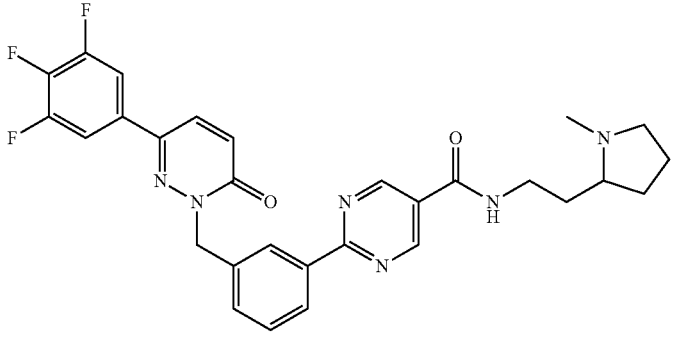 [SMILES: CN1CCCC1CCNC(=O)c1cnc(-c2cccc(Cn3nc(-c4cc(F)c(F)c(F)c4)ccc3=O)c2)nc1] |
| "A47" | 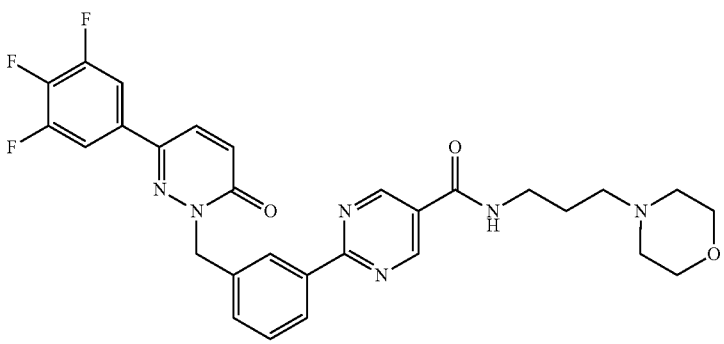 [SMILES: O=C(NCCCN1CCOCC1)c1cnc(-c2cccc(Cn3nc(-c4cc(F)c(F)c(F)c4)ccc3=O)c2)nc1] |
| "A48" | 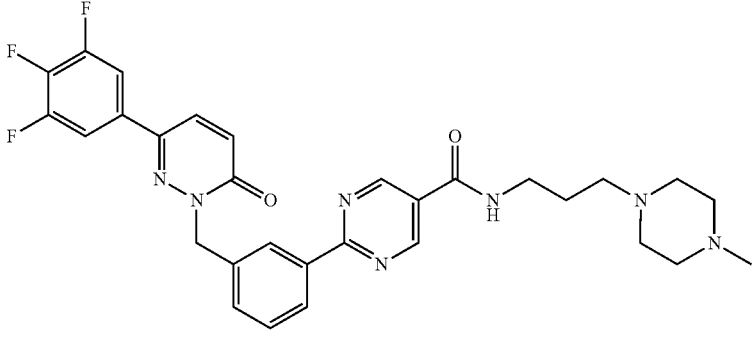 [SMILES: CN1CCN(CCCNC(=O)c2cnc(-c3cccc(Cn4nc(-c5cc(F)c(F)c(F)c5)ccc4=O)c3)nc2)CC1] |

| No. | Name and/or structure |
|---|---|
| "A49" | 6-(3,5-difluorophenyl)-2-[3-(2-{[4-(dimethylamino)butyl]carbamoyl}pyrimidin-5-yl... structure: 3,5-difluorophenyl-pyridazinone-CH2-phenyl-pyrimidine-C(O)NH-(CH2)4-N(CH3)2 |
| "A50" | 3,5-difluorophenyl-pyridazinone-CH2-phenyl-pyrimidine-C(O)NH-(CH2)4-pyrrolidin-1-yl |
| "A52" | 3,4,5-trifluorophenyl-pyridazinone-CH2-phenyl-pyrimidine-C(O)NH-(CH2)3-(1,2,4-triazol-1-yl) |
| "A53" | 3,4,5-trifluorophenyl-pyridazinone-CH2-phenyl-pyrimidine-C(O)NH-(CH2)3-(2-oxopyrrolidin-1-yl) |

-continued

| No. | Name and/or structure |
|---|---|
| "A59" | 6-(3,5-difluorophenyl)-2-{3-[4-(methylpiperidin-4-yl-amino)pyrimidin-2-yl]benzyl}-2H-pyridazin-3-one |
| "A63" | |
| "A71" | |
| "A72" | |
| "A73" | |

| No. | Name and/or structure |
|---|---|
| "A74" | |
| "A75" | 4-(2-{3-[3-(3,5-difluorophenyl)-6-oxo-6H-pyridazin-1-ylmethyl]-phenyl}pyrimidin-5-yl)morpholin-3-one |
| "A77" | 2-{3-[6-oxo-3-(3,4,5-trifluorophenyl)-6H-pyridazin-1-ylmethyl]-phenyl}pyrimidine-5-carbonitrile |
| "A78" | 6-[4-(3-dimethylaminopropoxy)-3,5-difluorophenyl]-2-[3-(5-methylpyrimidin-2-yl)benzyl]-2H-pyridazin-3-one |
| "A79" | 6-benzo-1,2,5-thiadiazol-5-yl-2-[3-(5-methylpyrimidin-2-yl)-benzyl]-2H-pyridazin-3-one |

| No. | Name and/or structure |
|---|---|
| "A84" | 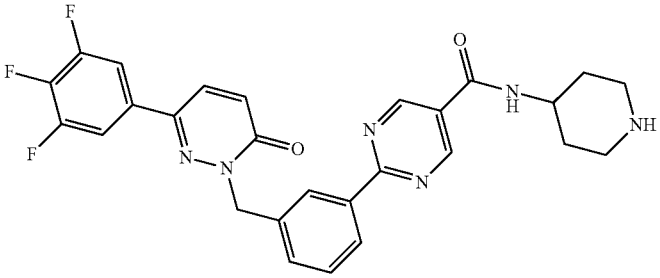 [SMILES: O=C(NC1CCNCC1)c1cnc(-c2cccc(Cn3nc(-c4cc(F)c(F)c(F)c4)ccc3=O)c2)nc1] |
| "A87" | N-(2-{3-[3-(3,5-difluorophenyl)-6-oxo-6H-pyridazin-1-ylmethyl]-phenyl}pyrimidin-5-yl)-4-dimethylaminobutyramide<br>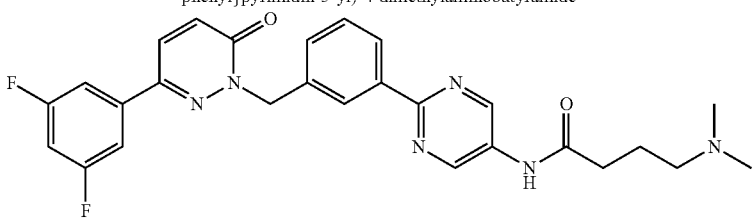 |
| "A88" | 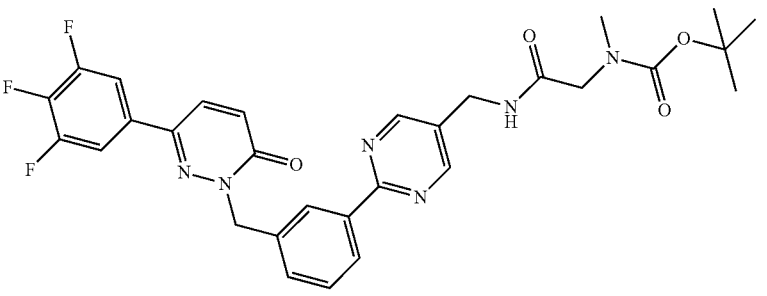 [SMILES: CN(CC(=O)NCc1cnc(-c2cccc(Cn3nc(-c4cc(F)c(F)c(F)c4)ccc3=O)c2)nc1)C(=O)OC(C)(C)C] |
| "A89" | 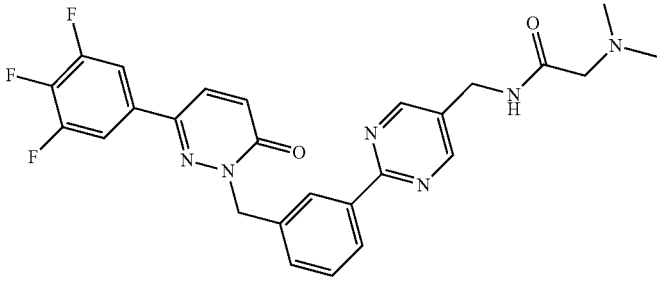 [SMILES: CN(C)CC(=O)NCc1cnc(-c2cccc(Cn3nc(-c4cc(F)c(F)c(F)c4)ccc3=O)c2)nc1] |
| "A90" | 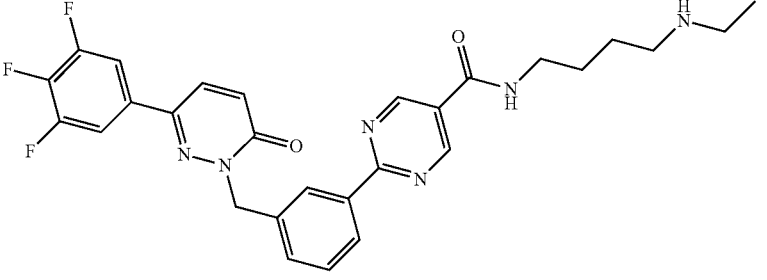 [SMILES: CCNCCCCNC(=O)c1cnc(-c2cccc(Cn3nc(-c4cc(F)c(F)c(F)c4)ccc3=O)c2)nc1] |

-continued

| No. | Name and/or structure |
|---|---|
| "A92" | 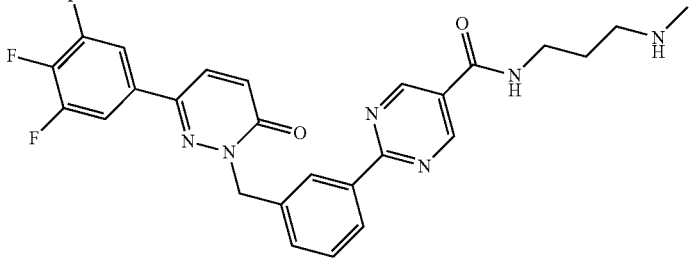 |
| "A95" | N-(2-{3-[3-difluorophenyl)-6-oxo-6H-pyridazin-1-ylmethyl]-phenyl}pyrimidin-5-yl)-3-dimethylaminopropionamide<br>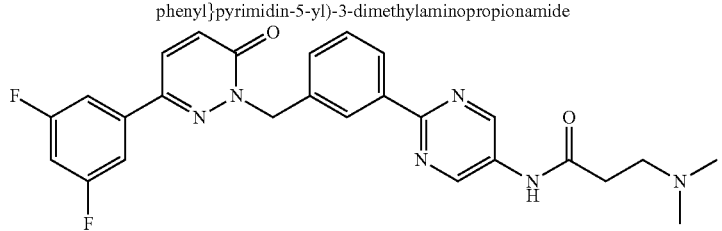 |
| "A96" | 3-(4-methylpiperazin-1-yl)-N-(2-{3-[6-oxo-3-(3,4,5-trifluoro-phenyl)-6H-pyridazin-1-ylmethyl]phenyl}pyrimidin-5-ylmethyl)-propionamide<br>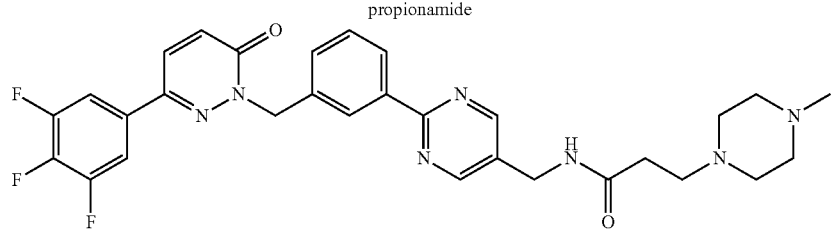 |
| "A97" | 2-(4-methylpiperazin-1-yl)-N-(2-{3-[6-oxo-3-(3,4,5-trifluoro-phenyl)-6H-pyridazin-1-ylmethyl]phenyl}pyrimidin-5-yl-methyl)acetamide<br>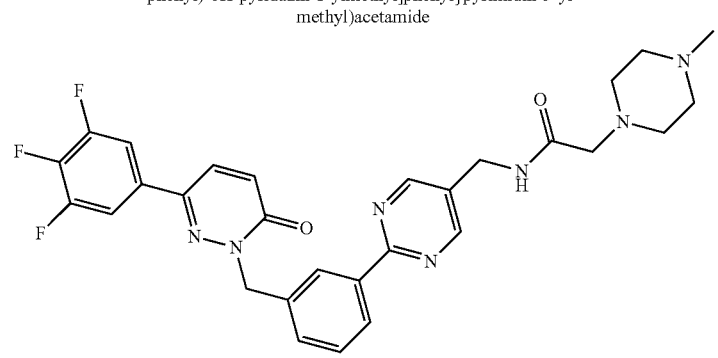 |
| "A98" | 2-methylamino-N-(2-{3-[6-oxo-3-(3,4,5-trifluorophenyl)-6H-pyridazin-1-ylmethyl]phenyl}pyrimidin-5-ylmethyl)acetamide<br>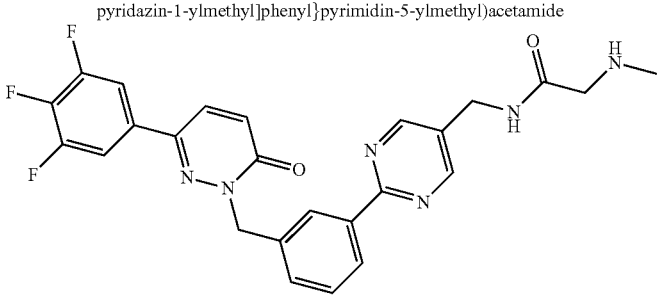 |

| No. | Name and/or structure |
|---|---|
| "A99" | 3-dimethylamino-N-(2-{3-[6-oxo-3-(3,4,5-trifluorophenyl)-6H-pyridazin-1-ylmethyl]phenyl}pyrimidin-5-ylmethyl)propionamide |
| "A103" | |
| "A104" | |
| "A105" | |
| "A106" | |

-continued

| No. | Name and/or structure |
|---|---|
| "A107" | 6-(3,5-difluorophenyl)-2-{3-[5-(1-(2-hydroxyethyl)-1H-pyrazol-4-yl)pyrimidin-2-yl]benzyl}pyridazin-3(2H)-one |
| "A108" | 6-(3,5-difluorophenyl)-2-{3-[5-(1-(2-morpholinoethyl)-1H-pyrazol-4-yl)pyrimidin-2-yl]benzyl}pyridazin-3(2H)-one |
| "A109" | 6-(3,5-difluorophenyl)-2-{3-[5-(1-(2-(dimethylamino)ethyl)-1H-pyrazol-4-yl)pyrimidin-2-yl]benzyl}pyridazin-3(2H)-one |
| "A110" | 6-(3,5-difluorophenyl)-2-{3-[5-(3-(pyrrolidin-1-yl)propoxy)pyrimidin-2-yl]benzyl}pyridazin-3(2H)-one |

-continued

| No. | Name and/or structure |
|---|---|
| "A111" | 6-(3,5-difluorophenyl)-2-{3-[5-(2-methylaminoethoxy)pyrimidin-2-yl]benzyl}-2H-pyridazin-3-one |
| "A112" | 6-(4-acetamidophenyl)-2-{3-(5-methylpyrimidin-2-yl)benzyl}-2H-pyridazin-3-one |
| "A113" | 6-(1-methyl-1H-pyrazol-4-yl)-2-{3-(5-methylpyrimidin-2-yl)benzyl}-2H-pyridazin-3-one |
| "A114" | 6-(3,5-difluorophenyl)-2-{3-[5-(3-pyrrolidin-1-ylpropoxy)pyrimidin-2-yl]benzyl}-2H-pyridazin-3-one |
| "A115" | 6-(3,5-difluorophenyl)-2-{3-[5-(2-(1-methylpyrrolidin-2-yl)ethoxy)pyrimidin-2-yl]benzyl}-2H-pyridazin-3-one |
| "A116" | 6-(3,5-difluorophenyl)-2-{3-[5-(1-methylazepan-4-yloxy)pyrimidin-2-yl]benzyl}-2H-pyridazin-3-one |
| "A117" | 6-(3,5-difluorophenyl)-2-{3-[5-(2-methoxyethoxy)pyrimidin-2-yl]benzyl}-2H-pyridazin-3-one |

| No. | Name and/or structure |
|---|---|
| "A118" | |
| "A119" | 6-(3,5-difluorophenyl)-2-{3-[5-(8-methyl-8-azabicyclo[3.2.1]oct-3-yloxy)pyrimidin-2-yl]benzyl}-2H-pyridazin-3-one |
| "A120" | |
| "A121" | 6-(3,5-difluorophenyl)-2-{3-[5-((S)-1-methylpyrrolidin-3-yloxy)-pyrimidin-2-yl]benzyl}-2H-pyridazin-3-one, |
| "A123" | |
| "A124" | |

| No. | Name and/or structure |
|---|---|
| "A125" | |
| "A126" | |
| "A129" | |
| "A131" | |
| "A142" | 2-{3-[5-(piperidin-4-yloxy)pyrimidin-2-yl]benzyl}-6-pyridin-4-yl-2H-pyridazin-3-one |
| "A143" | 4-(6-oxo-1-{3-[5-(piperidin-4-yloxy)pyrimidin-2-yl]benzyl}-1,6-dihydropyridazin-3-yl)benzonitrile |

-continued

| No. | Name and/or structure |
|---|---|
| "A149" | 2-{3-[5-(1-piperidin-4-yl-1H-pyrazol-4-yl)pyrimidin-2-yl]benzyl}-6-(3,4,5-trifluorophenyl)-2H-pyridazin-3-one |
| "A150" | 3-(6-oxo-1-{3-[5-(1-piperidin-4-yl-1H-pyrazol-4-yl)pyrimidin-2-yl]benzyl}-1,6-dihydropyridazin-3-yl)benzonitrile |
| "A151" | 6-(1-methyl-1H-pyrazol-4-yl)-2-{3-[5-(1-piperidin-4-yl-1H-pyrazol-4-yl)pyrimidin-2-yl]benzyl}-2H-pyridazin-3-one |
| "A154" | 6-(3,5-difluorophenyl)-2-{3-[5-(1H-pyrazol-4-yl)pyrimidin-2-yl]benzyl}-2H-pyridazin-3-one |

| No. | Name and/or structure |
|---|---|
| "A155" | 6-(3,5-difluorophenyl)-2-(3-{5-[1-(2-methylaminoethyl)-1H-pyrazol-4-yl]pyrimidin-2-yl}benzyl)-2H-pyridazin-3-one, |
| "A156" | 6-(3-chlorophenyl)-2-{3-[5-(1-piperidin-4-yl-1H-pyrazol-4-yl)-pyrimidin-2-yl]benzyl}-2H-pyridazin-3-one |
| "A157" | |
| "A158" | 6-(3,5-difluorophenyl)-2-(3-{5-[1-(3-methylaminopropyl)-1H-pyrazol-4-yl]pyrimidin-2-yl}benzyl)-2H-pyridazin-3-one |

-continued

| No. | Name and/or structure |
|---|---|
| "A159" | 3-[1-(3-{5-[1-(2-methylaminoethyl)-1H-pyrazol-4-yl]pyrimidin-2-yl}benzyl)-6-oxo-1,6-dihydropyridazin-3-yl]benzonitrile 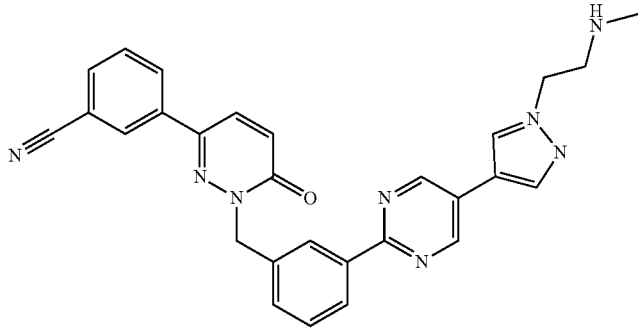 |
| "A160" | 6-(3,5-difluorophenyl)-2-(3-{5-[1-(2-piperazin-1-ylethyl)-1H-pyrazol-4-yl]pyrimidin-2-yl}benzyl)-2H-pyridazin-3-one 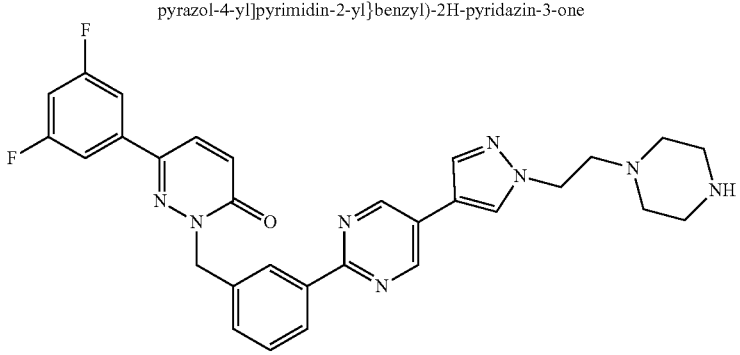 |
| "A161" | 3-(6-oxo-1-{3-[5-(1H-pyrazol-4-yl)pyrimidin-2-yl]benzyl}-1,6-dihydropyridazin-3-yl)benzonitrile 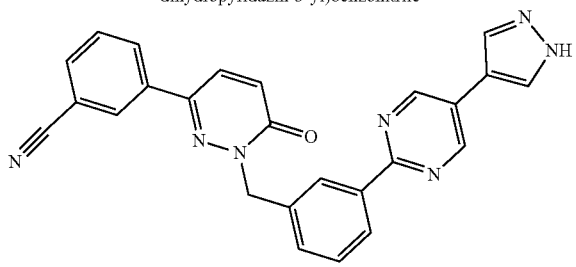 |
| "A162" | 3-[6-oxo-1-(3-{5-[1-(2-piperazin-1-ylethyl)-1H-pyrazol-4-yl]-pyrimidin-2-yl}benzyl)-1,6-dihydropyridazin-3-yl]benzonitrile 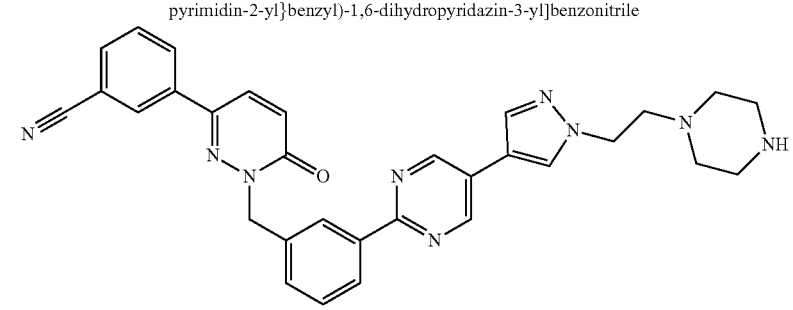 |

-continued

| No. | Name and/or structure |
|---|---|
| "A163" | N-(4-dimethylaminobutyl)-2-[3-(6-oxo-3-pyridin-4-yl-6H-pyridazin-1-ylmethyl)phenyl]pyrimidine-5-carboxamide |
| "A164" | N-(4-dimethylaminobutyl)-2-{3-[3-(4-cyanophenyl)-6-oxo-6H-pyridazin-1-ylmethyl]phenyl}pyrimidine-5-carboxamide |
| "A165" | |
| "A166" | |

-continued

| No. | Name and/or structure |
|---|---|
| "A167" | |
| "A168" | |
| "A169" | 6-(1-methyl-1H-pyrazol-4-yl)-2-(3-{5-[1-(2-pyrrolidin-1-ylethyl)-1H-pyrazol-4-yl]pyrimidin-2-yl}benzyl)-2H-pyridazin-3-one |
| "A170" | 6-(3,5-difluorophenyl)-2-(3-{5-[1-(2-morpholin-4-ylethyl)-1H-pyrazol-4-yl]pyrimidin-2-yl}benzyl)-2H-pyridazin-3-one |

-continued

| No. | Name and/or structure |
|---|---|
| "A171" | 6-(3,5-difluorophenyl)-2-(3-{5-[1-(2-dimethylaminoethyl)-1H-pyrazol-4-yl]pyrimidin-2-yl}benzyl)-2H-pyridazin-3-one |
| "A174" | 3-[1-(3-{5-[1-(2-morpholin-4-ylethyl)-1H-pyrazol-4-yl]pyrimidin-2-yl}benzyl)-6-oxo-1,6-dihydropyridazin-3-yl]benzonitrile |
| "A175" | 2-(3-{5-[1-(2-morpholin-4-ylethyl)-1H-pyrazol-4-yl]pyrimidin-2-yl}benzyl)-6-pyridin-3-yl-2H-pyridazin-3-one |
| "A176" | 6-(1-methyl-1H-pyrazol-4-yl)-2-(3-{5-[1-(2-morpholin-4-ylethyl)-1H-pyrazol-4-yl]pyrimidin-2-yl}benzyl)-2H-pyridazin-3-one |

-continued

| No. | Name and/or structure |
|---|---|
| "A180" | 4-[6-oxo-1-(3-{5-[1-(2-pyrrolidin-1-ylethyl)-1H-pyrazol-4-yl]-pyrimidin-2-yl]benzyl)-1,6-dihydropyridazin-3-yl]benzonitrile |
| "A182" | |
| "A184" | 6-(5-methyloxazol-2-yl)-2-(3-{5-[1-(2-pyrrolidin-1-ylethyl)-1H-pyrazol-4-yl]pyrimidin-2-yl}benzyl)-2H-pyridazin-3-one |
| "A186" | 6-(1-propyl-1H-pyrazol-4-yl)-2-(3-{5-[1-(2-[pyrrolidin-1-ylethyl)-1H-pyrazol-4-yl]pyrimidin-2-yl}benzyl)-2H-pyridazin-3-one |

| No. | Name and/or structure |
|---|---|
| "A187" | 2-(3-{5-[1-(2-pyrrolidin-1-ylethyl)-1H-pyrazol-4-yl]-pyrimidin-2-yl}benzyl)-6-thiophen-3-yl-2H-pyridazin-3-one |
| "A188" | |
| "A188a" | |
| "A190" | 2-{3-[5-(3-dimethylaminopropoxy)pyrimidin-2-yl]benzyl}-6-(1-methyl-1H-pyrazol-4-yl)-2H-pyridazin-3-one |

| No. | Name and/or structure |
|---|---|
| "A215" | N-[4-(1-{3-[5-(3-dimethylaminopropoxy)pyrimidin-2-yl]benzyl}-6-oxo-1,6-dihydropyridazin-3-yl)phenyl]acetamide |
| "A217" | 6-benzo-1,2,5-thiadiazol-5-yl-2-{3-[5-(3-dimethylaminopropoxy)-pyrimidin-2-yl]benzyl}-2H-pyridazin-3-one |
| "A225" | methyl 5-(1-{3-[5-(1-methylpiperidin-4-yloxy)pyrimidin-2-yl]-benzyl}-6-oxo-1,6-dihydropyridazin-3-yl)thiophene-2-carboxylate |
| "A227" | 2-{3-[5-(3-dimethylaminopropoxy)pyrimidin-2-yl]benzyl}-6-(5-oxo-4,5-dihydro-1,2,4-oxadiazol-3-yl)-2H-pyridazin-3-one |

-continued

| No. | Name and/or structure |
|---|---|
| "A228" | 2-{3-[5-(3-dimethylaminopropoxy)pyrimidin-2-yl]benzyl}-6-piperazin-1-yl-2H-pyridazin-3-one |
| "A244" | 2-(3-{5-[2-(4-methyl-3-oxopiperazin-1-yl)ethoxy]pyrimidin-2-yl}-benzyl)-6-(1-methyl-1H-pyrazol-4-yl)-2H-pyridazin-3-one |
| "A246" | 6-(1-methyl-1H-pyrazol-4-yl)-2-{3-[5-(2-morpholin-4-ylpropoxy)-pyrimidin-2-yl]benzyl}-2H-pyridazin-3-one |
| "A247" | 2-{3-[5-(1-methyl-2-morpholin-4-ylethoxy)pyrimidin-2-yl]-benzyl}-6-(1-methyl-1H-pyrazol-4-yl)-2H-pyridazin-3-one |
| "A249" | 2-{3-[5-(2-methyl-3-morpholin-4-ylpropoxy)pyrimidin-2-yl]-benzyl}-6-(1-methyl-1H-pyrazol-4-yl)-2H-pyridazin-3-one |
| "A252" | 6-(1-methyl-1H-pyrazol-4-yl)-2-{3-[5-(2-morpholin-4-yl-2-oxo-ethoxy)pyrimidin-2-yl]benzyl}-2H-pyridazin-3-one |

-continued
| No. | Name and/or structure |
|---|---|
| "A254" | 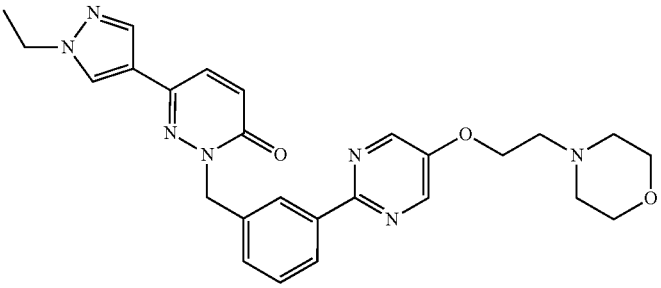 [SMILES: CCn1cc(-c2ccc(=O)n(Cc3cccc(-c4ncc(OCCN5CCOCC5)cn4)c3)n2)cn1] |
| "A255" | 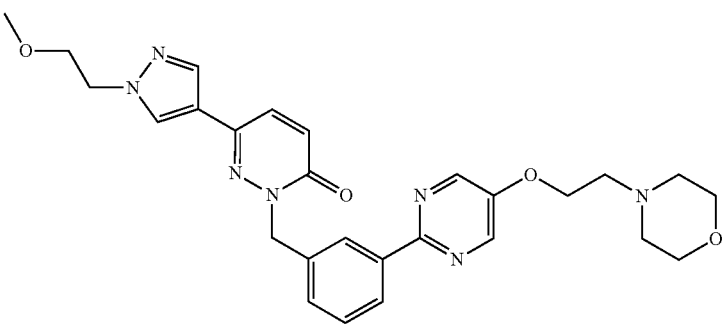 [SMILES: COCCn1cc(-c2ccc(=O)n(Cc3cccc(-c4ncc(OCCN5CCOCC5)cn4)c3)n2)cn1] |
| "A256" | 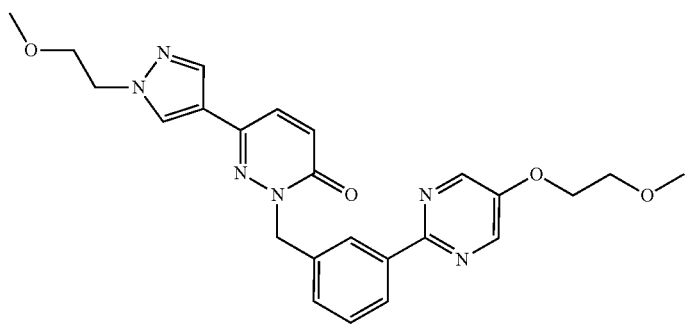 |
| "A261" | 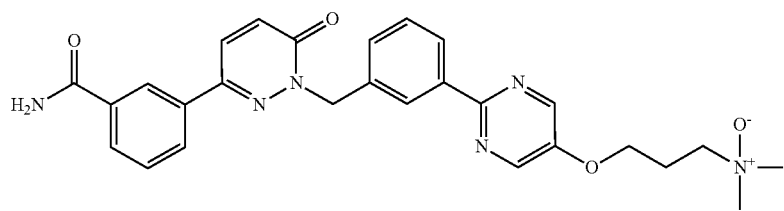 [SMILES: C[N+](C)([O-])CCCOc1cnc(-c2cccc(Cn3nc(-c4cccc(C(N)=O)c4)ccc3=O)c2)nc1] |
| "A268" | 3-(1-{3-[5-(3-methylaminopropoxy)pyrimidin-2-yl]benzyl}-6-oxo-1,6-dihydropyridazin-3-yl)benzonitrile<br>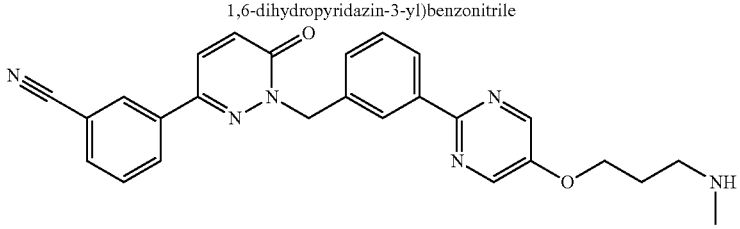 |

| No. | Name and/or structure |
|---|---|
| "A269" | 3-[1-(3-{5-[2-(4-methyl-3-oxopiperazin-1-yl)ethoxy]pyrimidin-2-yl}benzyl)-6-oxo-1,6-dihydropyridazin-3-yl]benzonitrile |
| "A276" | |
| "A276a" | |
| "A304" | |
| "A305" | |
| "A306" | |

| No. | Name and/or structure |
|---|---|
| "A307" | |
| "A308" | |
| "A309" | |
| "A310" | |
| "A311" | |
| "A312" | |

| No. | Name and/or structure |
|---|---|
| "A313" | 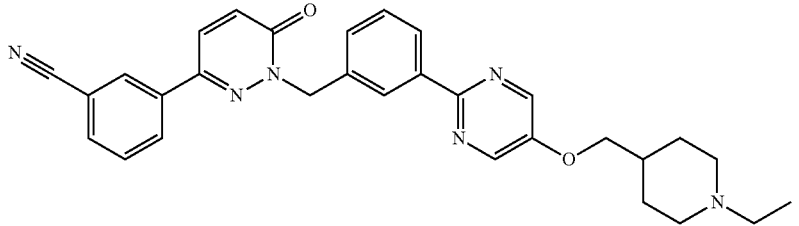 or |
| "A314" | 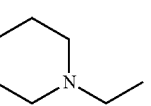 | or a pharmaceutically acceptable solvate, salt, tautomer or stereoisomer thereof.

22. A compound according to claim 1, which is 3-(1-{3-[5-(1-methylpiperidin-4-ylmethoxy)pyrimidin-2-yl]benzyl}-6-oxo-1,6-dihydropyridazin-3-yl)benzonitrile or a pharmaceutically acceptable solvate, salt, tautomer or stereoisomer thereof.

23. A compound according to claim 1, or a pharmaceutically acceptable salt thereof.

24. A compound according to claim 20, or a pharmaceutically acceptable salt thereof.

25. A compound according to claim 21, or a pharmaceutically acceptable salt thereof.

26. A compound according to claim 22, which is 3-(1-{3-[5-(1-methylpiperidin-4-ylmethoxy)pyrimidin-2-yl]benzyl}-6-oxo-1,6-dihydropyridazin-3-yl)benzonitrile, or a pharmaceutically acceptable salt thereof.

27. A compound according to claim 22, which is 3-(1-{3-[5-(1-methyl-piperidin-4-ylmethoxy)pyrimidin-2-yl]benzyl}-6-oxo-1,6-dihydropyridazin-3-yl)benzonitrile.

28. A compound according to claim 1, in which
$R^1$ denotes Ar or Het,
$R^2$ denotes pyrimidinyl, which is monosubstituted by Hal, A, $[C(R^3)_2]_nOR^3$, $N=CR^3N(R^3)_2$, CN, $COOR^3$, $[C(R^3)_2]_nN(R^3)_2$, $[C(R^3)_2]_n$Het, $O[C(R^3)_2]_pOR^3$, $O[C(R^3)_2]_nN(R^3)_2$, $O[C(R^3)_2]_nC\equiv C[C(R^3)_2]_nN(R^3)_2$, $O[C(R^3)_2]_nN^+O^-(R^3)_2$, $O[C(R^3)_2]_n$Het, $NR^3[C(R^3)_2]_nN(R^3)_2$, $NR^3[C(R^3)_2]_n$Het, $[C(R^3)_2]_n$NHCO$[C(R^3)_2]_{n-}$N$(R^3)_2$, $[C(R^3)_2]_n$NHCO$[C(R^3)_2]_n$Het, $CONR^3[C(R^3)_2]_nN(R^3)_2$, $CONR^3[C(R^3)_2]_nNR^3COOA$, $CONR^3[C(R^3)_2]_nOR^3$, $CONR^3[C(R^3)_2]_n$Het, COHet, CH=CH—COOR$^3$,
CH=CH—N(R$^3$)$_2$ and/or =O,
$R^3$ denotes H, methyl, ethyl or propyl,
$R^4$, $R^{4'}$ denote H, Ar denotes phenyl, naphthyl or biphenyl, each of which is unsubstituted or mono-, di- or trisubstituted by A, Hal, CN, $S(O)_mA$, $NR^3COA$, $CON(R^3)_2$, $O[C(R^3)_2]_nN(R^3)_2$, $[C(R^3)_2]_nOR^3$, $CONR^3[C(R^3)_2]_nN(R^3)_2$ and/or $CONR^3[C(R^3)_2]_n$Het, Het denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, azabicyclo[3.2.1]octyl, azabicyclo[2.2.2]octyl, imidazolidinyl, azepanyl or benzo-2,1,3-thiadiazolyl, each of which is unsubstituted or mono-, di-, tri-, tetra- or penta- substituted by A, CHO, $COOR^3$, $CON(R^3)_2$, $[C(R^3)_2]_n$Het$^1$, $[C(R^3)_2]_nOR^3$, $[C(R^3)_2]_nN(R^3)_2$, $O[C(R^3)_2]_n$Het$^1$ and/or =O, and where a ring nitrogen is optionally oxidized, Het$^1$ denotes pyrrolidine, piperidine, piperazine or morpholine, each of which is unsubstituted or mono- or disubstituted by A and/or =O, A denotes unbranched or branched alkyl having 1-8 C atoms, in which 1-7 H atoms are optionally replaced by F, Hal denotes F, Cl, Br or I, m denotes 0, 1 or 2, n denotes 0, 1, 2, 3 or 4, and p denotes 1, 2, 3 or 4, or a pharmaceutically acceptable solvate, salt, tautomer or stereoisomer thereof.

29. A compound according to claim 28, or a pharmaceutically acceptable salt thereof.

* * * * *

UNITED STATES PATENT AND TRADEMARK OFFICE
CERTIFICATE OF CORRECTION

PATENT NO. : 8,580,781 B2  
APPLICATION NO. : 12/668535  
DATED : November 12, 2013  
INVENTOR(S) : Dieter Dorsch et al.

Page 1 of 1

It is certified that error appears in the above-identified patent and that said Letters Patent is hereby corrected as shown below:

In the Claims:

Column 204, line 66 (Claim 1), reads as follows:  
-- $(R^3)_2]_nC\equiv C[C(R^3)_2]_nN(R^3)_2, O[C(R^3)_2]_nN^+O^{31}(R^3)_2$, --  
Should read as: -- $(R^3)_2]_nC\equiv C[C(R^3)_2]_nN(R^3)_2, O[C(R^3)_2]_nN^+O^-(R^3)_2$, --

Column 205, line 53 (Claim 2), reads as follows: -- $R^2$ denotes pyrimidines, which is monosubstituted by Hal, --  
Should read as: -- $R^2$ denotes pyrimidinyl, which is monosubstituted by Hal, --

Signed and Sealed this  
Eighth Day of July, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,580,781 B2  Page 1 of 1
APPLICATION NO. : 12/668535
DATED : November 12, 2013
INVENTOR(S) : Dorsch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 689 days.

Signed and Sealed this
Twenty-second Day of September, 2015

Michelle K. Lee
*Director of the United States Patent and Trademark Office*